US010220158B2

(12) United States Patent
Blondino et al.

(10) Patent No.: US 10,220,158 B2
(45) Date of Patent: Mar. 5, 2019

(54) DEVICES AND METHODS FOR DELIVERING OPIOID ANTAGONISTS INCLUDING FORMULATIONS FOR NALOXONE

(71) Applicant: kaleo, Inc., Richmond, VA (US)

(72) Inventors: Frank E. Blondino, Henrico, VA (US); Eric S. Edwards, Moseley, VA (US); Evan T. Edwards, Charlottesville, VA (US); Glen L. Kelley, Glen Allen, VA (US); Paul F. Meyers, Fishers, IN (US)

(73) Assignee: kaleo, Inc., Richmond, VA (US)

( * ) Notice: Subject to any disclaimer, the term of this patent is extended or adjusted under 35 U.S.C. 154(b) by 245 days.

(21) Appl. No.: 15/371,515

(22) Filed: Dec. 7, 2016

(65) Prior Publication Data

US 2017/0232206 A1  Aug. 17, 2017

Related U.S. Application Data

(62) Division of application No. 14/335,490, filed on Jul. 18, 2014, now Pat. No. 9,517,307.

(51) Int. Cl.
*A61M 5/32* (2006.01)
*A61M 5/20* (2006.01)
(Continued)

(52) U.S. Cl.
CPC ......... *A61M 5/3234* (2013.01); *A61K 9/0019* (2013.01); *A61K 31/485* (2013.01);
(Continued)

(58) Field of Classification Search
CPC .. A61M 5/3234; A61M 11/02; A61M 5/2053; A61M 5/3287; A61M 5/2033;
(Continued)

(56) References Cited

U.S. PATENT DOCUMENTS 2,960,087 A   11/1960   Uytenbogaart
3,055,362 A    9/1962   Uytenbogaart
(Continued)

FOREIGN PATENT DOCUMENTS

DE        2019296        11/1971
DE   20 2009 003 009     7/2009
(Continued)

OTHER PUBLICATIONS

"Insect Stings Auto-injector Pouches and Carry Cases," The Insect Stings On-Line Shop, [online] [retrieved on Jan. 24, 2007] Retrieved from the Internet <URL: http://www.insectstings.co.uk/acatalog/Auto Injector Pouches.html >, 3 pages.
(Continued)

*Primary Examiner* — Amber Stiles

(57) ABSTRACT

An apparatus includes a container, a needle, and an actuation assembly. The container contains a dose of a naloxone composition having a delivered volume of at least about 0.34 mL. The actuation assembly includes an energy storage member that produces a force on a movable member to move the needle and to deliver the dose of the naloxone composition. The 90% confidence interval of at least one of the relative mean maximum naloxone plasma concentration after dose delivery into the body ($C_{max}$), time to reach the maximum naloxone plasma concentration ($T_{max}$), area under the plasma concentration-time curve from pre-dose (time 0) extrapolated to infinity ($AUC_{0-\infty}$), or area under the plasma concentration-time curve from pre-dose (time 0) to the time of the last quantifiable concentration ($T_{last}$) ($AUC_{0-t}$) of the delivered dose to a delivered dose of a corresponding naloxone composition delivered via a manually-actuated syringe is within 80% to 125%.

21 Claims, 46 Drawing Sheets

(51) Int. Cl.
  *A61K 31/485* (2006.01)
  *A61K 9/00* (2006.01)
  *A61M 11/02* (2006.01)
(52) U.S. Cl.
  CPC ........ *A61M 5/2033* (2013.01); *A61M 5/2053* (2013.01); *A61M 5/3287* (2013.01); *A61M 11/02* (2013.01); *Y02A 50/465* (2018.01)
(58) Field of Classification Search
  CPC ... A61K 9/0019; A61K 31/485; Y02A 50/465
  See application file for complete search history.

(56) References Cited

U.S. PATENT DOCUMENTS

| | | |
|---|---|---|
| 3,115,133 A | 12/1963 | Morando |
| 3,426,448 A | 2/1969 | Sarnoff |
| 3,688,765 A | 9/1972 | Gasaway |
| 3,768,472 A | 10/1973 | Hodosh et al. |
| 3,795,061 A | 3/1974 | Sarnoff et al. |
| 3,945,379 A | 3/1976 | Pritz et al. |
| 4,031,889 A | 6/1977 | Pike |
| 4,108,177 A | 8/1978 | Pistor |
| 4,186,741 A | 2/1980 | Cesaro |
| 4,226,235 A | 10/1980 | Sarnoff et al. |
| 4,227,528 A | 10/1980 | Wardlaw |
| 4,258,713 A | 3/1981 | Wardlaw |
| 4,284,077 A | 8/1981 | Wagner |
| 4,360,019 A | 11/1982 | Portner et al. |
| 4,378,015 A | 3/1983 | Wardlaw |
| 4,394,863 A | 7/1983 | Bartner |
| 4,424,057 A | 1/1984 | House |
| 4,441,629 A | 4/1984 | Mackal |
| 4,484,910 A | 11/1984 | Sarnoff |
| 4,573,976 A | 3/1986 | Sampson et al. |
| 4,596,556 A | 6/1986 | Morrow et al. |
| 4,610,666 A | 9/1986 | Pizzino |
| 4,613,328 A | 9/1986 | Boyd |
| 4,617,557 A | 10/1986 | Gordon |
| 4,624,660 A | 11/1986 | Mijers et al. |
| 4,640,686 A | 2/1987 | Dalling et al. |
| 4,643,721 A | 2/1987 | Brunet |
| 4,666,430 A | 5/1987 | Brown et al. |
| 4,673,657 A | 6/1987 | Christian |
| 4,689,042 A | 8/1987 | Sarnoff et al. |
| 4,693,708 A | 9/1987 | Wanderer et al. |
| 4,755,172 A | 7/1988 | Baldwin |
| 4,781,697 A | 11/1988 | Slaughter |
| 4,782,841 A | 11/1988 | Lopez |
| 4,784,652 A | 11/1988 | Wikström |
| 4,795,433 A | 1/1989 | Sarnoff |
| 4,853,521 A | 8/1989 | Claeys et al. |
| 4,874,382 A | 10/1989 | Lindemann et al. |
| 4,894,054 A | 1/1990 | Miskinyar |
| 4,906,235 A | 3/1990 | Roberts |
| 4,906,463 A | 3/1990 | Cleary |
| 4,915,695 A | 4/1990 | Koobs |
| 4,941,880 A | 7/1990 | Burns |
| 4,955,871 A | 9/1990 | Thomas |
| 4,959,056 A | 9/1990 | Dombrowski et al. |
| 4,968,302 A | 11/1990 | Schluter et al. |
| 4,983,164 A | 1/1991 | Hook et al. |
| 5,000,736 A | 3/1991 | Kaufhold, Jr. et al. |
| 5,024,656 A | 6/1991 | Gasaway et al. |
| 5,037,306 A | 8/1991 | van Schoonhoven |
| 5,038,023 A | 8/1991 | Saliga |
| 5,041,088 A | 8/1991 | Ritson et al. |
| 5,062,603 A | 11/1991 | Smith et al. |
| 5,064,413 A | 11/1991 | McKinnon et al. |
| 5,071,353 A | 12/1991 | van der Wal |
| 5,085,642 A | 2/1992 | Sarnoff et al. |
| 5,092,843 A | 3/1992 | Monroe et al. |
| 5,096,715 A | 3/1992 | Sinclair |
| 5,125,898 A | 6/1992 | Kaufhold, Jr. et al. |
| 5,167,641 A | 12/1992 | Schmitz |
| 5,199,949 A | 4/1993 | Haber et al. |
| 5,224,936 A | 7/1993 | Gallagher |
| 5,240,146 A | 8/1993 | Smedley et al. |
| 5,271,527 A | 12/1993 | Haber et al. |
| 5,281,198 A | 1/1994 | Haber et al. |
| 5,286,258 A | 2/1994 | Haber et al. |
| 5,298,023 A | 3/1994 | Haber et al. |
| 5,312,326 A | 5/1994 | Myers et al. |
| 5,314,412 A | 5/1994 | Rex |
| 5,314,502 A | 5/1994 | McNichols et al. |
| 5,343,519 A | 8/1994 | Feldman |
| 5,344,407 A | 9/1994 | Ryan |
| 5,354,284 A | 10/1994 | Haber et al. |
| 5,354,286 A | 10/1994 | Mesa et al. |
| 5,356,376 A | 10/1994 | Milijasevic et al. |
| 5,358,489 A | 10/1994 | Wyrick |
| 5,363,842 A | 11/1994 | Mishelevich et al. |
| 5,380,281 A | 1/1995 | Tomellini et al. |
| 5,383,851 A | 1/1995 | McKinnon, Jr. et al. |
| 5,394,866 A | 3/1995 | Ritson et al. |
| 5,399,163 A | 3/1995 | Peterson et al. |
| 5,405,362 A | 4/1995 | Kramer et al. |
| 5,417,660 A | 5/1995 | Martin |
| 5,451,210 A | 9/1995 | Kramer et al. |
| 5,466,217 A | 11/1995 | Myers et al. |
| 5,478,316 A | 12/1995 | Bitdinger et al. |
| 5,514,097 A | 5/1996 | Knauer |
| 5,514,135 A | 5/1996 | Earle |
| 5,540,664 A | 7/1996 | Wyrick |
| 5,558,679 A | 9/1996 | Tuttle |
| 5,567,160 A | 10/1996 | Massino |
| 5,568,555 A | 10/1996 | Shamir |
| 5,569,192 A | 10/1996 | van der Wal |
| 5,584,815 A | 12/1996 | Pawelka et al. |
| 5,587,381 A | 12/1996 | Sinclair |
| 5,610,992 A | 3/1997 | Hickman |
| 5,615,771 A | 4/1997 | Hollister |
| 5,616,132 A | 4/1997 | Newman |
| 5,645,534 A | 7/1997 | Chanoch |
| 5,662,612 A | 9/1997 | Niehoff |
| 5,681,291 A | 10/1997 | Galli |
| 5,681,292 A | 10/1997 | Tober et al. |
| 5,692,492 A | 12/1997 | Bruna et al. |
| 5,695,476 A | 12/1997 | Harris |
| 5,697,916 A | 12/1997 | Schraga |
| 5,716,338 A | 2/1998 | Hjertman et al. |
| 5,728,074 A | 3/1998 | Castellano et al. |
| 5,772,635 A | 6/1998 | Dastur et al. |
| 5,792,190 A | 8/1998 | Olson et al. |
| 5,800,397 A | 9/1998 | Wilson et al. |
| 5,805,423 A | 9/1998 | Wever et al. |
| 5,809,997 A | 9/1998 | Wolf |
| 5,813,397 A | 9/1998 | Goodman et al. |
| 5,813,570 A | 9/1998 | Fuchs et al. |
| 5,814,020 A | 9/1998 | Gross |
| 5,823,346 A | 10/1998 | Weiner |
| 5,823,363 A | 10/1998 | Cassel |
| 5,832,488 A | 11/1998 | Eberhardt |
| 5,837,546 A | 11/1998 | Allen et al. |
| RE35,986 E | 12/1998 | Ritson et al. |
| 5,846,089 A | 12/1998 | Weiss et al. |
| 5,848,988 A | 12/1998 | Davis |
| 5,852,590 A | 12/1998 | de la Huerga |
| 5,853,292 A | 12/1998 | Eggert et al. |
| 5,858,001 A | 1/1999 | Tsals et al. |
| 5,865,795 A | 2/1999 | Schiff et al. |
| 5,866,154 A | 2/1999 | Bahal |
| 5,868,713 A | 2/1999 | Klippenstein |
| 5,868,721 A | 2/1999 | Marinacci |
| D407,487 S | 3/1999 | Greubel et al. |
| 5,925,021 A | 7/1999 | Castellano et al. |
| 5,928,195 A | 7/1999 | Malamud |
| 5,941,857 A | 8/1999 | Nguyen et al. |
| 5,964,739 A | 10/1999 | Champ |
| 5,970,457 A | 10/1999 | Brant et al. |
| 5,971,953 A | 10/1999 | Bachynsky |
| 5,991,655 A | 11/1999 | Gross et al. |
| 6,015,438 A | 1/2000 | Shaw |
| 6,030,363 A | 2/2000 | Kriesel |

(56) References Cited

U.S. PATENT DOCUMENTS

| | | |
|---|---|---|
| 6,039,713 A | 3/2000 | Botich et al. |
| 6,045,534 A | 4/2000 | Jacobsen et al. |
| 6,050,977 A | 4/2000 | Adams |
| 6,056,728 A | 5/2000 | von Schuckmann |
| 6,062,901 A | 5/2000 | Liu et al. |
| 6,063,053 A | 5/2000 | Castellano et al. |
| 6,074,213 A | 6/2000 | Hon |
| 6,077,106 A | 6/2000 | Mish |
| 6,083,199 A | 7/2000 | Thorley et al. |
| 6,084,526 A | 7/2000 | Blotky et al. |
| 6,086,562 A | 7/2000 | Jacobsen et al. |
| 6,096,002 A | 8/2000 | Landau |
| 6,099,504 A | 8/2000 | Gross et al. |
| 6,102,896 A | 8/2000 | Roser |
| 6,119,684 A | 9/2000 | Nöhl et al. |
| 6,149,626 A | 11/2000 | Rachynsky et al. |
| 6,158,613 A | 12/2000 | Novosel et al. |
| 6,161,281 A | 12/2000 | Dando et al. |
| 6,165,155 A | 12/2000 | Jacobsen et al. |
| 6,179,812 B1 | 1/2001 | Botich et al. |
| 6,192,891 B1 | 2/2001 | Gravel et al. |
| 6,193,695 B1 | 2/2001 | Rippstein, Jr. |
| 6,202,642 B1 | 3/2001 | McKinnon et al. |
| 6,210,359 B1 | 4/2001 | Patel et al. |
| 6,210,369 B1 | 4/2001 | Wilmot et al. |
| 6,219,587 B1 | 4/2001 | Ahlin et al. |
| 6,221,045 B1 | 4/2001 | Duchon et al. |
| 6,221,055 B1 | 4/2001 | Shaw et al. |
| 6,245,046 B1 | 6/2001 | Sibbitt |
| 6,258,063 B1 | 7/2001 | Haar et al. |
| 6,258,068 B1 | 7/2001 | Kirchhofer et al. |
| 6,259,654 B1 | 7/2001 | de la Huerga |
| 6,264,629 B1 | 7/2001 | Landau |
| 6,270,455 B1 | 8/2001 | Brown |
| 6,270,479 B1 | 8/2001 | Bergens et al. |
| 6,280,421 B1 | 8/2001 | Kirchhofer et al. |
| 6,284,765 B1 | 9/2001 | Caffrey |
| 6,312,412 B1 | 11/2001 | Saied et al. |
| 6,317,630 B1 | 11/2001 | Gross et al. |
| 6,321,070 B1 | 11/2001 | Clark et al. |
| 6,321,654 B1 | 11/2001 | Robinson |
| 6,321,942 B1 | 11/2001 | Krampen et al. |
| 6,323,780 B1 | 11/2001 | Morris |
| 6,334,070 B1 | 12/2001 | Nova et al. |
| 6,364,866 B1 | 4/2002 | Furr et al. |
| 6,371,939 B2 | 4/2002 | Bergens et al. |
| 6,377,848 B1 | 4/2002 | Garde et al. |
| 6,382,465 B1 | 5/2002 | Greiner-Perth |
| 6,387,078 B1 | 5/2002 | Gillespie, III |
| 6,405,912 B2 | 6/2002 | Giannou |
| 6,406,455 B1 | 6/2002 | Willis et al. |
| 6,411,567 B1 | 6/2002 | Niemiec et al. |
| 6,413,236 B1 | 7/2002 | Van Dyke |
| 6,425,499 B1 | 7/2002 | Guiffray |
| 6,425,897 B2 | 7/2002 | Overes et al. |
| 6,428,517 B1 | 8/2002 | Hochman et al. |
| 6,428,528 B2 | 8/2002 | Sadowski |
| 6,446,839 B1 | 9/2002 | Ritsche |
| 6,475,181 B1 | 11/2002 | Potter et al. |
| 6,478,769 B1 | 11/2002 | Parker |
| 6,478,771 B1 | 11/2002 | Lavi et al. |
| 6,482,186 B1 | 11/2002 | Douglas et al. |
| 6,494,863 B1 | 12/2002 | Shaw et al. |
| 6,500,150 B1 | 12/2002 | Gross et al. |
| 6,514,230 B1 | 2/2003 | Munk et al. |
| 6,529,446 B1 | 3/2003 | de la Huerga |
| 6,530,900 B1 | 3/2003 | Daily et al. |
| 6,530,904 B1 | 3/2003 | Edwards et al. |
| 6,535,714 B2 | 3/2003 | Melker et al. |
| 6,540,672 B1 | 4/2003 | Simonsen et al. |
| 6,540,675 B2 | 4/2003 | Aceti et al. |
| 6,544,234 B1 | 4/2003 | Gabriel |
| 6,551,276 B1 | 4/2003 | Mann et al. |
| 6,551,298 B1 | 4/2003 | Zhang |
| 6,554,798 B1 | 4/2003 | Mann et al. |
| 6,558,320 B1 | 5/2003 | Causey, III et al. |
| 6,565,533 B1 | 5/2003 | Smith et al. |
| 6,569,123 B2 | 5/2003 | Alchas |
| 6,572,584 B1 | 6/2003 | Shaw et al. |
| 6,574,166 B2 | 6/2003 | Niemiec |
| 6,575,939 B1 | 6/2003 | Brunel |
| RE38,189 E | 7/2003 | Walker et al. |
| 6,585,685 B2 | 7/2003 | Staylor et al. |
| 6,585,698 B1 | 7/2003 | Packman et al. |
| 6,589,158 B2 | 7/2003 | Winkler |
| 6,595,956 B1 | 7/2003 | Gross et al. |
| 6,599,272 B1 | 7/2003 | Hjertman et al. |
| 6,610,271 B2 | 8/2003 | Wermeling |
| 6,613,010 B2 | 9/2003 | Castellano |
| 6,616,627 B2 | 9/2003 | Willis et al. |
| 6,633,796 B1 | 10/2003 | Pool et al. |
| 6,641,566 B2 | 11/2003 | Douglas et al. |
| 6,645,171 B1 | 11/2003 | Robinson et al. |
| 6,645,181 B1 | 11/2003 | Lavi et al. |
| 6,648,850 B2 | 11/2003 | Landau |
| 6,659,980 B2 | 12/2003 | Moberg et al. |
| 6,673,035 B1 | 1/2004 | Rice et al. |
| 6,676,630 B2 | 1/2004 | Landau et al. |
| 6,679,862 B2 | 1/2004 | Diaz et al. |
| 6,689,093 B2 | 2/2004 | Landau |
| 6,692,469 B1 | 2/2004 | Weekes et al. |
| 6,702,778 B2 | 3/2004 | Hill et al. |
| 6,706,019 B1 | 3/2004 | Parker et al. |
| 6,707,763 B2 | 3/2004 | Osberg et al. |
| 6,708,050 B2 | 3/2004 | Carim |
| 6,708,846 B1 | 3/2004 | Fuchs et al. |
| 6,722,916 B2 | 4/2004 | Buccinna et al. |
| 6,723,077 B2 | 4/2004 | Pickup et al. |
| 6,726,657 B1 | 4/2004 | Dedig et al. |
| 6,726,661 B2 | 4/2004 | Munk et al. |
| 6,736,796 B2 | 5/2004 | Shekalim |
| 6,743,635 B2 | 6/2004 | Neel et al. |
| 6,749,437 B2 | 6/2004 | Chan |
| 6,752,781 B2 | 6/2004 | Landau et al. |
| 6,764,469 B2 | 7/2004 | Broselow |
| 6,767,336 B1 | 7/2004 | Kaplan |
| 6,770,052 B2 | 8/2004 | Hill et al. |
| 6,770,056 B2 | 8/2004 | Price et al. |
| 6,783,509 B1 | 8/2004 | Landau et al. |
| 6,784,798 B2 | 8/2004 | Morris |
| 6,786,875 B2 | 9/2004 | Barker et al. |
| 6,786,885 B2 | 9/2004 | Hochman et al. |
| 6,793,646 B1 | 9/2004 | Giambattista et al. |
| 6,803,856 B1 | 10/2004 | Murphy et al. |
| 6,805,686 B1 | 10/2004 | Fathallah et al. |
| 6,808,514 B2 | 10/2004 | Schneider et al. |
| 6,809,653 B1 | 10/2004 | Mann et al. |
| 6,817,986 B2 | 11/2004 | Slate et al. |
| 6,830,560 B1 | 12/2004 | Gross et al. |
| 6,839,304 B2 | 1/2005 | Niemiec et al. |
| 6,872,200 B2 | 3/2005 | Mann et al. |
| 6,875,195 B2 | 4/2005 | Choi |
| 6,883,222 B2 | 4/2005 | Landau |
| 6,923,764 B2 | 8/2005 | Aceti et al. |
| 6,936,029 B2 | 8/2005 | Mann et al. |
| 6,937,150 B2 | 8/2005 | Medema et al. |
| 6,942,646 B2 | 9/2005 | Langley et al. |
| 6,945,961 B2 | 9/2005 | Miller et al. |
| 6,946,299 B2 | 9/2005 | Neel et al. |
| 6,948,492 B2 | 9/2005 | Wermeling et al. |
| 6,949,082 B2 | 9/2005 | Langley et al. |
| 6,950,028 B2 | 9/2005 | Zweig |
| 6,952,604 B2 | 10/2005 | DeNuzzio et al. |
| 6,953,445 B2 | 10/2005 | Wilmot et al. |
| 6,953,693 B2 | 10/2005 | Neel et al. |
| 6,958,691 B1 | 10/2005 | Anderson et al. |
| 6,959,247 B2 | 10/2005 | Neel et al. |
| 6,961,285 B2 | 11/2005 | Niemiec et al. |
| 6,964,650 B2 | 11/2005 | Alexandre et al. |
| 6,969,259 B2 | 11/2005 | Pastrick et al. |
| 6,979,316 B1 | 12/2005 | Rubin et al. |
| 6,979,326 B2 | 12/2005 | Mann et al. |
| 6,985,870 B2 | 1/2006 | Martucci et al. |
| 6,997,911 B2 | 2/2006 | Klitmose |

(56) References Cited

U.S. PATENT DOCUMENTS

| | | |
|---|---|---|
| 7,014,470 B2 | 3/2006 | Vann |
| 7,074,211 B1 | 7/2006 | Heiniger et al. |
| 7,077,835 B2 | 7/2006 | Robinson et al. |
| 7,093,595 B2 | 8/2006 | Nesbitt |
| 7,102,526 B2 | 9/2006 | Zweig |
| 7,104,972 B2 | 9/2006 | Moller et al. |
| 7,113,101 B2 | 9/2006 | Peterson et al. |
| 7,116,233 B2 | 10/2006 | Zhurin |
| 7,118,553 B2 | 10/2006 | Scherer |
| 7,126,879 B2 | 10/2006 | Snyder |
| 7,158,011 B2 | 1/2007 | Brue |
| 7,158,040 B2 | 1/2007 | Morris |
| 7,190,988 B2 | 3/2007 | Say |
| 7,191,916 B2 | 3/2007 | Clifford et al. |
| 7,229,458 B2 | 6/2007 | Boecker et al. |
| 7,237,549 B2 | 7/2007 | Stradella |
| 7,278,983 B2 | 10/2007 | Ireland et al. |
| 7,299,981 B2 | 11/2007 | Hickle et al. |
| 7,343,914 B2 | 3/2008 | Abrams et al. |
| 7,357,790 B2 | 4/2008 | Hommann et al. |
| 7,416,540 B2 | 8/2008 | Edwards et al. |
| 7,465,294 B1 | 12/2008 | Vladimirsky |
| 7,500,963 B2 | 3/2009 | Westbye et al. |
| 7,500,967 B2 | 3/2009 | Thorley et al. |
| 7,503,907 B1 | 3/2009 | Lesch, Jr. |
| 7,544,188 B2 | 6/2009 | Edwards et al. |
| 7,648,482 B2 | 1/2010 | Edwards et al. |
| 7,648,483 B2 | 1/2010 | Edwards et al. |
| 7,654,983 B2 | 2/2010 | De La Serna et al. |
| 7,670,328 B2 | 3/2010 | Miller et al. |
| 7,674,246 B2 | 3/2010 | Gillespie et al. |
| 7,678,073 B2 | 3/2010 | Griffiths et al. |
| 7,682,155 B2 | 3/2010 | Raven et al. |
| 7,731,686 B2 | 6/2010 | Edwards et al. |
| 7,731,690 B2 | 6/2010 | Edwards et al. |
| 7,749,194 B2 | 7/2010 | Edwards et al. |
| 7,806,866 B2 | 10/2010 | Hommann et al. |
| 7,871,393 B2 | 1/2011 | Monroe |
| 7,901,377 B1 | 3/2011 | Harrison et al. |
| 7,910,599 B2 | 3/2011 | Sinclair |
| 7,918,823 B2 | 4/2011 | Edwards et al. |
| 7,938,802 B2 | 5/2011 | Bicknell et al. |
| 7,947,017 B2 | 5/2011 | Edwards et al. |
| 8,016,788 B2 | 9/2011 | Edwards et al. |
| 8,021,335 B2 | 9/2011 | Lesch, Jr. |
| 8,021,344 B2 | 9/2011 | Edwards et al. |
| 8,105,281 B2 | 1/2012 | Edwards et al. |
| 8,123,719 B2 | 2/2012 | Edwards et al. |
| 8,162,886 B2 | 4/2012 | Sadowski et al. |
| 8,198,291 B2 | 6/2012 | Wermeling |
| 8,206,360 B2 | 6/2012 | Edwards et al. |
| 8,226,610 B2 | 7/2012 | Edwards et al. |
| 8,231,573 B2 | 7/2012 | Edwards et al. |
| 8,313,466 B2 | 11/2012 | Edwards et al. |
| 8,348,096 B2 | 1/2013 | Greiner-Perth |
| 8,361,029 B2 | 1/2013 | Edwards et al. |
| 8,419,706 B2 | 4/2013 | Heldt et al. |
| 8,425,462 B2 | 4/2013 | Edwards et al. |
| 8,544,645 B2 | 10/2013 | Edwards et al. |
| 8,567,390 B2 | 10/2013 | Stadelhofer |
| 8,608,698 B2 | 12/2013 | Edwards et al. |
| 8,627,816 B2 | 1/2014 | Edwards et al. |
| 8,647,306 B2 | 2/2014 | Schwirtz et al. |
| 8,690,827 B2 | 4/2014 | Edwards et al. |
| 8,734,392 B2 | 5/2014 | Stadelhofer |
| 8,747,357 B2 | 6/2014 | Stamp et al. |
| 8,920,367 B2 | 12/2014 | Edwards et al. |
| 8,920,377 B2 | 12/2014 | Edwards et al. |
| 8,926,594 B2 | 1/2015 | Edwards et al. |
| 8,939,943 B2 | 1/2015 | Edwards et al. |
| 9,022,022 B2 | 5/2015 | Edwards et al. |
| 9,022,980 B2 | 5/2015 | Edwards et al. |
| 9,056,170 B2 | 6/2015 | Edwards et al. |
| 9,084,849 B2 | 7/2015 | Edwards et al. |
| 9,149,579 B2 | 10/2015 | Edwards et al. |
| 9,173,999 B2 | 11/2015 | Edwards et al. |
| 9,211,253 B2 | 12/2015 | Crystal et al. |
| 2001/0005781 A1 | 6/2001 | Bergens et al. |
| 2001/0037087 A1 | 11/2001 | Knauer |
| 2002/0042596 A1 | 4/2002 | Hartlaub et al. |
| 2002/0072784 A1 | 6/2002 | Sheppard, Jr. et al. |
| 2002/0074345 A1 | 6/2002 | Schneider et al. |
| 2002/0076679 A1 | 6/2002 | Aman |
| 2002/0079326 A1 | 6/2002 | Fuchs |
| 2002/0090601 A1 | 7/2002 | Strupat et al. |
| 2002/0095120 A1 | 7/2002 | Larsen et al. |
| 2002/0096543 A1 | 7/2002 | Juselius |
| 2002/0169439 A1 | 11/2002 | Flaherty |
| 2002/0183721 A1 | 12/2002 | Santini, Jr. et al. |
| 2003/0028145 A1 | 2/2003 | Duchon et al. |
| 2003/0040717 A1 | 2/2003 | Saulenas et al. |
| 2003/0060765 A1 | 3/2003 | Campbell et al. |
| 2003/0105430 A1 | 6/2003 | Lavi et al. |
| 2003/0106824 A1 | 6/2003 | Wilmot et al. |
| 2003/0120212 A1 | 6/2003 | Dedig et al. |
| 2003/0120222 A1 | 6/2003 | Vaillancourt |
| 2003/0132128 A1 | 7/2003 | Mazur |
| 2003/0135388 A1 | 7/2003 | Martucci et al. |
| 2003/0233070 A1 | 12/2003 | De La Serna et al. |
| 2004/0015125 A1 | 1/2004 | Alexandre et al. |
| 2004/0019326 A1 | 1/2004 | Gilbert et al. |
| 2004/0024361 A1 | 2/2004 | Fago et al. |
| 2004/0024367 A1 | 2/2004 | Gilbert |
| 2004/0039336 A1 | 2/2004 | Amark et al. |
| 2004/0039337 A1 | 2/2004 | Letzing |
| 2004/0039368 A1 | 2/2004 | Reilly et al. |
| 2004/0054327 A1 | 3/2004 | Gillespie, III |
| 2004/0078001 A1 | 4/2004 | Langley et al. |
| 2004/0084047 A1 | 5/2004 | Hickle |
| 2004/0092874 A1 | 5/2004 | Mazidji |
| 2004/0094146 A1 | 5/2004 | Schiewe et al. |
| 2004/0116854 A1 | 6/2004 | Abulhaj et al. |
| 2004/0138611 A1 | 7/2004 | Griffiths et al. |
| 2004/0143298 A1 | 7/2004 | Nova et al. |
| 2004/0159364 A1 | 8/2004 | Landau et al. |
| 2004/0180916 A1 | 9/2004 | Levine |
| 2004/0210199 A1 | 10/2004 | Atterbury et al. |
| 2004/0220524 A1 | 11/2004 | Sadowski et al. |
| 2004/0235731 A1 | 11/2004 | Lundgren et al. |
| 2004/0249358 A1 | 12/2004 | McWethy et al. |
| 2004/0267204 A1 | 12/2004 | Brustowicz |
| 2005/0027255 A1 | 2/2005 | Lavi et al. |
| 2005/0033234 A1 | 2/2005 | Sadowski et al. |
| 2005/0033386 A1 | 2/2005 | Osborn et al. |
| 2005/0038062 A1 | 2/2005 | Burns et al. |
| 2005/0055014 A1 | 3/2005 | Coppeta et al. |
| 2005/0062603 A1 | 3/2005 | Fuerst et al. |
| 2005/0088289 A1 | 4/2005 | Rochkind |
| 2005/0090781 A1 | 4/2005 | Baba et al. |
| 2005/0092679 A1 | 5/2005 | Warby |
| 2005/0101912 A1 | 5/2005 | Faust et al. |
| 2005/0134433 A1 | 6/2005 | Sweeney et al. |
| 2005/0137530 A1 | 6/2005 | Campbell et al. |
| 2005/0148931 A1 | 7/2005 | Juhasz |
| 2005/0148945 A1 | 7/2005 | Chen |
| 2005/0159705 A1 | 7/2005 | Crawford et al. |
| 2005/0165360 A1 | 7/2005 | Stamp |
| 2005/0168337 A1 | 8/2005 | Mahoney |
| 2005/0171477 A1 | 8/2005 | Rubin et al. |
| 2005/0177111 A1 | 8/2005 | Ozeri et al. |
| 2005/0182358 A1 | 8/2005 | Veit et al. |
| 2005/0183982 A1 | 8/2005 | Giewercer |
| 2005/0186221 A1 | 8/2005 | Reynolds et al. |
| 2005/0192530 A1 | 9/2005 | Castellano |
| 2005/0197654 A1 | 9/2005 | Edman et al. |
| 2005/0222539 A1 | 10/2005 | Gonzales et al. |
| 2005/0261742 A1 | 11/2005 | Nova et al. |
| 2005/0267403 A1 | 12/2005 | Landau et al. |
| 2005/0277891 A1 | 12/2005 | Sibbitt |
| 2006/0030819 A1 | 2/2006 | Young et al. |
| 2006/0053036 A1 | 3/2006 | Coffman et al. |
| 2006/0058848 A1 | 3/2006 | Piraino et al. |
| 2006/0083691 A1 | 4/2006 | Wermeling |
| 2006/0089592 A1 | 4/2006 | Kadhiresan et al. |

(56) References Cited

U.S. PATENT DOCUMENTS

| | | |
|---|---|---|
| 2006/0111666 A1 | 5/2006 | Hommann et al. |
| 2006/0111671 A1 | 5/2006 | Klippenstein |
| 2006/0116639 A1 | 6/2006 | Russell |
| 2006/0129090 A1 | 6/2006 | Moberg et al. |
| 2006/0189938 A1 | 8/2006 | Hommann et al. |
| 2006/0200077 A1 | 9/2006 | Righi et al. |
| 2006/0233778 A1 | 10/2006 | Lundgren et al. |
| 2006/0235354 A1 | 10/2006 | Kaal et al. |
| 2006/0247578 A1 | 11/2006 | Arguendas et al. |
| 2006/0247579 A1 | 11/2006 | Friedman |
| 2006/0265186 A1 | 11/2006 | Holland et al. |
| 2007/0008113 A1 | 1/2007 | Spoonhower et al. |
| 2007/0074722 A1 | 4/2007 | Giroux et al. |
| 2007/0100288 A1 | 5/2007 | Bozeman et al. |
| 2007/0129686 A1 | 6/2007 | Daily et al. |
| 2007/0135767 A1 | 6/2007 | Gillespie, III et al. |
| 2007/0148097 A1 | 6/2007 | Finn et al. |
| 2007/0149954 A1 | 6/2007 | Hood et al. |
| 2007/0166187 A1 | 7/2007 | Song et al. |
| 2007/0184847 A1 | 8/2007 | Hansen et al. |
| 2007/0185053 A1 | 8/2007 | Linn |
| 2007/0203247 A1 | 8/2007 | Phillips et al. |
| 2007/0210147 A1 | 9/2007 | Morrone et al. |
| 2007/0212307 A1 | 9/2007 | Wermeling et al. |
| 2007/0213598 A1 | 9/2007 | Howard et al. |
| 2007/0233001 A1 | 10/2007 | Burroughs et al. |
| 2007/0239116 A1 | 10/2007 | Follman et al. |
| 2007/0261695 A1 | 11/2007 | Kottayil et al. |
| 2007/0293826 A1 | 12/2007 | Wall et al. |
| 2008/0154200 A1 | 6/2008 | Lesch |
| 2008/0188798 A1 | 8/2008 | Weber |
| 2008/0228143 A1 | 9/2008 | Stamp |
| 2008/0230057 A1 | 9/2008 | Sutherland |
| 2008/0255513 A1 | 10/2008 | Kaal et al. |
| 2008/0262443 A1 | 10/2008 | Hommann et al. |
| 2009/0093759 A1 | 4/2009 | Judd et al. |
| 2009/0143761 A1 | 6/2009 | Cantor et al. |
| 2009/0176834 A1 | 7/2009 | Kottayil et al. |
| 2009/0192486 A1 | 7/2009 | Wilmot et al. |
| 2009/0221962 A1 | 9/2009 | Kaal et al. |
| 2009/0240200 A1 | 9/2009 | Heneveld et al. |
| 2009/0318361 A1 | 12/2009 | Noera et al. |
| 2010/0010454 A1 | 1/2010 | Marshall et al. |
| 2010/0049125 A1 | 2/2010 | James et al. |
| 2010/0152659 A1 | 6/2010 | Streit et al. |
| 2010/0160894 A1 | 6/2010 | Julian et al. |
| 2010/0185148 A1 | 7/2010 | Gillespie, III et al. |
| 2010/0185178 A1 | 7/2010 | Sharp et al. |
| 2010/0211005 A1 | 8/2010 | Edwards et al. |
| 2010/0212663 A1 | 8/2010 | Vedrine et al. |
| 2010/0286612 A1 | 11/2010 | Cirillo |
| 2010/0331354 A1 | 12/2010 | Wermeling et al. |
| 2011/0060274 A1 | 3/2011 | Kuhn |
| 2011/0098655 A1 | 4/2011 | Jennings et al. |
| 2011/0189259 A1 | 8/2011 | Vasisht et al. |
| 2011/0295215 A1 | 12/2011 | Nielsen et al. |
| 2012/0046613 A1 | 2/2012 | Plumptre |
| 2012/0056019 A1 | 3/2012 | Renz et al. |
| 2012/0071819 A1 | 3/2012 | Bruggemann et al. |
| 2012/0091026 A1 | 4/2012 | Chacornac et al. |
| 2012/0101444 A1 | 4/2012 | Muller-Pathle et al. |
| 2012/0101446 A1 | 4/2012 | Heald |
| 2012/0103328 A1 | 5/2012 | Smith et al. |
| 2012/0107783 A1 | 5/2012 | Julian et al. |
| 2012/0116319 A1 | 5/2012 | Grunhut |
| 2012/0125951 A1 | 5/2012 | Leak et al. |
| 2012/0136316 A1 | 5/2012 | Davies et al. |
| 2012/0172804 A1 | 7/2012 | Plumptre |
| 2012/0172817 A1 | 7/2012 | Bruggemann et al. |
| 2012/0172818 A1 | 7/2012 | Harms et al. |
| 2012/0191049 A1 | 7/2012 | Harms et al. |
| 2012/0191066 A1 | 7/2012 | Schabbach et al. |
| 2012/0197210 A1 | 8/2012 | Kuhn et al. |
| 2012/0209200 A1 | 8/2012 | Jones et al. |
| 2012/0217184 A1* | 8/2012 | Edwards ............ A61M 5/2033 206/571 |
| 2012/0220949 A1 | 8/2012 | Davies et al. |
| 2012/0226238 A1 | 9/2012 | Davies et al. |
| 2012/0233834 A1 | 9/2012 | Szechinski et al. |
| 2012/0238960 A1 | 9/2012 | Smith et al. |
| 2012/0253288 A1 | 10/2012 | Dasbach et al. |
| 2012/0259285 A1 | 10/2012 | Schabbach et al. |
| 2012/0270895 A1 | 10/2012 | Wermeling |
| 2012/0271243 A1 | 10/2012 | Plumptre et al. |
| 2012/0283648 A1 | 11/2012 | Veasey et al. |
| 2012/0283651 A1 | 11/2012 | Veasey et al. |
| 2012/0283662 A1 | 11/2012 | MacDonald et al. |
| 2012/0289906 A1 | 11/2012 | Jones et al. |
| 2012/0289929 A1 | 11/2012 | Boyd et al. |
| 2012/0302966 A1 | 11/2012 | Vedrine et al. |
| 2012/0310168 A1 | 12/2012 | Plumptre et al. |
| 2012/0310208 A1 | 12/2012 | Kouyoumjian et al. |
| 2012/0325865 A1 | 12/2012 | Forstreuter et al. |
| 2012/0330244 A1 | 12/2012 | Helmer et al. |
| 2013/0030367 A1 | 1/2013 | Wotton et al. |
| 2013/0060231 A1 | 3/2013 | Adlon et al. |
| 2013/0060232 A1 | 3/2013 | Adlon et al. |
| 2013/0079718 A1 | 3/2013 | Shang et al. |
| 2013/0079725 A1 | 3/2013 | Shang et al. |
| 2013/0081953 A1 | 4/2013 | Bruna et al. |
| 2013/0096512 A1 | 4/2013 | Ekman et al. |
| 2013/0110050 A1 | 5/2013 | Boyd et al. |
| 2013/0131602 A1 | 5/2013 | Kemp et al. |
| 2013/0138049 A1 | 5/2013 | Kemp et al. |
| 2013/0172822 A1 | 7/2013 | Ekman et al. |
| 2013/0236872 A1 | 9/2013 | Laurusonis et al. |
| 2013/0266919 A1 | 10/2013 | Baker et al. |
| 2013/0317477 A1 | 11/2013 | Edwards et al. |
| 2014/0296824 A1 | 10/2014 | Edwards et al. |
| 2015/0018379 A1 | 1/2015 | Strang et al. |
| 2015/0041496 A1 | 2/2015 | Kim et al. |
| 2015/0231334 A1 | 8/2015 | Buchine et al. |
| 2015/0231336 A1 | 8/2015 | Edwards et al. |
| 2015/0297840 A1 | 10/2015 | Edwards et al. |
| 2016/0015895 A1 | 1/2016 | Edwards et al. |
| 2017/0035957 A1 | 2/2017 | Edwards et al. |
| 2017/0333422 A1 | 11/2017 | Silverman et al. |
| 2018/0126082 A1 | 5/2018 | Edwards et al. |

FOREIGN PATENT DOCUMENTS

| | | |
|---|---|---|
| EP | 0429039 B1 | 3/1995 |
| EP | 0346830 B1 | 5/1995 |
| EP | 1084765 B1 | 3/2001 |
| EP | 1287840 A1 | 3/2003 |
| EP | 1462134 A1 | 9/2004 |
| EP | 1712178 A2 | 10/2006 |
| FR | 1514210 | 2/1968 |
| FR | 2506161 | 11/1982 |
| FR | 2509615 | 1/1983 |
| FR | 2700959 | 2/1993 |
| GB | 2195544 A1 | 4/1988 |
| WO | WO 91/04760 | 4/1991 |
| WO | WO 92/18176 | 10/1992 |
| WO | WO 93/02720 | 2/1993 |
| WO | WO 95/13838 | 5/1995 |
| WO | WO 95/26009 | 9/1995 |
| WO | WO 95/35126 | 12/1995 |
| WO | WO 96/25965 | 8/1996 |
| WO | WO 97/30742 | 8/1997 |
| WO | WO 98/52632 | 11/1998 |
| WO | WO 99/07425 | 2/1999 |
| WO | WO 99/10031 | 3/1999 |
| WO | WO 99/43283 | 9/1999 |
| WO | WO 99/52575 | 10/1999 |
| WO | WO 2001/024690 | 4/2001 |
| WO | WO 2001/026020 | 4/2001 |
| WO | WO 2001/041849 | 6/2001 |
| WO | WO 2001/088828 | 11/2001 |
| WO | WO 2001/093926 | 12/2001 |
| WO | WO 2002/011778 | 2/2002 |
| WO | WO 2002/024257 | 3/2002 |
| WO | WO 2002/051471 | 7/2002 |

(56) References Cited

FOREIGN PATENT DOCUMENTS

| | | |
|---|---|---|
| WO | WO 2002/083205 | 10/2002 |
| WO | WO 2002/083212 | 10/2002 |
| WO | WO 2003/011378 | 2/2003 |
| WO | WO 2003/013632 | 2/2003 |
| WO | WO 2003/057283 | 7/2003 |
| WO | WO 2003/070191 | 8/2003 |
| WO | WO 2003/095001 | 11/2003 |
| WO | WO 2003/097133 | 11/2003 |
| WO | WO 2004/041330 | 5/2004 |
| WO | WO 2004/047890 | 6/2004 |
| WO | WO 2004/047891 | 6/2004 |
| WO | WO 2004/047892 | 6/2004 |
| WO | WO 2004/047893 | 6/2004 |
| WO | WO 2004/054644 | 7/2004 |
| WO | WO 2005/020906 | 3/2005 |
| WO | WO 2005/050526 | 6/2005 |
| WO | WO 2005/070481 | 8/2005 |
| WO | WO 2005/077441 | 8/2005 |
| WO | WO 2006/045525 | 5/2006 |
| WO | WO 2006/085175 | 8/2006 |
| WO | WO 2006/085204 | 8/2006 |
| WO | WO 2006/109778 | 10/2006 |
| WO | WO 2006/125692 | 11/2006 |
| WO | WO 2007/032962 | 3/2007 |
| WO | WO 2007/075839 | 7/2007 |
| WO | WO 2007/083115 | 7/2007 |
| WO | WO 2007/088444 | 8/2007 |
| WO | WO 2008/005315 | 1/2008 |
| WO | WO 2008/034060 | 3/2008 |
| WO | WO 2008/082704 | 7/2008 |
| WO | WO 2008/148864 | 12/2008 |
| WO | WO 2009/040595 | 4/2009 |
| WO | WO 2013/044172 | 3/2013 |
| WO | WO 2013/086292 | 6/2013 |

OTHER PUBLICATIONS

"Anaphylaxis Canada Product Catalogue," Anaphylaxis Canada > Living with Anaphylaxis > Tools and Resources [online] [retrieved on Jan. 24, 2007] Retrieved from the Internet <URL: http://anaphylaxis.org/content/livingwith/product catalogue.asp >, 9 pages.
"Microfluidics Device Provides Programmed, Long-Term Drug Dosing," nano techwire.com [online] [retrieved on Nov. 28, 2006] Retrieved from the Internet <URL: http://nanotechwire.com/news.asp?nid=3141&ntid=124&pg=1 >, 3 pages.
Allan, R., "Medical Electronics: Technology Advances Will Revolutionize Healthcare," Sep. 30, 2002 [online] [retrieved on Nov. 28, 2006] Retrieved from the Internet <URL: http://www.elecdesign.com/Articles/Index.cfm?AD=1&ArticleID=2041>, 3 pages.
RFID Gazette, "Smart Labels in Healthcare," Sep. 29, 2005 [online] [retrieved on Nov. 28, 2006] Retrieved from the Internet <URL: http://www.rfidagazeete.org/2005/09/smart labels in.html >, 2 pages.
"Merck Serono Launches easypod(R), First Electronic Growth Hormone Injection Device," Jan. 30, 2007 [online] [retrieved on Feb. 5, 2007] Retrieved from the Internet <URL: http://www.biz.yahoo.com/pmews/070130/ukm028.html?.v=8>, 3 pages.
Scholz, O., "Drug depot in a tooth," [online] [retrieved on Feb. 6, 2007] Retrieved from the Internet <URL: http://www.fraunhofer.de/fhg/EN/press/pi/2007/02Mediendienst22007Thema2.jsp?print=true>, 1 page.
Heartsine Technology, samaritan™ Pad Accessories [online] [retrieved on Jun. 1, 2007] Retrieved from the Internet <URL: http://www.heartsine.com/aboutsam-accessories.htm>, 4 pages.
CliniSense Corporation, "Drug delivery devices a potentially harsh environment for drugs," Stability [online] [retrieved on Jun. 1, 2007] Retrieved from the Internet <URL: http://www.clinisense.com/devices.htm>, 2 pages.
CliniSense Corporation, "LifeTrack Technology a new method to detect improper storage." Stability [online] [retrieved on Jun. 1, 2007] Retrieved from the Internet <URL: http://www.clinisense.com/tech.htm>, 2 pages.

Ruppar, D., "Implant Technologies Expected to Remain a Niche but Effective Method of Drug Delivery," Drug Delivery Technology, Feb. 2007, vol. 7, No. 2 [online] [retrieved on Jun. 1, 2007] Retrieved from the Internet <URL: http://www.drugdeliverytech-online.com/drugdelivery/200702/templates/pageviewer_print?pg=44&pm=8 >, 8 pages.
O'Hagan, D. et al., "Novel approaches to pediatric vaccine delivery," Advanced Drug Delivery Reviews, 58:29-51 (2006).
Meridian Medical Technologies, Inc., "Pralidoxime Chloride Trainer," 2006. [retrieved on Feb. 16, 2007] Retrieved from the Internet <URL: http://www.meridianmeds.com/auto-injectors/2pamcl_trainer.html/>, 1 pages.
Gosbee, L. L., "Nuts! I Can't Figure Out How to Use My Life-Saving Epinephrine Auto-Injector," Joint Commision Journal on Quality and Safety, 30(4):220-223 (Apr. 2004).
Amgen, "Using Aranesp prefilled SureClick autoinjector is a simple 3-step process," 2006. [retrieved on Feb. 16, 2007] Retrieved from the Internet <URL: http://www.aranesp.com/patient/cia/sureclick/using_three_steps.jsp/>, 4 pages.
Boseley, S., "Families to receive antidote to help drug users who overdose," Guardian News and Media, Jun. 25, 2009. [retrieved on May 27, 2011] Retrieved from the Internet <URL: http://www.guardian.co.uk/society/2009/jun/25/drug-overdose-antidote-naloxone-families>.
McDougall, L., "Addicts to be given personal supply of anti-overdose drug," The Herald Scotland, May, 28, 2006. Retrieved from the Internet <URL: http://www.heraldscotland.com/sport/spl/aberdeen/addicts-to-be-given-personal-supply-of-anti-overdose-drug-heroin-controversial-lifesaving-plan-projects-aim-to-cut-rising-death-toll-by-making-naloxone-treatment-more-readily-avaliable-1.19181>, 3 pages.
BD Accuspray™ Nasal Spray System, 2004, Retrieved from the Internet <URL: http://www.bd.com/press/pdfs/flu/bd_accuspray.pdf>, 1 page.
Colliver, V., "Naloxone saves lives of overdosed opiate users" San Francisco Chronicle, Oct. 14, 2010 [retrieved Aug. 14, 2013] Retrieved from the Internet <URL: http://www.sfgate.com/health/article/Naloxone-saves-lives-of-overdosed-opiate-users-3249978.php>.
Terry, D., "A Shot That Saves the Lives of Addicts Is Now in Their Hands," The New York Times, Jul. 24, 2010 [retrieved Aug. 14, 2013] Retrieved from the Internet <URL: http://www.nytimes.com/2010/07/25/us/25cncnaloxone.html>.
Szalavitz, M., "Should an Overdose Antidote Be Made More Accessible?" TIME, Dec. 9, 2010 [retrieved on Aug. 14, 2013] Retrieved from the Internet <URL: http://healthland.time.com/2010/12/09/should-an-overdose-antidote-be-made-more-accessible/>.
Okie, S., "A Flood of Opioids, a Rising Tide of Deaths," The New England Journal of Medicine, Nov. 18, 2010, 363:1981-1985 [online], [retrieved on Aug. 14, 2013] Retrieved from the Internet <URL: http://www.nejm.org/doi/full/10.1056/NEJMp1011512>.
Wermeling, D. P., "A response to the opioid overdose epidemic: naloxone nasal spray," Drug Deliv. and Transl. Res., 3:63-74 (2013).
Wermeling, D. P., "Opioid Harm Reduction Strategies: Focus on Expanded Access to Intranasal Naloxone," Pharmacotherapy, 30(7):627-631 (2010).
Djupesland, P. G., "Nasal drug delivery devices: characteristics and performance in a clinical perspective—a review," Drug Deliv. and Transl. Res., Published online: Oct. 18, 2012, 21 pages.
"Martindale Pharma Launches Prenoxad Injection in UK for Emergency Treatment of Opioid Overdose," Pharmabiz.com, May 6, 2013 [online], [retrieved on Nov. 26, 2014] Retrieved from the Internet <URL: http://www.pharmabiz.com/NewsDetails.aspx?aid=75187&sid=2, 1 page.
"Therapeutic Intranasal Drug Delivery: Needleless Treatment Options for Medical Problems," Intranasal.net [online], [retrieved on Dec. 16, 2010] Retrieved from the Internet <URL: http://intranasal.net/OpiateOverdose/>, 10 pages.
Prenoxad Injection: Client's Guide to Prenoxad Injection, Martindale Pharma, Apr. 2013, 16 pages.
Prenoxad Injection: Pharmacists's Guide, Martindale Pharma, Apr. 2013, 6 pages.

(56) References Cited

OTHER PUBLICATIONS

Prenoxad Injection: Packaging Leaflet: Information for the User, Martindale Pharma, Nov. 2012, 2 pages.
Prenoxad Injection: Summary of Product Characteristics, Martindale Pharma, Apr. 2013, 4 pages.
Edwards, E. S., Dissertation: "Development of a novel approach to assess qualitative and quantitative dynamics associated with the subcutaneous or intramuscular administration of pharmaceuticals and associated parenteral delivery systems," B.S. Biology, Virginia Commonwealth University (Dec. 2011), 316 pages.
Bennett, J. et al., "Subcutaneous administration of midazolam: A comparison of the bioject jet injector with the conventional syringe and needle," J Oral Maxillofac Surg, 56(11):1249-1254 (1998).
Brearley, C. et al., "Pharmacokinetics of recombinant human growth hormone administered by cool.clickTM 2, a new needle-free device, compared with subcutaneous administration using a conventional syringe and needle," BMC Clin Pharmacol, 7:10 (2007), 7 pages.
Simons, F. E. R. et al., "Epinephrine absorption in adults: intramuscular versus subcutaneous injection," J Allergy Clin Immunol, 108(5), 871-873 (2001).
Kerum, G. et al., "Blood glucose and free insulin levels after the administration of insulin by conventional syringe or jet injector in insulin treated type 2 diabetics," Horm. Metabol. Res., 19:422-425 (1987).
Halle, J.-P. et al., "Twice daily mixed regular and NPH insulin injections with new jet injector versus conventional syringes: pharmacokinetics of insulin absorption," Diabetes Care, 9(3):279-282 (1986).
Taylor, R. et al., "Plasma free insulin profiles after administration of insulin by jet and conventional syringe injection," Diabetes Care, 4(3):377-379 (1981).
Biocryst Pharmaceuticals, Inc., Biocryst Press Release, "Biocryst reports preliminary results from a phase II clinical trial of peramivir in subjects with acute influenza," Retrieved from the Internet: <http://investor.shareholder.com/biocryst/releasedetail.cfm?ReleaseID=264815> (Sep. 19, 2007), 3 pages.
Marx, D. et al., "Multi-Dose Container for Nasal and Ophthalmic Drugs: A Preservative Free Future?," Chapter 20 of Drug Development—A Case Study Based Insight into Modern Strategies, isBN: 978-953-307-257-9 (Nov. 2011).
Harm Reduction Coalition, "How to Give Nasal Spray Naloxone," [online], [retrieved on May 27, 2015] Retrieved from the Internet: <http://http://harmreduction.org/wp-content/uploads/2014/10/OD-Response-administer-naloxone-intranasal-instructions.pdf> (undated).
Elsemiek, E.C. et al., "Improved Pharmacokinetic and Pharmacodynamic Profile of Rapid-Acting Insulin Using Needle-Free Jet Injection Technology," Emerging Treatments and Technologies, *Diabetes Care* 34:1804-1808 (Aug. 2011).
Lewis, J. et al., "Needle-Free Subcutaneous Sumatriptan (Sumavel™ DosePro™ Bioequivalence and Ease of Use," *Headache*, 2009;49:1435-1444 (Nov./Dec. 2009).
Schram, J. et al., "Transdermal Drug Delivery by Jet Injectors: Energetics of Jet Formation and Penetration," *Pharmaceutical Research*, vol. 19, No. 11 (Nov. 2002).
Verhagen, A. et al.,A1032:C1038 "Pharmacokinetics and pharmacodynamics of a single dose of recombinant human growth hormone after subcutaneous administration by jet-injection: comparison with conventional needle-injection," Eur J Cin Pharmacol 49:69-72 (Feb. 10, 1995).

Dahan, Albert et al., "Incidence, Reversal, and Prevention of Opioid-induced Respiratory Depression," *Anesthesiology* vol. 112, No. 1: 226-238 (Jan. 2010).
Clarke, S.F.J. et al., "Naloxone in Opioid Poisoning: Walking the tightrope," *Emerg Med J* vol. 22: 612-616 (2005).
Engwerda, Elsemiek E.C. et al, "Improved Pharmacokinetic and Pharmacodynamic Profile of Rapid-Acting Insulin Using Needle-Free Jet Injection Technology," *Diabetes Care* vol. 34: 1804-1808 (Aug. 2011).
Sarno, Mark A. et al, "Pharmacokinetics and Glucodynamics of Rapid-, Short-, and Intermediate-Acting Insulins: Comparison of Jet Injection to Needle Syringe," *Diabetes Technology & Therapeutics* vol. 4, No. 6: 863-866 (2002).
Agerso, Henrik et al., "Pharmacokinetics and Pharmacodynamics of a New Formulation of Recombinant Human Growth Hormone Administered by ZomaJet 2 Vision, a New Needle-Free Device, Compared to Subcutaneous Administration Using a Conventional Syringe," *Journal of Clinical Pharmacology*, vol. 42: 1262-1268 (2002).
Apley, M.D. et al., "Ampicillin pharmacokinetics in swine following needle-free, intramuscular and intravenous administration," *J. vet. Pharmacol. Therap.* 30: 417-421 (2007).
True, Andrea L. et al., "Pharmacokinetic Bioequivalence of Enfuvirtide Using a Needle-Free Device versus Standard Needle Administration," *Pharmacotherapy* vol. 26, No. 12: 1679-1686 (2006).
Reutens, Anne T. et al., "A Pilot Study to Examine the Tolerability and Device Preference in Type 1 Diabetes of Insulin Aspart Administered by InsuJet Compared with Subcutaneous Injection," *Diabetes Technology & Therapeutics*, vol. 16, No. 4: 235-240 (2014).
International Search Report and Written Opinion for International Patent Application No. PCT/US06/03415, dated Jul. 13, 2006, 10 pages.
Examination Report for Australian Patent Application No. 2011218756, dated Nov. 1, 2011.
Examination Report for Australian Patent Application No. 2011213756, dated Feb. 1, 2013.
Notice of Acceptance for Australian Patent Application No. 2011218756, dated Apr. 12, 2013.
Non-Final Office Action for U.S. Appl. No. 13/036,720, dated May 17, 2013.
Final Office Action for U.S. Appl. No. 13/036,720, dated Nov. 5, 2013.
International Search Report and Written Opinion for International Application No. PCT/US2012/026708, dated Jun. 7, 2012.
International Preliminary Report on Patentability for International Patent Application No. PCT/US2012/026708, dated Oct. 22, 2013.
Non-Final Office Action for U.S. Appl. No. 14/062,516, dated Apr. 22, 2014.
Final Office Action for U.S. Appl. No. 14/062,516, dated Sep. 23, 2014.
Office Action for U.S. Appl. No. 14/153,575, dated Jan. 30, 2015.
Office Action for U.S. Appl. No. 14/335,490, dated May 8, 2015.
Office Action for U.S. Appl. No. 14/694,725, dated Dec. 17, 2015.
Office Action for British Patent Application No. 1315737.5, dated Feb. 28, 2017.
Search Report for European Patent Application No. 12751771,2, dated Jun. 13, 2017.
Office Action for U.S. Appl. No. 14/605,512, dated Aug. 10, 2017
Office Action for U.S. Appl. No. 15/797,844, dated Sep. 21, 2018.

* cited by examiner

DEVICES AND METHODS FOR DELIVERING OPIOID ANTAGONISTS INCLUDING FORMULATIONS FOR NALOXONE

CROSS-REFERENCE TO RELATED APPLICATIONS

This application is a divisional of pending U.S. patent application Ser. No. 14/335,490, entitled "Devices and Methods for Delivering Opioid Antagonists Including Formulations for Naloxone," filed Jul. 18, 2014, which is incorporated herein by reference in its entirety.

BACKGROUND

The embodiments described herein relate generally to medical devices and pharmaceutical compositions, and more particularly to a drug product for injection of opioid antagonists, including formulations for naloxone.

Opioid antagonists are medicaments that prevent and/or reverse the effects of opioids. Known opioid antagonists, such as naltrexone and naloxone, can be used, for example, to treat respiratory depression and other indications that result from opioid toxicity. For example, known formulations for naloxone can be used to reverse and/or mitigate the effects of an overdose of a drug containing opioids, such as, for example, heroin. In such situations, it is desirable to deliver the naloxone formulation quickly and in a manner that will produce a rapid onset of action. Accordingly, known formulations of naloxone are often delivered either intranasally or via injection.

The delivery of naloxone intranasally or via injection, however, often involves completing a series of operations that, if not done properly, can limit the effectiveness of the naloxone formulation. For example, prior to delivering the naloxone, the user must first determine whether the patient's symptoms warrant the delivery of naloxone, and then couple a needle (or an atomizer) to a syringe containing the naloxone formulation. After the device is prepared for delivery, the user then selects the region of the body in which the naloxone is to be delivered, and manually produces a force to deliver the naloxone. In some situations, such as, for example, when the patient is in an ambulance or a hospital setting, the user then inserts an intravenous catheter to administer the naloxone. Additionally, after the delivery of the naloxone formulation, the user must dispose of the device properly (e.g., to prevent needle sticks in instances where the naloxone is injected) and seek further medical attention for the patient. Accordingly, known formulations of naloxone are often delivered by a healthcare provider in a controlled environment (e.g. a hospital, physician's office, clinic or the like). Access to emergency medical facilities and/or trained health care providers, however, is not always available when an individual is suffering from an overdose. Moreover, because naloxone is often administered during an emergency situation, even experienced and/or trained users may be subject to confusion and/or panic, thereby compromising the delivery of the naloxone formulation.

The use of some known devices for delivering naloxone compositions generally involves a user manually generating a force and/or pressure that is sufficient to convey the naloxone from the device into the body. For example, to deliver naloxone using known syringes, the user manually inserts a needle into the body (e.g., intramuscularly) and following insertion, manually depresses a plunger into the syringe body. The force generated by the user to insert the needle and/or manually depress the plunger, however, can vary depending on the user (e.g., based on a user's strength, comfort level, experience, etc.), thus resulting in undesirable fluctuations in the flow of the naloxone and/or incomplete delivery of the full dose. Such fluctuations and variability can be particularly undesirable when the naloxone is being atomized for intranasal delivery. For example, in some instances, the user may be unable to generate sufficient force to provide the desired flow rate and/or flow characteristics (e.g., for an atomizer) of the naloxone. Moreover, in certain situations, a user could inadvertently insert a needle of a syringe containing a dose of a naloxone composition at an angle relative to a target injection site, which can result in failure to deliver the dose intramuscularly. For example, in some such situations, the dose may be delivered subcutaneously, which can affect the release of the drug into the body and thus, the desired pharmacokinetics (PK) of the naloxone composition. In addition, most manually actuated syringes do not include an automatic retraction of the needle and/or otherwise include a needle covering mechanism that is automatically deployed upon removal of the needle from the body, which can result in inadvertent needle sticks or the like.

To mitigate at least some of the challenges presented above, some known devices such as, for example, autoinjectors, can be arranged to automatically perform some or all of the steps for delivering a dose of an opioid antagonist. Some known autoinjectors, however, deliver a dose at a much faster rate and/or at higher pressures than a manually actuated syringe. The higher pressure and/or faster rate of delivery can result in a difference in the delivery of the drug, thereby affecting the pharmacokinetic characteristics of the drug upon delivery. Similarly stated, changing the mechanism of delivery of a known drug can influence the drug performance. In particular, studies have demonstrated differences in the bioavailability of an injectable drug product between different pharmaceutical delivery technologies (Bennett, Nichols, Rosenblum, & Condry, 1998; Brearly, Priestley, Leighton-Scott, & Christen, 2007; Simons, Gu, Simons, 2001). For example, the study by Bennett et al. investigated midazolam administered by a conventional syringe and needle compared to administration via a jet injection system, and found that the delivery via the jet injector produced peak midazolam plasma concentrations over 30% faster with a significantly greater overall peak level than delivery via the conventional syringe (Bennett, et al., 1998). Similar studies with insulin have demonstrated substantial pharmacokinetic differences between different delivery systems (Kerum, Profozic, Granic, & Skrabalo, 1987; Halle, Lambert, Lindmayer, Menassa, Coutu, Moghrabi, Legendre, Legault, & Lalumiere, 1986; Taylor, Home, & Alberti, 1981). More importantly, there have been reports of undesirable outcomes as a result of choosing the wrong delivery system for the desired clinical response. As one example, the drug peramivir, which was being developed for seasonal flu, failed to meet the primary endpoint in the mid-stage trial "because too-short needles failed to deliver the drug to the muscle in all of the patients" (Biocryst, 2007).

In the "Development of a Novel Approach to Assess Qualitative and Quantitative Dynamics Associated with the Subcutaneous or Intramuscular Administration of Pharmaceuticals and Associated Parenteral Delivery Systems," the kinematics of an injection by standard manual syringe is compared with an injection by auto-injector. The dispersion of a contrast agent (iohexol) into the body after injection was observed in real-time by the use of computed tomography (CT) scanning. It was found that iohexol delivered subcutaneously by an auto-injector resulted in notable qualitative and quantitative dispersion differences, including a higher rate of iohexol loss from the extravascular tissue, as well as differences in early plasma exposure as compared to a pre-filled syringe delivery system.

Therefore, the effectiveness of a dose of a naloxone composition formulated to be delivered via a manually actuated syringe can be dependent on the pharmacokinetic characteristics associated with the delivery modality.

Thus, a need exists for improved methods and devices for delivering opioid antagonists, such as, for example, devices that provide for at least a partially automatic delivery of naloxone compositions while maintaining, for example, pharmacokinetic characteristics of delivery via a manually actuated syringe.

SUMMARY

In some embodiments, an apparatus includes a housing, a medicament container, a needle, and an actuation assembly. The medicament container is disposed within the housing and contains a dose of a naloxone composition having a delivered volume of at least about 0.34 ml. The actuation assembly includes an energy storage member and a movable member. The energy storage member is configured to produce a force on the movable member to move the needle from a first needle position, in which the needle is disposed within the housing, and a second needle position, in which the needle is placed in fluid communication with the medicament container and a portion of the needle extends from the housing. The actuation assembly is configured to deliver the dose of the naloxone composition from the medicament container via the needle such that the 90% confidence interval of at least one of the relative mean maximum naloxone plasma concentration after the dose is delivered into the body ($C_{max}$), the time to reach the maximum naloxone plasma concentration ($T_{max}$), area under the concentration-time curve from pre-dose (time 0) extrapolated to infinity ($AUC_{0-\infty}$), or area under the concentration-time curve from pre-dose (time 0) to the time of the last quantifiable concentration ($T_{last}$) ($AUC_{0-t}$) of the delivered dose to a delivered dose of a corresponding naloxone composition delivered via a manually-actuated syringe is within 80% to 125%.

DETAILED DESCRIPTION

Figure 3:
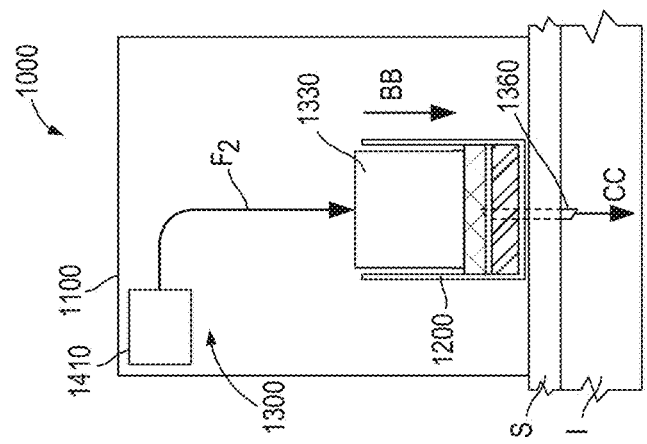
FIGS. 1-3 are schematic illustrations of a medicament delivery device according to an embodiment, in a first, a second and a third configuration, respectively.

Medicament delivery devices for administration of opioid antagonists and chemical compositions used within such devices are described herein. In some embodiments, a naloxone composition can be formulated for use in a delivery device of the types shown and described herein. The naloxone composition includes an effective amount of naloxone (i.e., 4,5-epoxy-3,14-dihydroxy-17-(2-propenyl) morphinan-6-one), or a pharmaceutically acceptable salt and/or ester thereof. As used herein, an "effective amount" Is an amount sufficient to provide a desired therapeutic effect. In some embodiments, the naloxone composition can include a pH-adjusting agent, such as, for example, at least one of hydrochloric acid, citric acid, acetic acid, phosphoric acid, or combinations thereof. In some embodiments, the naloxone composition can include one or more tonicity-adjusting agents, such as, for example, at least one of dextrose, glycerin, mannitol, potassium chloride, sodium chloride, or combinations thereof. In some embodiments, a medicament container can be filled with a naloxone composition that includes naloxone or salts thereof, a tonicity-adjusting agent, and a pH-adjusting agent, whereby the osmolality of the naloxone composition ranges from about 250 to about 350 mOsm and the pH ranges from about 3 to about 5. Because the naloxone composition may be stored in the medicament container of a delivery device for extended periods of time under varying storage conditions, in some embodiments, the naloxone composition can include stabilizers to prevent or inhibit decomposition of the naloxone during storage. Moreover, in some embodiments, an elastomeric member disposed within a medicament container containing a naloxone composition is configured to be compatible with the naloxone composition and can, for example, can be formulated to prevent undesired leaching and/or reaction with the naloxone composition. In some embodiments, the elastomeric member is formulated to include a polymer and a curing agent. The polymer includes at least one of bromobutyl or chlorobutyl, and the curing agent includes at least one of sulfur or metal compounds, e.g., metal oxides such as zinc oxide or magnesium oxide, etc.

In some embodiments, an apparatus includes a housing, a medicament container, a needle, and an actuation assembly. The medicament container is disposed within the housing and contains a dose of a naloxone composition (such as those described above) having a delivered volume of at least about 0.34 ml. The actuation assembly includes an energy storage member and a movable member. The energy storage member is configured to produce a force on the movable member to move the needle from a first needle position, in which the needle is disposed within the housing, and a second needle position, in which the needle is placed in fluid communication with the medicament container and a portion of the needle extends from the housing. The actuation assembly is configured to deliver the dose of the naloxone composition from the medicament container via the needle such that the 90% confidence interval of at least one of the relative mean maximum naloxone plasma concentration after the dose is delivered into the body ($C_{max}$), time to reach the maximum naloxone plasma concentration ($T_{max}$), area under the concentration-time curve from pre-dose (time 0) extrapolated to infinity ($AUC_{0-\infty}$), or area under the concentration-time curve from pre-dose (time 0) to the time of the last quantifiable concentration ($T_{last}$) ($AUC_{0-t}$) of the delivered dose to a delivered dose of a corresponding naloxone composition delivered via a manually-actuated syringe is within 80% to 125%.

In some embodiments, an apparatus includes a housing, a medicament container, a needle, and an actuation assembly. The medicament container is disposed within the housing and contains a dose of a naloxone composition. The dose of the naloxone composition has a delivered volume of at least about 0.34 ml. The needle is configured to be placed in fluid communication with the medicament container when an end portion of the needle is extended outside of the housing. The actuation assembly includes an energy storage member and a movable member. The energy storage member is configured to produce a force on the movable member to deliver the dose of the naloxone composition from the medicament container via the needle. The actuation assembly delivers the dose of the naloxone composition into a body such that at least one pharmacokinetic parameter of the naloxone composition is bioequivalent to the corresponding pharmacokinetic parameter resulting from the delivery of a corresponding dose of a corresponding naloxone composition via a manually actuated syringe. An amount of the corresponding dose is substantially the same as the amount of the naloxone composition.

In some embodiments, a method for delivering a naloxone composition to a body includes placing a medicament injector against a body. The medicament injector includes a housing, a medicament container, a needle, and an actuation assembly. The medicament container is disposed within the housing and contains a dose of a naloxone composition that has a delivered volume of at least about 0.34 ml. The needle is movable between a first needle position and a second needle position. A portion of the needle extends from the housing and the needle is in fluid communication with the medicament container when the needle is in the second needle position. The actuation assembly includes an energy storage member and a movable member. The method includes actuating the medicament injector such that the energy storage member produces a force on the movable member to move the needle from the first needle position to the second needle position and to deliver the dose of the naloxone composition from the medicament container via the needle into the body. The dose of the naloxone composition is delivered in a manner such that the 90% confidence interval of at least one of the relative mean maximum naloxone plasma concentration after the dose is delivered into the body ($C_{max}$), time to reach the maximum naloxone plasma concentration ($T_{max}$), area under the concentration-time curve from pre-dose (time 0) extrapolated to infinity ($AUC_{0-\infty}$), or area under the concentration-time curve from pre-dose (time 0) to the time of the last quantifiable concentration ($T_{last}$) ($AUC_{0-t}$) of the delivered dose to a delivered dose of a corresponding naloxone composition delivered via a manually-actuated syringe is within 80% to 125%.

In some embodiments, an apparatus includes a housing, a medicament container, a delivery member and a medicament delivery assembly. The medicament container is disposed at least partially within the housing, and includes an elastomeric member disposed therein. The medicament container contains a dose of a naloxone composition having a delivered volume of at least about 0.34 ml. The delivery member, which can be, for example, a needle, a nozzle or the like, has a distal end portion disposed outside of the housing. The delivery member us configured to be placed in fluid communication with the medicament container. The medicament delivery assembly includes a movable member and a deformable portion. The movable member is configured to receive an actuation force, and the deformable portion is configured to deform in response to the force. The movable member is configured to move the elastomeric member within the medicament container to deliver the naloxone composition into a body via the delivery member after deformation of the deformable portion. The medicament delivery assembly is configured to deliver the dose of the naloxone composition into a body such that a confidence interval of at least one of a maximum naloxone plasma concentration after the dose is delivered into the body (Cmax), a time to reach the maximum naloxone plasma concentration (Tmax), or an area under a curve of the naloxone plasma concentration as a function of time from a first time after the dose is delivered into the body to a second time after administration (AUC) is between about 80 percent and about 125 percent of a corresponding confidence interval resulting from the delivery of a corresponding dose of a corresponding naloxone composition via a manually-actuated syringe, an amount of the corresponding dose being substantially the same as an amount of the dose.

In some embodiments, a method includes placing a medicament delivery device against a body. The medicament delivery device includes a housing, a medicament container, a delivery member and a medicament delivery assembly. The medicament container is disposed within the housing, and includes an elastomeric member disposed therein. The medicament container contains a dose of a naloxone composition having a delivered volume of at least about 0.34 ml. The delivery member has a distal end portion disposed outside of the housing, and is configured to be placed in fluid communication with the medicament container. The medicament delivery assembly includes a movable member and a deformable portion. A force is applied to the movable member of the medicament delivery assembly to deform the deformable portion of the medicament delivery assembly and move the elastomeric member within the medicament container. This causes delivery of the naloxone composition via the delivery member into the body in a manner such that a confidence interval of at least one of a maximum naloxone plasma concentration after the dose is delivered into the body (Cmax), a time to reach the maximum naloxone plasma concentration (Tmax) or an area under a curve of the naloxone plasma concentration as a function of time after the dose is delivered into the body (AUC) is between about 80 percent and about 125 percent of a corresponding confidence interval resulting from the delivery of a corresponding dose of a corresponding naloxone composition via a manually-actuated syringe, an amount of the corresponding dose being substantially the same as an amount of the naloxone composition.

In some embodiments, the medicament delivery device can include an electronic circuit system coupled to the housing. The electronic circuit system is configured to produce an output when the electronic circuit system is actuated. The output can be, for example, an audible or visual output related to the naloxone composition (e.g., an indication of the expiration date, the symptoms requiring treatment with naloxone, or the like), the use of the medicament delivery device, and/or post-administration procedures (e.g., a prompt to call 911, instructions for the disposal of the device, or the like).

As used in this specification and the appended claims, the singular forms "a," "an" and "the" include plural referents unless the context clearly dictates otherwise. Thus, for example, the term "a member" is intended to mean a single member or a combination of members, "a material" is intended to mean one or more materials, or a combination thereof. Furthermore, the words "a" or "an" and the phrase "one or more" may be used interchangeably.

As used herein, the words "proximal" and "distal" refer to direction closer to and away from, respectively, an operator of the medical device. Thus, for example, the end of the medicament delivery device contacting the patient's body would be the distal end of the medicament delivery device, while the end opposite the distal end would be the proximal end of the medicament delivery device.

As used herein, the terms "about" and/or "approximately" when used in conjunction with numerical values and/or ranges generally refer to those numerical values and/or ranges near to a recited numerical value and/or range. For example, in some instances, "about 40 [units]" can mean within ±25% of 40 (e.g., from 30 to 50). In some instances, the terms "about" and "approximately" can mean within ±10% of the recited value. In other instances, the terms "about" and "approximately" can mean within ±9%, ±8%, ±7%, ±6%, ±5%, ±4%, ±3%, ±2%, ±1%, less than ±1%, or any other value or range of values therein or therebelow. The terms "about" and "approximately" may be used interchangeably.

In a similar manner, term "substantially" when used in connection with, for example, a geometric relationship, a numerical value, and/or a range is intended to convey that the geometric relationship (or the structures described thereby), the number, and/or the range so defined is nominally the recited geometric relationship, number, and/or range. For example, two structures described herein as being "substantially parallel" is intended to convey that, although a parallel geometric relationship is desirable, some non-parallelism can occur in a "substantially parallel" arrangement. By way of another example, a structure defining a volume that is "substantially 0.50 milliliters (mL)" is intended to convey that, while the recited volume is desirable, some tolerances can occur when the volume is "substantially" the recited volume (e.g., 0.50 mL). Such tolerances can result from manufacturing tolerances, measurement tolerances, and/or other practical considerations (such as, for example, minute imperfections, age of a structure so defined, a pressure or a force exerted within a system, and/or the like). As described above, a suitable tolerance can be, for example, of ±1%, ±2%, ±3%, ±4%, ±5%, ±6%, ±7%, ±8%, ±9%, ±10%, or more of the stated geometric construction, numerical value, and/or range. Furthermore, although a numerical value modified by the term "substantially" can allow for and/or otherwise encompass a tolerance of the stated numerical value, it is not intended to exclude the exact numerical value stated.

While numerical ranges are provided for certain quantities, it is to be understood that these ranges can include all subranges therein. Thus, the range "from 50 to 80" includes all possible ranges therein (e.g., 51-79, 52-78, 53-77, 54-76, 55-75, 70-70, etc.). Furthermore, all values within a given range may be an endpoint for the range encompassed thereby (e.g., the range 50-80 includes the ranges with endpoints such as 55-80, 50-75, etc.).

The embodiments described herein define volumes that contain a gas (e.g., air or the like). The gas contained within the volumes can have characteristics (e.g., pressure, temperature, etc.) that are dependent on, for example, a point in time during an injection event and/or the like. Similarly, the volumes so defined can also be dependent on time (e.g., the volumes can increase or decrease over time). In general, fluid dynamic principles can be used to determine and/or define such characteristics and/or relationships therebetween. For example, the devices described herein define volumes that contain and/or receive air, nitrogen, argon, or other gases, which, in fluid dynamics, are generally considered to be an "ideal gas." As such, characteristics of the subject gas can be determined and/or approximated using the ideal gas law mathematically expressed below:

$$PV = nRT$$

where P is pressure, V is volume, n is the number of moles of the gas, R is the gas constant (8.3145 Joules per moles-Kelvin $$\left(\frac{J}{mol \cdot K}\right)\right),$$

and T is temperature.

As used herein, the ideal gas law can be applied to determine a relationship between two volumes of the same gas (e.g., air). Specifically, when assuming a substantially constant temperature and considering that the volumes contain the same gas, the terms "nRT" (from the ideal gas law) are substantially equal and thus, a relationships between the two volumes can be defined as $P_1V_1 = P_2V_2$. In this manner, when portions of the devices described herein have a pre-determined pressure and volume at a time prior to an injection event (e.g., $P_1V_1$), a pressure and a volume (e.g., $P_2V_2$) of the portions at a given time during an injection event can be determined and/or approximated.

The embodiments described herein can be formed or constructed of one or more biocompatible materials. Examples of suitable biocompatible materials include metals, glasses, ceramics, or polymers. Examples of suitable metals include pharmaceutical grade stainless steel, gold, titanium, nickel, iron, platinum, tin, chromium, copper, and/or alloys thereof. A polymer material may be biodegradable or non-biodegradable. Examples of suitable biodegradable polymers include polylactides, polyglycolides, polylactide-co-glycolides (PLGA), polyanhydrides, polyorthoesters, polyetheresters, polycaprolactones, polyesteramides, poly(butyric acid), poly(valeric acid), polyurethanes, and/or blends and copolymers thereof. Examples of non-biodegradable polymers include nylons, polyesters, polycarbonates, polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, and/or blends and copolymers thereof.

As used herein, the terms "bioequivalent," "bioequivalence," "bioequivalency," when used to describe to compositions generally means the compositions and the PK characteristics of the compositions are substantially the same. More specifically, the term "bioequivalence" is defined by the Food and Drug Administration (FDA) as, "the absence of a significant difference in the rate and extent to which the active ingredient or active moiety in pharmaceutical equivalents or pharmaceutical alternatives becomes available at the site of drug action when administered at the same molar dose under similar conditions in an appropriately designed study."

In certain embodiments, a first dosage form and a second dosage form are bioequivalent if the 90% confidence interval of the relative mean $C_{max}$ of the second dosage form to the first dosage form is within 80% to 125%. In further embodiments, a first dosage form and a second dosage form are bioequivalent if the 90% confidence interval of the relative mean $AUC_{(0-t)}$ of the second dosage form to the first dosage form is within 80% to 125%. In yet further embodiments, a first dosage form and a second dosage form are bioequivalent if the 90% confidence interval of the relative mean $AUC_{(0-\infty)}$ of the second dosage form to the first dosage form is within 80% to 125%. In still further embodiments of the invention, a first dosage form and a second dosage form are bioequivalent if the 90% confidence intervals of the relative mean $C_{max}$, $AUC_{(0-t)}$, and $AUC_{(0-\infty)}$ of the second dosage form to the first dosage form is within 80% to 125%.

As used herein, $AUC_{(0-\infty)}$ is the area under the plasma concentration-time curve from pre-dose (time 0) extrapolated to infinity.

As used herein, $AUC_{(0-t)}$ is the area under the plasma concentration-time curve from pre-dose (time 0) to the time of the last quantifiable concentration ($T_{last}$).

As used herein, $C_{max}$ is the maximum plasma naloxone concentration determined directly from the plasma concentration-time profile.

As used herein, $T_{max}$ is the time of maximum plasma naloxone concentration determined directly from the plasma concentration-time profile.

As used herein, the term "pharmacokinetic" refers generally to the characteristic interactions of a drug and the body in terms of the absorption, distribution, metabolism, and excretion of the drug. By way of example, the terms "pharmacokinetic parameter" or "pharmacokinetic parameters" can include, but are not limited to parameters such as $C_{max}$, $T_{max}$, $AUC_{(0-t)}$, and $AUC_{(0-\infty)}$.

Figure 2:
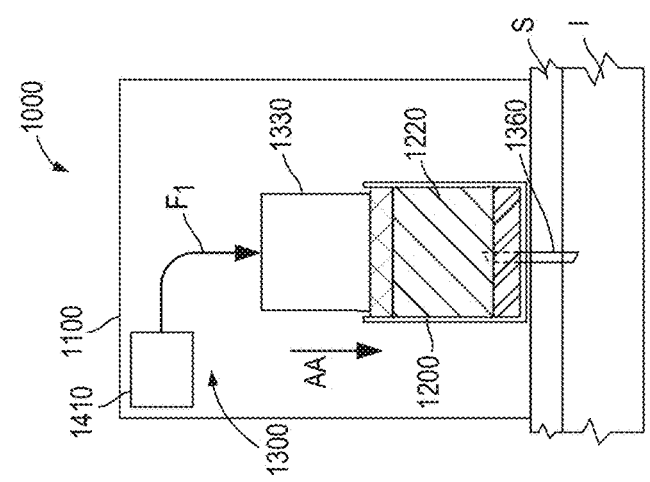
Figure 1:
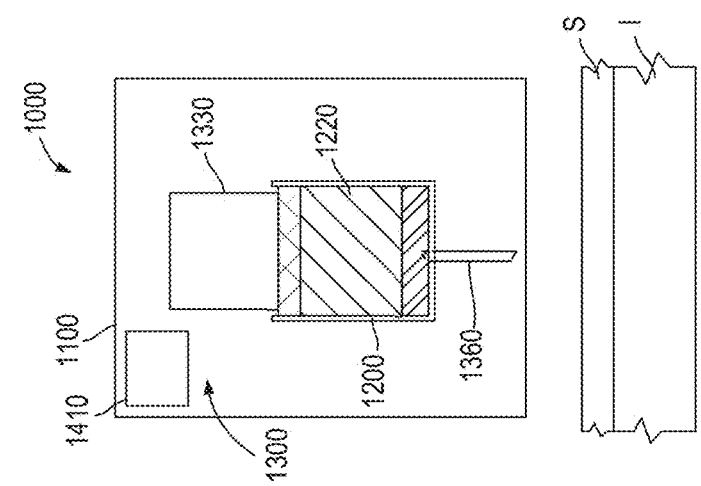

FIGS. 1-3 are schematic illustrations of a medicament delivery device 1000 according to an embodiment in a first, second, and third configuration, respectively. The medicament delivery device 1000 (also referred to herein as "delivery device" or a "drug product") includes a housing 1100, a medicament container 1200, a needle 1360, and an actuation assembly 1300. The housing 1100 can be any suitable size, shape, or configuration and can be made of any suitable material. For example, in some embodiments, the housing 1100 is an assembly of multiple parts formed from a plastic material that are coupled together to form a substantially rectangular shape when assembled. In some embodiments, the parts and/or components of the housing 1100 can be coupled via, for example, ultrasonic welding, friction welding, an adhesive, an epoxy, and/or the like. In some embodiments, at least some of the parts of the housing 1100 can be coupled together to form substantially fluid tight seals or the like. In such embodiments, the housing 1100 can define, for example, volumes and/or portions that define a flow path through which a fluid can flow from one portion of the housing 1100 to a different portion of the housing 1100, as described in further detail herein.

As shown in FIGS. 1-3, the medicament container 1200 is disposed within the housing 1100 and can be moved between a first position and a second position within the housing 1100 in response to an applied force (e.g., exerted by the actuation assembly 1300). Although the medicament container 1200 is shown as moving between the first position and the second position to facilitate needle insertion and medicament delivery, in other embodiments, a device and/or drug product can include a medicament container that does not move relative to the housing. The medicament container 1200 can be any container suitable for storing the medicament. In some embodiments, the medicament container 1200 can be, for example, a vial, cartridge, ampule, prefilled syringe or the like formed from a biocompatible material such as, for example, a pharmaceutical grade metal or alloy, glass, polymer, ceramic, and/or the like. The medicament container 1200 can have, for example, a proximal end portion and a distal end portion and can define an inner volume.

The inner volume of the medicament container 1200 can include, receive, and/or otherwise contain (i.e., is filled or partially filled with) a medicament 1220 such as, for example, an opioid antagonist. More specifically, in some embodiments, the medicament 1220 disposed within the medicament container 1200 can be a naloxone composition such as those described herein. For example, the naloxone composition can include an effective amount of naloxone (i.e., 4,5-epoxy-3,14-dihydroxy-17-(2-propenyl) morphinan-6-one), or a pharmaceutically acceptable salt and/or ester thereof. In some embodiments, the naloxone composition can include one or more pH-adjusting agents (e.g., at least one of hydrochloric acid, citric acid, acetic acid, phosphoric acid, or combinations thereof), one or more tonicity-adjusting agents (e.g., at least one of dextrose, glycerin, mannitol, potassium chloride, sodium chloride, or combinations thereof), one or more stabilizing agents, and/or the like. In some embodiments, the naloxone composition can have an osmolality between about 250 to about 350 mOsm and a pH between about 3 to about 5.

The medicament container 1200 can include an elastomeric member (also referred to herein as a "plunger") that can be formulated to be compatible with the medicament housed within the medicament container 1200 (i.e., the naloxone composition). Similarly stated, the elastomeric member can be formulated to minimize any reduction in the efficacy of the medicament 1220 that may result from contact (either direct or indirect) between the elastomeric member and the medicament 1220. For example, in some embodiments, the elastomeric member can be formulated to minimize any leaching or out-gassing of compositions that may have an undesired effect on the medicament 1220. The elastomeric member is disposed within the medicament container 1200, for example, to seal the proximal end portion thereof. In some embodiments, the elastomeric member can be formulated to maintain its chemical stability, flexibility, and/or sealing properties when in contact (either direct or indirect) with a medicament 1220 over a long period of time (e.g., for up to six months, one year, two years, five years, or longer). In some embodiments, the elastomeric member can be any of the elastomeric members shown and described in U.S. Pat. No. 8,627,816 entitled "Medicament Delivery Device for Administration of Opioid Antagonists Including Formulations for Naloxone," which is incorporated herein by reference in its entirety.

The needle 1360 of the delivery device 1000 can be any suitable shape, size, or configuration. For example, the needle 1360 can have any diameter and/or length to facilitate the injection of the medicament 1220 (i.e., the naloxone composition). In some embodiments, the needle 1360 can have a length suitable to penetrate clothing and deliver the medicament via an intramuscular injection. In some embodiments, the needle 1360 can have a length of greater than about 1 inch, greater than about 1.5 inches, greater than about 2 inches, greater than about 2.5 inches or greater than about 3 inches. In other embodiments, the needle 1360 can have a length of less than about 1 inch. Moreover, the needle 1360 can have any suitable outer diameter and/or inner diameter (i.e., a diameter of a lumen defined by the needle 1360). For example, the needle 1360 can have a lumen diameter of approximately between 19-gauge and 31-gauge.

The needle 1360 is movable between a first needle position and a second needle position relative to the housing 1100. More specifically, the first needle position is, for example, a proximal position in which the needle 1360 is disposed in the housing 1100 (see e.g., FIG. 1) and the second needle position is, for example, a distal position in which a portion of the needle 1360 is disposed substantially outside of the housing 1100 (see e.g., FIGS. 2 and 3). In addition, the arrangement of the medicament container 1200 and the needle 1360 within the housing 1100 can be such that the needle 1360 is fluidically isolated from the medicament 1220 contained in the medicament container 1200 when the needle 1360 is in the first needle position and the needle 1360 is placed in fluid communication with the medicament 1220 contained in the medicament container 1200 when the needle 1360 is in the second need position. Thus, the medicament 1220 can be expelled through the needle 1360, as described in further detail herein. In other embodiments, however, the needle 1360 can be in fluid communication with the medicament container 1200 when the needle is in both the first needle position and the second needle position. For example, in some embodiments, the medicament container 1200 can a prefilled syringe with a staked needle that remains in fluid communication with the interior volume of the syringe regardless of the needle position.

Although not shown in FIGS. 1-3, in some embodiments, the needle 1360 can be coupled to, for example, a carrier or the like and maintained in a substantially fixed position relative thereto. The carrier can be movably disposed in the housing, for example, between a proximal position and a distal position. Expanding further, with the needle 1360 maintained in a substantially fixed position relative to the carrier, the proximal position of the carrier within the housing can be associated with the first needle position and the distal position of the carrier within the housing can be associated with the second needle position. The carrier can also be in contact with and/or can otherwise carry the medicament container 1200, which can be movable in an axial direction relative to the carrier. For example, the medicament container 1200 can be disposed within a portion of the carrier and movable in the axial direction between a proximal position relative to the carrier and a distal position relative to the carrier. Therefore, the arrangement of the medicament container 1200, the needle 1360, and the carrier can be such that when the medicament container 1200 is in its proximal position relative to the carrier and the needle 1360 is in the first needle position, the needle 1360 is fluidically isolated from the medicament 1220 contained in the medicament container 1200. Conversely, when the needle 1360 is in the second needle position and the medicament container 1200 is placed in its distal position relative to the carrier, the needle 1360 is placed in fluid communication with the medicament 1220 contained in the medicament container 1200, as described in further detail herein.

The actuation assembly 1300 of the medicament delivery device 1000 can be any suitable assembly, mechanism, and/or device that can be configured, for example, to move a portion of the medicament container 1200 and/or the needle 1360 relative to the housing 1100. As shown in FIGS. 1-3, the actuation assembly 1300 includes a movable member 1330 and an energy storage member 1410. The movable member 1330 is movably disposed within the housing 1100 such that, a distal portion of the movable member 1330 is in contact with the medicament container 1200. In this manner, a force can be exerted (e.g., a force produced by the energy storage member 1410) to move the movable member 1330 substantially concurrently with medicament container 1200 (see e.g., FIG. 2) and/or the needle 1360 or relative to the medicament container 1200 and the needle 1360 (see e.g., FIG. 3).

The energy storage member 1410 of the actuation assembly 1300 can be any suitable device or mechanism that, when actuated, produces a force to move the needle 1360 from the first needle position (FIG. 1) to the second needle position (FIGS. 2 and 3) and/or to deliver the medicament 1220. For example, in some embodiments, the energy storage member 1410 can be a mechanical energy storage member, such as a spring; a device containing compressed gas; a device containing a vapor pressure-based propellant; and/or the like. In some embodiments, the energy storage member 1410 can be and/or can otherwise include an electrical energy storage member, such as a battery, a capacitor, a magnetic energy storage member, and/or the like. In other embodiments, the energy storage member 1410 can be a chemical energy storage member, such as a container containing two substances that, when mixed, react to produce energy. The energy storage member 1410 can be disposed within the housing in any position and/or orientation relative to the medicament container 1200. In some embodiments, for example, the energy storage member 1410 can be positioned within the housing 1100 spaced apart from the medicament container 1200. Moreover, in some embodiments, the energy storage member 1410 can be positioned such that a longitudinal axis of the energy storage member 1410 is offset from a longitudinal axis of the medicament container 1200. In other embodiments, the energy storage member 1410 can substantially surround the medicament container 1200. In this manner, the energy storage member 1410 can be any suitable device, mechanism, and/or member configured to exert a force on the movable member 1330 to deliver the medicament 1220 from the medicament container 1200 to the body of the patient via the needle 1360.

As shown in FIG. 1, in some instances, the delivery device 1000 can be stored in the first configuration in which the needle 1360 is in the first needle position. In the event of a medical emergency associated with, for example, a patient experiencing an opioid overdose, a user (e.g., a patient, a friend or family member, an untrained bystander, a medical professional, etc.) can manipulate the delivery device 1000 to administer the medicament 1220 (e.g., an opioid antagonist such as any of the naloxone formulations described herein) to the patient. As shown in FIG. 2, the user can manipulate the delivery device 1000 to actuate the actuation assembly 1300, for example, by placing at least a portion of the delivery device 1000 in contact with a surface of the body of the patient, and transitioning the delivery device 1000 to the second configuration. The delivery device 1000 can be actuated (or transitioned to its second configuration) by any suitable mechanism, such as, for example, by depressing the distal end surface of the delivery device 1000 against the surface S, by depressing a button disposed at a proximal end of the device, or the like.

More specifically, the actuation assembly 1300 can be actuated such that the energy storage member 1410 exerts a force $F_1$ on the movable member 1330 sufficient to move the needle 1360 from the first needle position to the second needle position, as indicated by the arrow AA in FIG. 2. In some embodiments, the force $F_1$ exerted on the movable member 1330 moves at least the movable member 1330, the medicament container 1200, and the needle 1360 substantially concurrently. With the needle 1360 in the second needle position, a portion of the needle 1360 extends in the distal direction from the housing 1100. Moreover, with the delivery device 1000 in contact with the surface of the body of the patient and with the needle 1360 in the second needle position, a portion (i.e., a distal end portion) of the needle 1360 extends through a subcutaneous portion S of the body and into an intramuscular portion I of the body.

With the medicament container 1200 in its distal position and with the needle 1360 in the second needle position, at least a portion of the force exerted by the energy storage member 1410 on the movable member 1330 (represented as $F_2$ in FIG. 3) can move the movable member 1330 relative to the medicament container 1200, as shown in FIG. 3. Thus, the movement of the movable member 1330 increases a pressure within a portion of the medicament container 1200 (for example, between an elastomeric member and a surface of the medicament container 1200 through which the needle 1360 extends). Thus, the portion of the force $F_2$ can act to expel the medicament 1220 from the medicament container 1200, as indicated by the arrow CC in FIG. 3. Although described as including an elastomeric member that is distinct from the movable member 1330, in some embodiments, the movable member 1330 can be the elastomeric member (i.e., the plunger or "stopper" in the medicament container). In such embodiments, the energy storage member 1410 can produce a force to act directly or indirectly on the elastomeric member (i.e., the movable member 1330) to perform the functions described herein.

The arrangement of the energy storage member 1410, the needle 1360, and the composition of the medicament 1220 and/or any other suitable portion of the delivery device 1000 (or drug product) can be such that the medicament 1220, when delivered, provides a desired set of delivery and/or pharmacokinetic (PK) characteristics. In some embodiments, the specific characteristics of the delivery device 1000 (or drug product) are such that a dose of the medicament 1220 (i.e., the naloxone formulation) is delivered from the medicament container 1200 and into the body of the patient (as indicated by the arrow CC in FIG. 3) such that at least one pharmacokinetic parameter of the naloxone composition is bioequivalent to the corresponding pharmacokinetic parameter resulting from the delivery of a corresponding dose of a corresponding naloxone formulation via a manually-actuated syringe. Similarly stated, the delivery device 1000 (or drug product) is configured such that delivery of the medicament 1220 (i.e., the naloxone formulation) from the medicament container 1200 to the body provides naloxone bioavailability that is bioequivalent to naloxone bioavailability resulting from the delivery of a corresponding naloxone formulation from a manually actuated syringe. In some embodiments, the actuation assembly 1300 is configured to deliver the dose of the medicament 1220 (i.e., the naloxone formulation) into the body such that the 90% confidence interval of at least one of the relative mean maximum naloxone plasma concentration after the dose is delivered into the body ($C_{max}$), time to reach the maximum naloxone plasma concentration ($T_{max}$), area under the plasma concentration-time curve from pre-dose (time 0) extrapolated to infinity ($AUC_{0-\infty}$), or area under the plasma concentration-time curve from pre-dose (time 0) to the time of the last quantifiable concentration ($T_{last}$) ($AUC_{0-t}$) of the delivered dose to a delivered dose of a corresponding naloxone composition delivered via a manually-actuated syringe is within 80% to 125%.

In yet other embodiments, the specific characteristics of the delivery device 1000 (or drug product) are such that a dose of the medicament 1220 (i.e., the naloxone formulation) is delivered from the medicament container 1200 and into the body of the patient such that the 90% confidence interval of at least one of the relative mean maximum naloxone plasma concentration after the dose is delivered into the body ($C_{max}$), time to reach the maximum naloxone plasma concentration ($T_{max}$), area under the plasma concentration-time curve from pre-dose (time 0) extrapolated to infinity ($AUC_{0-\infty}$), or area under the plasma concentration-time curve from pre-dose (time 0) to the time of the last quantifiable concentration ($T_{last}$) ($AUC_{0-t}$) of the delivered dose to a delivered dose of a corresponding naloxone composition delivered via a manually-actuated syringe is within 80% to 125%.

For example, in some embodiments, the actuation assembly 1300 is configured to deliver a dose of the naloxone composition (i.e., any of the naloxone compositions described herein) having a delivered volume of at least about 0.34 ml at a faster delivery rate and/or at a higher delivery pressure than would result from the delivery of a corresponding dose via a manually-actuated syringe. As described in the examples herein, such faster delivery rate and/or higher delivery pressures can be implemented to produce certain desired performance characteristics associated with the delivery device 1000 (or drug product). Such characteristics can include, for example, a minimum time for insertion of the needle 1360, a repeatable needle insertion depth, repeatable placement of the needle 1360 into fluid communication with the medicament container 1200, a consistent delivery volume, and the like. As further described herein, unexpectedly, even when delivered at a faster delivery rate and/or higher delivery pressure, the delivery device 1000 (or drug product) delivers the dose of the naloxone composition such that at least one pharmacokinetic parameter of the naloxone composition is bioequivalent to the corresponding pharmacokinetic parameter resulting from the delivery of a corresponding dose of a corresponding naloxone formulation via a manually-actuated syringe.

By way of an example, in some embodiments the energy storage member 1410 is and/or otherwise includes a container or a device containing a compressed gas to produce a force to move the needle 1360 and deliver the dose of the naloxone composition 1220. In such embodiments, the arrangement of the housing 1100 can be such that portions of the housing 1100 form a fluid flow path through which the compressed gas can flow after the energy storage member 1410 has been actuated (e.g., after puncturing a seal and/or otherwise releasing at least a portion of the compressed gas from the container). Moreover, a proximal end portion of the movable member 1330 can include a seal member or the like that can be in contact with an inner surface of a portion of the housing 1100 such that a substantially fluid-tight seal is defined therebetween. Thus, at least a portion of the housing 1100 can define an inner volume that is substantially fluidically isolated from a remaining volume defined by the housing 1100 and/or other structure of the delivery device 1000. As such, when the delivery device 1000 is actuated, the compressed gas flows from the container having a relatively small volume and a relatively high pressure into the inner volume of the portion of the housing 1100 having a relatively large volume and a relatively low pressure (e.g., atmospheric pressure).

The expansion of the gas as it enters the substantially fluidically sealed inner volume of the portion of the housing 1100 exerts the force $F_1$ on the movable member 1330 to move the needle 1360 from the first needle position (FIG. 1) to the second needle position (FIGS. 2 and 3). Similarly, a portion of the force (identified as $F_2$) resulting from the expansion of the gas can move the movable member 1330 relative to the medicament container 1200 to deliver the medicament 1220 (e.g., a naloxone composition, such as those described herein) contained within the medicament container 1200 into a body of a patient via the needle 1360, as described in further detail herein. A volume of the substantially fluidically sealed portion of the housing 1100 increases as the movable member 1330 is moved relative to the housing 1100 in response to the force exerted by the expansion of the gas. Thus, a pressure within the inner volume of the housing decreases as the volume increases in response to the movement of the movable member 1330 (e.g., as determined by, for example, the ideal gas law expressed as $P_1V_1=P_2V_2$, wherein P is pressure and V is volume). Thus, the force $F_2$ exerted by the energy storage member 1410 (i.e., in this embodiment, the expansion of the gas) on the movable member 1330 decreases from a first amount at the start of an injection event to a second amount at the end of an injection event. In some embodiments, the force exerted on the movable member 1330 can decrease in a substantially linear manner from the first amount at the start of the injection event to the second amount at the end of the injection event. In other embodiments, the decrease in the force can be non-linear, exponential, and/or logarithmic over the duration of the injection event. Because of the decrease in the injection force $F_2$, in some embodiments, the actuation assembly 1300 can be configured to produce a higher initial injection force to ensure that the desired delivered volume is delivered having the desired characteristics (e.g., that the delivered volume is repeatably delivered within a desired tolerance, that the needle 1360 is repeatably placed into fluid communication with the medicament container 1200, that there is no "dribbling" at the end of delivery due to a drop in the injection force, or the like).

In contrast, a force exerted on a plunger of a manually-actuated syringe to deliver a medicament contained therein can be substantially constant throughout the stroke of the syringe. Moreover, the force exerted on the plunger of a manually-actuated syringe to deliver the medicament is independent from a force exerted to insert the needle into the patient. The forces exerted by the energy storage member 1410 ($F_1$ and $F_2$), however, are not independent and are not constant. Thus, in some instances, the larger force (i.e., $F_1$) is exerted at the start of an injection event to ensure proper insertion of the needle 1360 while the smaller force (e.g., $F_2$) is exerted at the end of the injection event to deliver of the dose of the medicament 1220. As described herein, unexpectedly, even when delivered with a different injection and/or force profile, the delivery device 1000 (or drug product) delivers the dose of the naloxone composition such that at least one pharmacokinetic parameter of the naloxone composition is bioequivalent to the corresponding pharmacokinetic parameter resulting from the delivery of a corresponding dose of a corresponding naloxone formulation via a manually-actuated syringe.

While the energy storage member 1410 is described above as being a device containing a compressed gas, in other embodiments, the energy storage member 1410 can be a mechanical member such as, for example, a spring or the like. In some embodiments, the spring can be configured to exert a substantially constant force throughout an injection event. In other embodiments, the spring can be configured to exert a varied force dependent on a time during an injection event (e.g., which can result from the changing length of the spring). Moreover, the energy storage member 1410, so configured, can exert a force that is such that the medicament 1220 is delivered with the desired PK characteristics as described herein.

Although not shown in FIG. 1, in some embodiments, the delivery device 1000 can include the can include a retraction member or the like. The retraction member can be any suitable device and/or mechanism configured to move the needle 1360 from the second needle position toward the first needle position. More specifically, the retraction member can be, for example, an energy storage member and/or a bias member that, once actuated, exerts a force to move the needle 1360 from the second needle position to the first needle position. In some embodiments, at least a portion of the force exerted by the energy storage member 1410 (e.g., the force $F_1$) can transition the retraction member from a first configuration having a first amount of potential energy to a second configuration having a second, larger amount of potential energy. Thus, when the potential energy of the retraction member is greater than the force exerted by the energy storage member 1410 (e.g., the force $F_2$ at the end of an injection event), the retraction spring can exert a force in substantially the opposite direction (i.e., opposite to the direction indicated in FIG. 3 by the arrow BB) associated with the transition of the potential energy to a kinetic energy, thereby moving the needle 1360 towards the first needle position to be disposed within the housing 1100. In this manner, the likelihood of an inadvertent needle stick or the like can be reduced or substantially eliminated.

In some embodiments, the retraction member can be preloaded with a predetermined amount force. In such embodiments, the retraction member can exert a force on the medicament container 1200 and/or on a carrier (as described above) supporting the medicament container 1200 that is sufficient to prevent a distal movement of the medicament container 1200 and/or the needle 1360 in response, for example, to gravity or the like, prior to the actuating of the actuation assembly 1300. Moreover, the medicament container 1200 and/or the carrier can include a locking feature of the like that can engage a portion of the housing 1100 to substantially limit a proximal movement of the medicament container 1200, the needle 1360, the movable member 1330, and/or the retraction member prior to actuating the actuation assembly 1300.

Figure 4:
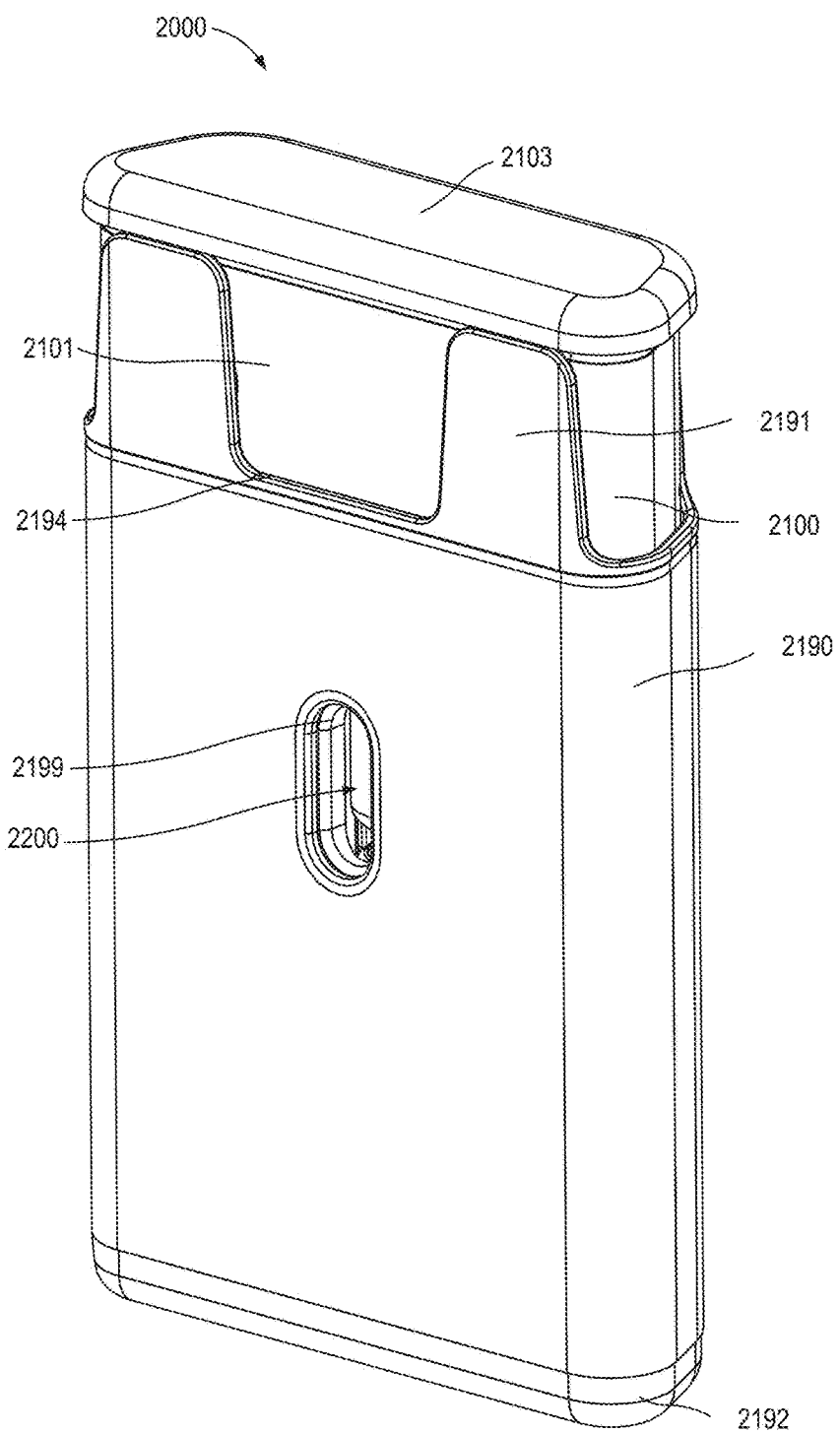
FIGS. 4 and 5 are perspective views of a medicament delivery device according to an embodiment, in a first configuration.
Figure 5:
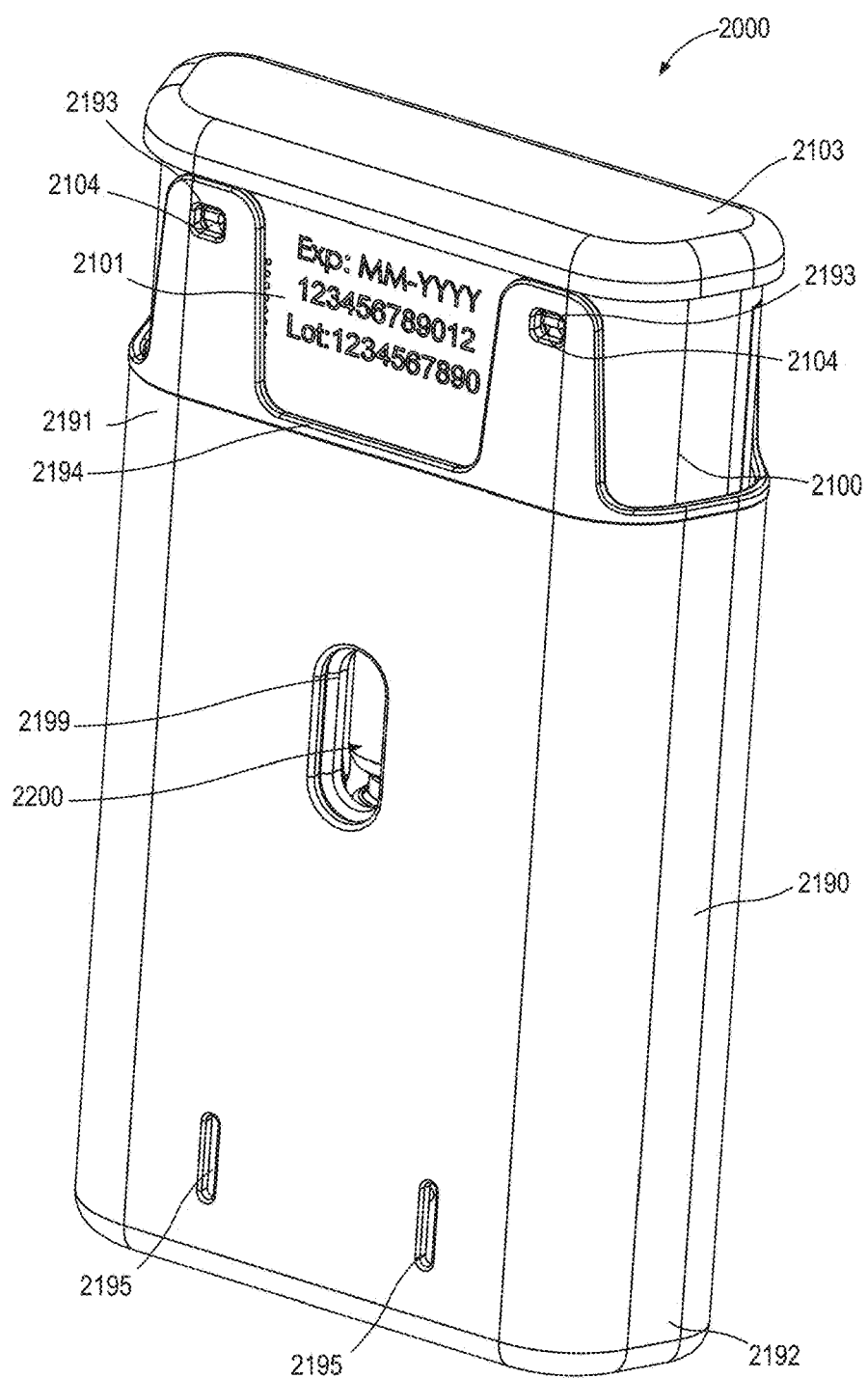
Figure 6:
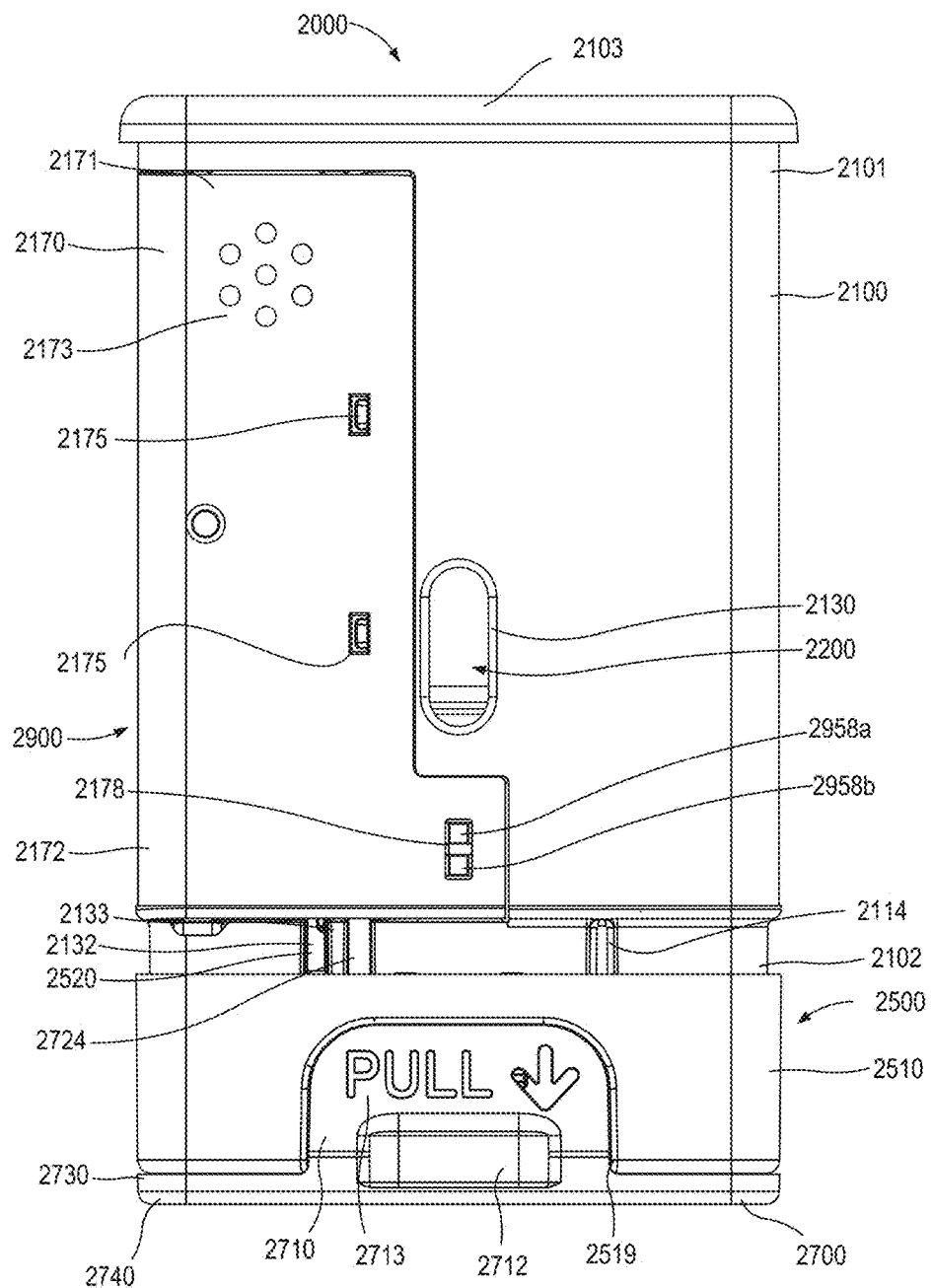
FIGS. 6 and 7 are a front view and a rear view, respectively, of the medicament delivery device illustrated in FIG. 4 with a cover removed.
Figure 7:
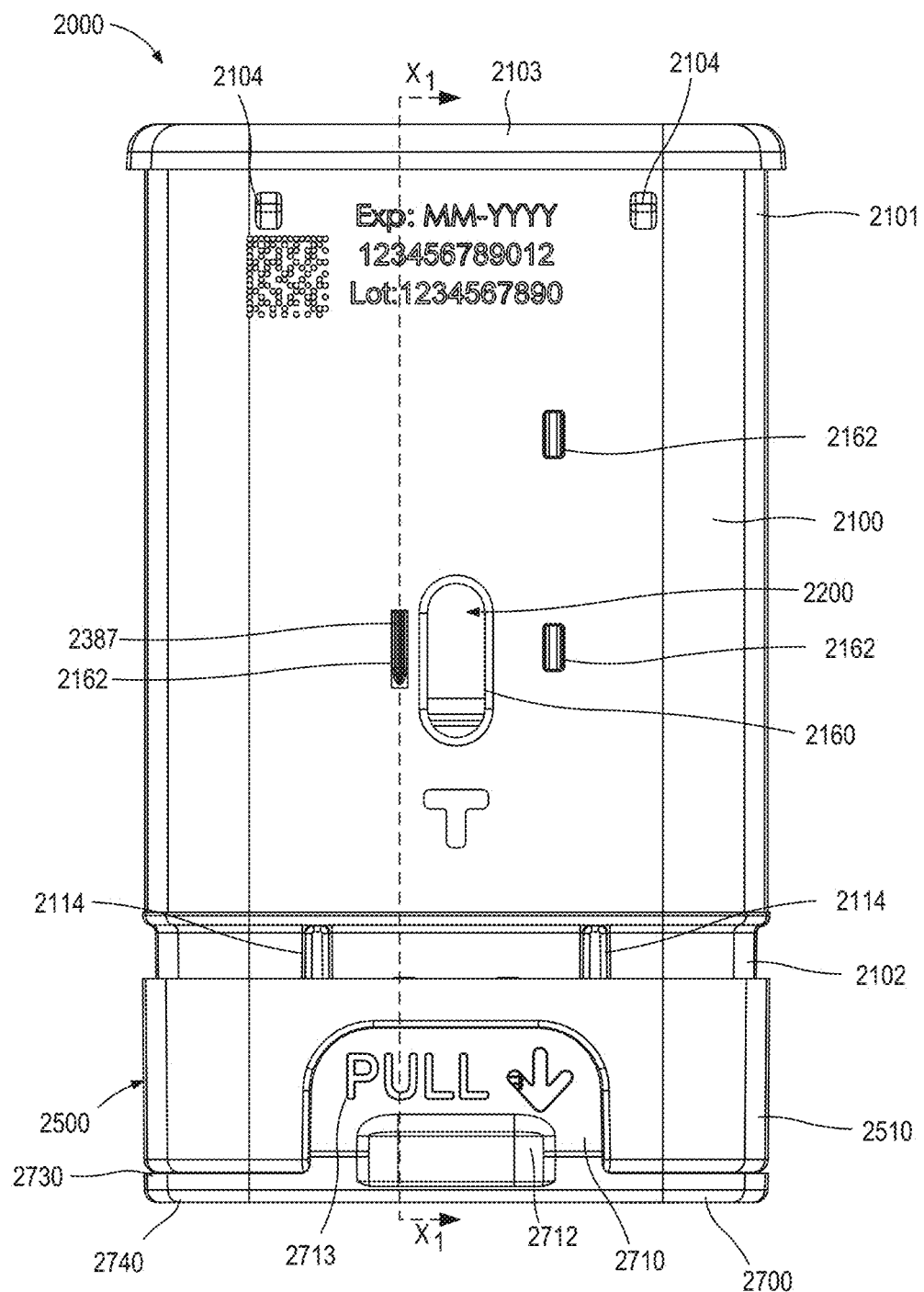
Figure 8:
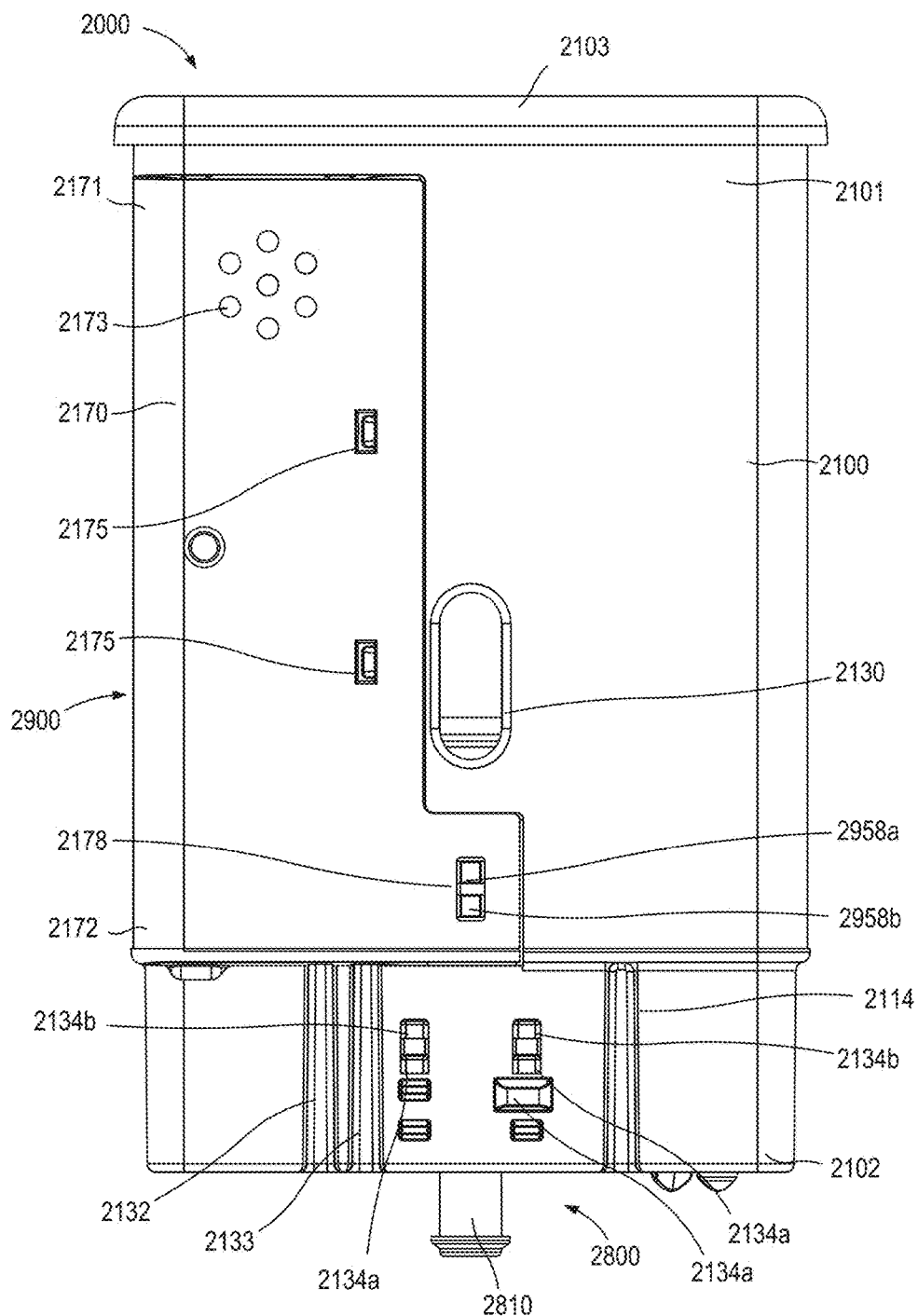
FIG. 8 is a front view of a portion of the medicament delivery device illustrated in FIG. 4.

In some embodiments, a medicament delivery device or drug product can be configured to automatically deliver a medicament such as, for example, an opioid antagonist, contained within a medicament container. For example, FIGS. 4-52 show a medicament delivery device 2000, according to an embodiment. FIGS. 4 and 5 are perspective views of the medicament delivery device 2000 (also referred to herein as "delivery device" or "drug product") in a first configuration (i.e., prior to use). The delivery device 2000 includes a housing 2100 (see e.g., FIGS. 6-12), a system actuation assembly 2500 (see e.g., FIGS. 13-18), a medicament container 2200 containing a medicament 2220 (see e.g., FIGS. 19 and 20), a medicament delivery mechanism 2300 (see e.g., FIGS. 22-26), an electronic circuit system 2900 (see e.g., FIGS. 27-36), a cover 2190 (see e.g., FIGS. 37 and 38), and a safety lock 2700 (see e.g., FIGS. 39-42). A discussion of the components of the delivery device 2000 will be followed by a discussion of the operation of the delivery device 2000.

As shown in FIGS. 6-12, the housing 2100 has a proximal end portion 2101 and a distal end portion 2102. The proximal end portion 2101 of the housing 2100 is fixedly coupled to a proximal cap 2103 (see e.g., FIG. 10) and the distal end portion 2102 of the housing 2100 engages and/or is selectively or at least temporarily coupled to a base 2510 included in the system actuation assembly 2500 and the safety lock 2700, as described in further detail herein. The housing 2100 defines a first status window 2130 and a second status window 2160 (see e.g., FIGS. 6-9). The first status window 2130 defined by the housing 2100 is located on a first side of the housing 2100, and the second status window 2160 of the housing 2100 is located on a second side of the housing 2100. The status indicator windows (or apertures) 2130, 2160 can allow a patient to monitor the status and/or contents of the medicament container 2200 contained within the housing 2100. For example, by visually inspecting the status windows 2130, 2160, a patient can determine whether the medicament container 2200 contains a medicament 2220 and/or whether the medicament 2220 has been dispensed. More specifically, in some instances, the status windows 2130 and 2160 can allow a patient and/or user to monitor the status and/or position of, for example, a plunger or the like disposed in the medicament container 2200. Thus, based on the position of the plunger the patient and/or user can determine the status of the delivery device 2000. In some embodiments, the delivery device 2000 (e.g., the housing 2100, the medicament container 2200, and/or any other suitable structure) can include a status indicator, which is viewable through the status indicator apertures 2130 and is configured to change one or more characteristics thereof over time (e.g., color, image, and/or the like).

Figure 9:
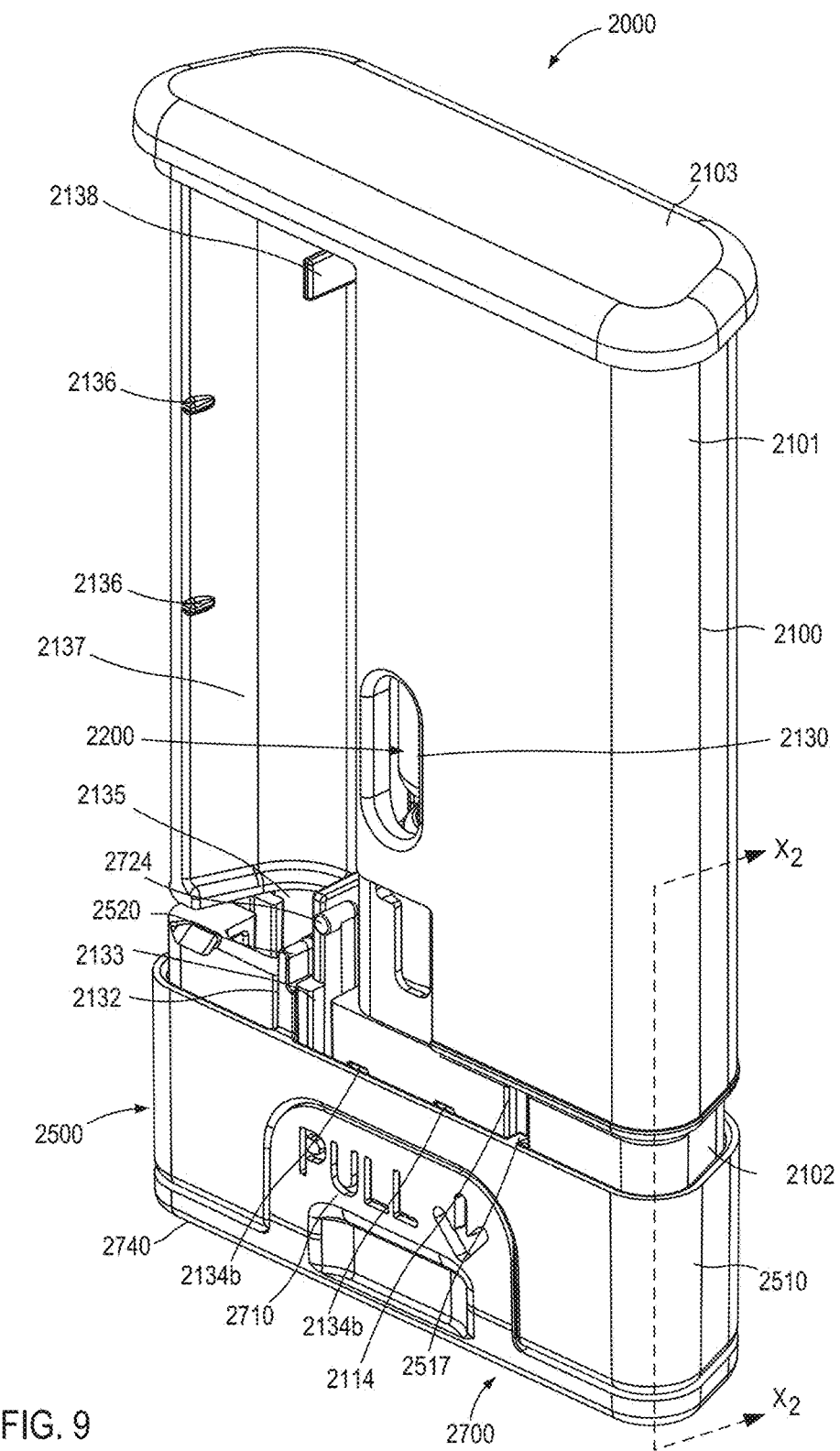
FIG. 9 is a perspective view of a portion of the medicament delivery device illustrated in FIG. 4.

The proximal end portion 2101 of the housing 2100 includes a set of cover retention protrusions 2104 (see e.g., FIGS. 5 and 7) and a speaker protrusion 2138 (see e.g., FIG. 9). The cover retention protrusions 2104 are configured to be received within corresponding openings 2193 defined by the cover 2190 (see e.g., FIG. 5) to at least temporarily retain the cover 2190 in a substantially fixed position about the housing 2100. In this manner, as described in more detail herein, the cover 2190 can be removably coupled to and disposed about at least a portion of the housing 2100. The speaker protrusion 2138 extends from a surface of the housing 2100 and can maintain a position of an audio output device 2956 of the electronic circuit system 2900 relative to the housing 2100 when the electronic circuit system 2900 is attached to the housing 2100, as described herein.

The proximal end portion 2101 of the housing 2100 is fixedly coupled to a proximal cap 2103 (see e.g., FIGS. 4-10). More particularly, the proximal end portion 2101 of the housing 2100 includes a proximal surface 2106 that includes and/or that defines a surface finish configured to facilitate the coupling of the proximal end portion 2101 of the housing 2100 to the proximal cap 2103. For example, as shown in FIG. 11, the proximal surface 2106 can define and/or can include a surface finish or the like with a track of protrusions and/or discontinuities. During a manufacturing process or the like, the proximal cap 2101 can be disposed adjacent to the proximal surface 2106 and coupled thereto via, for example, ultrasonic welding, friction welding, an adhesive, and/or the like. Thus, the track of protrusions and/or discontinuities can be transitioned, for example, from a first physical state (e.g., a solid physical state) to a second physically state (e.g., an amorphous physical state), in which the track of protrusions and/or discontinuities is at least partially reconstituted, thereby fixedly coupling (i.e., welding) the proximal cap 2103 to the proximal surface 2106 of the housing 2100. Moreover, the arrangement of the track of protrusions and/or discontinuities of the proximal surface 2106 can be such that portions of the coupling between the proximal surface 2106 and the proximal cap 2103 form a substantially fluid tight seal while other portions of the proximal surface 2106 (e.g., portions of the proximal surface 2106 not including the track of protrusions and/or discontinuities) do not form a substantially fluid tight seal with the proximal cap 2103, as described in further detail herein.

Figure 10:
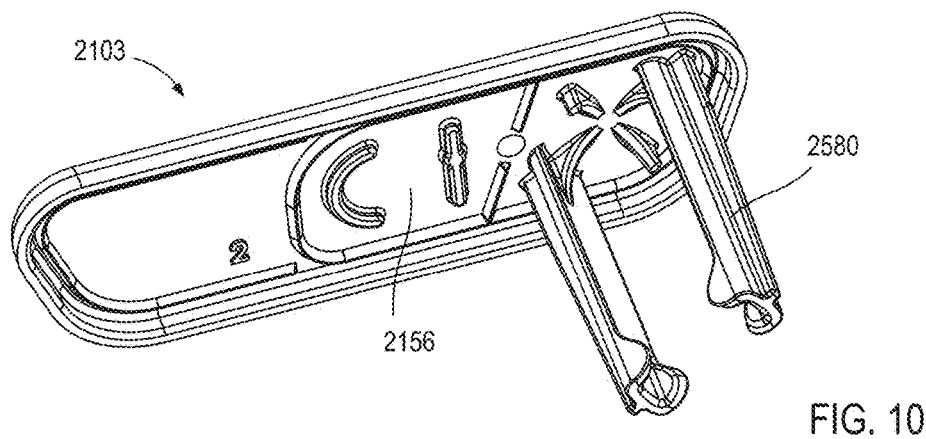
FIG. 10 is a perspective view of a proximal cap of the medicament delivery device illustrated in FIG. 4.
Figure 11:
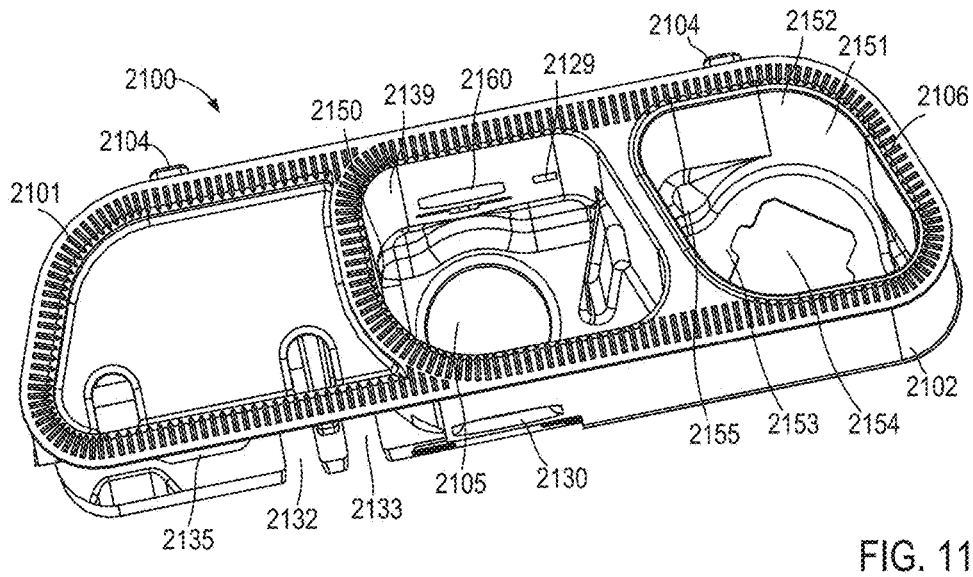
FIG. 11 is a top perspective view of a housing of the medicament delivery device illustrated in FIG. 4.

As shown in FIG. 10, the proximal cap 2103 includes a retention member 2580 and defines a passageway 2156. The retention member 2580 is configured to receive and/or retain an energy storage member 2410 such as, for example, a device containing a compressed and/or pressurized gas (see e.g., FIG. 13). As described in further detail herein, in this embodiment, the energy storage member 2410 is a device containing a compressed and/or pressurized gas, when the delivery device 2000 is actuated, pressurized gas from the energy storage member 2410 (also referred to herein as "gas container 2410") is conveyed from the gas container 2410 and into portions of the housing 2100 via the gas passageway 2156, as further described herein.

As shown in FIGS. 6-9, the distal end portion 2102 of the housing 2100 defines a battery isolation protrusion aperture 2135, a needle aperture 2105, a safety lock actuator groove 2133, a release member contact surface 2126, a release member aperture 2154, a base protrusion groove 2132, base retention recesses 2134A, 2134B, base rail grooves 2114, and a safety lock retention recess 2134C. The battery isolation protrusion aperture 2135 receives a battery isolation protrusion 2197 of the cover 2190 (see e.g., FIG. 39) when the cover 2190 is disposed about at least a portion of the housing 2100. The needle aperture 2105 is the opening through which a needle 2360 of the medicament delivery mechanism 2300 and/or a needle sheath 2810 can extend (see e.g., FIGS. 8, 46-51), as described in further detail herein.

Figure 12:
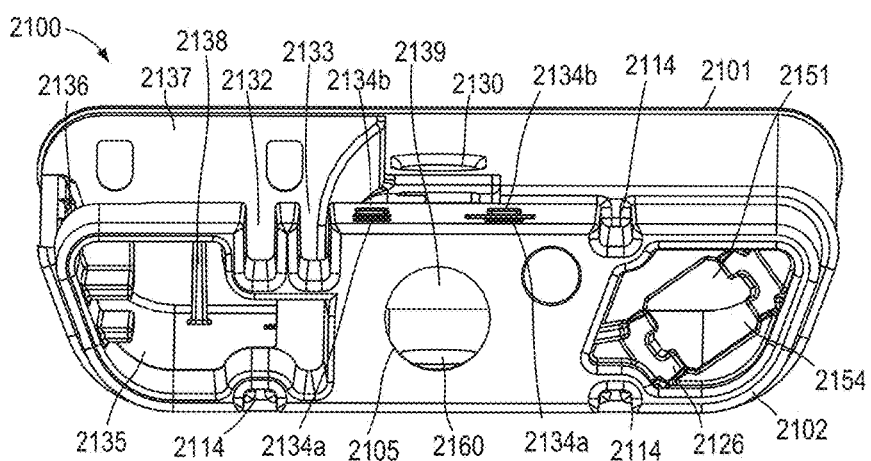
FIG. 12 is a bottom perspective view of a housing of the medicament delivery device illustrated in FIG. 4.

The safety lock actuator groove 2133 receives an actuator 2724 of the safety lock 2700 (see e.g., FIGS. 6 and 8 and FIGS. 40 and 41). As described in more detail herein, the actuator 2724 of the safety lock 2700 is configured to move within the safety lock groove 2133 to engage and/or activate a portion of the electronic circuit system 2900 when the safety lock 2700 is moved with respect to the housing 2100. The release member contact surface 2126 defines the release member aperture 2154. As shown in FIG. 12 and as described in further detail herein, the release member aperture 2154 receives a distal end portion 2552 of a release member 2550 included in the system actuation assembly 2500. Moreover, a safety lock protrusion 2702 (see e.g., FIGS. 40-43) is disposed within an opening 2556 between extensions 2553 of the release member 2550 (see e.g., FIG. 18) such that an engagement surface 2554 of the extensions 2553 is engaged with the release member contact surface 2126 to prevent activation of the delivery device 2000. The safety lock 2700, its components, and its functions are described in more detail below.

The distal base retention recesses 2134A are each configured to receive a different base connection knobs 2518 of the base 2510 (also referred to herein as "actuator," see e.g., FIG. 16) when the base 2510 is in a first position relative to the housing 2100. The proximal base retention recesses 2134B are configured to receive the base connection knobs 2518 of the base 2510 when the base 2510 is in a second position relative to the housing 2100. The base retention recesses 2134A, 2134B have a tapered proximal sidewall and a non-tapered distal sidewall. Thus, the base retention recesses 2134A, 2134B can receive the base connection knobs 2518 to allow the base 2510 to move proximally relative to the housing 2100, but substantially limit a distal movement of the base relative to the housing 2100. Said another way, the distal base retention recesses 2134A are configured to prevent the base 2510 from moving distally when the base 2510 is in a first position and the proximal base retention recesses 2134B are configured to prevent the base 2510 from moving distally when the base 2510 is in a second position. Similarly stated, the proximal base retention recesses 2134B and the base connection knobs 2518 cooperatively to limit movement of the base to prevent undesirable movement of the base 2510 after the delivery device 2000 is actuated. The proximal base retention recesses 2134B and the base connection knobs 2518 also provide a visual cue to the user that the delivery device 2000 has been used. In a similar manner, the safety lock retention recess 2134C is configured to receive a retention protrusion 2711 (see e.g., FIGS. 40 and 42) of the safety lock 2700 to at least temporarily retain the safety lock 2700 in a substantially fixed position relative to the housing 2100.

The base actuator groove 2132 receives an electronics actuator 2520 of the base 2510. As described in more detail herein, the electronics actuator 2520 of the base 2510 is configured to engage the electronic circuit system 2900 when the base 2510 is moved with respect to the housing 2100. The base rail grooves 2114 receive the guide members 2517 of the base 2510 (see FIG. 16). The guide members 2517 of the base 2510 and the base rail grooves 2114 of the housing 2100 engage each other in a way that allows the guide members 2517 of the base 2510 to slide in a proximal and/or distal direction within the base rail grooves 2114 while limiting lateral movement of the guide members 2517. This arrangement allows the base 2510 to move in a proximal and/or distal direction with respect to the housing 2100 but prevents the base 2510 from moving in a lateral direction with respect to the housing 2100.

As shown in FIGS. 11 and 12, the housing 2100 defines an electronic circuit system cavity 2137 (also referred to herein as "electronics cavity"), a medicament cavity 2139, and a gas cavity 2151. The electronic circuit system cavity 2137 receives and/or houses the electronic circuit system 2900. The housing 2100 has protrusions 2136 (see e.g., FIG. 9) configured to stabilize the electronic circuit system 2900 when disposed within the electronics cavity 2137. An outer surface of the housing 2100 is configured to receive a set of connection protrusions 2174A and connection protrusion 2174B of the electronic circuit system 2900 (see e.g., FIG. 32). In this manner, the electronic circuit system 2900 can be coupled to the housing 2100 within the electronics cavity 2137. In other embodiments, the electronic circuit system 2900 can be coupled to the housing 2100 and disposed within the electronics cavity 2137 by other suitable means such as an adhesive, a clip, a label and/or the like.

The electronics cavity 2137 is fluidically and/or physically isolated from the gas cavity 2151 and/or the medicament cavity 2139 by a sidewall 2150. The sidewall 2150 can be any suitable structure to isolate the electronics cavity 2137 within the housing 2100 from the gas cavity 2151 and/or the medicament cavity 2139 within the housing 2100. More specifically, the sidewall 2150 defines at least a portion of the electronics cavity 2137 and the medicament cavity 2139, as shown in FIG. 11. Furthermore, the proximal end portion 2101 of the housing 2100 is coupled to the proximal cap 2103 such that a substantially fluid tight seal is defined therebetween. Thus, the arrangement of the sidewall 2150 of the housing 2100, the proximal end portion 2101 of the housing 2100, and the proximal cap 2103 physically and/or fluidically isolates the electronics cavity 2137 from the medicament cavity 2139 and/or the gas cavity 2151. In this manner, the electronics cavity 2137 can, along with other aspects of the device 2000, produce the desired acoustic performance, as described in U.S. Pat. No. 8,021,344, entitled "Medicament Delivery Device Configured to Produce an Audible Output," which is incorporated herein by reference in its entirety. In other embodiments, the electronics cavity 2137 can be fluidically and/or physically isolated from the gas cavity 2151 and the medicament cavity 2139 by any suitable means. In yet other embodiments, the electronics cavity 2137 need not be physically and/or fluidically isolated from the medicament cavity 2139 and/or the gas cavity 2151.

The medicament cavity 2139 receives and/or houses the medicament container 2200 and at least a portion of the medicament delivery mechanism 2300. In particular, as described below, the medicament delivery mechanism 2300 includes a carrier 2370 and movable member 2330 movably disposed in the medicament cavity 2139. At least a portion of the medicament cavity 2139 is separated from the gas cavity 2151 by a sidewall 2155. Said another way, the sidewall 2155 defines at least a portion of the medicament cavity 2139 and the gas cavity 2151, as shown in FIG. 11. The arrangement of the sidewall 2155, the proximal end portion 2101 of the housing 2100, and the proximal cap 2103 is such that at least a portion of the medicament cavity 2139 is in fluid communication with the gas cavity 2151 via the gas passageway 2156 defined by the proximal cap 2103 (see e.g., FIG. 10), as described in further detail herein. Moreover, the medicament cavity 2139 is open to a region substantially outside of the housing 2100 via a needle aperture 2105 (see e.g., FIGS. 11 and 12) and/or the status windows 2130, 2160.

The gas cavity 2151 has a proximal end portion 2152 and a distal end portion 2153. The gas cavity 2151 is configured to receive an energy storage member 2410 such as, for example, a device containing a compressed gas and a portion of the system actuator assembly 2500 (e.g., a release member 2550 and a spring 2576, see e.g., FIGS. 13-15 and FIG. 18), as described in further detail herein. The proximal end portion 2152 of the gas cavity 2151 receives and/or houses a retention member 2580 included in and/or extending from a proximal cap 2103 of the housing 2100. As described above, the gas cavity 2151 is in fluid communication with the medicament cavity 2139 via the gas passageway 2156. The gas cavity 2151 is open to a region substantially outside of the housing 2100 via a release member aperture 2154 (see e.g., FIGS. 11 and 12).

Figure 13:
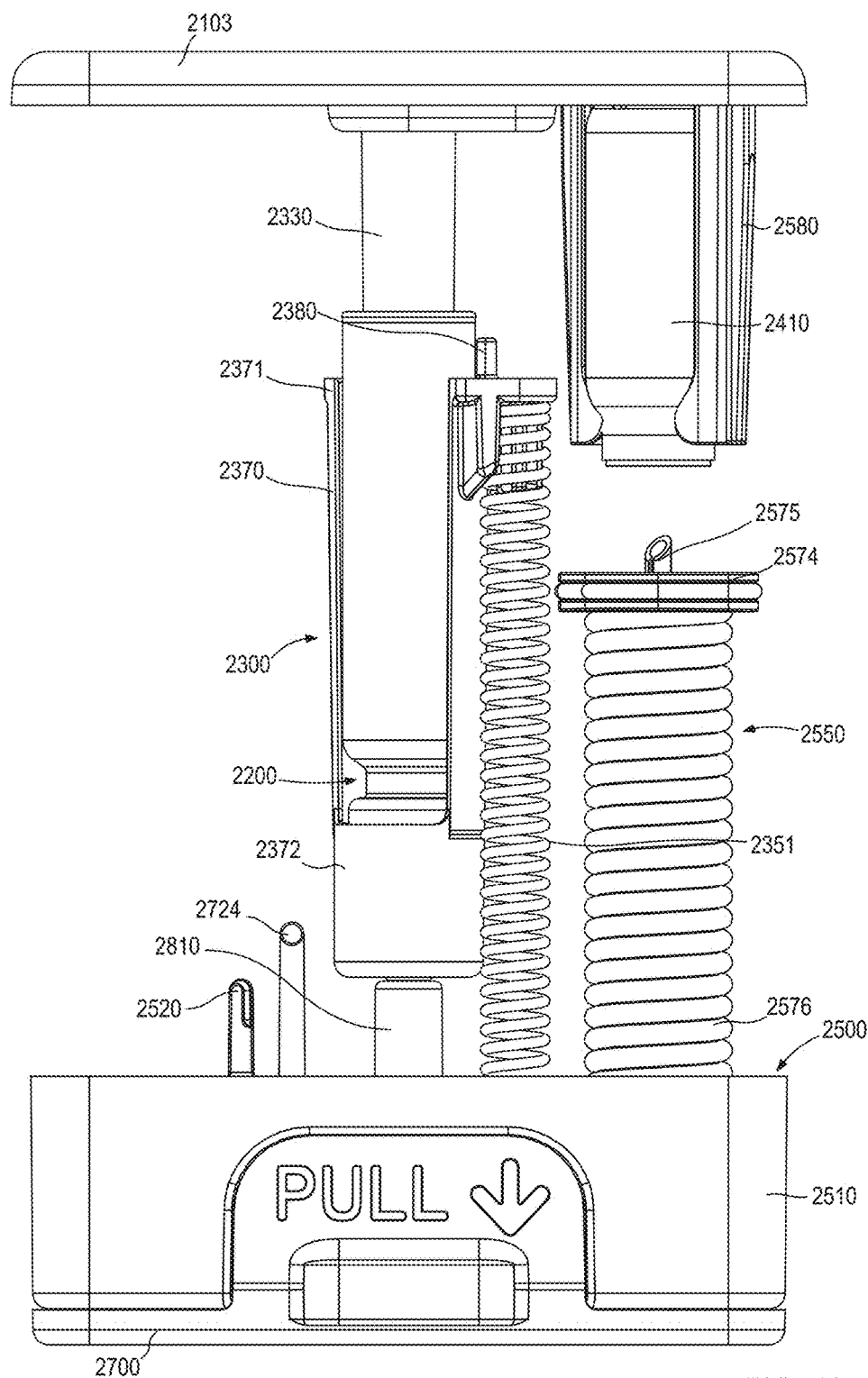
FIGS. 13 and 14 illustrate a medicament container, a medicament delivery mechanism, and a system actuator included in the medicament delivery device of FIG. 4.
Figure 14:
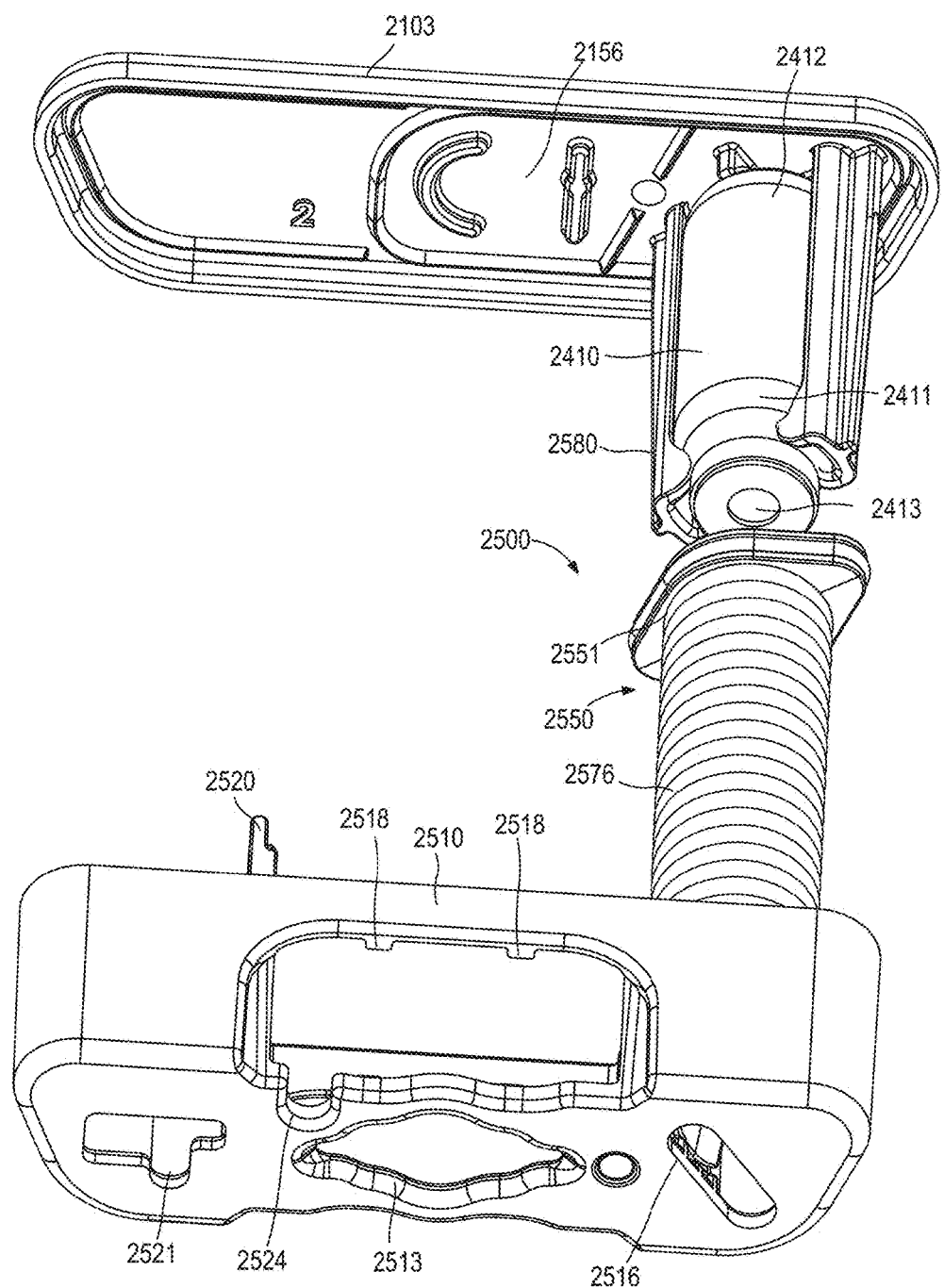

FIGS. 13-26 show the system actuator assembly 2500, the medicament delivery mechanism 2300, and the medicament container 2200 of the delivery device 2000. The system actuator assembly 2500 includes the energy storage member 2410 (i.e., the gas container 2410), the base 2510, a release member 2550, and a spring 2576. As shown in FIGS. 13 and 14, the gas container 2410 is coupled to the proximal cap 2103 of the housing 2100 via the retention member 2580. For example, in some embodiments, the retention member 2580 can include one or more surfaces that have a shape associated with a contour of the gas container 2410. In this manner, the gas container 2410 can be positioned within the retention member 2580 such that the one or more surfaces selectively engage the gas container 2410, thereby at least temporarily maintaining the gas container 2410 in a fixed position relative to the proximal cap 2103. Moreover, when the proximal cap 2103 is coupled to the proximal end portion 2101 of the housing 2100, the gas container 2410 is disposed within the gas cavity 2151, as described in detail above.

The gas container 2410 includes a distal end portion 2411 and a proximal end portion 2412, and defines an inner volume that contains a pressurized gas (e.g., prior to actuation). The distal end portion 2411 of the gas container 2410 includes and/or defines a frangible seal 2413 that can be transitioned between a first, substantially sealed configuration and a second, substantially open configuration. For example, the release member 2550 of the system actuator assembly 2500 can be moved within the gas cavity 2151 and into contact with the frangible seal 2413 to transition the frangible seal 2413 from its first configuration to its second configuration, as described in further detail herein. Furthermore, the length of the retention member 2580 and the length of the release member 2550 collectively define a distance between a proximal end portion 2551 of the release member 2550 and the frangible seal 2413 of the gas container 2410 when the delivery device 2000 is in the storage configuration. Accordingly, this distance, which is the distance through which the release member 2550 travels when the delivery device 2000 is actuated, can be adjusted by changing the length of the retention member 2580 and/or the length of the release member 2550. In some embodiments, the actuation time and/or the force exerted by the release member to, for example, puncture the frangible seal 2413 can be adjusted by changing the distance between the proximal end portion 2551 of the release member 2550 and the frangible seal 2413.

As described above, the gas container 2410 is configured to contain a pressurized gas prior to the frangible seal 2413 being transitioned to the second configuration. The gas contained within the gas container 2410 can be stored with any suitable pressure. Similarly, the inner volume defined by the gas container 2410, within which the pressurized gas is disposed), can be any suitable volume. For example, in some embodiments, the inner volume can be about 0.0625 cubic inches (in$^3$). In other embodiments, the inner volume of the gas container 2410 can be less than about 0.0625 in$^3$ or greater than about 0.0625 in$^3$. In some embodiments, the gas container 2410 can contain and/or store the pressurized gas (e.g., prior to actuation of the gas container 2410) at any suitable pressure, such as a pressure of about 900 pounds per square inch (psi), about 1000 psi, or about 1100 psi. More specifically, in this embodiment, the gas container 2410 can store the pressurized gas at about 1100 psi at a temperature of about 70 degrees Fahrenheit.

As described above, the arrangement of the housing 2100 can be such that portions thereof define a substantially sealed fluid flow path through which gas can flow from the gas container 2410 to a portion of the medicament cavity 2139. The pressure within the portion of the housing 2100 defining the fluid flow path is substantially equal to atmospheric pressure (e.g., about 14.7 psi) prior to the actuation of the gas container 2410. In addition, the fluid flow path defined by the housing 2100 can have a volume that is much greater than the volume defined by the gas container 2410. For example, in this embodiment, the volume of the fluid flow path can be about 0.5 in$^3$, prior to the actuation of the gas container 2410. Thus, when the gas container 2410 is transitioned to an actuated state or the like (e.g., when the frangible seal 2413 is transitioned to its second, open configuration), the compressed gas flows from the gas container 2410 having a volume of about 0.0625 in$^3$ and a pressure of about 1100 psi into the volume (e.g., the fluid flow path) defined by the portion of the housing 2100 having the larger volume of about 0.5 in$^3$ and the lower pressure of about one atmosphere (e.g., about 14.7 psi). Thus, the gas expands as it enters the substantially sealed fluid flow path defined by the portion of the housing 2100. The expansion of the gas, in turn, increases the pressure within the fluid flow path defined by the portion of the housing 2100 and as a result, exerts a force on the movable member 2330 to move the movable member 2330 within the medicament cavity 2139 from a first, proximal position to a second, distal position, as described in further detail herein.

As shown in FIGS. 13-16, the base 2510 of the system actuation assembly 2500 includes the base connection knobs 2518 and has a proximal surface 2511 and a distal surface 2523. The base connection knobs 2518 engage the base retention recesses 2134A, 2134B in a way that allows proximal movement of the base 2510 but limits distal movement of the base 2510, as described above. The distal surface 2523 is configured to be placed in contact with a patient to actuate the delivery device 2000. The proximal surface 2511 of the base 2510 includes an electronics actuator 2520, guide members 2517 and protrusions 2515. The electronics actuator 2520 is configured to engage a portion of the electronic circuit system 2900, as described in further detail herein. The guide members 2517 of the base 2510 engage and/or slide within the base rail grooves 2114 of the housing 2100, as described above. The protrusions 2515 of the base 2510 engage the tapered surfaces 2557 of the extensions 2553 of the release member 2550 when the base 2510 is moved in a proximal direction relative to the housing 2100 and/or the release member 2550. By way of example, when the safety lock 2700 is removed and the base 2510 is moved in a proximal direction with respect to the housing 2100, the protrusions 2515 of the base 2510 are placed in contact with a bifurcated portion of the release member 2550 in such a way that each side is brought closer to the other, thereby actuating the delivery device 2300, as described in further detail herein.

Figure 15:
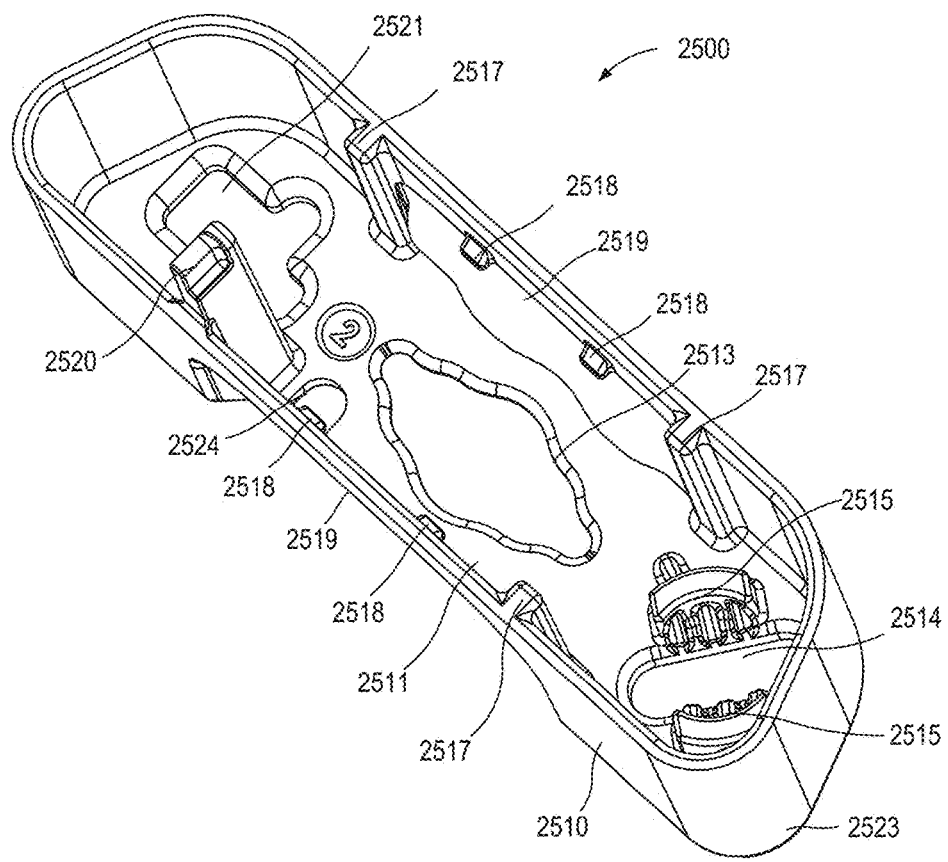
FIGS. 15 and 16 are a top perspective view and a front view, respectively, of a base included in the system actuation assembly illustrated in FIG. 13.
Figure 16:
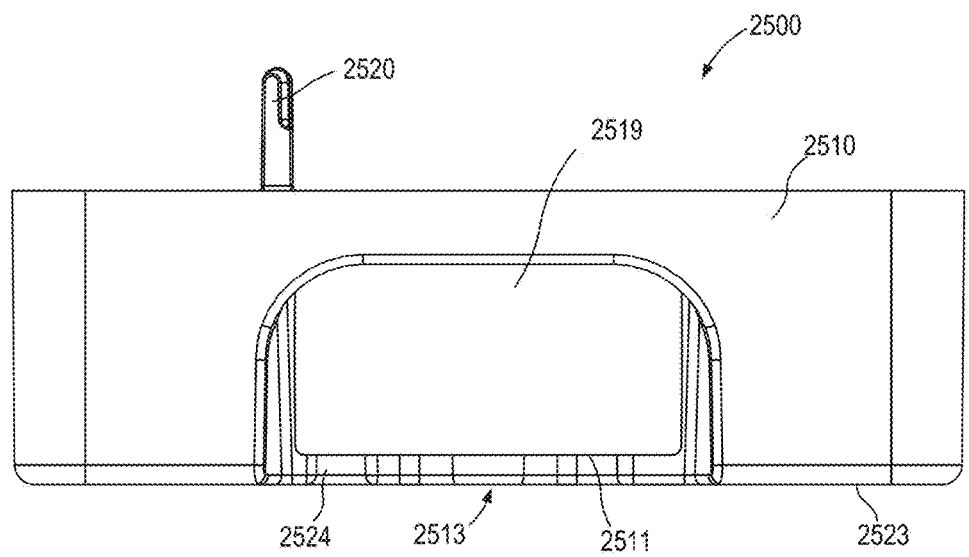

The base 2510 defines a needle aperture 2513, a safety lock protrusion aperture 2514, a battery isolation protrusion aperture 2521, a safety lock actuator opening 2524, and pull-tab openings 2519 (see e.g., FIGS. 14-16). As described in further detail herein, the needle aperture 2513 receives the needle 2360 when the delivery device 2000 is actuated; the safety lock protrusion aperture 2514 receives a safety lock protrusion 2702 of the safety lock 2700 when the safety lock 2700 is coupled to the housing 2100 and/or the base 2510 (see e.g., FIG. 13); the battery isolation protrusion aperture 2521 receives a battery isolation protrusion 2197 of the cover 2190 and a stopper 2727 of the safety lock 2700; the safety lock actuator opening 2524 receives a safety lock actuator 2724 of the safety lock 2700; and the pull-tab openings 2519 receive pull-tabs 2710 of the safety lock 2700.

Figure 17:
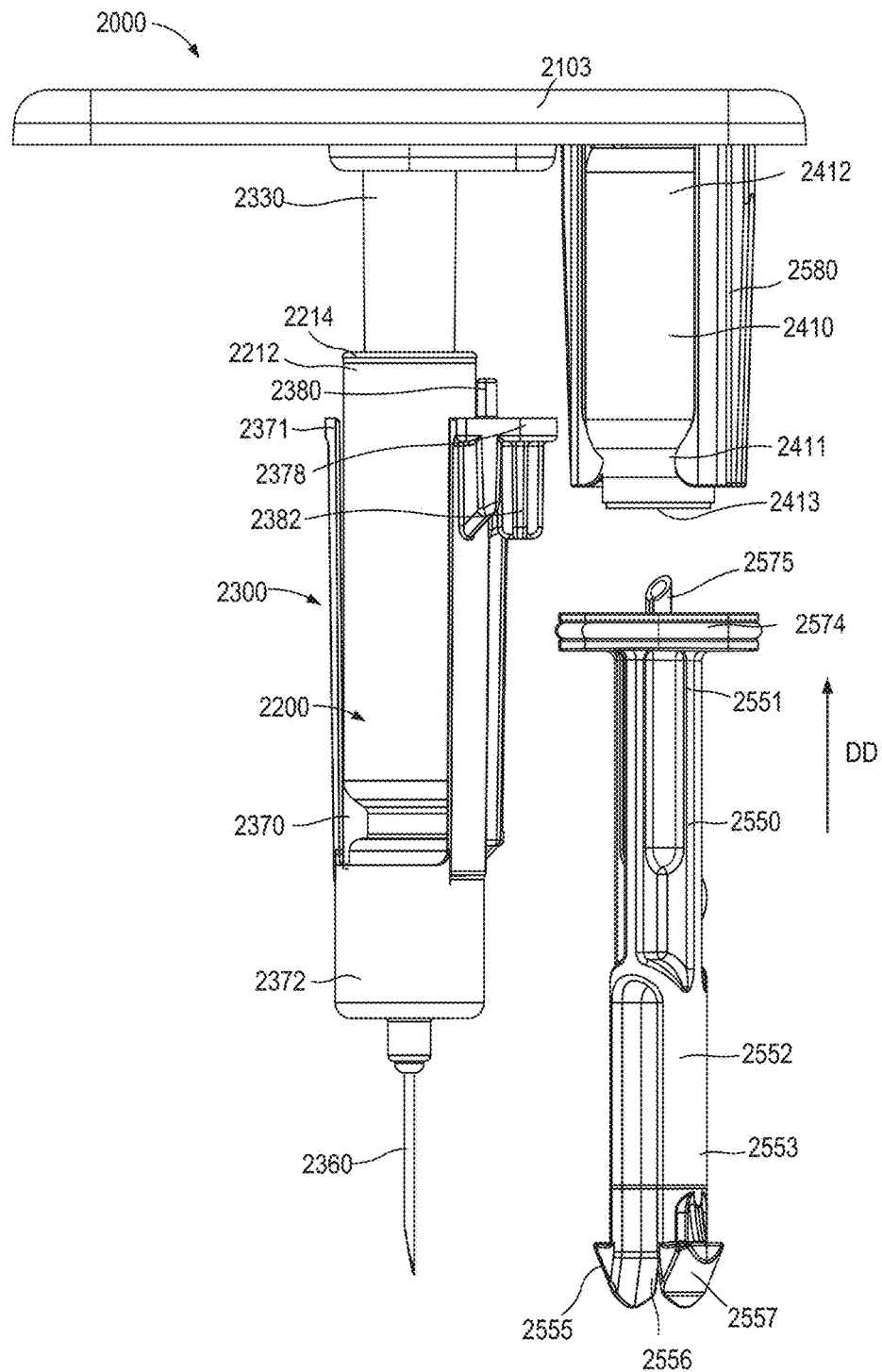
FIG. 17 is a front view of a portion of the medicament delivery device of FIG. 4.

FIG. 17 shows certain components of the system actuation assembly 2500, the medicament delivery mechanism 2300, and the medicament container 2200 without the base 2510 and the spring 2576 so that the release member 2550 can be more clearly shown. The release member 2550 is movably disposed within the distal end portion 2153 of the gas cavity 2151. The release member 2550 has the proximal end portion 2551 and a distal end portion 2552. The proximal end portion 2551 includes a seal member 2574 and a puncturer 2575. The release member 2550 is disposed within the gas cavity 2151 in such a manner that the seal member 2574 engages an inner surface of the housing 2100 that defines at least a portion of the gas cavity 2151 (e.g., the sidewall 2155 and/or any other wall of the housing 2100 defining the gas cavity 2151). More specifically, the seal member 2574 is in contact with the inner surface of the housing 2100 that defines the gas cavity 2151 to form and/or define a substantially fluid tight seal therebetween. Thus, the proximal end portion 2152 of the gas cavity 2151 is fluidically isolated from the distal end portion 2153 of the gas cavity 2151 via the fluidic seal defined between the inner surface of the housing 2100 and the seal member 2574.

The puncturer 2575 of the proximal end portion 2551 of the release member 2550 is configured to contact and puncture the frangible seal 2413 on the gas container 2410 when the release member 2550 moves proximally within the gas cavity 2151, as shown by the arrow DD in FIG. 17. In this manner, when gas is released from the gas container 2410, the seal member 2574 substantially prevents the gas contained in the proximal end portion 2152 of the gas cavity 2151 from entering the distal end portion 2153 of the gas cavity 2151. As described above and in further detail herein, a pressure within the gas cavity 2151 is lower than the pressure within the gas container 2410, prior to the frangible seal 2413 being punctured, and a volume defined by at least a portion of the gas cavity 2151 is larger than the volume defined by the gas container 2410. Thus, upon puncturing the frangible seal 2413, the gas escapes the gas container 2410 and expands within the gas cavity 2151, thereby exerting a force on the release member 2550. In some instances, the force exerted on the release member 2550 can be sufficient to move the release member 2550 in the distal direction (e.g., opposite the arrow DD in FIG. 17), which in turn, compresses the spring 2576 disposed about a portion of the release member 2550 (see e.g., FIGS. 13 and 14). In some such instances, the force exerted by the expansion of the gas can be sufficient to compress the spring 2576 to a substantially solid configuration (e.g., completely compressed). As such, the spring 2576 and the release member 2550 can act, for example, as an accumulator or the like based at least in part on a force exerted by the expansion of the gas as it leaves the gas container 2410, as described in further detail herein.

Figure 18:
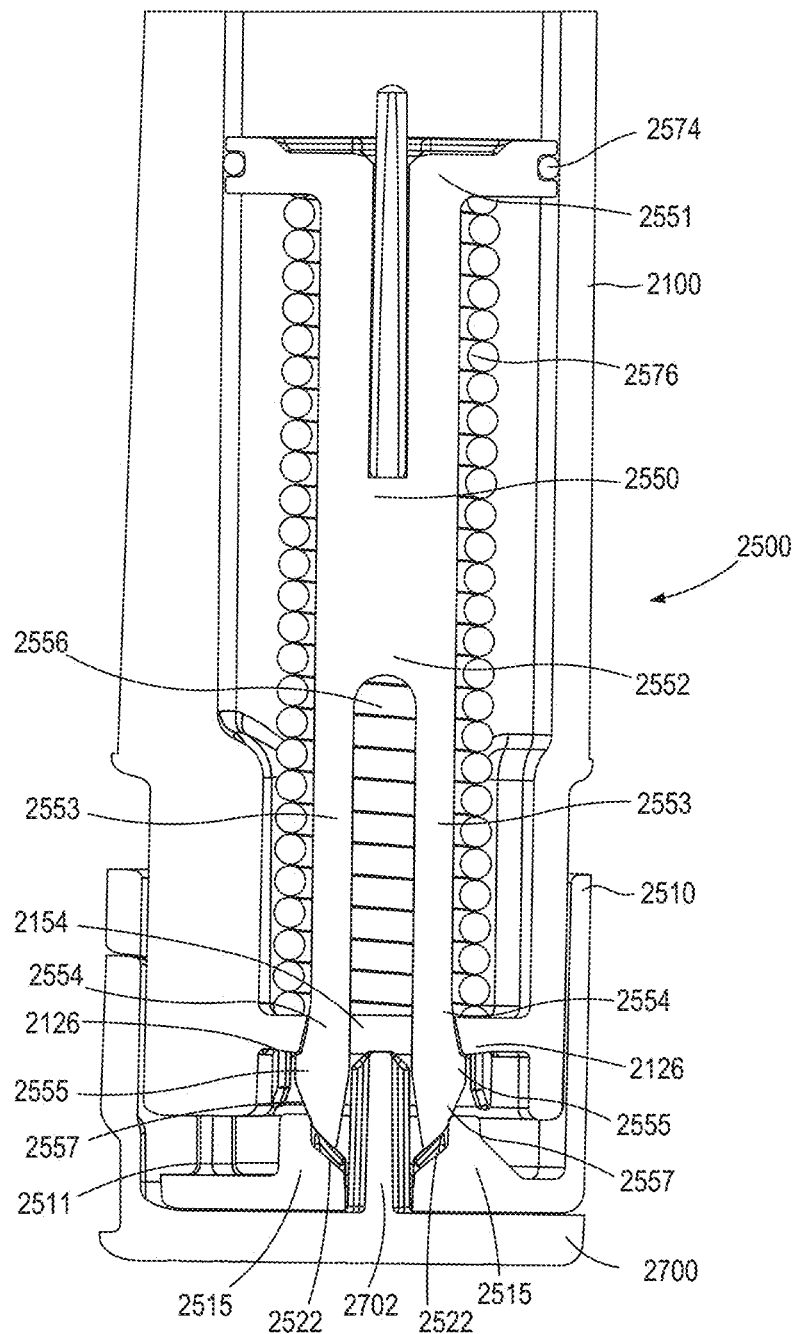
FIG. 18 is an enlarged cross-sectional view of a portion of the medicament delivery device illustrated in FIG. 4, taken along the line $X_2$-$X_2$ in FIG. 9.

The distal end portion 2552 of the release member 2550 includes extensions 2553. As described above, the extensions 2553 can form, for example, a bifurcated portion of the release member 2550. Each extension 2553 includes a projection 2555 with a tapered surface 2557 and an engagement surface 2554. Further, the extensions 2553 define an opening 2556 therebetween. The projections 2555 are configured to extend through the release member aperture 2154 of the housing 2100 in such a manner that the engagement surfaces 2554 are placed in contact the release member contact surface 2126 of the housing 2100, as shown in FIG. 18. In this manner, the engagement surfaces 2554 of the projections 2555 limit proximal movement of the release member 2550 when the engagement surfaces 2554 are in contact with the release member contact surface 2126 of the housing 2100.

The opening 2556 defined by the extensions 2553 receives the safety lock protrusion 2702 of the safety lock 2700 (see e.g., FIGS. 18 and 40-43) when the safety lock 2700 is coupled to the housing 2100 and/or the base 2510. With the safety lock protrusion 2702 disposed between the extensions 2553, radial (or inward) movement of the extensions 2553 towards each other is limited and/or substantially prevented. Said another way, the safety lock protrusion 2702 is configured to ensure that the extensions 2553 remain spaced apart and the engagement surfaces 2554 of the projections 2555 remain in contact with the release member contact surface 2126 of the housing 2100. Moreover, as shown in FIG. 18, the system actuation assembly 2500 and the housing 2100 is such that the spring 2576 is disposed between the proximal end portion 2551 of the release member 2550 (e.g., a flange, a surface, and/or the like included in the proximal end portion 2551) and a surface of the housing 2100 that defines a distal surface of the gas cavity 2151. Thus, with the engagement surface 2554 of each extension 2553 in contact with the release member contact surface 2126 of the housing 2100, the spring 2576 is maintained in a configuration having, for example, a relatively high potential energy (e.g., in a compressed configuration). In this manner, the engagement surface 2554 of each extension 2553 contacts the release member contact surface 2126 and in turn, exerts a reaction force in response to a force exerted by the spring 2576 associated with the configuration of relatively high potential energy. As such, the puncturer 2575 can be at least temporarily retained in a position within the gas cavity 2151 that is spaced apart from the gas container 2410. In some embodiments, for example, the release member 2550 and/or the extensions 2553 can be constructed from any suitable material configured to withstand deformation that may occur when exposed to a load over an extended period of time (e.g., exerted by and/or otherwise associated with the spring 2576 in the configuration having relatively high potential energy). In some embodiments, for example, the release member 2550 and/or the extensions 2553 can be constructed from and/or include a surface constructed from brass or the like. Thus, the release member 2550 and/or the extensions 2553 can have a stiffness and/or hardness sufficient to withstand fatigue associated with the force exerted by the spring 2576.

The tapered surfaces 2557 of the projections 2555 are configured to contact tapered surfaces 2522 of contact protrusions 2515 extending from the proximal surface 2511 of the base 2510, as shown in FIG. 18. Accordingly, when the base 2510 is moved proximally relative to the housing 2100, the extensions 2553 are moved together by the tapered surfaces 2522 of the contact protrusions 2515. The inward movement of the extensions 2553 causes the release member 2550 to disengage the release member contact surface 2126 of the housing 2100, thereby allowing the release member 2550 to be moved proximally along its longitudinal axis. More specifically, by disengaging the engagement surface 2554 of the extensions 2553 from the release member contact surface 2126, the reaction force exerted in response to the force exerted by the spring 2576 is removed and thus, the spring 2576 converts the potential energy into kinetic energy, resulting in expansion of the spring 2576.

Figure 20:
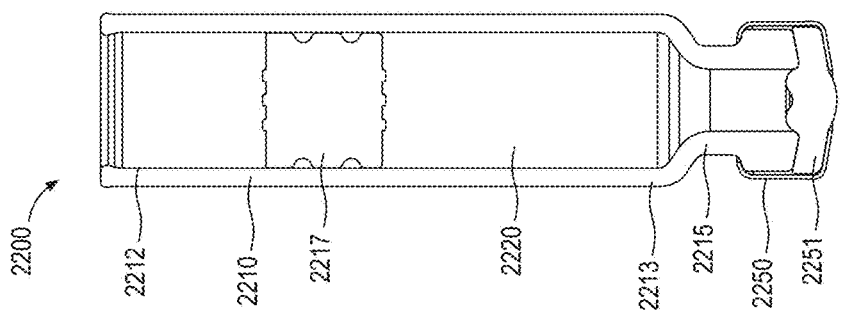
FIG. 20 is a cross-sectional view of the medicament container of FIG. 19, taken along the line $X_3$-$X_3$.
Figure 19:
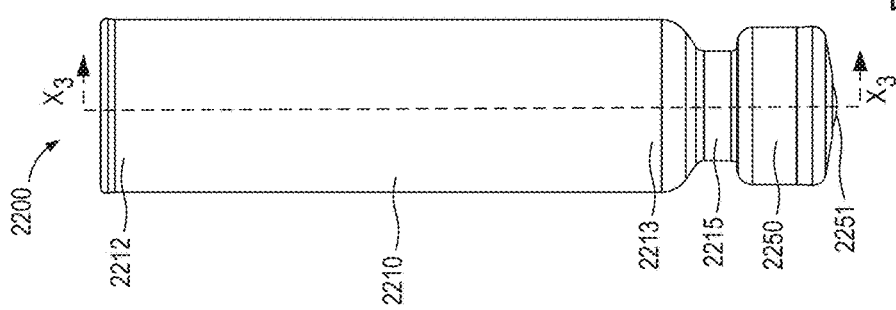
FIG. 19 is a front view of the medicament container illustrated in FIG. 13.
Figure 21:
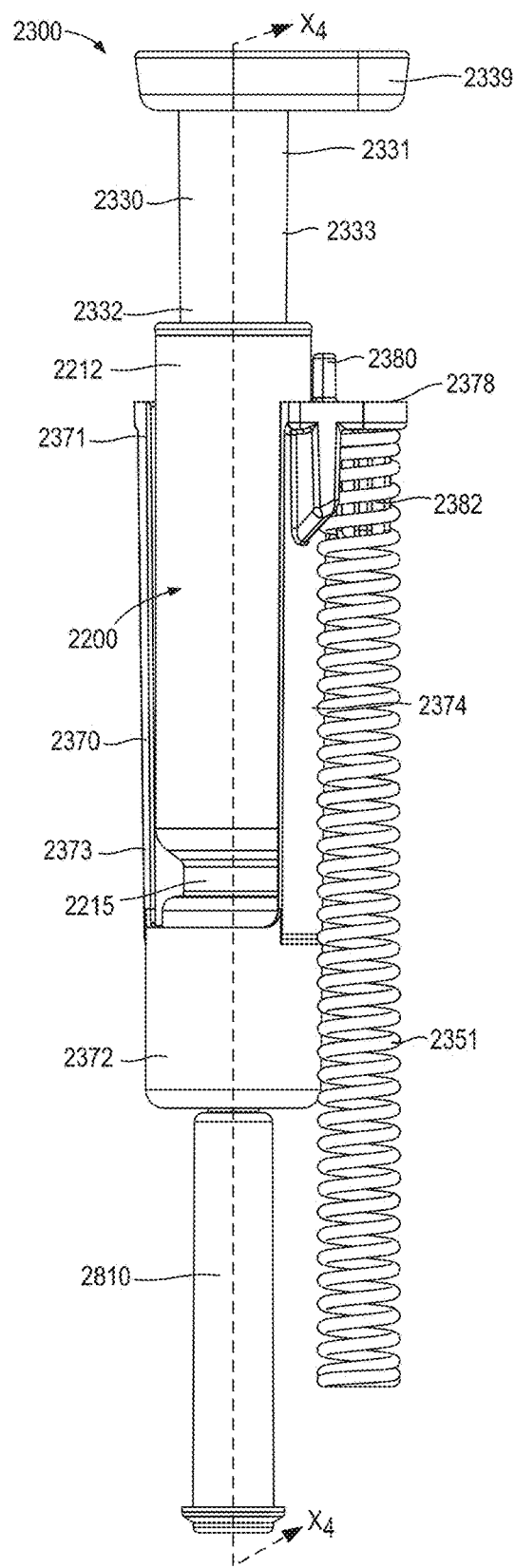
FIG. 21 is a front view of the medicament container and the medicament delivery mechanism of FIG. 13.

As shown in FIGS. 19-21, the medicament container 2200 of the delivery device 2000 has a body 2210 with a proximal end portion 2212 and a distal end portion 2213. The body 2210 defines a volume that contains (i.e., is filled with or partially filled with) a naloxone composition 2220 such as those described herein. The distal end portion 2213 of the medicament container 2200 includes a neck 2215, a cap 2250, and a seal 2251. The cap 2250, which can be, for example, an 8-I crimp seal or the like, is fixedly coupled about a portion of the neck 2215 and includes a seal 2251. The cap 2250 is disposed about the neck 2215 of the medicament container 2200 such that the seal 2251 and, for example, a distal surface of the medicament container 2200 form a substantially fluid tight seal. As such, the seal 2251 can limit and/or substantially prevent leaching of a portion of the naloxone composition 2200 through the distal end portion 2213 of the medicament container 2200. Moreover, the cap 2250 can be crimped, molded, and/or otherwise disposed about the medicament container 2200 during a manufacturing process with a force that is sufficient to maintain the cap 2250 about the portion of the medicament container 2200 regardless of an increase in pressure within the medicament container 2200 in response to an injection event. Said another way, the cap 2250 can be fixedly coupled to the portion of the medicament container 2200 and can be maintained thereabout with sufficient force (e.g., a friction force, a force resulting from an internal stress with the cap 2250 and/or medicament container 2200, and/or any other suitable force) to resist a decoupling of the cap 2250 from the portion of the medicament container 2200 as the pressure therein is increased during an injection event.

With the seal 2251 disposed between an inner surface of the cap 2250 and, for example, a distal surface of the medicament container 2200 (see e.g., FIG. 20), a portion of the force that couples the cap 2250 to the medicament container 2200 deforms a portion of the seal 2251. Thus, in some embodiments, the seal 2251 can have a first portion (e.g., an annular portion substantially aligned with the distal surface of the medicament container 2200) having a first thickness and a second portion (e.g., a portion substantially aligned with an opening defined by the distal surface of the medicament container 2200) having a second thickness that is thicker than the first thickness, as shown in FIG. 20. As described in further detail herein, a distal portion of the needle 2360 can have a length that is sufficient to puncture the seal 2251 (e.g., the second portion of the seal 2251) in such a manner that a lumen defined by the needle 2360 is substantially unobstructed by the seal 2251 and placed in fluid communication with the naloxone composition 2220.

The proximal end portion 2212 of the medicament container 2200 is substantially open to receive a portion of the movable member 2330. Similarly, during a manufacturing process and/or the like, an elastomeric member 2217 (also referred to here as "plunger") can be inserted through the open proximal end portion 2212 to be movably disposed within the medicament container 2200. For example, the plunger 2217 can be disposed in the medicament container 2200 such that the naloxone composition is disposed between a distal surface of the plunger 2217 and a proximal surface of the seal 2251 (described above). Thus, when the medicament container 2200 is assembled in the delivery device 1000, a force can be exerted on the movable member 2330, which in turn, exerts a force on the plunger 2217 to move the plunger 2217 within the medicament container 2200, as described in further detail herein.

The medicament container 2200 can have any suitable size (e.g., length and/or diameter) and can define an inner region (e.g., between the distal surface of the plunger 2217 disposed therein and the proximal surface of the seal 2251) having any suitable volume, within which a volume of the naloxone composition 2220 is disposed. Moreover, the medicament container 2200 and the movable member 2330 can be collectively configured such that the movable member 2330 travels a desired distance within the medicament container 2200 (i.e., the "stroke") during an injection event. In this manner, the medicament container 2200 can provide, for example, a desired fill volume and/or a desired delivery volume of the naloxone composition 2220. In some embodiments, for example, the size of the medicament container 2200 and the length of the movable member 2330 can be such that the fill volume of the naloxone composition 2220 is approximately between about 0.3 milliliters (mL) and about 2 mL. In other embodiments, the fill volume of the naloxone composition 2220 can be about 0.4 mL, about 0.5 mL, about 0.6 mL, about 0.7 mL, about 0.8 mL, about 0.9 mL, about 1 mL, about 1.25 mL, about 1.5 mL, about 1.75 mL, about 2.0 mL, or any fraction therebetween. In at least one embodiment, the fill volume of the naloxone composition 2220 can be about 0.34 mL. In other embodiments, the fill volume of the naloxone composition 2220 can be about 0.41 mL. In still other embodiments, the fill volume of the naloxone composition 2220 can be about 0.76 mL. In other embodiments, the fill volume of the naloxone composition 2220 can be less than about 0.3 mL or greater than about 2.0 mL.

In some embodiments, the arrangement of the movable member 2330 and/or the medicament container 2200 can be such that the delivered volume of the naloxone composition 2220 after an injection event (i.e., a volumetric amount delivered to a patient) is less than the fill volume of the naloxone composition 2220. For example, in some embodiments, the delivered volume of the naloxone composition 2220 can be between about 0.3 mL and about 2.0 mL. In other embodiments, the delivered volume of the naloxone composition 2220 can be about 0.4 mL, about 0.5 mL, about 0.6 mL, about 0.7 mL, about 0.8 mL, about 0.9 mL, about 1 mL, about 1.25 mL, about 1.5 mL, about 1.75 mL, about 2.0 mL, or any fraction therebetween. In some embodiments, the delivered volume of the naloxone composition 2220 can be between about 0.34 mL and about 0.46 mL. In at least one embodiment, the delivered volume of the naloxone composition 2220 can be about 0.34 mL. In other embodiments, the delivered volume of the naloxone composition 2220 can be about 0.4 mL. In still other embodiments, the delivered volume of the naloxone composition 2220 can be less than about 0.3 mL or greater than about 2.0 mL. In at least one embodiment, the fill volume of the naloxone composition 2220 can be about 0.58 mL and the delivered volume of the naloxone composition 2220 can be about 0.4 mL. In some embodiments, the medicament container 2200 and/or the movable member 2330 can be arranged such that a ratio of a delivered volume of the naloxone composition 2220 to a fill volume of the naloxone composition 2220 is about 0.1, about 0.2, about 0.3, about 0.4, about 0.5, about 0.6, about 0.7, about 0.8, about 0.9, or about 1.0.

Moreover, the length of the medicament container 2200 and the length of the movable member 2330 can be configured such that the medicament delivery mechanism 2300 can fit in the same housing 2100 regardless of the fill volume, the delivery volume and/or the ratio of the fill volume to the delivery volume. In this manner, the same housing and production tooling can be used to produce devices having various volumes of the naloxone composition. For example, in a first embodiment (e.g., having a fill volume to delivery volume ratio of 0.4), the medicament container has a first length and the movable member has a first length. In a second embodiment (e.g., having a fill volume to delivery volume ratio of 0.6), the medicament container has a second length shorter than the first length, and the movable member has a second length longer than the first length. In this manner, the stroke of the device of the second embodiment is longer than that of the device of the first embodiment, thereby allowing a greater volume of the naloxone composition 2220 to be delivered. The medicament container of the device of the second embodiment, however, is shorter than the medicament container of the device of the first embodiment, thereby allowing the components of both embodiments to be disposed within the same housing and/or a housing having the same length.

The naloxone composition 2220 contained within the medicament container 2200 can be any of the naloxone compositions described herein, and in U.S. Pat. No. 8,627,816 entitled "Medicament Delivery Device for Administration of Opioid Antagonists Including Formulations for Naloxone," which is incorporated herein by reference in its entirety. In particular, the naloxone composition 2220 can include at least an effective dosage of naloxone or salts thereof. In some embodiments, the naloxone composition 2220 can include an effective dosage of naloxone or salts thereof, a tonicity-adjusting agent, pH-adjusting agent, a stabilizing agent, and/or the like. The naloxone composition 2220 can be formulated such that the osmolality of the naloxone composition 2220 ranges from about 250-350 mOsm and the pH ranges from about 3-5.

In some embodiments, the naloxone composition 2220 can include any suitable concentration of 4,5-epoxy-3,14-dihydroxy-17-(2-propenyl) morphinan-6-one. In some embodiments, for example, the naloxone composition 2220 has a concentration of 4,5-epoxy-3,14-dihydroxy-17-(2-propenyl)morphinan-6-one between approximately 0.01 milligrams per milliliter (mg/mL) and approximately 50 mg/mL. In other embodiments, the naloxone composition 2220 has a concentration of 4,5-epoxy-3,14-dihydroxy-17-(2-propenyl)morphinan-6-one between approximately 0.05 mg/mL and approximately 2 mg/mL.

In some embodiments, the naloxone composition 2220 has a dose of 4,5-epoxy-3,14-dihydroxy-17-(2-propenyl) morphinan-6-one between approximately about 0.2 mg and about 10 mg. In other embodiments, the amount of the dose can be about 0.4 mg, about 0.5 mg, about 0.6 mg, about 0.7 mg, about 0.8 mg, about 0.9 mg, about 1 mg, about 1.25 mg, about 1.5 mg, about 1.75 mg, about 2.0 mg, about 3.0 mg, about 4.0 mg, about 5.0 mg, about 6.0 mg, about 7.0 mg, about 8.0 mg, about 9.0 mg, about 10.0 mg, or any fraction therebetween. In at least one embodiment, the amount of the dose can be about 0.4 mg. In other embodiments, the amount of the dose can be less than about 0.2 mg or greater than about 10.0 mg.

The tonicity-adjusting agent can be any of the tonicity-adjusting agents described herein, and can be included within the naloxone composition 2220 in any suitable amount and/or concentration. For example, in some embodiments, the tonicity-adjusting agent includes at least one of dextrose, glycerin, mannitol, potassium chloride or sodium chloride. In other embodiments, the tonicity-adjusting agent includes sodium chloride in an amount such that a concentration of sodium chloride is between approximately 0.1 mg/mL and approximately 20 mg/mL.

The pH-adjusting agent can be any of the pH-adjusting agents described herein, and can be included within the naloxone composition 2220 in any suitable amount and/or concentration. For example, in some embodiments, the pH-adjusting agent includes at least one of hydrochloric acid, citric acid, citrate salts, acetic acid, acetate salts, phosphoric acid or phosphate salts. In other embodiments, the pH-adjusting agent includes a dilute hydrochloric acid.

The elastomeric member 2217 can be of any design or formulation suitable for contact with the naloxone composition 2220. For example, the elastomeric member 2217 can be formulated to minimize any reduction in the efficacy of the naloxone composition 2220 that may result from contact (either direct or indirect) between the elastomeric member 2217 and the naloxone composition 2220. For example, in some embodiments, the elastomeric member 2217 can be formulated to minimize any leaching or out-gassing of compositions that may have an undesired effect on the naloxone composition 2220. In other embodiments, the elastomeric member 2217 can be formulated to maintain its chemical stability, flexibility and/or sealing properties when in contact (either direct or indirect) with naloxone over a long period of time (e.g., for up to six months, one year, two years, five years or longer).

In some embodiments, the elastomeric member 2217 can be formulated to include a polymer and a curing agent. In such embodiments, the polymer can include at least one of bromobutyl or chlorobutyl. In such embodiments, the curing agent can include at least one of sulfur, zinc or magnesium.

In some embodiments, the elastomeric member 2217 can be constructed from multiple different materials. For example, in some embodiments, at least a portion of the elastomeric member 2217 can be coated. Such coatings can include, for example, polydimethylsiloxane. In some embodiments, at least a portion of the elastomeric member 2217 can be coated with polydimethylsiloxane in an amount of between approximately 0.02 mg/cm2 and approximately 0.80 mg/cm2. In other embodiments, the elastomeric member 2217 can include multiple materials in any suitable manner, blend or composition. For example, in some embodiments, at least a portion of the elastomeric member 2217 can include polydimethylsiloxane in any suitable amount (e.g., in an amount of between approximately 0.02 mg/cm2 and approximately 0.80 mg/cm2.)

Figure 22:
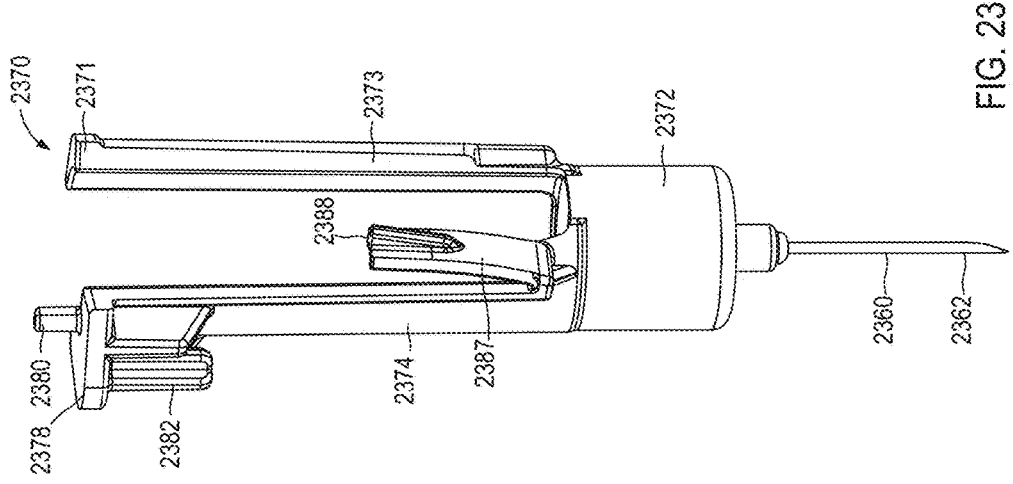
FIGS. 22 and 23 are perspective views of a carrier included in the medicament delivery mechanism illustrated in FIG. 13.
Figure 25:
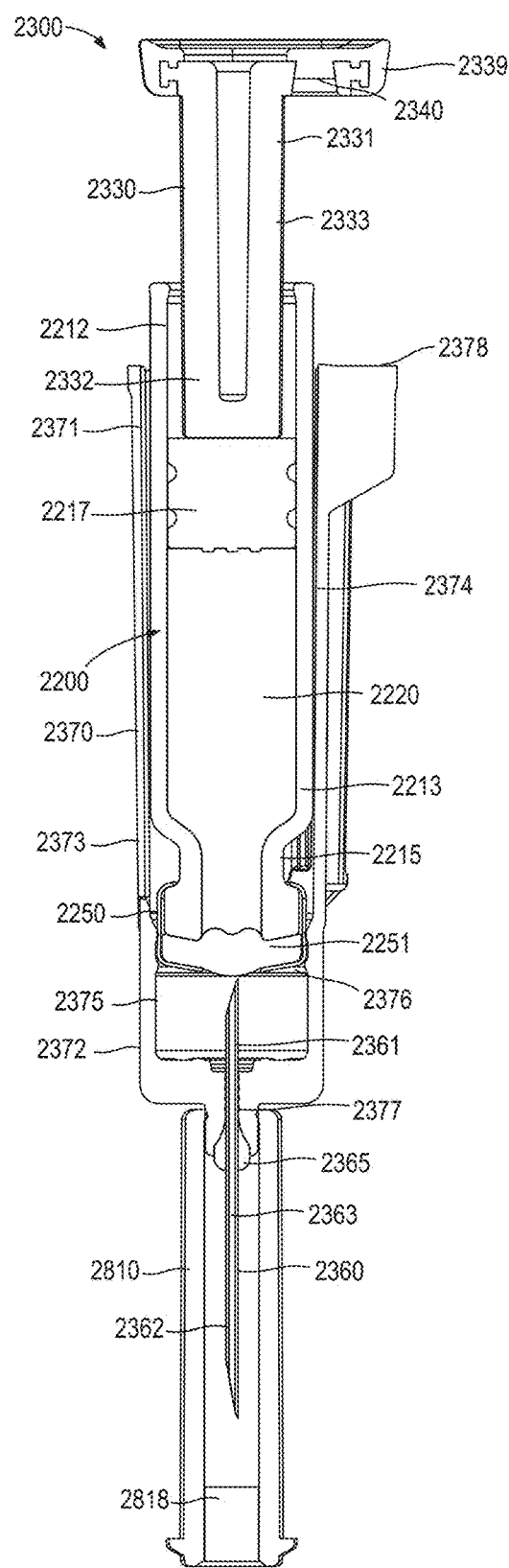
FIG. 25 is a cross-sectional view of the medicament container and the medicament delivery mechanism of FIG. 21, taken along the line $X_5$-$X_5$ in FIG. 22.
Figure 26:
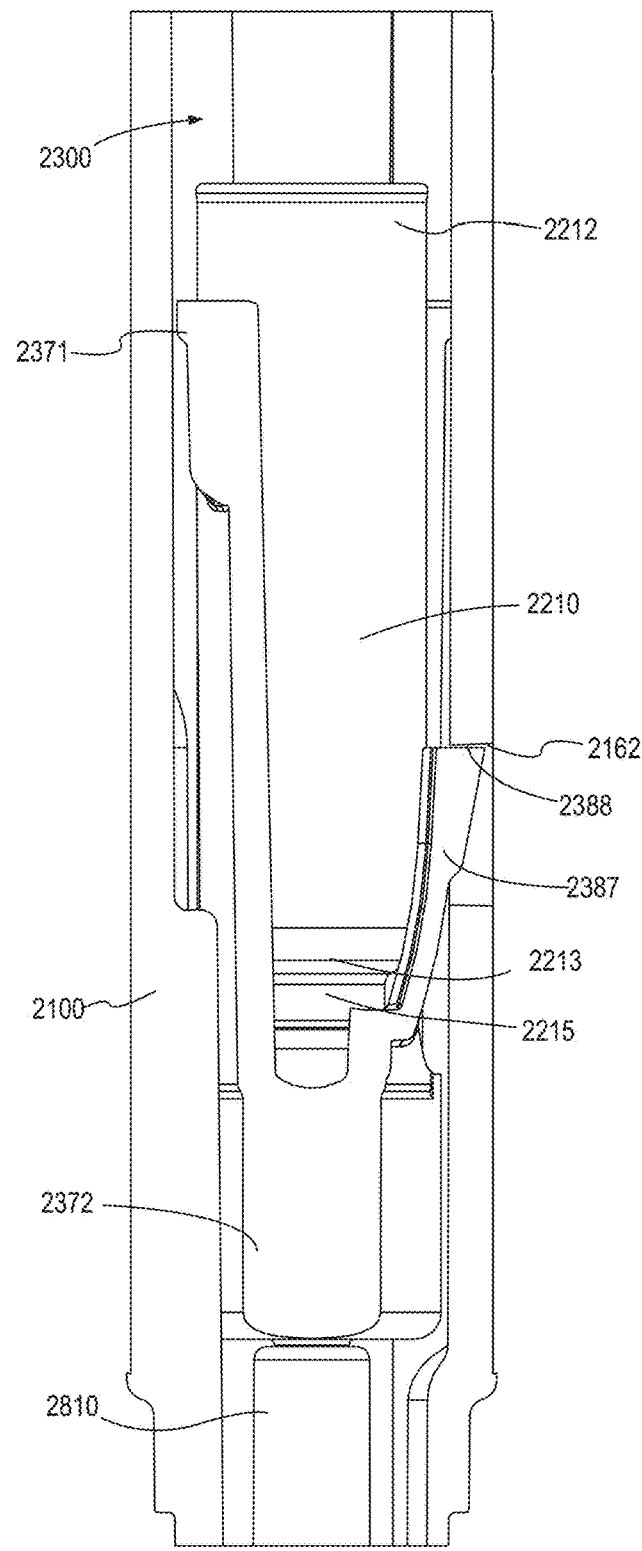
FIG. 26 is an enlarged side cross-sectional view of a portion of the medicament delivery device illustrated in FIG. 4, taken along the line $X_1$-$X_1$ in FIG. 7.

The medicament delivery mechanism 2300 of the delivery device 2000 includes the carrier 2370, the movable member 2330, and a retraction spring 2351. As described above, the carrier 2370 and the movable member 2330 are each movably disposed within the medicament cavity 2139 of the housing 2100. In addition, the carrier 2370 movably receives at least a portion of the medicament container 2200 in such a way that allows the medicament container 2200 to move contemporaneously with the carrier 2370 or relative to the carrier 2370. As shown in FIGS. 22 and 25, the movable member 2330 includes a piston rod 2333, and has a proximal end portion 2331 and a distal end portion 2332. The movable member 2330 can be constructed of a resilient, durable, and/or sealing material or combination of materials, such as a rubber. The distal end portion 2332 of the movable member 2330 is disposed within the proximal end portion 2212 of the medicament container 2200 and in contact with the plunger 2217. As described in further detail herein, the movable member 2330 can be moved within the medicament cavity 2139 to collectively move the carrier 2370, the medicament container 2200, and the plunger 2217; to collectively move the medicament container 2200 and the plunger 2217 relative to the carrier 2370; and to move the plunger 2217 relative to the medicament container 2200.

The proximal end portion 2331 includes a seal member 2339. The seal member 2339 engages the sidewall of the housing 2100 to define a substantially fluidic seal therebetween. Thus, a portion of the medicament cavity 2139 that is disposed on proximal to the seal member 2339 (e.g., a gas chamber) is fluidically isolated from a portion of the medicament cavity 2139 that is disposed on distal to the seal member 2339. Moreover, the portion of the medicament cavity 2139 disposed proximal to the seal member 2339 is in fluid communication with the portion of the gas cavity 2151 that is proximal to the seal member 2574 of the release member 2550 via the gas passageway 2151, as described in detail above. The proximal end portion 2331 and/or the seal member 2339 also includes a gas relief valve 2340 (see e.g., FIG. 25) that can be selectively actuated to allow fluid communication between the portion of the medicament cavity 2139 proximal to the seal member 2339 and the portion the portion of the medicament cavity 2139 distal to the seal member 2339. As described in more detail below, the gas relief valve 2340 allows a gas pressure within the gas chamber to be reduced upon completion of the injection event.

As shown in FIGS. 21-26, the carrier 2370 includes a proximal end portion 2371, a distal end portion 2372, a first side portion 2373, a second side portion 2374, and a locking protrusion (or leg) 2387. The distal end portion 2372 forms a cup or the like (see e.g., FIGS. 24 and 25). That is to say, the distal end portion 2372 can include a substantially annular wall (or set of walls) that extends a distance from a distal surface of the carrier 2370. In this manner, the distal end portion 2372 has an inner surface 2375 that substantially circumscribes a volume configured to receive, for example, the distal end portion 2213 of the medicament container 2200. The inner surface 2375 includes a ribbed portion 2376 that is configured to selectively engage the distal end portion 2213 of the medicament container 2200 (see e.g., FIG. 25). For example, the ribbed portion 2376 of the inner surface 2375 can contact the medicament container 2200 to define and/or form a "snap-fit" connection that can allow the medicament container 2200 to be selectively moved relative to the carrier 2370 between a first position and a second position during an injection event. In the first position (e.g., a proximal position), the carrier 2370 can be moved within the medicament cavity 2139 such that movement of the carrier 2370 within the medicament cavity 2139 results in contemporaneous movement of the medicament container 2200 within the medicament cavity 2139. More specifically, the ribbed portion 2376 is in contact with, for example, a distal surface of the medicament container 2200 in such a manner that at least temporarily retains the medicament container 2200 in a substantially fixed position relative to the carrier 2370. Thus, the carrier 2370 and the medicament container 2200 are moved concurrently.

When the carrier 2370 and the medicament container 2200 are moved to the second position (e.g., a distal position), a force can be exerted on a portion of the carrier 2370 that can limit and/or otherwise substantially prevent further movement (e.g., distal movement) of the carrier 2370 and thus, the carrier 2370 is at least temporarily maintained in its second position. The force, however, is not exerted on the medicament container 2200 and as a result, in the presence of the gas pressure on the movable member 2300, the medicament container 2200 is moved relative to the carrier 2370. As the distal end portion 2213 of the medicament container 2200 moves along the inner surface 2375, the distal end portion 2213 of the medicament container 2200 is, for example, released from the snap-fit, thereby allowing the medicament container 2200 to move relative to the carrier 2370 (e.g., in the distal direction).

Figure 23:
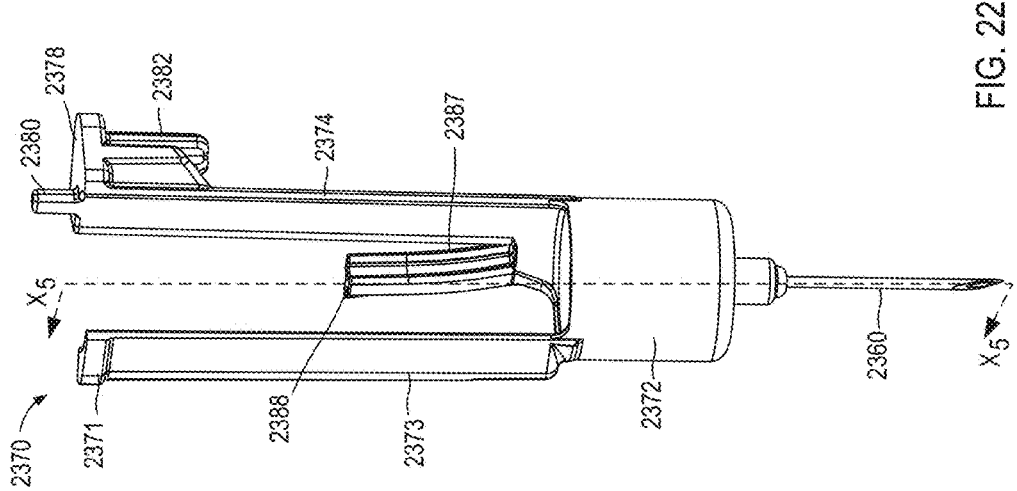
Figure 24:
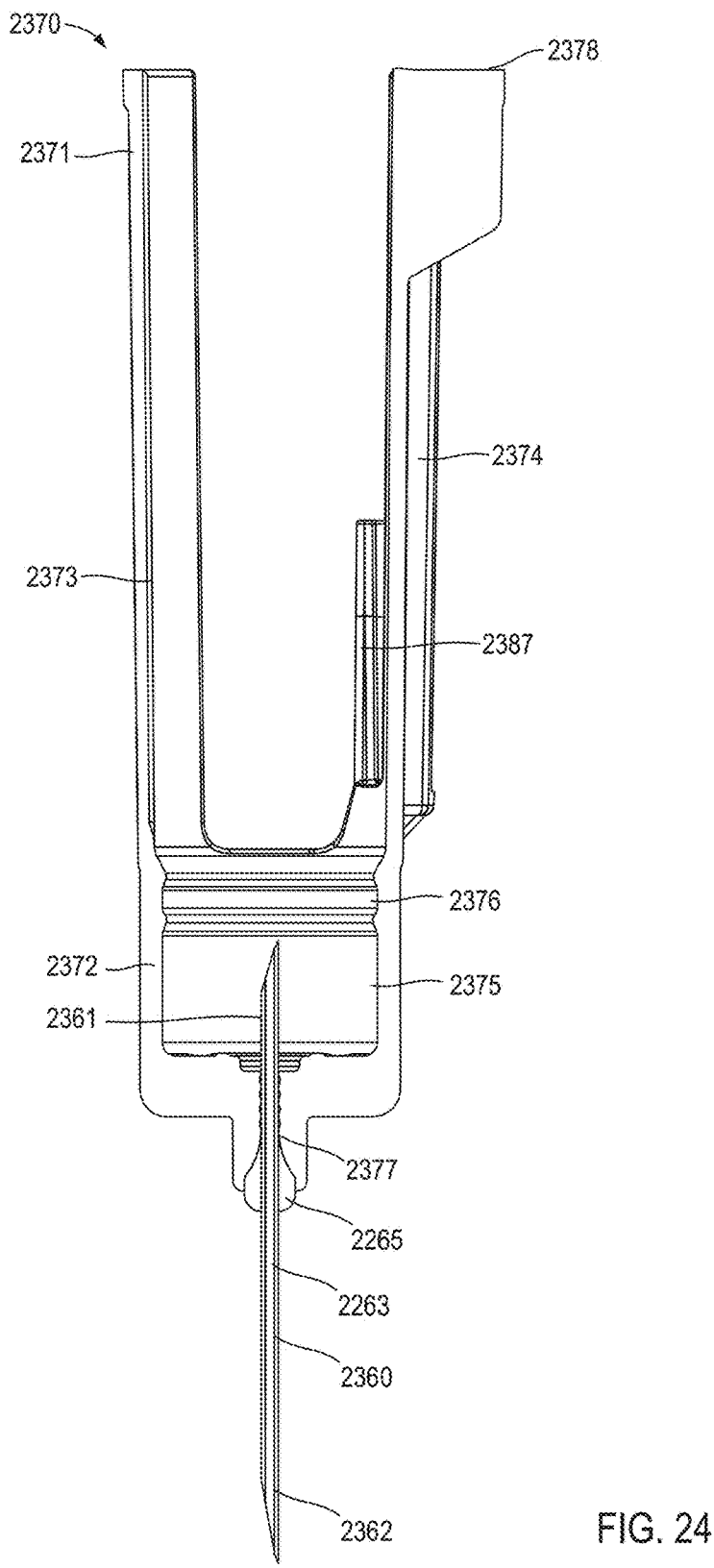
FIG. 24 is a cross-sectional view of the carrier of FIG. 22, taken along the line $X_4$-$X_4$ in FIG. 21.

As shown in FIGS. 22-25, the distal end portion 2372 of the carrier 2370 is coupled to the needle 2360. More specifically, the distal end portion 2372 defines an opening 2377 through which the needle 2360 extends such that a proximal end portion 2361 of the needle 2360 is disposed within the volume that is circumscribed by the annular wall of the distal end portion 2372. In some embodiments, the needle 2360 can be fixedly coupled to the carrier 2370 via an adhesive 2365 or the like, as shown in FIGS. 24 and 25. The arrangement of the carrier 2370, the needle 2360, and the medicament container 2200 can be such that the proximal end portion 2361 of the needle 2360 is spaced apart from the seal 2251 of the medicament container 2200 (see e.g., FIG. 25) when the carrier 2370 and the medicament container 2200 are collectively in the first position (e.g., prior to an injection event). When the medicament container 2200 is moved relative to the carrier 2370 (e.g., when the carrier 2370 is its second position during the injection event), the proximal end portion 2361 of the needle 2360 pierces the seal 2251 such that substantially an entire proximal surface of the needle 2360 is in a proximal position relative to the seal 2251. In this manner, a lumen 2364 of the needle 2360 can be selectively placed in fluid communication with the medicament container 2200 to define a medicament delivery path through which the naloxone composition 2220 can flow. Moreover, the needle 2360 can be any suitable size or gauge (e.g., 18 gauge, 24 gauge, 27 gauge, 32 gauge, etc.) to deliver the naloxone composition 2220 through the lumen 2364 and into the body of the patient with a desired set of pharmacokinetic characteristics, as described in further detail herein.

The first side portion 2373 and the second side portion 2374 of the carrier 2370 extend from the distal end portion 2372 to the proximal end portion 2371. Moreover, the first side portion 2373 and the second side portion 2374 from a bifurcated region of the carrier 2370, as shown in FIGS. 21-23. This arrangement allows at least the distal end portion 2213 of the medicament container 2200 to be disposed within (and/or removed from) the carrier 2370. In some embodiments, the first side portion 2373 and the second side portion 2374 can define a distance therebetween that is slightly smaller than a diameter of the medicament container 2200 and thus, when the medicament container 2200 is disposed within the carrier 2370, the first side portion 2373 and the second side portion 2374 can exert a substantially lateral force on a surface of the medicament container 2200 that is sufficient to maintain the medicament container 2200 within the carrier 2370, while allowing the medicament container 2200 to move relative to the carrier 2370, as described above. The bifurcated arrangement of the carrier 2370 also allows at least a portion of the medicament container 2200 to be visible via the status windows 2130, 2160 of the housing (substantially unobstructed by the carrier 2370).

The proximal end portion 2371 of the carrier 2370 includes a gas valve actuator 2380 and a retraction spring protrusion 2382. More specifically, as shown in FIGS. 21-23, the second side 2374 of the carrier 2370 includes a shoulder 2378 having a proximal surface from which the gas valve actuator 2380 extends, and a distal surface from which the retraction spring protrusion 2382 extends. The gas valve actuator 2380 is configured to engage a gas relief valve 2340 of the movable member 2330 to allow the pressurized gas contained within the gas chamber (i.e., the volume within the medicament cavity 2139 between the proximal end of the housing 2100 and the proximal end of the movable member 2330) to escape when the injection event is complete.

The retraction spring protrusion 2382 extends from the distal surface of the shoulder 2378 to engage the retraction spring 2351. More particularly, a portion of the retraction spring 2351 is disposed about the retraction spring protrusion 2382. In other embodiments, the retraction spring protrusion 2382 can include any suitable features for engaging and/or retaining the retraction spring 2351 (e.g., a recess or the like). In this manner, the retraction spring 2351 can be disposed between the shoulder 2378 of the carrier 2370 and a distal surface of the housing 2100 and can be transitioned from a first configuration having a first potential energy to a second configuration having a second, higher potential energy. Moreover, when the retraction spring 2351 is placed in its second configuration and the gas valve actuator 2380 engages the gas relief valve 2340 of the movable member 2330, a gas pressure within the medicament cavity 2139 can be decreased below a threshold, such that the force exerted by the retraction spring 2351 on the carrier 2370 (e.g., as a result of being placed in its second configuration) is sufficient to move the carrier 2370 in a proximal direction within the housing 2100 (i.e., to retract), as described in further detail herein. In addition, this arrangement results in there being substantially no residual force within the housing, which decreases stress on the components after the injection event.

As described above, the carrier 2370 includes a locking leg 2387 that extends from the distal end portion 2372 towards the proximal end portion 2371. The locking leg 2387 can be a relatively flexible extension or the like that can selectively bend, flex, deform (e.g., elastic deformation or plastic deformation), and/or otherwise reconfigure between a first configuration and a second configuration. For example, as shown in FIGS. 22 and 23, the locking leg 2387 extends from the second side portion 2374 of the carrier 2370 at angle. As such, in some instances, a force can be exerted the locking leg 2387 that can increase or decrease the angle.

The locking leg 2387 includes a protrusion 2388 that is selectively disposed in a retraction lock aperture 2162 defined by a sidewall of the housing 2100 defining a portion of the medicament cavity 2139 (see e.g., FIG. 26) when the carrier 2370 and the medicament container 2200 are in the first (i.e., storage) position. More specifically, the protrusion 2388 is in contact with a surface of the housing 2100 defining and/or otherwise bounding the retraction lock aperture 2162 in the proximal direction. This arrangement limits movement of the carrier 2370 and the medicament container 2200 in the proximal direction. In this manner, the retraction spring 2351 can be preloaded with a desired amount force prior to an injection event (e.g., during a manufacturing process). Thus, when the retraction spring 2351 is in contact with the shoulder 2378 of the carrier 2370 (e.g., disposed about the retraction spring protrusion 2382), a force exerted by the retraction spring 2351 in response to the preload is offset by a reaction force in the opposite direction exerted by the proximal surface of the housing 2100 defining the portion of the retraction lock aperture 2162 on the protrusion 2388 of the locking leg 2387.

In some instances, the arrangement of the medicament container 2200 and/or the movable member 2300 can be such that an amount of preloaded force in the retraction spring 2351 is varied. For example, in some instances, the length of the piston rod 2333 of the movable member 2330 and/or a length of the medicament container 2200 can be increased or decreased based at least in part on a volume of the naloxone composition 2220 disposed in the medicament container 2200 and/or the desired delivery volume. In some embodiments, such a change can result in a change in the initial position of the movable member 2330, the carrier 2370, and/or the medicament container 2200 relative to the housing 2100. This, in turn, can result in a change in the preloaded force in the retraction spring 2351 and/or an increase or decrease in a distance of retraction, a point during an injection event in which the retraction spring 2351 is actuated, and/or the like. Thus, regardless of the amount of preloaded force in the retraction spring 2351 corresponding the arrangement of the medicament delivery mechanism 2300 and the medicament container 2200, the protrusion 2388 of the locking leg 2387 can engage the proximal surface of the housing 2100 to substantially prevent a proximal movement of the medicament delivery mechanism 2300 and/or the medicament container 2200. This arrangement also limits proximal motion of the medicament delivery mechanism 2300 during assembly (e.g., when the needle sheath 2810 is being pressed about the needle 2360).

Figure 34:
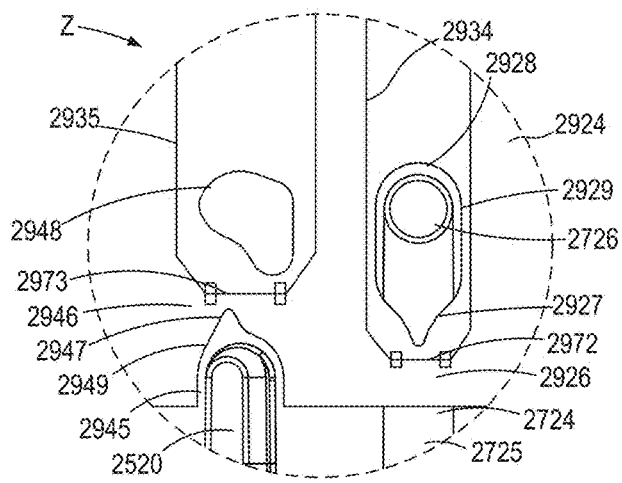
FIGS. 34-36 are front views of a portion of the electronic circuit system labeled as Region Z in FIG. 33 in a first, a second, and a third configuration, respectively.

FIGS. 27-36 show the electronic circuit system 2900 of the delivery device 2000. The electronic circuit system 2900 includes an electronic circuit system housing 2170, a printed circuit board 2922, a battery assembly 2962, an audio output device 2956, two light emitting diodes (LEDs) 2958A, 2958B, and a battery clip 2910. As shown in FIG. 34, the electronic circuit system 2900 is disposed within the electronic circuit system cavity 2137 of the housing 2100. As described herein, the electronic circuit system 2900 is configured to output an electronic output associated with the use of the delivery device 2000.

Figure 29:
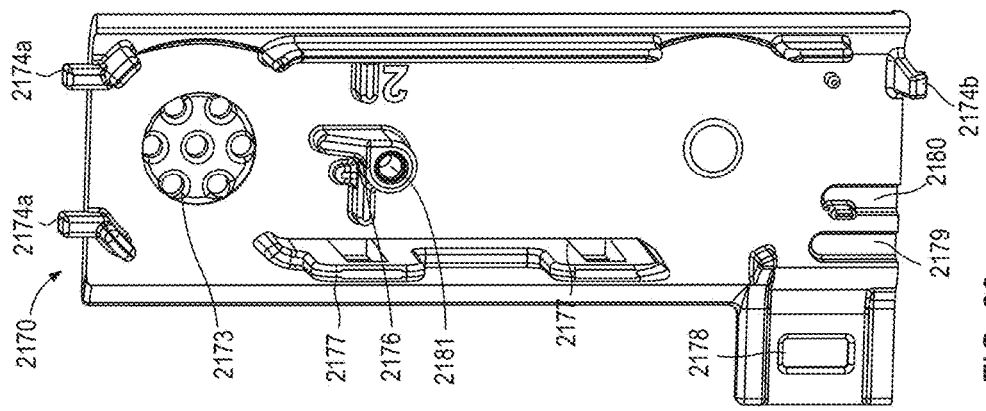
FIG. 29 is a rear perspective view of an electronic circuit system housing of the electronic circuit system illustrated in FIG. 27.
Figure 28:
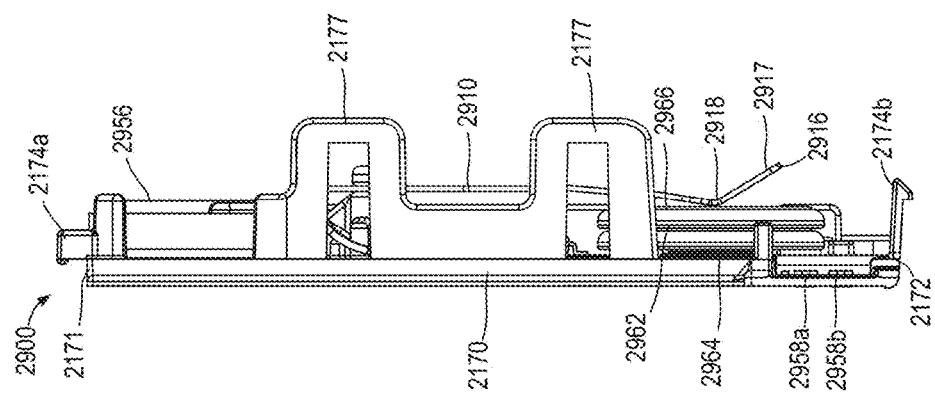
FIGS. 27 and 28 are a front view and a side view, respectively, of a portion of an electronic circuit system of the medicament delivery device illustrated in FIG. 4.
Figure 27:
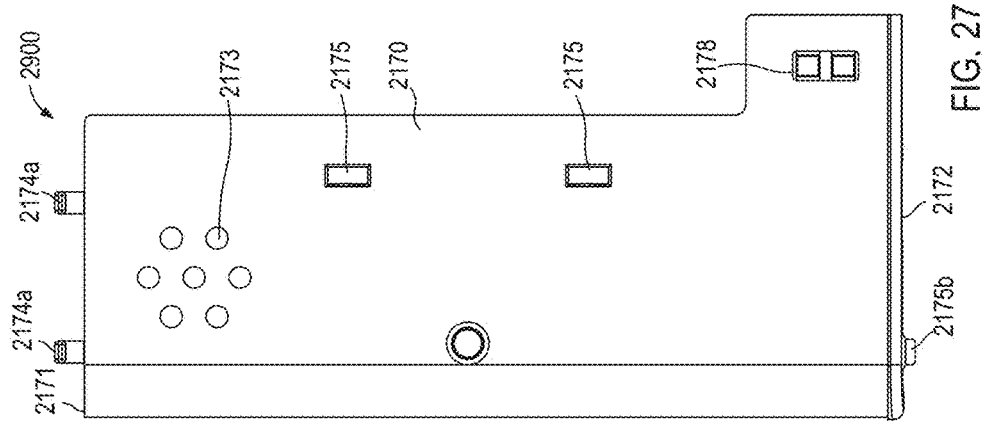
Figure 30:
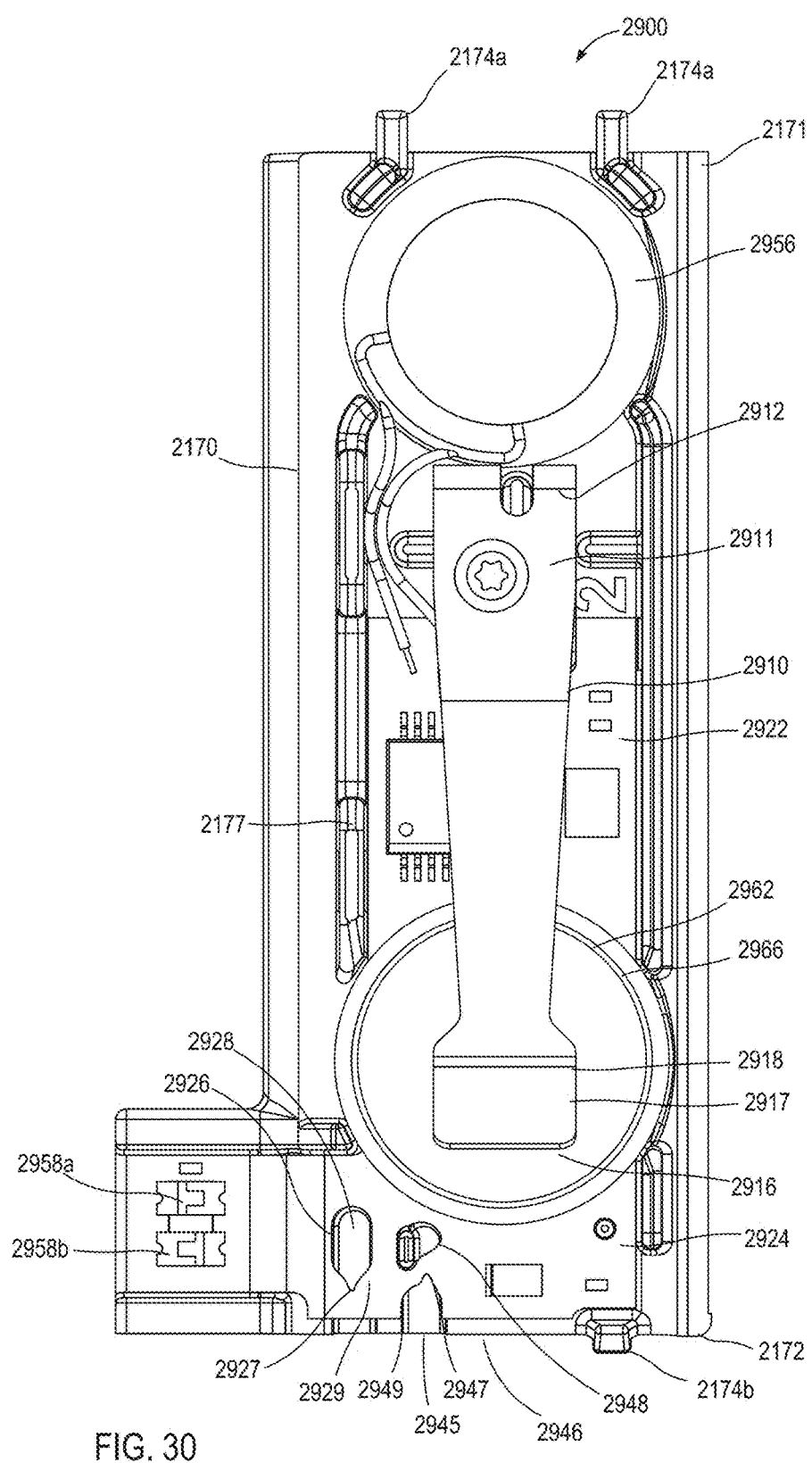
FIG. 30 is a rear view of the electronic circuit system illustrated in FIG. 27.
Figure 31:
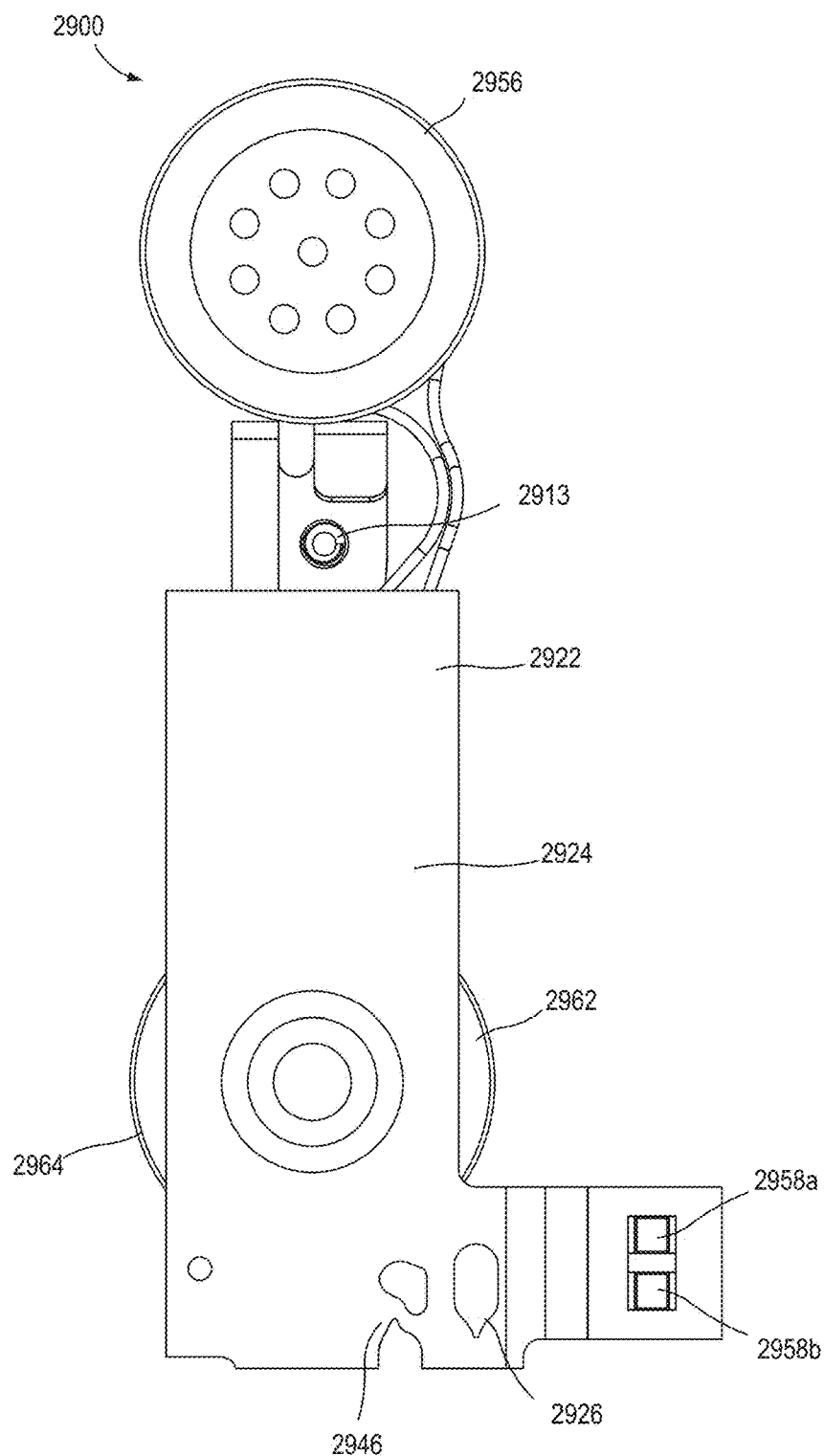
FIG. 31 is a front view of a portion of the electronic circuit system illustrated in FIG. 27.
Figure 32:
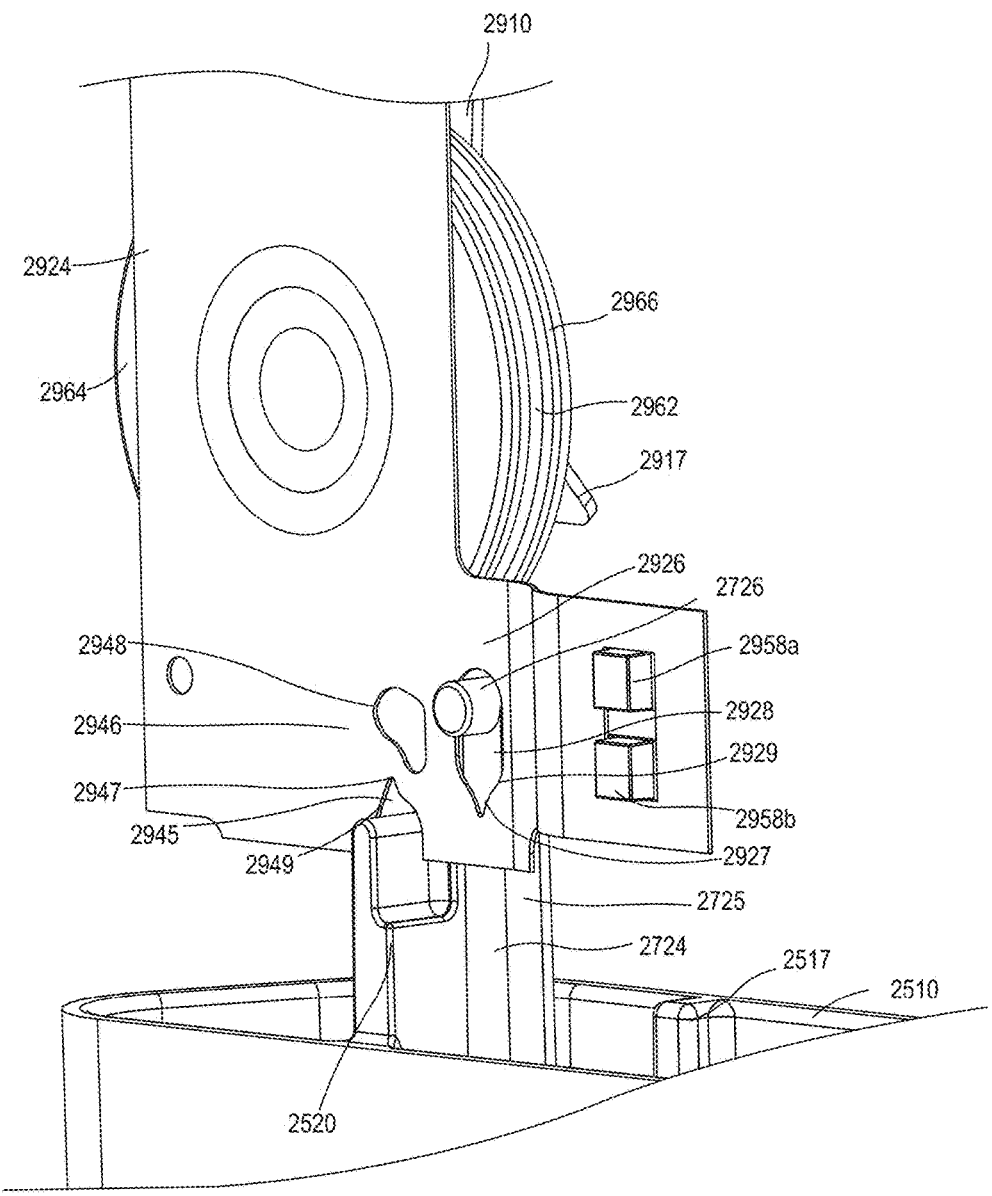
FIG. 32 is a perspective view of a portion of the electronic circuit system of FIG. 27 and a portion of the medicament delivery mechanism of FIG. 12, in a first configuration.
Figure 33:
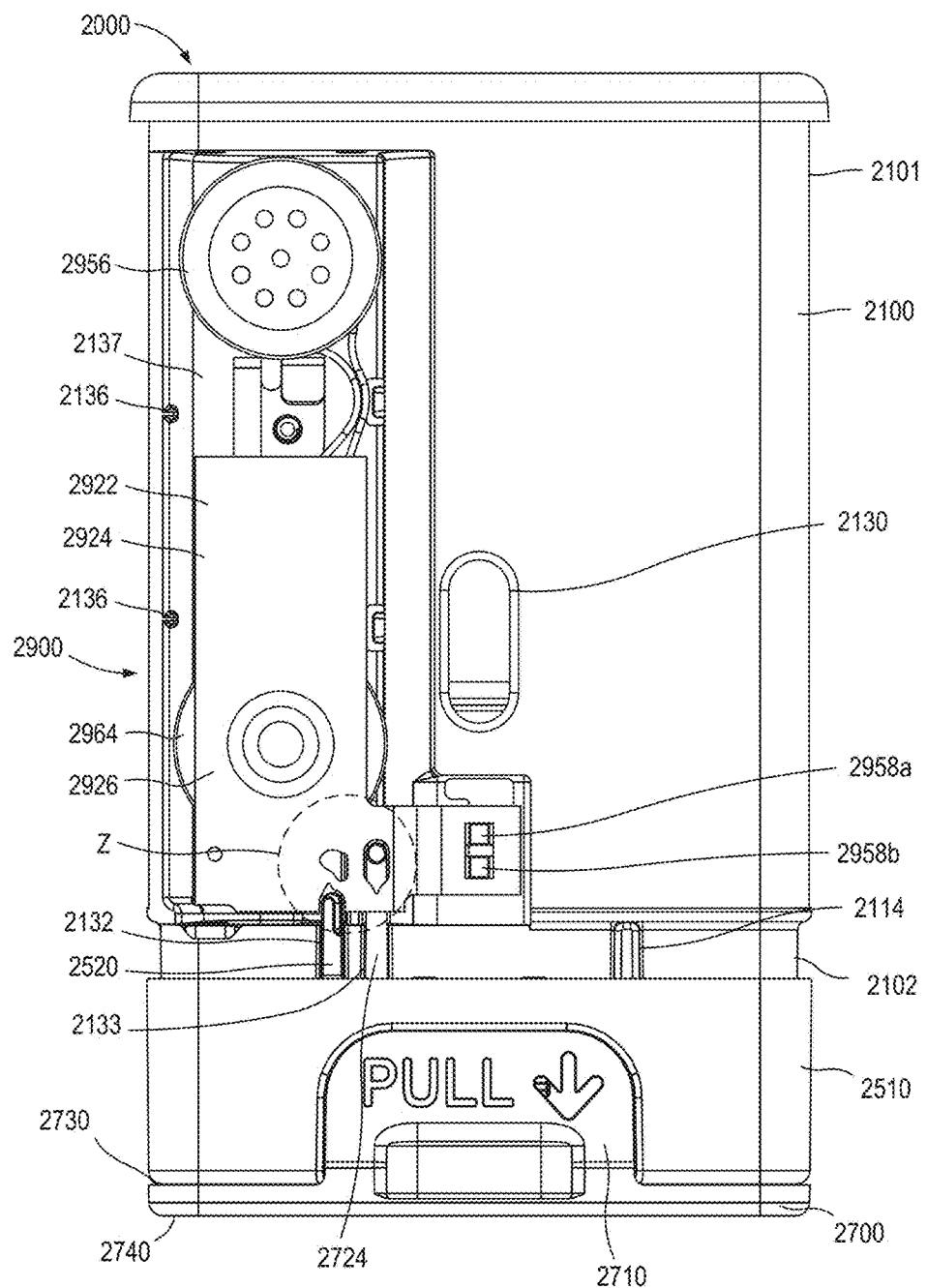
FIG. 33 is a front view of the medicament delivery device illustrated in FIG. 4 in a first configuration showing the electronic circuit system.

As shown in FIGS. 27-29, the electronic circuit system housing 2170 of the electronic circuit system 2900 includes a distal end portion 2172 and a proximal end portion 2171. The proximal end portion 2171 of the electronic circuit system housing 2170 defines multiple sound apertures 2173. The audible output device 2956 is disposed against the proximal end portion 2171 of the electronic circuit system housing 2170 such that the front face of the audible output device 2956 is disposed adjacent the sound apertures 2173. In this manner, the sound apertures 2173 can allow sound produced by the audio output device 2956 to pass from the audio output device 2956 to a region outside of the housing 2100.

The proximal end portion 2171 also includes connection protrusions 2174A and a battery clip protrusion 2176 (see e.g., FIG. 29). The connection protrusions 2174A are configured to matingly engage a surface of the sidewalls of the housing 2100 that define the electronic cavity 2137, as described above. In this manner, the electronic circuit system 2900 can be coupled to the housing 2100 and at least partially disposed within the electronic circuit system cavity 2137. In other embodiments, the electronic circuit system 2900 can be coupled to the housing 2100 by other suitable means such as an adhesive, a clip, a label and/or the like. As described in more detail herein, the battery clip protrusion 2176 is configured to hold the battery clip 2910 in place.

As shown in FIGS. 27-29, the distal end portion 2172 of the electronic circuit system housing 2170 includes the connection protrusion 2174B, a stiffening protrusion 2177 and defines an LED aperture 2178, apertures 2175, a safety lock actuator groove 2179 and a base actuator groove 2180. The LED aperture 2178 is configured to receive the LEDs 2958A, 2958B such that a user can view the LEDs 2958A, 2958B, which are described in more detail herein. The connection protrusion 2174B extends from the distal end portion 2172 of the electronic circuit system housing 2170, and is configured to attach the electronic circuit system 2900 to the housing 2100, as described above. The stiffening protrusion 2177 is configured to engage a portion of the housing 2100 (e.g., a protrusion, tab, and/or the like) that can be accessible via the apertures 2175. The stiffening protrusion 2177 is configured to limit bending (e.g., buckling) of the electronic circuit system housing 2170 when the electronic circuit system housing 2170 is coupled to the housing 2100. Moreover, the stiffening protrusion 2177 can be disengaged from the portion of the housing 2100 via the apertures 2175.

As shown in FIG. 29, the safety lock actuator groove 2179 of the electronic circuit system housing 2170 is configured to be disposed adjacent the safety lock actuator groove 2133 of the distal end portion 2102 of the housing 2100. In this manner, the safety lock actuator groove 2179 of the electronic circuit system housing 2170 and the safety lock actuator groove 2133 of the distal end portion 2102 of the housing 2100 collectively receive the electronic circuit system actuator 2724 (also referred to simply as the "actuator" 2724) of the safety lock 2700, which is described in more detail herein. Similarly, the base actuator groove 2180 of the electronic circuit system housing 2170 is configured to be disposed adjacent the base actuator groove 2132 of the distal end portion 2102 of the housing 2100. The base actuator groove 2180 of the electronic circuit system housing 2170 and the base actuator groove 2132 of the distal end portion 2102 of the housing 2100 collectively receive the electronics actuator 2520 of the base 2510, which is described in more detail herein.

The battery assembly 2962 of the electronic circuit system 2900 includes two batteries stacked on top of one another. In other embodiments, the electronic circuit system can include any number of batteries and/or any suitable type of power source. In some embodiments, for example, the battery assembly can include Lithium batteries such as, for example, CR1616, CR2016s, type AAA or the like. The battery assembly 2962 has a first surface 2964 and a second surface 2966. The first surface 2964 of the battery assembly 2962 can contact an electrical contact (not shown) disposed on the substrate 2924. The second surface 2966 of the battery assembly 2962 is configured to contact a contact portion 2918 of a distal end portion 2916 of a battery clip 2910. When both the electrical contact of the substrate 2924 and the contact portion 2918 of the distal end portion 2916 of the battery clip 2910 contact the battery assembly 2962, the batteries of the battery assembly 2962 are placed in electrical communication with the electronic circuit system 2900. Said another way, when the electrical contact of the substrate 2924 and the contact portion 2918 of the distal end portion 2916 of the battery clip 2910 contact the battery assembly 2962, the battery assembly 2962 is configured to supply power to the electronic circuit system 2900.

The battery clip 2910 (shown in FIGS. 28 and 30) includes a proximal end portion 2912 and a distal end portion 2916. The proximal end portion 2912 defines a retention aperture 2913. The retention aperture 2913 is configured to receive a screw 2911 to couple the battery clip 2910 to the battery clip protrusion 2176 of the electronic circuit system housing 2170. In this manner, the battery clip protrusion 2176 maintains the position of the battery clip 2910 with respect to the electronic circuit system housing 2170 and/or the battery assembly 2962.

The distal end portion 2916 of the battery clip 2910 includes a contact portion 2918 and an angled portion 2917. The contact portion 2918 is configured to contact the second surface 2966 of the battery assembly 2962 to place the battery assembly 2962 in electrical communication with the electronic circuit system 2900. The angled portion 2917 of the distal end portion 2916 of the battery clip 2910 is configured to allow a proximal end portion 2236 of a battery isolation protrusion 2197 (see e.g., FIG. 38) to be disposed between the second surface 2966 of the battery assembly 2962 and the contact portion 2918 of the distal end portion 2916 of the battery clip 2910. When the battery isolation protrusion 2197 is disposed between the second surface 2966 of the battery assembly 2962 and the contact portion 2918 of the distal end portion 2916 of the battery clip 2910, the electrical path between the battery assembly 2962 and the remainder of the electrical circuit system 2900 is disrupted, thereby removing power from the electronic circuit system 2900. The contact portion 2918 of the distal end portion 2916 of the battery clip 2910 is biased such that when the battery isolation protrusion 2197 is removed, the contact portion 2918 will move into contact the second surface 2966 of the battery assembly 2962, thereby restoring electrical communication between the battery assembly 2962 and the electronic circuit system 2900. In some embodiments, the battery isolation protrusion 2197 can be repeatedly removed from between the second surface 2966 of the battery assembly 2962 and the contact portion 2918 of the distal end portion 2916 of the battery clip 2910 and reinserted. Said another way, the battery isolation protrusion 2197 and the battery clip 2910 collectively form a reversible on/off switch.

The audio output device 2956 of the electronic circuit system 2900 is configured to output audible sound to a user in response to use of the delivery device 2000. In some embodiments, the audible output device 2956 can be a speaker. In some embodiments, the audible sound can be, for example, associated with a recorded message and/or a recorded speech. In other embodiments, the audible instructions can be an audible beep, a series of tones and/or or the like.

In some embodiments, the delivery device 2000 can have a network interface device (not shown) configured to operatively connect the electronic circuit system 2900 to a remote device (not shown) and/or a communications network (not shown). In this manner, the electronic circuit system 2900 can send information to and/or receive information from the remote device. The remote device can be, for example, a remote communications network, a computer, a compliance monitoring device, a cell phone, a personal digital assistant (PDA) or the like. Such an arrangement can be used, for example, to download replacement processor-readable code from a central network to the electronic circuit system 2900. In some embodiments, for example, the electronic circuit system 2900 can download information associated with a delivery device 2000, such as an expiration date, a recall notice, updated use instructions or the like. Similarly, in some embodiments, the electronic circuit system 2900 can upload information associated with the use of the delivery device 2000 via the network interface device (e.g., compliance information or the like).

The printed circuit board 2922 of the electronic circuit system 2900 includes a substrate 2924, a first actuation portion 2926 and a second actuation portion 2946. The substrate 2924 of the printed circuit board 2922 includes the electrical components for the electronic circuit system 2900 to operate as desired. For example, the electrical components can be resistors, capacitors, inductors, switches, microcontrollers, microprocessors and/or the like. The printed circuit board may also be constructed of materials other than a flexible substrate such as a FR4 standard board (rigid circuit board).

As shown in FIGS. 30-36, the first actuation portion 2926 includes a first electrical conductor 2934 and defines an opening 2928 having a boundary 2929. The opening 2928 of the first actuation portion 2926 is configured to receive a protrusion 2726 of the electronic circuit system actuator 2724 of the safety lock 2700. The boundary 2929 of the first opening 2928 has a discontinuous shape, such as, for example, a teardrop shape, that includes a stress concentration riser 2927. The discontinuity and/or the stress concentration riser 2927 of the boundary 2929 can be of any suitable shape to cause the substrate 2924 to deform in a predetermined direction when the protrusion 2726 of the actuator 2724 of the safety lock 2700 is moved relative to the opening 2928.

The opening 2928 is defined adjacent the first electrical conductor 2934 that electronically couples the components included in the electronic circuit system 2900. The first electrical conductor 2934 includes a first switch 2972, which can be, for example a frangible portion of the first electrical conductor 2934. In use, when the safety lock 2700 is moved from a first position (see e.g., FIG. 34) to a second position (see e.g., FIG. 35), the actuator 2724 moves in a direction substantially parallel to a plane defined by a surface of the first actuation portion 2926 of the substrate 2924. The movement of the actuator 2724 causes the protrusion 2726 to move within the first opening 2928, as indicated by the arrow EE in FIG. 35. The movement of the protrusion 2726 tears the first actuation portion 2926 of the substrate 2924, thereby separating the portion of the first electrical conductor 2934 including the first switch 2972. Said another way, when the safety lock 2700 is moved from its first position to its second position (see e.g., FIG. 44), the actuator 2724 moves irreversibly the first switch 2972 from a first state (e.g., a state of electrical continuity) to a second state (e.g., a state of electrical discontinuity). Said yet another way, when the safety lock 2700 is moved from its first position to its second position, the actuator 2724 disrupts the first electrical conductor 2934.

Figure 35:
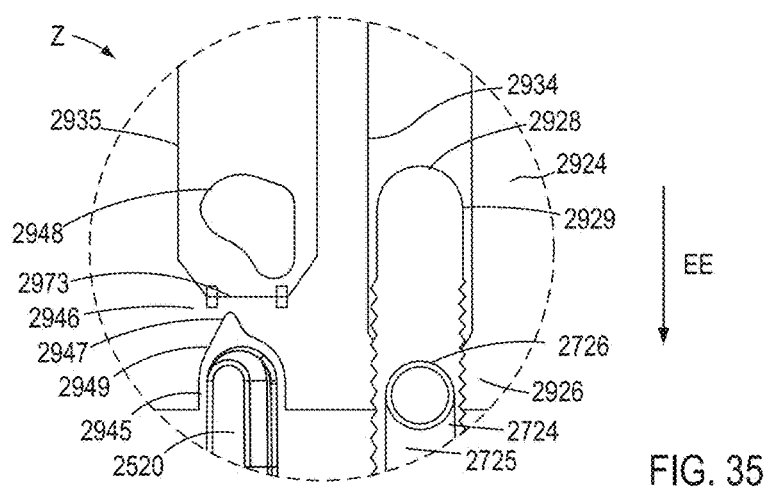
Figure 36:
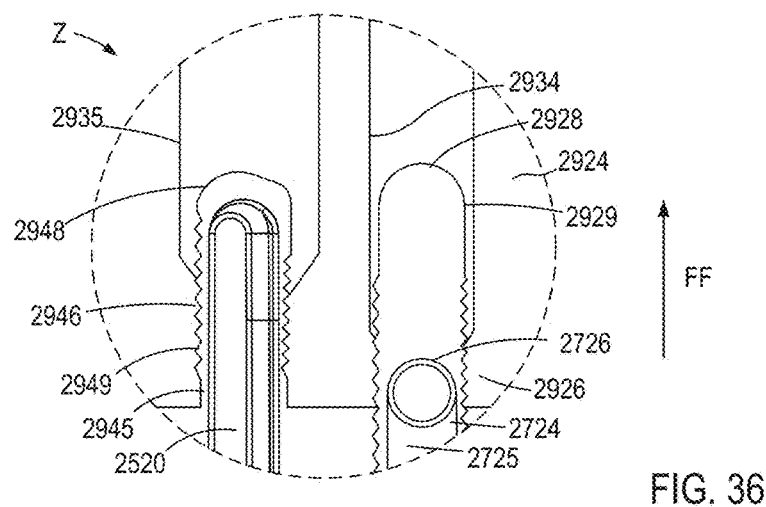

The second actuation portion 2946 includes a second electrical conductor 2935 and defines an opening 2945, having a boundary 2949 and a tear propagation limit aperture 2948. As shown in FIGS. 34-36, the opening 2945 of the second actuation portion 2946 is configured to receive a portion of an actuator 2520 of the base 2510. The boundary 2949 of the opening 2945 has a discontinuous shape that includes a stress concentration riser 2947. The discontinuity and/or the stress concentration riser 2947 of the boundary 2949 can be of any suitable shape to cause the substrate 2924 to deform in a predetermined direction when the actuator 2520 of the base 2510 is moved in a proximal direction relative to the opening 2945, as shown by the arrow FF in FIG. 36.

The second electrical conductor 2935 includes a second switch 2973 disposed between the opening 2945 and the tear propagation limit aperture 2948, which can be, for example, a frangible portion of the second electrical conductor 2935. In use, when the base 2510 is moved from its first position to its second position (see e.g., FIGS. 45 and 47), the actuator 2520 moves in a proximal direction, substantially parallel to a plane defined by a surface of the second actuation portion 2946 of the substrate 2924. The proximal movement of the actuator 2520 tears the second actuation portion 2946 of the substrate 2924, thereby separating the portion of the second electrical conductor 2935 including the second switch 2973. Said another way, when the base 2510 is moved from its first position to its second position, the actuator 2520 moves irreversibly the second switch 2973 from a first state (e.g., a state of electrical continuity) to a second state (e.g., a state of electrical discontinuity). The tear propagation limit aperture 2948 is configured to limit the propagation of the tear in the substrate 2924 in the proximal direction. Said another way, the tear propagation limit aperture 2948 is configured to ensure that the tear in the substrate 2924 does not extend beyond the tear propagation limit aperture 2948. The tear propagation limit aperture 2948 can be any shape configured to stop the propagation of a tear and/or disruption of the substrate 2924. For example, the tear propagation limit aperture 2948 can be oval shaped. In other embodiments, the proximal boundary of the tear propagation limit aperture 2948 can be reinforced to ensure that the tear in the substrate 2924 does not extend beyond the tear propagation limit aperture 2948. Although specifically described above, in other embodiments, the safety lock 2700 and base 2510 can be configured to interact with mechanical and/or optical switches to produce an electronic output in a reversible manner.

Figure 37:
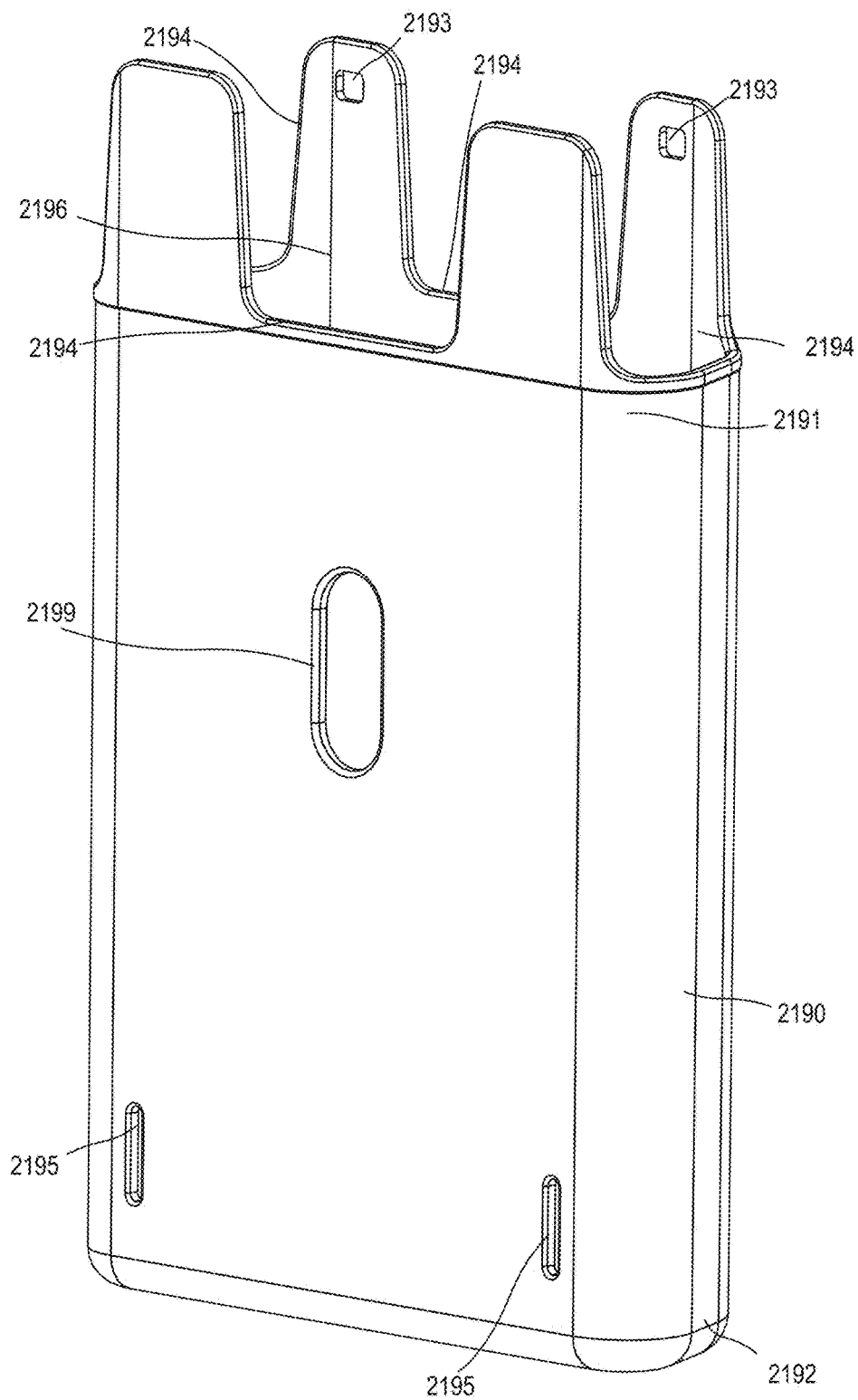
FIGS. 37 and 38 are perspective views of a cover of the medicament delivery device illustrated in FIG. 4.
Figure 38:
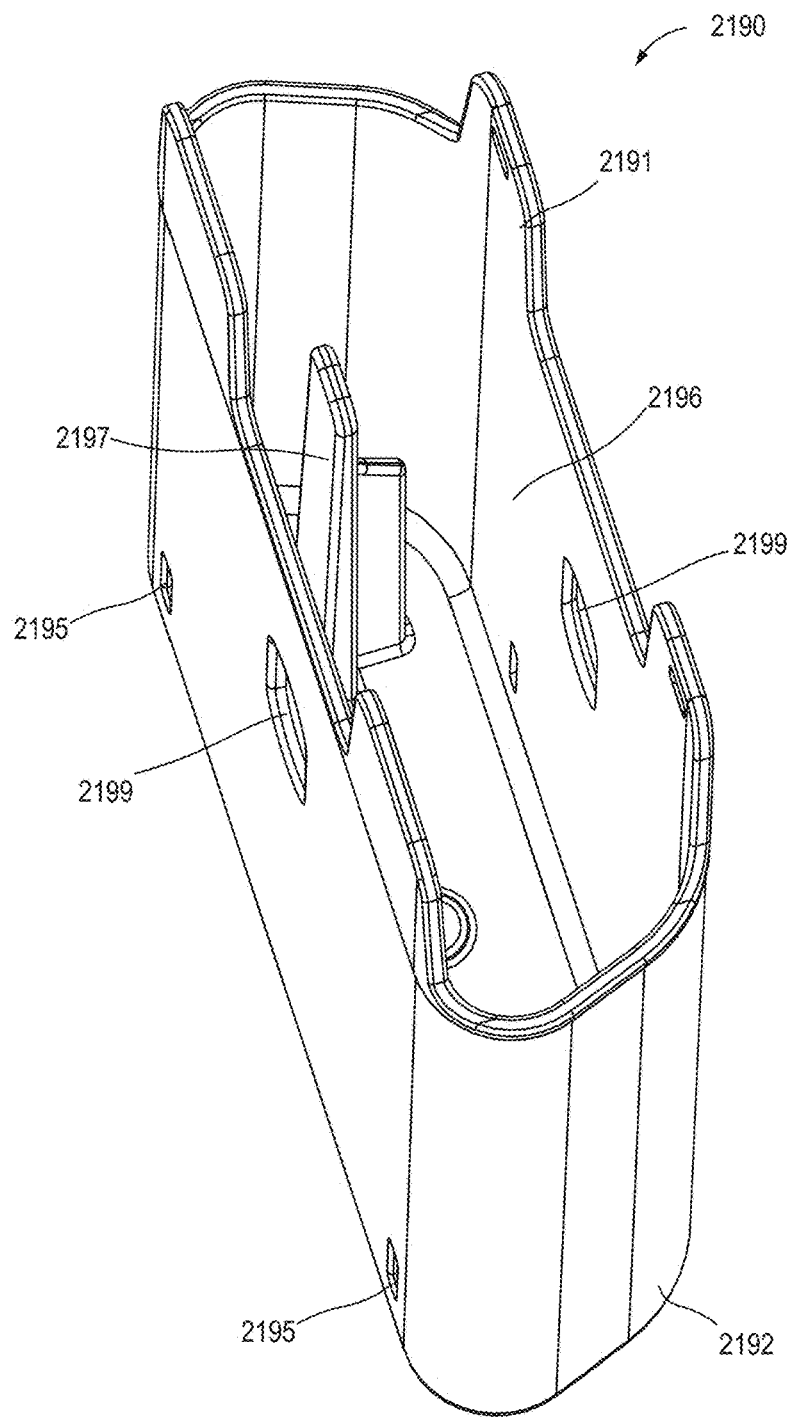
Figure 39:
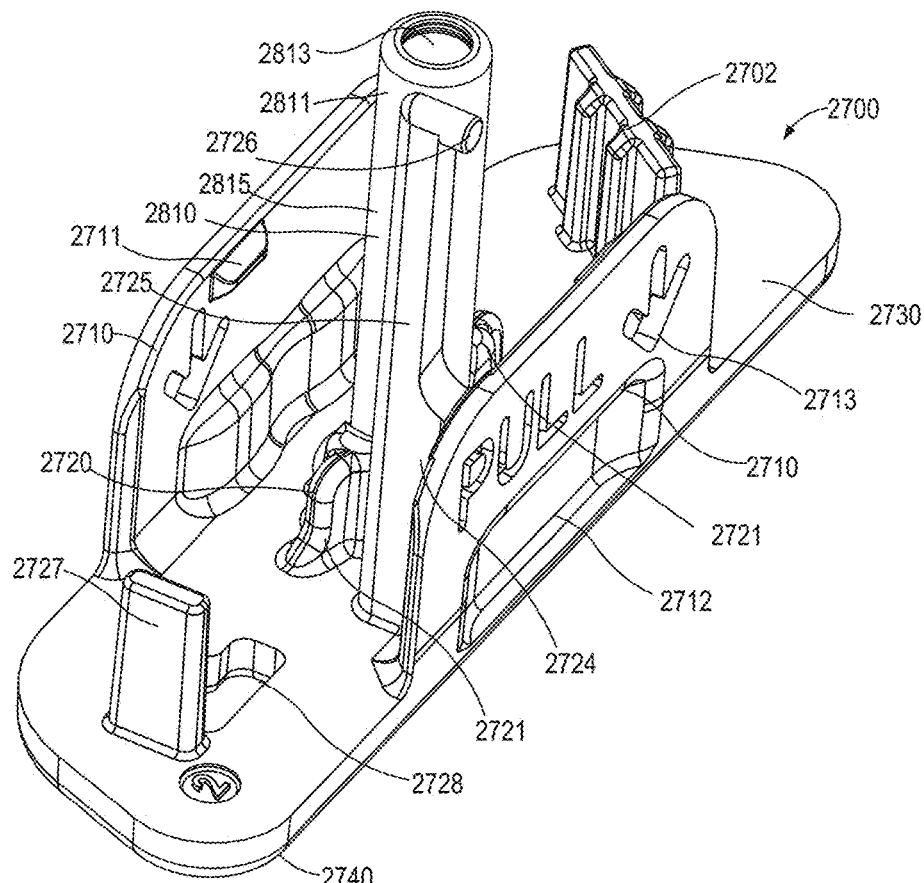
FIGS. 39-41 are a perspective view, a front view, and a bottom view, respectively, of a safety lock included the medicament delivery device illustrated in FIG. 4.
Figure 40:
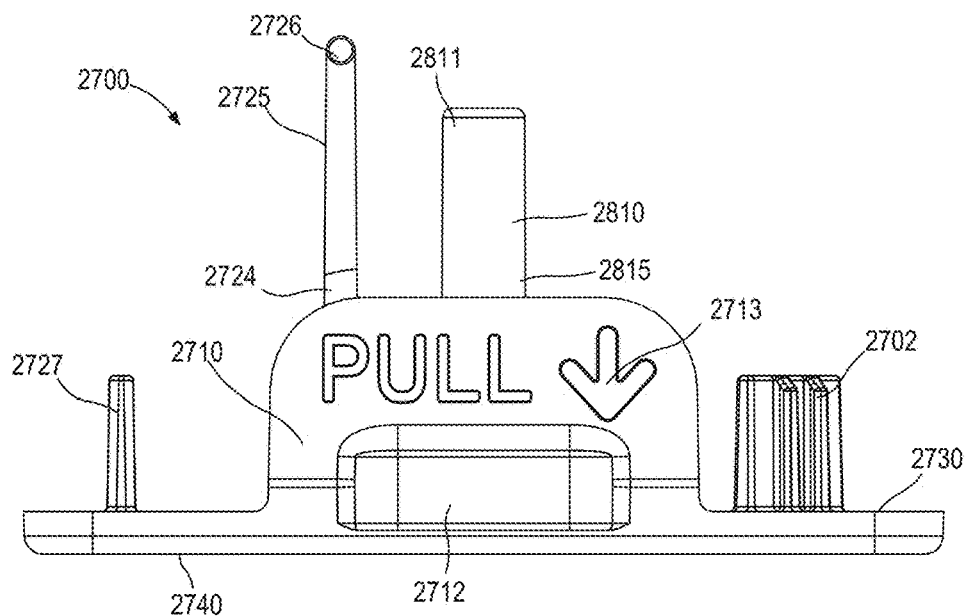
Figure 41:
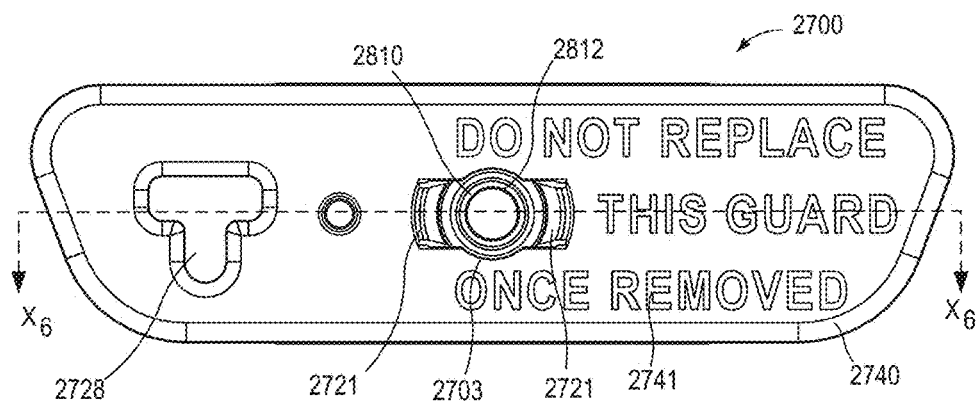

FIGS. 37 and 38 show the cover 2190 of the delivery device 2000. The cover 2190 can be any suitable configuration and can include any suitable feature. For example, the cover 2190 includes openings 2195 and notches 2194. In some embodiments, the openings 2195 can receive inserts (not shown). The inserts can be flexible inserts and can increase friction between the cover 2190 and a surface. For example, the inserts can increase the friction between the cover 2190 and a surface on which the delivery device 2000 is placed, to prevent sliding. The notches 2194 are disposed at the proximal end of the cover 2190. In some embodiments, the notches 2194 can be used to reduce the material needed to manufacture the cover 2190.

The cover 2190 includes a proximal end portion 2191 and a distal end portion 2192, and defines a cavity 2196, and status windows 2199. The cavity 2196 of the cover 2190 is configured to receive at least a portion of the housing 2100. When the portion of the housing 2100 is disposed within the cover 2190, the status windows 2199 are substantially aligned with the status windows 2130 and 2160 defined by the housing 2100. Thus, a user can visually inspect a status of the delivery device 2000 and/or the naloxone composition 2220 via the status windows of the cover 2190 and the status windows 2130 and 2160 of the housing 2100. In other embodiments, however, such as those containing a medicament that is sensitive to ultraviolet (UV) radiation, the cover 2190 need not include status windows 2199.

The proximal end portion 2191 of the cover 2190 defines apertures 2193 configured to receive the cover retention protrusions 2104 of the housing 2100 (shown in FIG. 5). In this manner, the apertures 2193 and the cover retention protrusions 2104 of the housing 2100 removably retain the cover 2190 about at least a portion of the housing 2100. Said another way, the apertures 2193 and the cover retention protrusions 2104 of the housing 2100 are configured such that the cover 2190 can be removed from a portion of the housing 2100 and then replaced about the portion of the housing 2100.

As described above, the electronic circuit system 2900 can be actuated when the housing 2100 is at least partially removed from the cover 2190. More particularly, the distal end portion 2192 of the cover 2190 includes the battery isolation protrusion 2197. The battery isolation protrusion 2197 is configured to be removably disposed between the second surface 2966 of the battery assembly 2962 and the contact portion 2918 of the distal end portion 2916 of the battery clip 2910, as described above.

FIGS. 39-42 show the safety lock 2700 of the delivery device 2000. The safety lock 2700 of the delivery device 2000 includes a proximal surface 2730, a distal surface 2740 opposite the proximal surface 2730, and a needle sheath 2810. The safety lock 2700 defines a needle sheath aperture 2703 and a battery isolation protrusion aperture 2728. The battery isolation protrusion aperture 2728 is configured to receive the battery isolation protrusion 2197 of the cover 2190 to allow the battery isolation protrusion 2197 to be disposed within the electronic circuit system cavity 2137 and/or in engagement with the electronic circuit system 2900, as described above. Similarly stated, the battery isolation protrusion aperture 2728 of the safety lock 2700 is aligned with the battery isolation protrusion aperture 2135 of the housing 2100 and thus, the battery isolation protrusion 2197 can extend therethrough to be disposed within the electronic circuit system cavity 2137 when the cover 2190 is disposed about a portion of the housing 2100.

The proximal surface 2730 of the safety lock 2700 includes a safety lock protrusion 2702, a stopper 2727, an electronic circuit system actuator 2724, two opposing pull-tabs 2710, and an engagement portion 2720. As described above, when the safety lock 2700 is in a first (locked) position, the safety lock protrusion 2702 is configured to be disposed in the space 2556 defined between the extensions 2553 of the distal end portion 2552 of the release member 2550 (see e.g., FIG. 18). Accordingly, the safety lock protrusion 2702 is configured to prevent the extensions 2553 from moving closer to each other, thereby preventing proximal movement of the release member 2550 and/or delivery of the medicament 2220. The stopper 2727 of the safety lock 2700 is a protrusion extending from the proximal surface 2730 of the safety lock 2700. The stopper 2727 is configured to contact a portion of the housing 2100 to limit the proximal movement of the safety lock 2700 relative to the housing 2100 and therefore, and inadvertent delivery of a portion of the naloxone composition 2220. In other embodiments, the stopper 2727 can be any structure configured to limit the proximal movement of the safety lock 2700.

The electronic circuit system actuator 2724 of the safety lock 2700 has an elongated portion 2725 and a protrusion 2726. The elongated portion 2725 extends in a proximal direction from the proximal surface 2730. In this manner, the elongated portion 2725 can extend through a safety lock actuator opening 2524 of the base 2510 (see e.g., FIGS. 14 and 15) and within the safety lock actuator groove 2133 of the housing 2100 and the safety lock actuator groove 2179 of the electronic circuit system housing 2170. The protrusion 2726 extends in a direction substantially transverse to the elongated portion 2725 and/or substantially parallel to the proximal surface 2730 of the safety lock 2700. As described above, the opening 2928 of the first actuation portion 2926 of the printed circuit board 2922 is configured to receive the protrusion 2726 of the actuator 2724 of the safety lock 2700.

The pull-tabs 2710 of the safety lock 2700 include a grip portion 2712 and indicia 2713. The grip portion 2712 of the pull-tabs 2710 provides an area for the user to grip and/or remove the safety lock 2700 from the rest of the medicament delivery system 2700. The indicia 2713 provide instruction on how to remove the safety lock 2700. In some embodiments, the indicia 2713 can be extruded through the pull-tabs 2710 (e.g., cut-outs defined by the pull-tabs 2710), thereby allowing a user to visually inspect a portion of the base 2510 and/or the housing 2100 while the safety lock 2700 is coupled thereto. In some embodiments, for example, indicia 2713 can indicate the direction the user should pull the safety lock 2700 to remove the safety lock 2700. The distal end surface 2740 also includes indicia 2741 (see e.g., FIG. 40).

The engagement portion 2720 of the safety lock 2700 includes engagement members 2721. The engagement members 2721 extend in a proximal direction from the proximal surface 2730. The engagement members 2721 have tabs 2722 that extend from a surface of the engagement members 2721. The tabs 2722 are configured to engage an outer surface 2815 of the needle sheath 2810.

Figure 42:
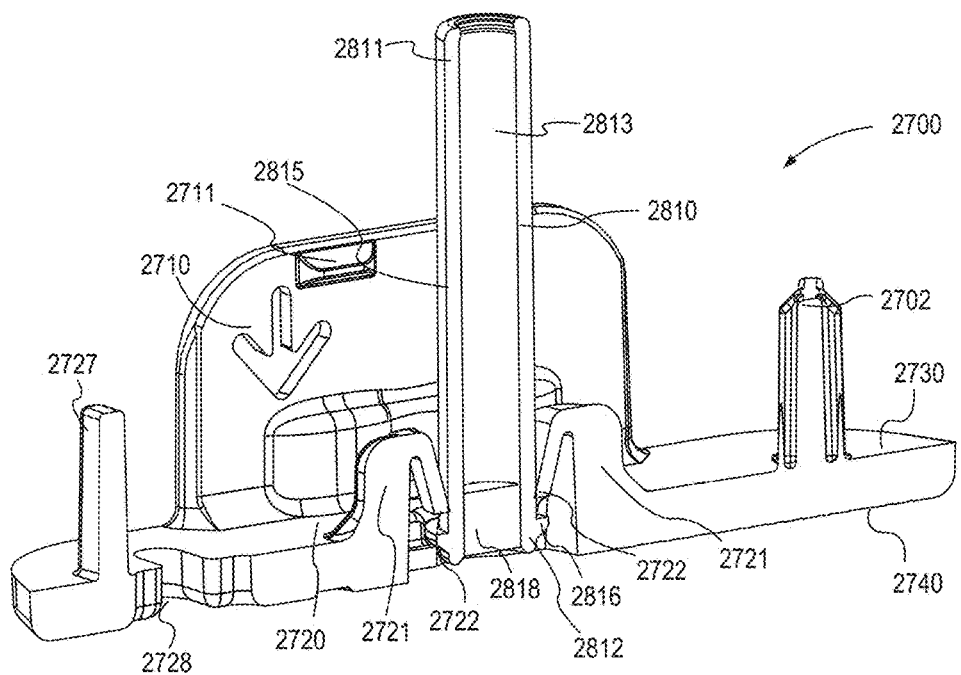
FIG. 42 is a cross-sectional view of the safety lock illustrated in FIG. 39, taken along the line $X_6$-$X_6$ in FIG. 41.
Figure 43:
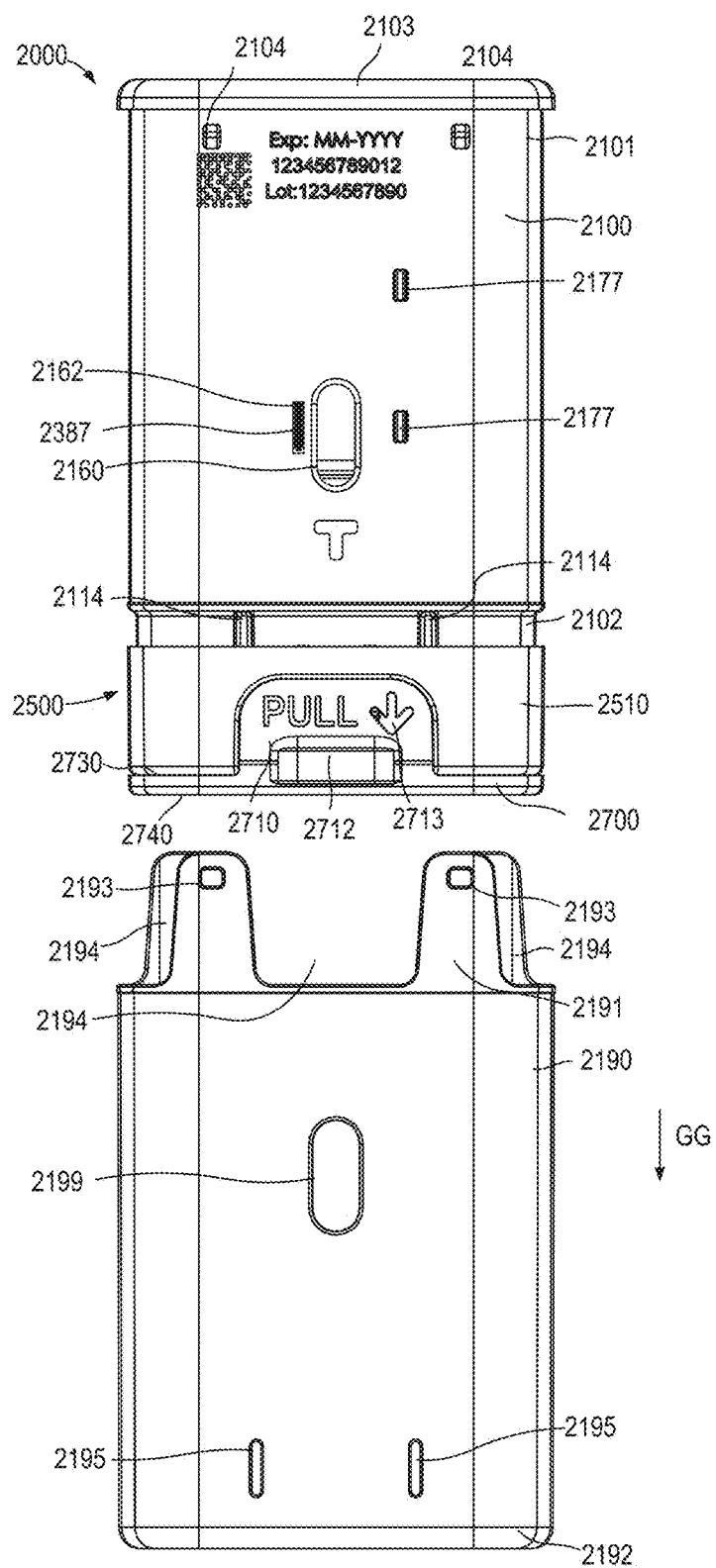
FIG. 43 is a rear view of the medicament delivery device illustrated in FIG. 4 in a second configuration.
Figure 44:
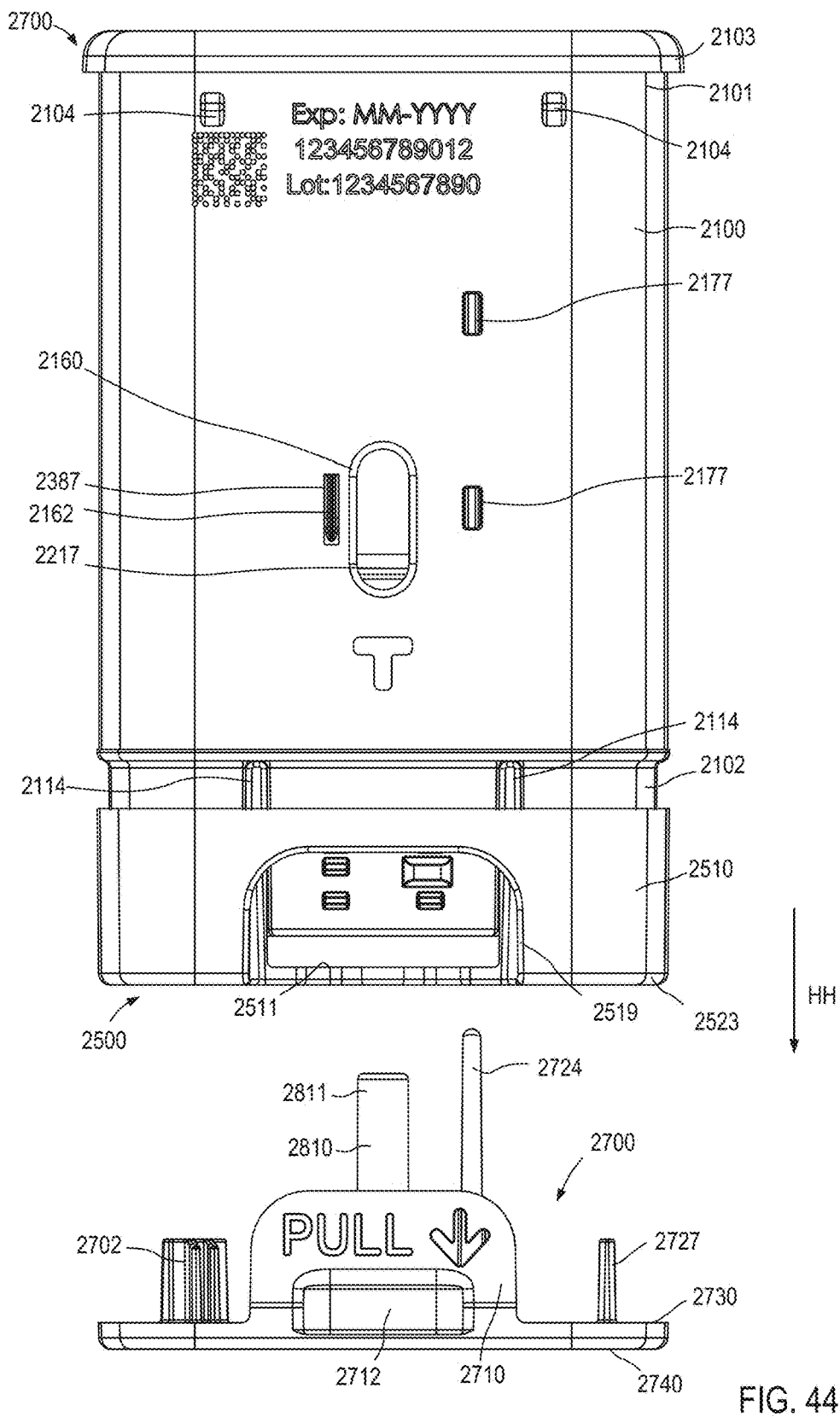
FIG. 44 is a rear view of the medicament delivery device illustrated in FIG. 4 in a third configuration.
Figure 45:
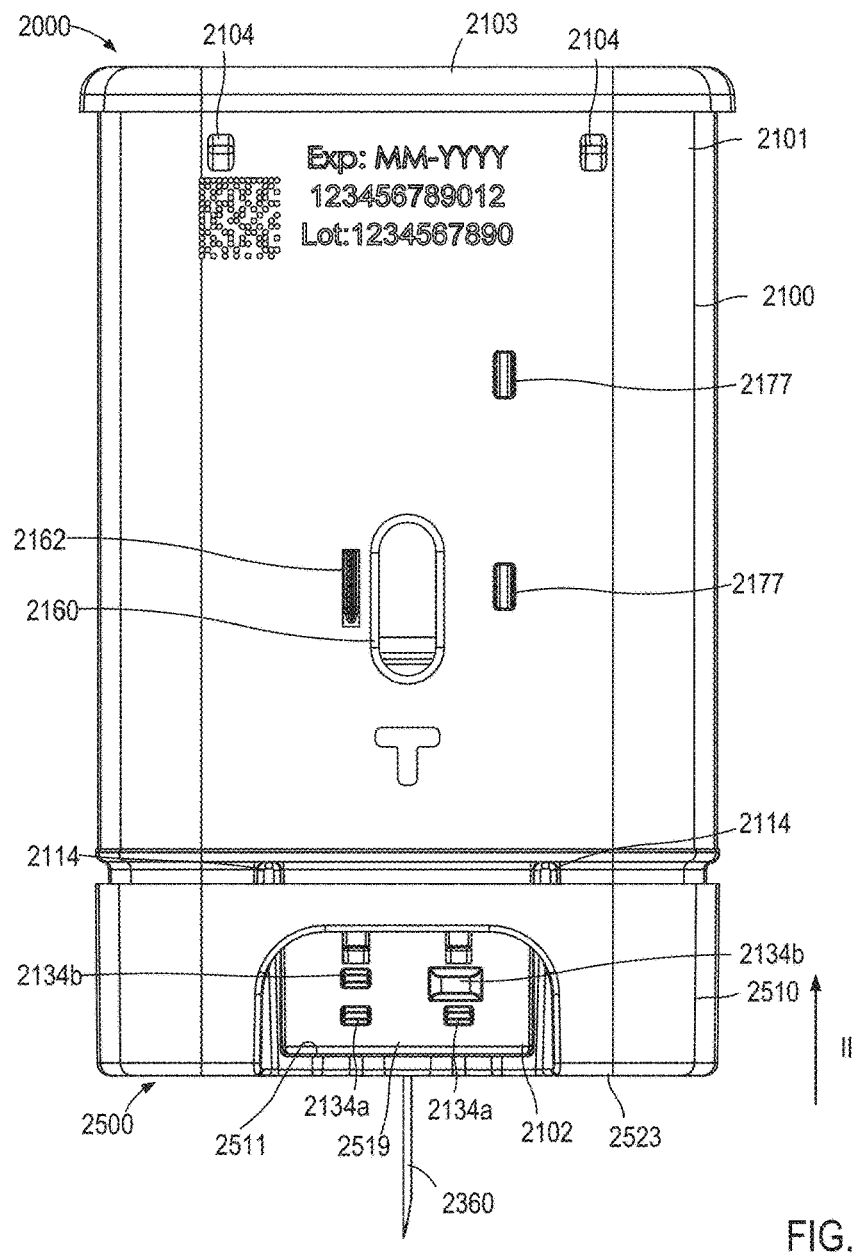
FIG. 45 is a rear view of the medicament delivery device illustrated in FIG. 4 in a fourth configuration (i.e., the needle insertion configuration).
Figure 46:
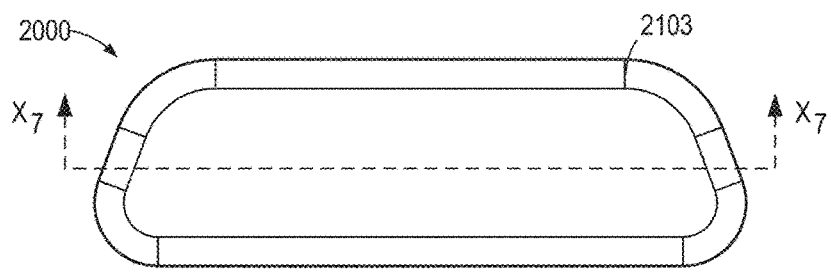
FIG. 46 is a top view of the medicament delivery device illustrated in FIG. 4.
Figure 47:
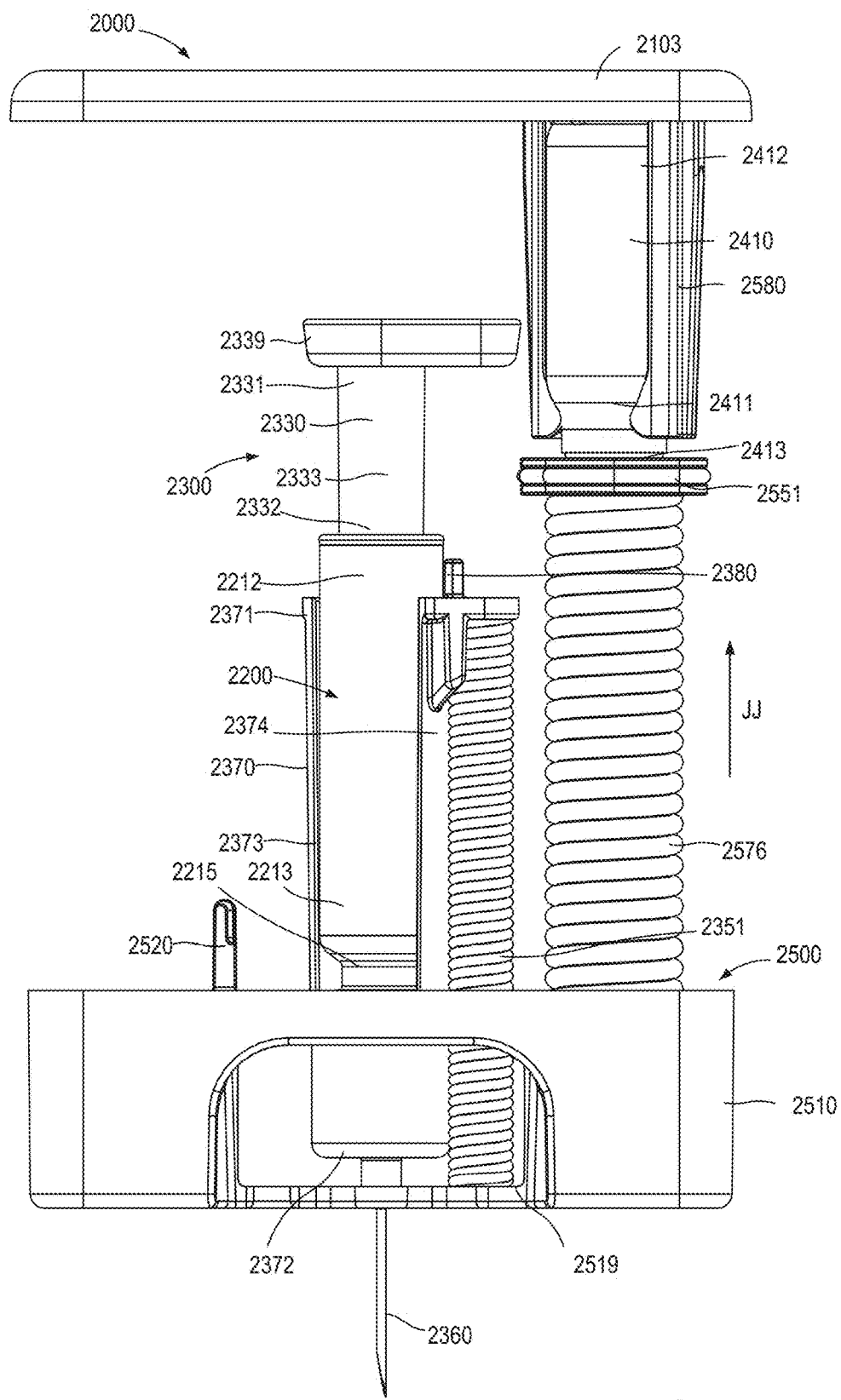
FIG. 47 is a front view of a portion of the medicament delivery device illustrated in FIG. 4 in the fourth configuration (i.e., the needle insertion configuration).
Figure 48:
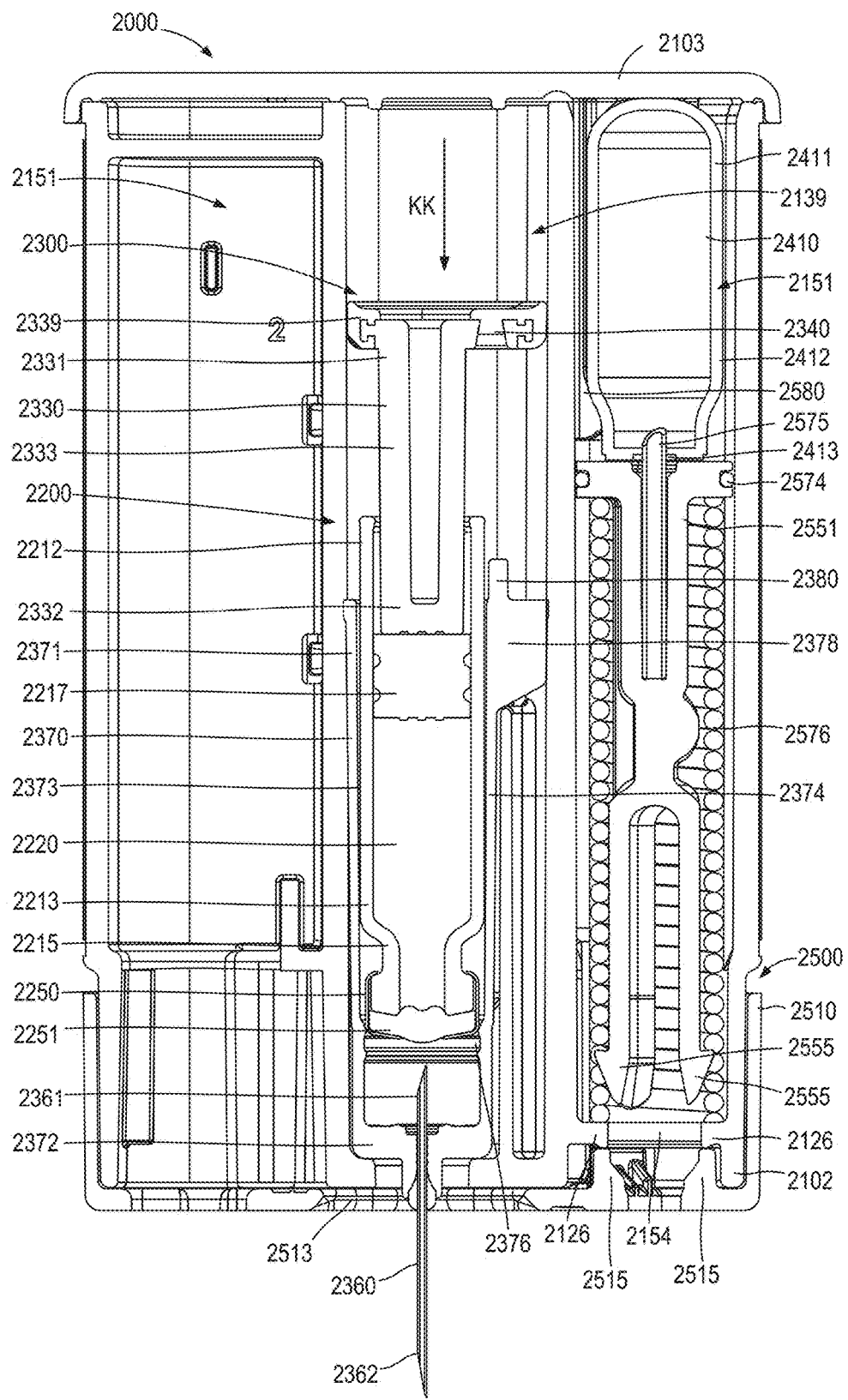
FIG. 48 is a cross-sectional view of the medicament delivery device illustrated in FIG. 4 in the fourth configuration (i.e., the needle insertion configuration), taken along the line $X_7$-$X_7$ in FIG. 46.

As shown in FIG. 42, the needle sheath 2810 includes the distal end portion 2812, a proximal end portion 2811 and a rib 2816. The needle sheath 2810 also defines a bore 2813. The bore 2813 is configured to receive the needle 2360 and/or a distal end portion of the 2372 of the carrier 2370. In some embodiment, an inner surface of the needle sheath 2810 defining bore 2813 forms a friction fit with the distal end portion 2370 of the carrier 2370. The bore 2813 also receives a distal plug (e.g., a porex plug or the like) disposed at or near the distal end portion 2812 of the needle sheath 2810. In this manner, the needle sheath 2810 can protect the user from the needle 2360 and/or can keep the needle 2360 sterile before the user actuates the delivery device 2000.

The distal end portion 2812 of the needle sheath 2810 is configured to be inserted into a space defined between the tabs 2722 of the engagement members 2721 of the safety lock 2700. The tabs 2722 are angled and/or bent towards the distal direction to allow the distal end portion 2812 of the needle sheath 2810 to move between the engagement members 2721 in a distal direction, but not in a proximal direction. Similarly stated, the tabs 2722 include an edge that contacts the outer surface 2815 of the needle sheath 2810 to prevent the safety lock 2700 from moving in a distal direction relative to the needle sheath 2810. More specifically, the needle sheath 2810 is disposed between the tabs 2722 in such a way that the rib 2816 is disposed in a distal position relative to the tabs 2722. In this manner, the needle sheath 2810 is removed from the needle 2360 when the safety lock 2700 is moved in a distal direction with respect to the housing 2100 (see e.g., FIG. 44).

An operation of the delivery device 2000 (or drug product 2000) is described below with reference to FIGS. 43-52. The delivery device 2000 is first enabled by moving the medicament delivery device 2000 from a first configuration to a second configuration by moving the cover 2190 from a first position to a second position relative to the housing 2100, as indicated by the arrow GG in FIG. 43. When the cover 2190 is moved with respect to the housing 2100 in the direction GG, the battery isolation protrusion 2197 is removed from the area between the battery clip 2910 and the second surface 2966 of the battery assembly 2962. In this manner, the battery assembly 2962 is operatively coupled (e.g., electrically coupled or connected) to the electronic circuit system 2900 when the cover 2190 is removed, thereby providing power to the electronic circuit system 2900. Similarly stated, this arrangement allows the electronic circuit system 2900 to be actuated when the cover 2190 is removed.

When power is provided, as described above, the electronic circuit system 2900 can output one or more predetermined electronic outputs. For example, in some embodiments, the electronic circuit system 2900 can output an electronic signal associated with recorded speech to the audible output device 2956. Such an electronic signal can be, for example, associated with a .WAV file that contains a recorded instruction, instructing the user in the operation of the delivery device 2000. Such an instruction can state, for example, "Remove the safety tab near the base of the auto-injector." The electronic circuit system 2900 can simultaneously output an electronic signal to one and/or both of the LEDs 2958A, 2958B thereby causing one and/or both of the LEDs 2958A, 2958B to flash a particular color. In this manner, the electronic circuit system 2900 can provide both audible and visual instructions to assist the user in the initial operation of the delivery device 2000.

In other embodiments, the electronic circuit system 2900 can output an electronic output associated with a description and/or status of the delivery device 2000 and/or the naloxone composition 2220 contained therein. For example, in some embodiments, the electronic circuit system 2900 can output an audible message indicating the symptoms for which the naloxone composition 2220 should be administered, the expiration date of the naloxone composition 2220, the dosage of the naloxone composition 2220, and/or the like. In some embodiments, the electronic circuit system 2900 can output an audible message stating, "If ready to use the delivery device, pull off the red safety guard." The electronic circuit system 2900 can also simultaneously output an electronic signal to one and/or both of the LEDs 2958A, 2958B, thereby causing one and/or both of the LEDs 2958A, and 2958B to stop flashing, change color or the like.

As described above, the delivery device 2000 can be repeatedly moved between the first configuration and the second configuration when the cover 2190 is moved repeatedly between the first position and the second position respectively. Said another way, the cover 2190 can be removed and replaced about the housing 2100 any number of times. When the cover 2190 is moved from the second position to the first position, the battery isolation protrusion 2197 is inserted between the battery clip 2910 and the second surface 2966 of the battery assembly 2962, deactivating the electronic circuit system 2900. When the cover is moved from the first position to the second position a second time, the electronic circuit system 2900 is once again activated. In this manner, the cover 2190 can be removed and the electronic circuit system 2900 can output the electronic output without compromising the sterility of the needle 2360.

After the cover 2190 is removed from the housing 2100, the delivery device 2000 can be moved from the second configuration (FIG. 43) to a third configuration (FIG. 44) by moving the safety lock 2700 from a first position to a second position. The safety lock 2700 is moved from a first position to a second position by moving the safety lock 2700 with respect to the housing 2100 in the direction shown by the arrow HH in FIG. 44. When the safety lock 2700 is moved from the first position to the second position, the safety lock protrusion 2702 is removed from between the extensions 2553 of the release member 2550, thereby enabling the medicament delivery mechanism 2300. Moreover, as shown in FIGS. 34 and 35, when the safety lock 2700 is moved from the housing 2100, the actuator 2724 of the safety lock 2700 moves in the direction EE as shown in FIG. 35, irreversibly moving the first switch 2972 from a first state (e.g., a state of electrical continuity) to a second state (e.g., a state of electrical discontinuity). When the actuator 2724 of the safety lock 2700 irreversibly moves the first switch 2972 of the electronic circuit system 2900 to the second state, the electronic circuit system 2900 can output one or more predetermined electronic outputs. For example, in some embodiments, a processor (not shown) can output an electronic signal associated with recorded speech to the audible output device 2956. Such an electronic signal can be, for example, associated with a recorded message notifying the user of the status of the delivery device 2000. The electronic circuit system 2900 can also simultaneously output an electronic signal to one and/or both of the LEDs 2958A, 2958B, thereby causing one and/or both of the LEDs 2958A, and 2958B to stop flashing, change color or the like.

In some embodiments, the first actuation portion 2926 and the actuator 2724 can be configured such that the actuator 2724 must move a predetermined distance before the actuator 2724 engages the boundary 2929 of the opening 2928. For example, in some embodiments, the actuator 2724 must move approximately 0.200 inches before the actuator 2724 engages the boundary 2929 of the opening 2928. In this manner, the safety lock 2700 can be moved slightly without irreversibly moving the first switch 2972 of the electronic circuit system 2900 to the second state. Accordingly, this arrangement will permit the user to inadvertently and/or accidentally move the safety lock 2700 a predetermined distance without actuating the electronic circuit system 2900.

In some embodiments, the electronic circuit system 2900 can be configured to output the status message for a predetermined time period, such as, for example, five seconds. After the predetermined time period has elapsed, the electronic circuit system 2900 can output an audible message further instructing the user in the operation of the delivery device 2000. Such an instruction can state, for example, "Place the base of the auto-injector against the patient's thigh. To complete the injection, press the base firmly against the patient's thigh." In some embodiments, the electronic circuit system 2900 can simultaneously output an electronic signal to one and/or both of the LEDs 2958A, 2958B, thereby causing one and/or both of the LEDs 2958A, and 2958B to flash a particular color. In this manner, the electronic circuit system 2900 can provide both audible and/or visual instructions to assist the user in the placement and actuation of the delivery device 2000. In some embodiments, the electronic circuit system 2900 can be configured to repeat the instructions after a predetermined time period has elapsed.

As described above, in other embodiments, the delivery device 2000 and/or the electronic circuit system 2900 can have a network interface device (not shown) configured to operatively connect the electronic circuit system 2900 to a remote device (not shown) and/or a communications network (not shown). For example, in some embodiments, the electronic circuit system 2900 can include a wireless network interface having the structure and function as shown and described in U.S. Pat. No. 8,226,610, entitled "Medical Injector with Compliance Tracking and Monitoring," which is incorporated herein by reference in its entirety. In some embodiments, the electronic circuit system 2900 can include a radio is configured to electronically communicate with a computing device via a wireless protocol (e.g., Bluetooth®) as shown and described in U.S. patent application Ser. No. 14/142,287, entitled "Devices, Systems and Methods for Locating and Interacting with Medicament Delivery Systems," filed on Dec. 27, 2013, which is incorporated herein by reference in its entirety. In this manner, the electronic circuit system 2900 can send a wireless signal notifying a remote device that the safety lock 2700 of the delivery device 2000 has been removed and that the delivery device 2000 has been armed. In other embodiments, the electronic circuit system 2900 can send a wireless signal (e.g., a wireless 911 call) notifying an emergency responder that the delivery device 2000 has been armed, for example, via removal of the safety lock 2700.

In other embodiments, the protrusion 2726 extending from the actuator 2724 of the safety lock 2700 can include a conductive element or the like that can engage a first actuation portion structurally and/or functionally similar to the first actuation portion 2926. In this manner, the movement of the conductive element relative to the first actuation portion can actuate an electronic circuit system to output an electronic output. For example, in some embodiments, the conductive element can be in electrical communication with the first actuation portion thereby causing a short, a fault, and/or completing a circuit. Thus, when the safety lock 2700 is moved relative to the housing 2100 the short, fault, and/or completed circuit can be transitioned to a second electrical state operable in outputting the electrical output.

After the safety lock 2700 is moved from the first position to the second position, the delivery device 2000 can be moved from the third configuration (FIG. 44) to a fourth configuration (FIGS. 45-48) by moving the base 2510 from a first position to a second position. Similarly stated, the delivery device 2000 can be actuated by the system actuator assembly 2500 by moving the base 2510 proximally relative to the housing 2100. In some instances, the base 2510 is moved from its first position to its second position by placing the delivery device 2000 against the body of the patient and moving the base 2510 with respect to the housing 2100 in the direction shown by the arrow II in FIG. 45.

As described above, the electronics actuator 2520 of the base 2510 actuates the electronic circuit 2900 to trigger a predetermined output or sequence of outputs when the base 2510 is moved from its first position to its second position. When the electronics actuator 2520 is moved in a proximal direction relative to the opening 2945, as shown by the arrow FF in FIG. 36, the electronic circuit system 2900 is actuated to output one or more predetermined electronic outputs. For example, in some embodiments, the electronic circuit system 2900 can output an electronic signal associated with recorded speech to the audible output device 2956. Such an electronic signal can be, for example, associated with an audible countdown timer, instructing the user on the duration of the injection procedure. Said another way, if it takes, for example, ten seconds to complete an injection, an audible countdown timer can count from ten (or five) to zero ensuring that the user maintains the delivery device 2000 in place for the full ten (or five) seconds. In other embodiments, the electronic signal can be, for example, associated with a recorded message notifying the user that the injection is complete, instructing the user on post-injection disposal and safety procedures, instructing the user on post-injection medical treatment or the like. Such a status message can state, for example, "The injection is now complete. Please seek further medical attention from a doctor."

The electronic circuit system 2900 can also simultaneously output an electronic signal to one and/or both LEDs 2958A, 2958B, thereby causing one and/or both LEDs 2958A and 2958B to stop flashing, change color or the like, to provide a visual indication that the injection is complete. In other embodiments, the electronic circuit system 2900 can send a wireless signal notifying a remote device that the injection is complete. In this manner, a patient's compliance and/or adherence with the use of the system can be monitored.

In some embodiments, the second actuation portion 2946 and the electronics actuator 2520 of the base 2510 can be configured such that the base 2510 and/or the actuator 2520 is moved a predetermined distance before the electronics actuator 2520 engages the boundary 2949 of the opening 2945. For example, in some embodiments, the electronics actuator 2520 must move approximately 0.200 inches before the actuator 2520 engages the boundary 2949 of the opening 2945. In this manner, the base 2510 can be moved a predetermined distance without irreversibly moving the second switch 2973 of the electronic circuit system 2900 to the second state. Accordingly, this arrangement will permit the user to inadvertently and/or accidentally move the base 2510 without actuating the electronic circuit system 2900.

In a substantially concurrent process, moving the base 2510 from the first position to the second position places the protrusions 2515 on the proximal surface 2511 of the base 2510 into contact with the tapered surfaces 2557 of the extensions 2553 of the release member 2550, thereby moving the extensions 2313 together. The inward movement of the extensions 2553 results in the engagement surfaces 2554 of the release member 2550 being disengaged from the base release surface 2126 of the housing 2100, thereby allowing the release member 2550 to be moved proximally along its longitudinal axis as the spring 2576 expands, as shown by the arrow JJ in FIG. 47.

When the base 2510 is moved from the first position to the second position, the system actuator assembly 2500 actuates the medicament delivery mechanism 2300, thereby placing the delivery device 2000 in its fourth configuration (i.e., the needle insertion configuration), as shown in FIGS. 45-48. More particularly, when the delivery device 2000 is placed in its fourth configuration, the puncturer 2575 of the release member 2550 is placed in contact with and/or disposed through the frangible seal 2413 of the gas container 2410. After the frangible seal 2413 has been punctured, an actuating volume of the compressed gas flows from the gas container 2410, into the portion of the gas cavity 2151 proximal to the seal member 2574 of the release member 2550 and into the portion of the medicament cavity 2139 proximal to the seal member 2339 of the movable member 2330 via the gas passageway 2156 of the proximal cap 2103. Thus, the gas exerts a force (e.g., associated with an increase in pressure in the medicament cavity 2139) on the movable member 2330 that is sufficient to move the movable member 2330, the carrier 2370 (and the needle 2360), and the medicament container 2200 in the distal direction within the medicament cavity 2139, as shown by the arrow KK in FIG. 48.

When the carrier 2370 moves distally within the medicament cavity 2139 in response to movement of the movable member 2330, the carrier 2370 and the medicament container 2200 are in a first configuration and collectively move toward a second configuration. In this manner, the medicament container 2200 and the needle 2360 contemporaneously move with the movable member 2330 and/or the carrier 2370 in a distal direction. The movement of the needle 2360 in a distal direction results in a distal end portion 2362 of the needle 2360 exiting the housing 2100 and entering the body of a patient via the needle aperture 2513 defined by the base 2510.

Since the retraction spring 2351 is disposed between the shoulder 2378 of the carrier 2370 and the distal surface of the housing 2100 (as described above), the force exerted by the expansion of the gas is sufficient to overcome a force exerted by the retraction spring 2351 and as such, the retraction spring 2351 is transitioned toward a compressed configuration. In addition, the cap 2250 of the medicament container 2200 is in contact with the ribbed portion 2376 of the carrier 2370 in such a manner that an amount of force sufficient to move the cap 2250 relative to the ribbed portion 2376 in the distal direction is greater than an amount of force exerted to transition the retraction spring 2351 towards its compressed configuration. Thus, the movable member 2330, the medicament container 2200, and the carrier 2370 are moved concurrently within the medicament cavity 2139 in response to the force exerted by the expansion of the gas.

More specifically, in this embodiment, the inner volume of the gas container 2410 is about 0.0625 in$^3$ and can contain and/or store the pressurized gas (e.g., prior to the frangible seal 2413 being punctured) at about 1100 psi. In some instances, the pressure and/or volume of the gas container 2410 can be selected in association with, for example, a volume of the naloxone composition 2220 disposed in the medicament container 2200, a length of the medicament container 2200, a position of the medicament container 2200 within the medicament cavity 2139, and/or a stroke length of the movable member 2330. In this manner, the drug product 2000 can produce certain desired performance characteristics during the delivery of the naloxone composition 2220. Such characteristics can include, for example, a minimum time for insertion of the needle 2360, a repeatable needle insertion depth, a consistent delivery volume, and the like.

Figure 49:
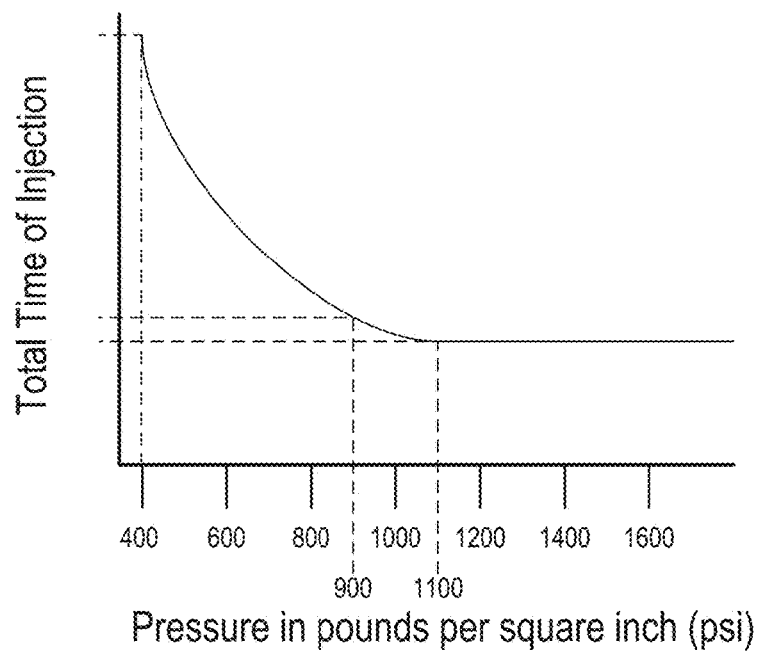
FIG. 49 is a graph illustrating a relationship between pressure and a time of an injection event of the delivery device illustrated in FIG. 4.

For example, in some embodiments, the volume and/or pressure of the gas within the gas container 2410 can be configured to generate a desired amount of pressure and/or force within the medicament cavity 2139 to reduce an amount of time to deliver the naloxone composition 2220 to the patient. For example, the pressure at which the gas is stored within the gas container 2410 prior to the actuation of the delivery device 2000 can be associated with a time of injection, wherein an increase in the gas pressure results in a decrease in time of injection. In some embodiments, the system actuation assembly 2500, the medicament delivery mechanism 2300 and/or the drug product 2000 is configured to deliver the dose of naloxone composition 2220 in less than about two seconds. In some embodiments, the system actuation assembly 2500, the medicament delivery mechanism 2300 and/or the drug product 2000 is configured to deliver the dose of naloxone composition 2220 in less than about 0.5 seconds. The increase in pressure, however, can reach a point (e.g., about 1100 psi) at which only a nominal reduction in the time of injection occurs as the gas pressure increases, as shown in the graph of FIG. 49 (which is a representative graph of a relationship between pressure and a time of an injection event of the delivery device 2000). In some embodiments, further reductions in the time of injection can be achieved via an increase in the size or gauge of the needle 2360.

After the carrier 2370 has been moved within the medicament cavity 2139 a predetermined distance (e.g., associated with the insertion of the needle 2360 into the patient), the carrier 2370 and the medicament container 2200 are then moved from the first configuration to the second configuration. For example, in some embodiments, the retraction spring 2351 can be fully compressed (e.g., a solid configuration) and can prevent the carrier 2370 from moving further in the distal direction. In other embodiments, a portion of the carrier 2370 and/or a portion of the medicament container 2200 can contact the housing 2100 when the needle insertion operation is completed, thereby limiting further distal movement of the carrier 2370 and the needle 2360 coupled thereto. With the distal movement of the carrier 2370 prevented, the pressure within the gas chamber continues to exert the force on the movable member 2330 and as such, the movable member 2330 continues to transmit the portion of the force on the elastomeric member 2217 disposed in the medicament container 2200.

With the naloxone composition 2220 under pressure and with at least a portion of the naloxone composition 2220 being an incompressible fluid (as described herein), the movable member 2330 and the medicament container 2200 act as a substantially solid rod. The force exerted by the expansion of the gas on the movable member 2330 is, therefore, transferred through the movable member 2330 and the medicament container 2200 and in turn, the force is exerted by the cap 2250 on the ribbed portion 2376 of the carrier 2370. The force exerted by the cap 2550 on the ribbed portion 2376 is sufficient to overcome a friction force or the like associated with the "snap fit" between the cap 2250 and the ribbed portion 2376. Thus, when the distal movement of the carrier 2370 is prevented, the force exerted by the expansion of the gas on the movable member 2330 is sufficient to move the medicament container 2200 in the distal direction relative to the carrier 2370 to a distal position, as indicated by the arrow LL in FIG. 51. In some embodiments, the movement of the medicament container 2200 relative to the carrier 2370 can be substantially immediately after the carrier 2370 is placed in the distal most position within the medicament cavity 2139. Thus, substantially the same force is exerted to move the medicament container 2200 relative to the carrier 2370 as was exerted at the end of the distal movement of the carrier 2370 (e.g., at the end of the needle insertion).

Figure 51:
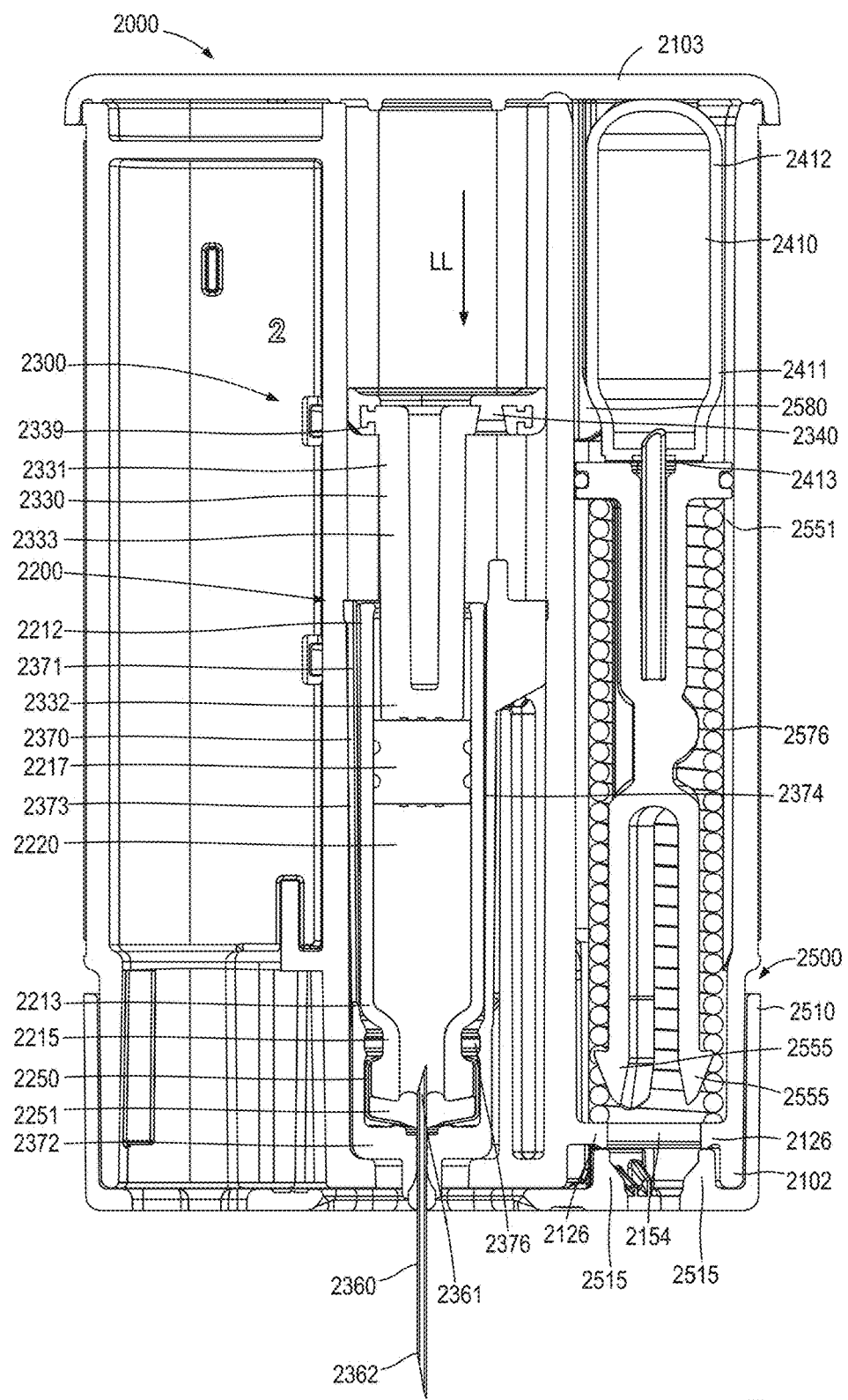
FIG. 51 is a cross-sectional view of the medicament delivery device illustrated in FIG. 4 in a fifth configuration (i.e., the fluid communication configuration), taken along the line $X_7$-$X_7$ in FIG. 46.

As the medicament container 2200 moves relative to the carrier 2370, the proximal end portion 2361 of the needle 2360 contacts and punctures the seal 2251 of the medicament container 2200 to establish fluid communication between the lumen 2363 of the needle 2360 and the inner volume of the medicament container 2200 containing the naloxone composition 2220. After the medicament container 2200 is placed in contact with a distal surface of the carrier 2370, the medicament container 2200 is prevented from moving in the distal direction relative to the carrier 2370, thereby placing the delivery device 2000 in a fifth configuration as shown in FIG. 51.

With the distal movement of the medicament 2200 prevented, the pressure within the gas chamber continues to exert a force on the movable member 2330 and as such, the movable member 2330 continues to transmit a portion of the force on the elastomeric member 2217 disposed in the medicament container 2200, to transition the delivery device 2000 from the fifth configuration to a sixth configuration (i.e., the injection event). With the lumen 2363 of the needle 2360 in fluid communication with the medicament container 2200, the force exerted by the movable member 2330 (e.g., in response to the force exerted by the expansion of the gas) on the elastomeric member 2217 is sufficient to move the elastomeric member 2217 within the medicament container 2200 in the distal direction, as indicated by the arrow MM in FIG. 52. As the piston rod 2333 of the movable member 2330 moves within the medicament container 2200, the elastomeric member 2217 generates a pressure acting upon the naloxone composition 2220 contained within the medicament container 2200, thereby allowing at least a portion of the naloxone composition 2220 to flow out of the medicament container 2200, through the lumen 2360 defined by the needle 2360, and into the body of the patient.

The portion of the gas cavity 2151 proximal to the seal member 2574 of the release member 2550, the gas passageway 2156 of the proximal cap 2103, and the portion of the medicament cavity 2139 proximal to the seal member 2339 of the movable member 2330 (collectively referred to as "gas chamber") define a volume that is about 0.5 in$^3$, prior to the frangible seal 2413 being punctured and that has a pressure substantially equal to atmospheric pressure (e.g., 14.7 psi) prior to actuation of the device. Thus, when the gas container 2410 is transitioned to an actuated state such as, for example, when the puncturer 2575 punctures the frangible seal 2413, the compressed gas flows from the gas container 2410 having a volume of about 0.0625 in$^3$ and a pressure of about 1100 psi into the gas chamber having a larger volume of about 0.5 in$^3$ and a lower pressure about 14.7 psi. Thus, the gas expands in the gas chamber which, in turn, increases the pressure therein, and the increase in pressure exerts a force on the movable member 2330 to move the movable member 2330 within the medicament cavity 2139, as described above.

Figure 52:
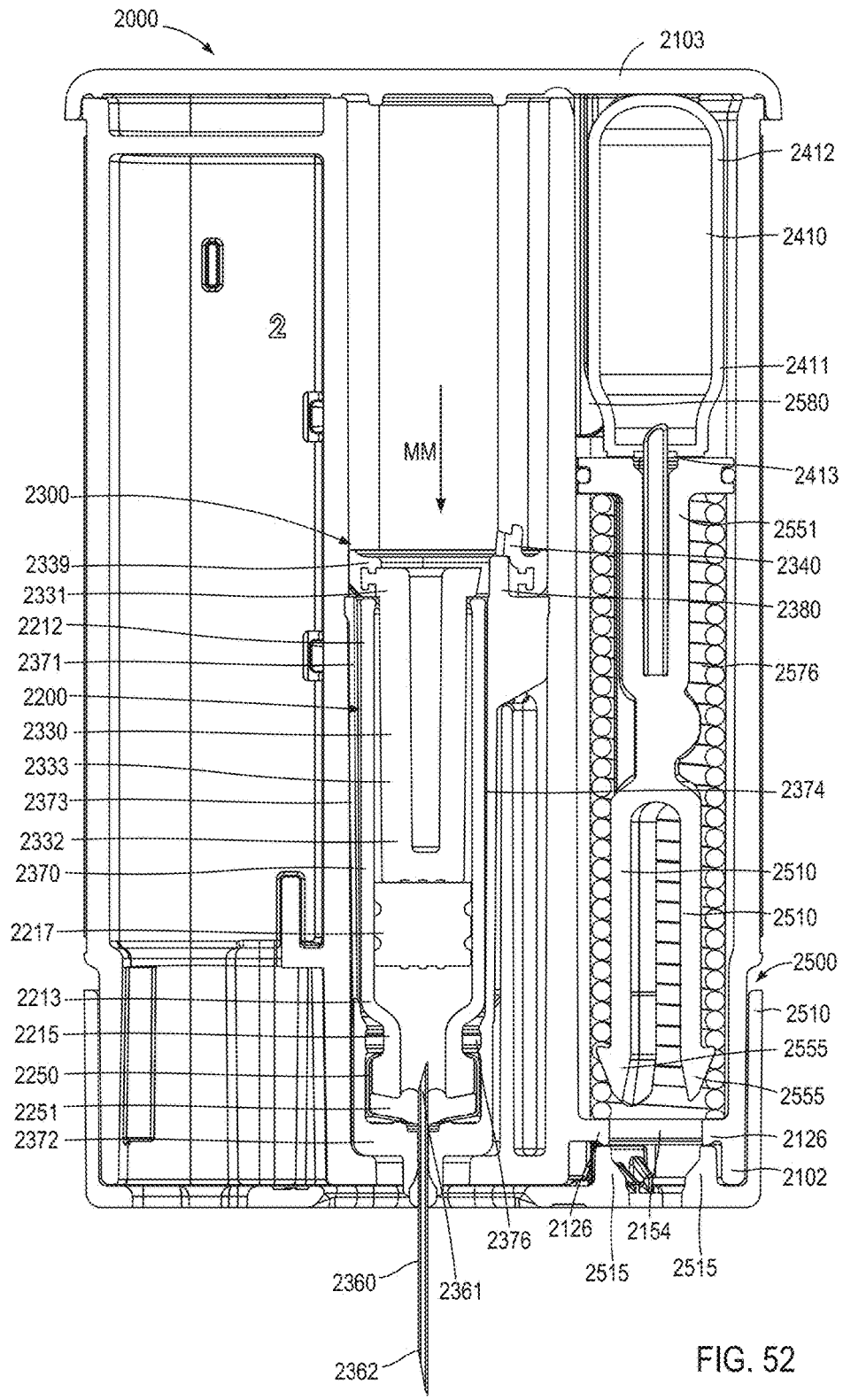
FIG. 52 is a cross-sectional view of the medicament delivery device illustrated in FIG. 4 in a sixth configuration (i.e., the injection configuration), taken along the line $X_7$-$X_7$ in FIG. 46.

The movement of the movable member 2330 in response to the increase in pressure within the gas chamber, however, increases the volume of the gas chamber. Similarly, in some instances, the increase in pressure within the gas chamber can exert a force on the release member 2550 that is sufficient to move the release member 2550 in the distal direction which in turn, compresses the spring 2576 disposed about the release member 2550 to a substantially solid configuration (e.g., completely compressed). Thus, the movement of the release member 2550 in response to the increase in the pressure within the gas chamber also increases the volume of the gas chamber. As a result, pressure within the gas chamber decreases as the volume of the gas chamber increases in response to the movement of the movable member 2330 and the release member 2550 (e.g., as determined and/or approximated by the ideal gas law expressed as $P_1V_1=P_2V_2$, described above). Thus, the force exerted by the expansion of the gas on the movable member 2330 decreases from a first amount at the start of an injection event to a second amount at the end of an injection event (i.e., the sixth configuration as shown in FIG. 52).

For example, in some embodiments, the force exerted on the movable member 2330 at the start of the injection event can be between about 30 pounds-force ($lb_f$) and about 38 $lb_f$, and the force exerted on the movable member 2330 at the end of the injection event (e.g., immediately after the dose of the naloxone composition 2220 is delivered through the needle 2360) can be between about 23 $lb_f$ and about 31 $lb_f$, respectively. More specifically, in this embodiment, the pressure within the gas chamber at the start of the injection event (assuming a negligible time of gas expansion and distribution) is about 160 psi, which corresponds to about 34 $lb_f$ exerted on the movable member 2330, and the pressure within the gas chamber at the end of the injection event is about 130 psi, which corresponds to about 27 $lb_f$. In some embodiments, the force exerted on the movable member 2330 can decrease in a substantially linear manner from the first amount at the start of the injection event to the second amount at the end of the injection event. In other embodiments, the decrease in the force can be non-linear, exponential, and/or logarithmic over the duration of the injection event.

Similarly, the movable member 2330 transmits at least a portion of the force exerted by the expansion of the gas to the elastomeric member 2217 disposed within the medicament container 2200, thereby increasing a pressure within the medicament container 2200 between the elastomeric member 2217 and the seal 2251. More specifically, in some embodiments, at least a portion of the naloxone composition 2220 can be, for example, an incompressible fluid. Thus, the force exerted by the movable member 2330 on the elastomeric member 2217 places the naloxone composition 2220 under pressure within the medicament container 2200. In some embodiments, the pressure within the medicament container 2200 can be between about 525 psi and about 670 psi at the start of the injection event, and between about 400 psi and about 545 psi at the end of the injection event. Specifically, in this embodiment, the pressure within the medicament container 2200 in response to the movable member 2330 exerting a force on the elastomeric member 2217 is about 600 psi at the start of the injection event and the pressure within the medicament container 2200 is about 490 psi at the end of the injection event.

Figure 50:
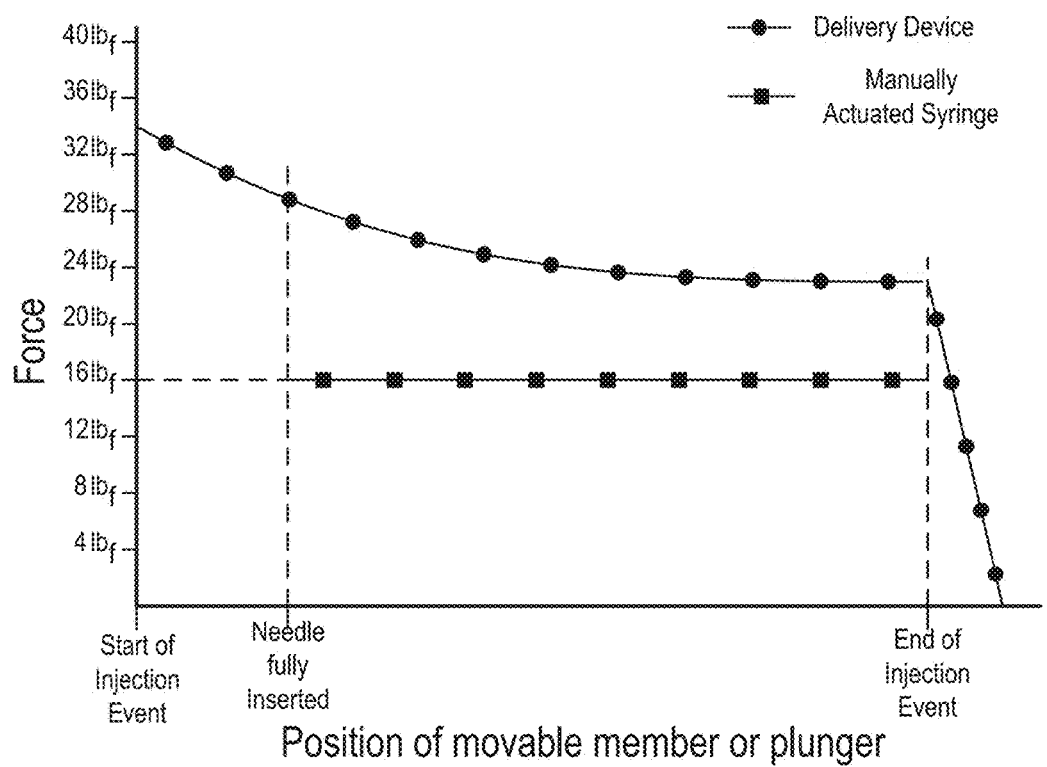
FIG. 50 is a graph illustrating a relationship between a force and a time of an injection event of the delivery device illustrated in FIG. 4.

FIG. 50 shows a representative graph of the force exerted on the movable member 2330 by the gas pressure within the gas chamber as a function of position of the movable member 2330 (as calculated using nominal dimensional specifications with the gas container 2410 having a volume of about 0.0625 in$^3$ and a pressure of about 1100 psi). As discussed above, the force is proportional to the pressure within the medicament container 2200 (i.e., the injection pressure). As shown, the graph illustrates the decrease in the force exerted on the movable member 2330 during an injection event resulting from the increased volume of the gas chamber, as described herein. This graph also includes representative data for the average amount of force that can be exerted on a plunger of a manually-actuated syringe by a user's thumb. In particular, as described in the Experimental Study entitled, "A Biomedical Evaluation of the Epidural Neurolysis Procedure," published in 2012 in the 15th edition of the *Pain Physician Journal*, the thumb force applied by orthopedic surgeons on a plunger of a manually actuated syringe was about 16 lb$_f$ (with a range of between about 9 lb$_f$ and about 22.5 lb$_f$). Although this thumb force data is not actual data taken in connection with a manually-actuated syringe containing a naloxone formulation, it nevertheless provides an illustration of the dynamic differences between injection via the device 2000 and a manually-actuated syringe. In particular, the thumb force exerted on a plunger of a manually-actuated syringe is generally constant from the start of an injection event to the end of the injection event. Moreover, the thumb force is applied independently from any force for inserting the needle.

In contrast, as described herein, the system actuation assembly 2500, the medicament delivery mechanism 2300 and/or the drug product 2000 includes a single energy storage member that produces a force that both inserts the needle and injects the naloxone formulation. Thus, the desired characteristics of the needle insertion for the drug product 2000 can affect the characteristics of the drug delivery. In other words, increasing the force applied to the movable member 2330 to decrease the needle insertion time and/or to produce a more repeatable needle insertion can result in faster initial delivery of the naloxone (due to the increased force at the beginning of injection). Conversely, decreasing the force to reduce the rate of naloxone delivery (e.g., in an effort to reduce the rate of system absorption and/or adjust a PK characteristics of a delivery of the naloxone composition 2220) can impact the needle insertion performance of the drug product 2000, the repeatability with which the seal 2251 is punctured to establish fluid communication between the needle 2360 and the medicament container 2200, and the like. Thus, in some embodiments, the drug product 2000 is configured to produce certain desired performance characteristics during the delivery of the naloxone composition 2220. Such characteristics can include, for example, a minimum time for insertion of the needle 2360, a repeatable needle insertion depth, a consistent delivery volume, and the like.

In some embodiments, the specific characteristics of, for example, the housing 2100, the energy storage member 2410, the movable member 2330, the medicament container 2200, and/or the needle 2360 are such that the naloxone composition 2220 is delivered from the medicament container 2200 and into the body of the patient with at least one pharmacokinetic (PK) parameter of the naloxone composition is bioequivalent to the corresponding PK parameter resulting from the delivery of a corresponding dose of a corresponding naloxone formulation via a manually-actuated syringe. Similarly stated, the delivery device 2000 (or drug product) is configured such that delivery of the naloxone composition 2220 from the medicament container 2200 to the body produces naloxone bioavailability that is bioequivalent to naloxone bioavailability resulting from the delivery of a corresponding naloxone formulation from a manually actuated syringe, as described in further detail herein.

For example, in some instances, the relatively high pressure at which the compressed gas is stored within the gas container 2410 prior to being actuated and/or the relatively high pressure within the gas chamber resulting from the expansion of the gas as it exits the gas chamber 2410 can be such the delivery of the naloxone composition 2220 resulting from the injection event achieves bioequivalent PK characteristics of a delivery of the naloxone composition 2220 otherwise resulting from a delivery of the naloxone composition 2220 via a manually actuated syringe. For example, in some embodiments, a dose of the naloxone composition 2220 can be delivered into a body such that the 90% confidence interval of at least one of the relative mean maximum naloxone plasma concentration after the dose is delivered into the body ($C_{max}$), time to reach the maximum naloxone plasma concentration ($T_{max}$), area under the plasma concentration-time curve from pre-dose (time 0) extrapolated to infinity ($AUC_{0-\infty}$), or area under the plasma concentration-time curve from pre-dose (time 0) to the time of the last quantifiable concentration ($T_{last}$) ($AUC_{0-t}$) of the delivered dose to a delivered dose of a corresponding naloxone composition delivered via a manually-actuated syringe is within 80% to 125%. In some embodiments, a dose of the naloxone composition 2220 can be delivered into a body such that the 90% confidence interval of at least one of the relative mean maximum naloxone plasma concentration after the dose is delivered into the body ($C_{max}$), time to reach the maximum naloxone plasma concentration ($T_{max}$), area under the plasma concentration-time curve from pre-dose (time 0) extrapolated to infinity ($AUC_{0-\infty}$), or area under the plasma concentration-time curve from pre-dose (time 0) to the time of the last quantifiable concentration ($T_{last}$) ($AUC_{0-t}$) of the delivered dose to a delivered dose of a corresponding naloxone composition delivered via a manually-actuated syringe is within 100% to 125%. In some embodiments, a dose of the naloxone composition 2220 can be delivered into a body such that the 90% confidence interval of at least one of the relative mean maximum naloxone plasma concentration after the dose is delivered into the body ($C_{max}$), time to reach the maximum naloxone plasma concentration ($T_{max}$), area under the plasma concentration-time curve from pre-dose (time 0) extrapolated to infinity ($AUC_{0-\infty}$), or area under the plasma concentration-time curve from pre-dose (time 0) to the time of the last quantifiable concentration ($T_{last}$) ($AUC_{0-t}$) of the delivered dose to a delivered dose of a corresponding naloxone composition delivered via a manually-actuated syringe is within 110% to 125%. In some embodiments, a dose of the naloxone composition 2220 can be delivered into a body such that the 90% confidence interval of at least one of the relative mean maximum naloxone plasma concentration after the dose is delivered into the body ($C_{max}$), time to reach the maximum naloxone plasma concentration ($T_{max}$), area under the plasma concentration-time curve from pre-dose (time 0) extrapolated to infinity ($AUC_{0-\infty}$), or area under the plasma concentration-time curve from pre-dose (time 0) to the time of the last quantifiable concentration ($T_{last}$) ($AUC_{0-t}$) of the delivered dose to a delivered dose of a corresponding naloxone composition delivered via a manually-actuated syringe is within 115% to 125%. In other words, the delivery of the naloxone composition 2220 via the delivery device 2000 is substantially bioequivalent to the delivery of the same naloxone composition 2220 via a manually actuated syringe.

Figure 53:
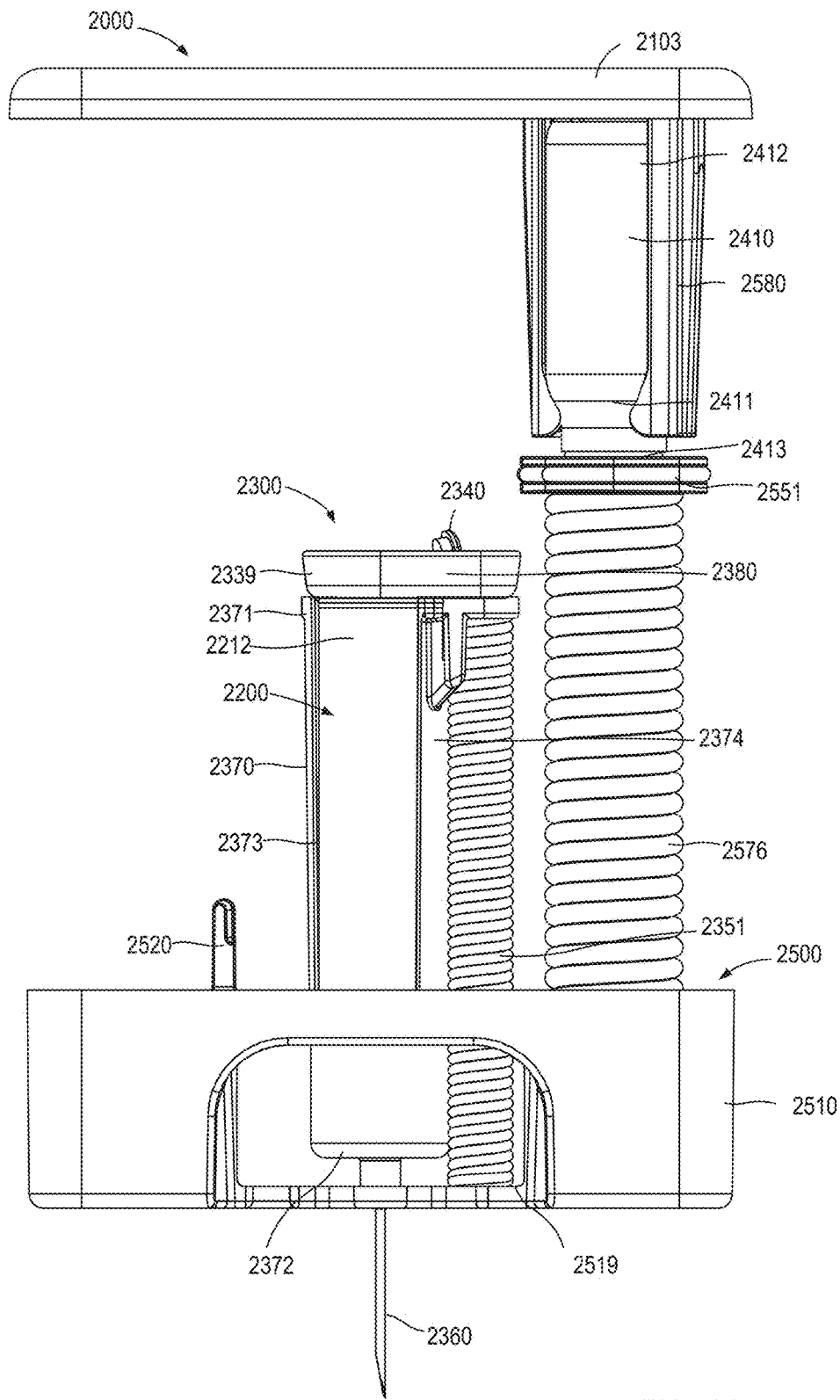
FIG. 53 is a front view of a portion of the medicament delivery device illustrated in FIG. 4 in the sixth configuration (i.e., the injection configuration).
Figure 54:
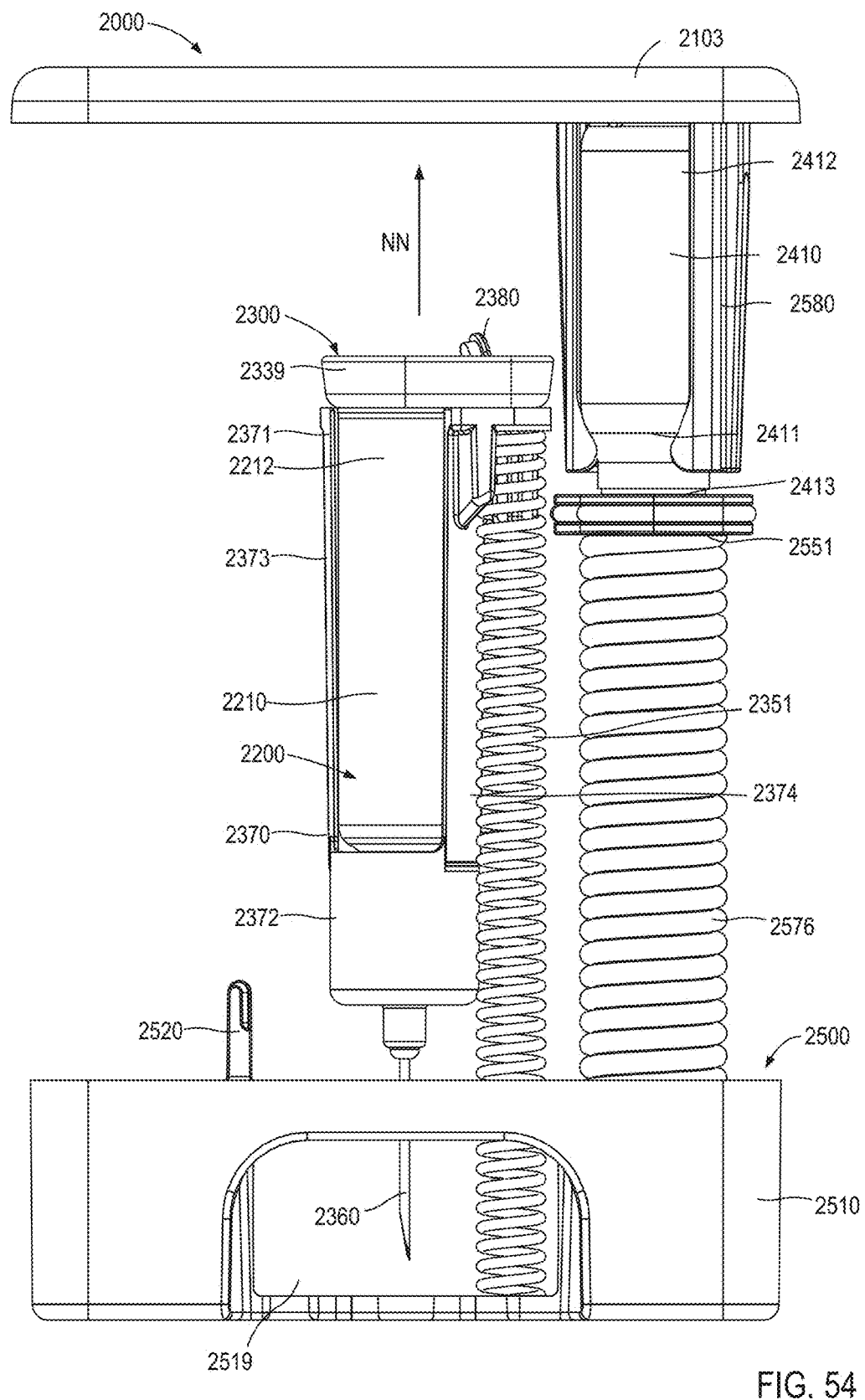
FIG. 54 is a front view of the medicament delivery device illustrated in FIG. 4 in a seventh configuration (i.e., the retraction configuration).

As shown in FIGS. 53 and 54, after the movable member 2330 moves a predetermined distance within the medicament container 2200, the gas valve actuator 2380 of the carrier 2370 engages the gas relief valve 2340 (FIG. 54) of the movable member 2330 thereby allowing the pressurized gas contained within the gas chamber to escape the gas chamber. Similarly stated, the gas valve actuator 2380 of the carrier 2370 engages the gas relief valve 2340 of the movable member 2330, thereby allowing the pressurized gas contained in the gas chamber and/or on the proximal side of the seal member 2339 to pass through the gas relief valve 2340 to be disposed on a distal side of the seal member 2340. Thus, the pressure within the gas chamber (i.e., on the proximal side of the seal member 2339 is reduced, thereby ending the injection event. In some embodiments, the pre-injection distance between the proximal end portion of the movable member 2330 and the gas valve actuator 2380 of the carrier 2370 can be adjusted to control the amount and/or the delivered volume of the naloxone composition 2220 to be injected and/or control a point in time during the injection event at which the gas relief valve 2340 is transitioned to an open state. After the gas pressure within the medicament cavity 2139 decreases below a certain level, the force exerted by the retraction spring 2351 on the carrier 2370 can be sufficient to overcome any residual pressure within the gas chamber and thus, the carrier 2370 is moved proximally within the housing 2100 (i.e., to retract), as shown by the arrow NN in FIG. 54. Moreover, as shown, the retraction of the carrier 2370 moves the needle 2360 in the proximal direction such that substantially the entire needle 2360 is disposed in a proximal position relative to the distal surface 2523 of the base 2510. Thus, the risk of accidental needle sticks and/or the like after the delivery of the naloxone composition 2220 to the body of the patient is reduced or substantially eliminated.

Figure 55:
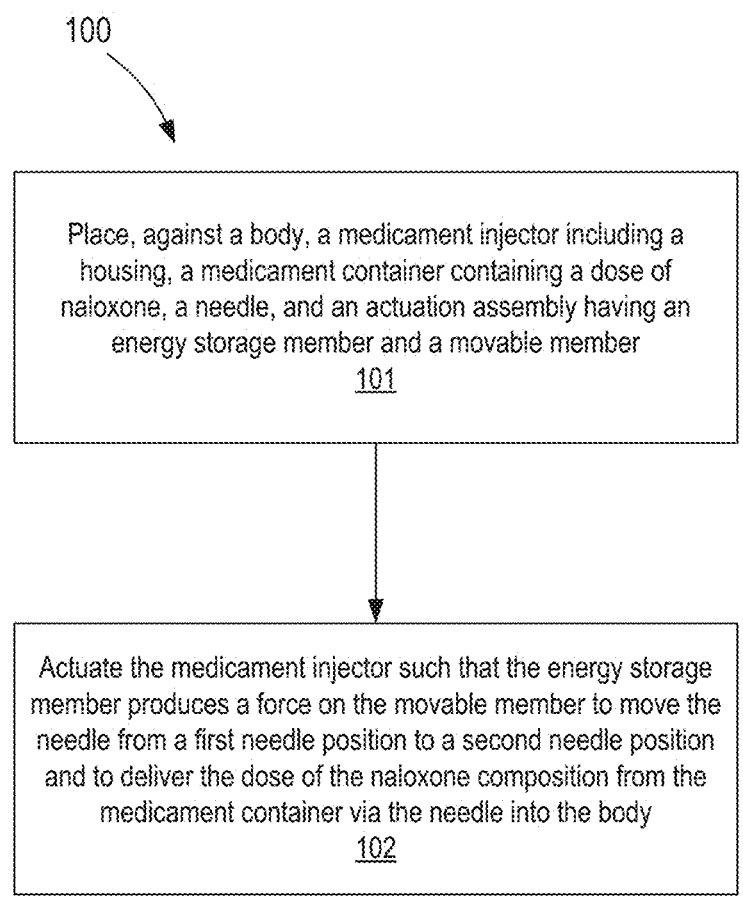
FIG. 55 is a flowchart illustrating a method of delivering an opioid antagonist to a body according to an embodiment.

Referring now to FIG. 55, a flowchart is illustrated describing a method of using a delivery device to deliver a naloxone composition to a patient according to an embodiment. For example, a method 100 includes placing a medicament injector against a body, at 101. The medical injector can be, for example substantially similar to and/or the same as the delivery device 1000 and/or 2000 described herein. Thus, the medical injector includes a housing, a medicament container, a needle, and an actuation assembly. The medicament container contains and/or stores a dose of the naloxone composition, such as those described herein, having a delivered volume of at least about 0.34 ml. In other embodiments, the dose of the naloxone composition can have any suitable delivered volume and/or fill volume such as, for example, a volume between about 0.3 ml and about 2.0 ml. The needle is configured to be moved between a first needle position and a second needle position. In some embodiments, the first needle position can be such that substantially the entire needle is disposed within, for example, the housing and fluidically isolated from the medicament container. In some embodiments, the second needle position can be such that a portion of the needle extends in a distal direction from the housing and a lumen defined by the needle is placed in fluid communication with the medicament container. The actuator assembly includes an energy storage member, such as the gas container 2410 described above, and a movable member, such as the movable member 2330 described above.

The medicament injector is actuated such that the energy storage member produces a force on the movable member to move the needle from a first needle position to a second needle position to deliver the dose of the naloxone composition from the medicament container via the needle into the body, at 102. As described above with reference to the delivery device 2000, the naloxone composition can be delivered in a manner such that the 90% confidence interval of at least one of the relative mean maximum naloxone plasma concentration after the dose is delivered into the body ($C_{max}$), time to reach the maximum naloxone plasma concentration ($T_{max}$), area under the plasma concentration-time curve from pre-dose (time 0) extrapolated to infinity ($AUC_{0-\infty}$), or area under the plasma concentration-time curve from pre-dose (time 0) to the time of the last quantifiable concentration ($T_{last}$) ($AUC_{0-t}$) of the delivered dose to a delivered dose of a corresponding naloxone composition delivered via a manually-actuated syringe is within 80% to 125%. In some embodiments, the naloxone composition can be delivered in a manner such that the 90% confidence interval of at least one of the relative mean maximum naloxone plasma concentration after the dose is delivered into the body ($C_{max}$), time to reach the maximum naloxone plasma concentration ($T_{max}$), area under the plasma concentration-time curve from pre-dose (time 0) extrapolated to infinity ($AUC_{0-\infty}$), or area under the plasma concentration-time curve from pre-dose (time 0) to the time of the last quantifiable concentration ($T_{last}$) ($AUC_{0-t}$) of the delivered dose to a delivered dose of a corresponding naloxone composition delivered via a manually-actuated syringe is within 100% to 125%. In some embodiments, the naloxone composition can be delivered in a manner such that the 90% confidence interval of at least one of the relative mean maximum naloxone plasma concentration after the dose is delivered into the body ($C_{max}$), time to reach the maximum naloxone plasma concentration ($T_{max}$), area under the plasma concentration-time curve from pre-dose (time 0) extrapolated to infinity ($AUC_{0-\infty}$), or area under the plasma concentration-time curve from pre-dose (time 0) to the time of the last quantifiable concentration ($T_{last}$) ($AUC_{0-t}$) of the delivered dose to a delivered dose of a corresponding naloxone composition delivered via a manually-actuated syringe is within 110% to 125%. In some embodiments, the naloxone composition can be delivered in a manner such that the 90% confidence interval of at least one of the relative mean maximum naloxone plasma concentration after the dose is delivered into the body ($C_{max}$), time to reach the maximum naloxone plasma concentration ($T_{max}$), area under the plasma concentration-time curve from pre-dose (time 0) extrapolated to infinity ($AUC_{0-\infty}$), or area under the plasma concentration-time curve from pre-dose (time 0) to the time of the last quantifiable concentration ($T_{last}$) ($AUC_{0-t}$) of the delivered dose to a delivered dose of a corresponding naloxone composition delivered via a manually-actuated syringe is within 115% to 125%. Thus, in some embodiments, the delivery of the naloxone composition via the medical injector can be substantially bioequivalent to a delivery of the naloxone composition (e.g., substantially the same dose) via the manually actuated syringe.

Figure 56:
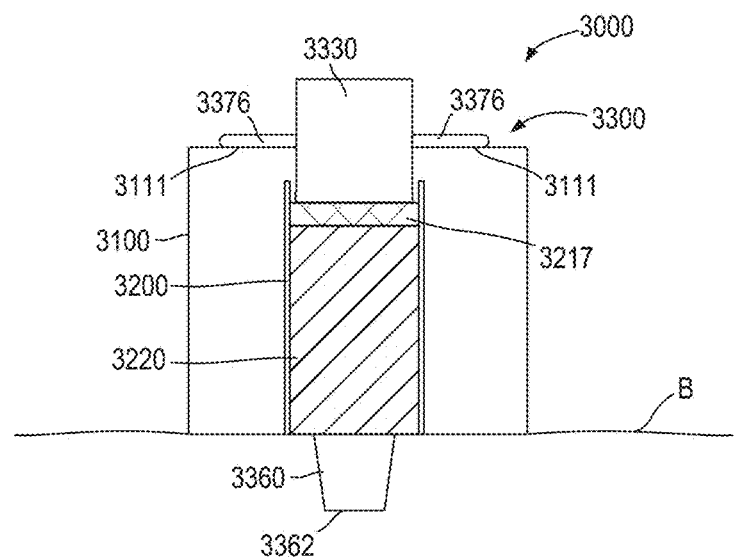
FIGS. 56 and 57 are schematic illustrations of a medicament delivery device according to an embodiment, in a first and a second configuration, respectively.
Figure 57:
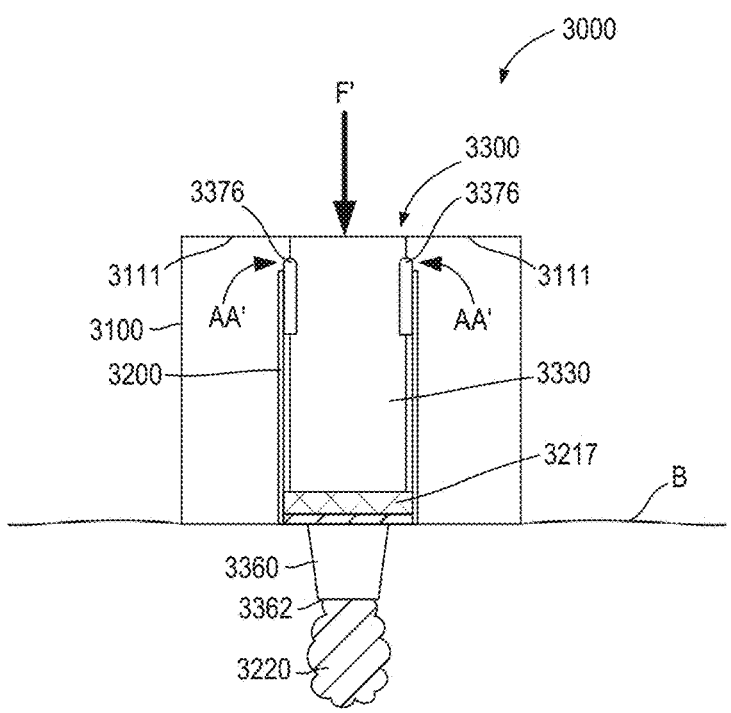

Although the devices described above, such as the medicament delivery device 2000, deliver the naloxone composition via a needle (e.g., needle 2360), in other embodiments, a device can deliver a naloxone composition via any suitable delivery member. Such delivery members can include, for example, a delivery nozzle (e.g., for a jet injection device, nasal spray delivery device or the like). For example, FIGS. 56 and 57 are schematic illustrations of a medicament delivery device 3000 according to an embodiment in a first and a second configuration, respectively. The medicament delivery device 3000 (also referred to herein as "delivery device" or a "drug product") includes a housing 3100, a medicament container 3200, a delivery member 3360, and a medicament delivery assembly 3300. The housing 3100 can be any suitable size, shape, or configuration and can be made of any suitable material. For example, in some embodiments, the housing 3100 is an assembly of multiple parts formed from a plastic material that are coupled together to form a substantially rectangular shape when assembled. As described in more detail below, the housing 3100 includes shoulders 3111 that engage and/or contact a portion of the medicament delivery assembly 3300.

As shown in FIGS. 56-57, the medicament container 3200 is disposed within the housing 3100, and can be any container suitable for storing the medicament. In some embodiments, the medicament container 3200 can be, for example, a vial, cartridge, ampule, prefilled syringe or the like formed from a biocompatible material such as, for example, a pharmaceutical grade metal or alloy, glass, polymer, ceramic, and/or the like. The medicament container 3200 can have, for example, a proximal end portion and a distal end portion and can define an inner volume.

The inner volume of the medicament container 3200 can include, receive, and/or otherwise contain (i.e., is filled or partially filled with) a medicament 3220 such as, for example, an opioid antagonist. More specifically, in some embodiments, the medicament 3220 disposed within the medicament container 3200 can be a naloxone composition such as those described herein. For example, the naloxone composition can include an effective amount of naloxone (i.e., 4,5-epoxy-3,14-dihydroxy-17-(2-propenyl) morphinan-6-one), or a pharmaceutically acceptable salt and/or ester thereof. In some embodiments, the naloxone composition can include one or more pH-adjusting agents (e.g., at least one of hydrochloric acid, citric acid, acetic acid, phosphoric acid, or combinations thereof), one or more tonicity-adjusting agents (e.g., at least one of dextrose, glycerin, mannitol, potassium chloride, sodium chloride, or combinations thereof), one or more stabilizing agents, and/or the like. In some embodiments, the naloxone composition can have an osmolality between about 250 to about 350 mOsm and a pH between about 3 to about 5.

The medicament container 3200 includes an elastomeric member 3217 (also referred to herein as a "plunger") formulated to be compatible with the medicament housed within the medicament container 3200 (i.e., the naloxone composition). Similarly stated, the elastomeric member 3217 is formulated to minimize any reduction in the efficacy of the medicament 3220 that may result from contact (either direct or indirect) between the elastomeric member 3217 and the medicament 3220. For example, in some embodiments, the elastomeric member 3217 can be formulated to minimize any leaching or out-gassing of compositions that may have an undesired effect on the medicament 3220. The elastomeric member is disposed within the medicament container 3200, for example, to seal the proximal end portion thereof. In some embodiments, the elastomeric member 3217 can be formulated to maintain its chemical stability, flexibility, and/or sealing properties when in contact (either direct or indirect) with a medicament 3220 over a long period of time (e.g., for up to six months, one year, two years, five years, or longer). In some embodiments, the elastomeric member 3217 can be any of the elastomeric members shown and described in U.S. Pat. No. 8,627,816 entitled "Medicament Delivery Device for Administration of Opioid Antagonists Including Formulations for Naloxone," which is incorporated herein by reference in its entirety.

The delivery member 3360 is configured to be placed in fluid communication with the interior of the medicament container 3200, and provides a pathway through which the medicament (e.g., the naloxone composition) 3220 can be conveyed. A distal end portion 3362 of the delivery member 3360 is disposed outside of the housing 3100, and is configured be disposed within, engage and/or otherwise interact with a portion of the body B. In this manner, the medicament 3220 can be delivered from the medicament container 3200 into the body B via the distal end portion 3362 of the delivery member 3360.

The delivery member 3360 can be any suitable structure for delivering the medicament 3220, in conjunction with the medicament delivery assembly 3300, in a manner that provides a desired set of delivery and/or pharmacokinetic (PK) characteristics. In some embodiments, for example, the delivery member 3360 can be a nozzle and/or atomizer through which the medicament 3220 can be delivered intranasally or intraorally. In other embodiments, the delivery member 3360 can be a nozzle through which the medicament 3220 can be delivered via a jet injection process. In yet other embodiments, the delivery member 3360 can be a needle of the types shown and described herein.

The delivery member 3360 can be any suitable shape, size, or configuration. For example, in some embodiments, the delivery member 3360 is a needle having any diameter and/or length to facilitate the delivery of the medicament 3220 (i.e., the naloxone composition). In other embodiments, the delivery member 3360 can be a nozzle and/or atomizer having a diverging flow area configured to produce a spray having a desired droplet size. In yet other embodiments, the delivery member 3360 can be a mouthpiece having an engagement portion configured to facilitate delivery of the medicament 3220 via inhalation. Although the delivery member 3360 is show in FIGS. 56 and 57 as being in a fixed position within the housing 3100, in other embodiments, the delivery member 3360 can be movable within the housing 3100, as described herein.

The medicament delivery assembly 3300 can be any suitable assembly, mechanism, and/or device that can transfer a force to the elastomeric member 3217 to deliver a dose of the medicament 3220 (e.g., naloxone), as described herein. As shown in FIGS. 56 and 57, the medicament delivery assembly 3300 includes a movable member 3330 having a deformable portion 3376 (although two distinct deformable portions are shown, in other embodiments, the movable member 3330 can include only one, contiguous deformable portion). The movable member 3330 is movably disposed within the housing 3100 such that, a distal portion of the movable member 3330 is in contact with the elastomeric member 3217. In this manner, a force F' can be exerted by the movable member 3330 to move the elastomeric member 3217, thereby delivering the medicament 3220.

The force F' can be produced in any suitable fashion. In some embodiments, the force F' can be produced by an energy storage member (not shown in FIGS. 56 and 57) of the types shown and described herein. Similarly stated, in some embodiments, the medicament delivery device 3000 can automatically produce the force F' that produces delivery of the medicament 3220. An "automatically produced" force is a force that is not directly produced by a human. Examples of automatic delivery devices include an apparatus having a compressed gas source to provide the delivery force, an apparatus having a spring to provide the delivery force, and an apparatus having an electric motor to provide the delivery force. An apparatus for automatically delivering a medicament, however, can include a manual actuator (e.g., an on/off switch, a push button, or the like) to initiate the "automatic" delivery. In other embodiments, the force F' can be produced manually, such as by a user directly depressing the movable member 3330 with sufficient force to deliver the medicament 3220.

In the event of a medical emergency associated with, for example, a patient experiencing an opioid overdose, a user (e.g., a patient, a friend or family member, an untrained bystander, a medical professional, etc.) can manipulate the delivery device 3000 to administer the medicament 3220 (e.g., an opioid antagonist such as any of the naloxone formulations described herein) to the patient. As shown in FIG. 57, the user can manipulate the delivery device 3000 to actuate the medicament delivery assembly 3300, for example, by placing at least a portion of the delivery device 3000 in contact with or adjacent a surface of the body B of the patient, and transitioning the delivery device 3000 to the second configuration. The delivery device 3000 can be actuated (or transitioned to its second configuration) by any suitable mechanism, such as, for example, by manually application of the force F' against the movable member 3330, by depressing a button disposed at a proximal end of the device, or the like.

Before actuation of the delivery device 3300 and before the force F' reaches a threshold value, the deformable portion 3376 is in contact with the shoulders 3111 of the housing to limit and/or prevent movement of the movable member 3330 within the medicament container 3200. As shown by the arrows AA' in FIG. 57, when the force F' exceeds a threshold value, at least a portion of the force F' exerted on the movable member 3330 can deform the deformable portion 3376 of the movable member 3330. Similarly stated, when the force F' exceeds a threshold value, the deformable portion 3376 can deform against the shoulders 3111 to move from a first configuration to a second configuration. With the deformable portion 3376 in the second configuration, the force F' can move the movable member 3330 relative to the medicament container 3200, as shown in FIG. 57. The movement of the movable member 3330 increases a pressure within a portion of the medicament container 3200 (for example, between the elastomeric member 3217 and a surface of the medicament container 3200 through which the delivery member 3360 extends) to expel the medicament 3220 from the medicament container 3200, as indicated in FIG. 57. Although described as including the elastomeric member 3217 that is distinct from the movable member 3330, in some embodiments, the movable member 3330 can be the elastomeric member 3217. In such embodiments, the force F' can act directly or indirectly on the elastomeric member 3217 to perform the functions described herein.

The arrangement of the delivery mechanism 3300, the movable member 3330 (including the deformable portion 3376), the delivery member 3360, and the composition of the medicament 3220 and/or any other suitable portion of the delivery device 3000 (or drug product) can be such that the medicament 3220, when delivered, provides a desired set of delivery and/or pharmacokinetic (PK) characteristics. In some embodiments, the specific characteristics of the delivery device 3000 (or drug product) are such that a dose of the medicament 3220 (i.e., the naloxone formulation) is delivered from the medicament container 3200 and into the body of the patient (as indicated by the spray in FIG. 57) such that at least one pharmacokinetic parameter of the naloxone composition is bioequivalent to the corresponding pharmacokinetic parameter resulting from the delivery of a corresponding dose of a corresponding naloxone formulation via a manually-actuated syringe. Similarly stated, the delivery device 3000 (or drug product) is configured such that delivery of the medicament 3220 (i.e., the naloxone formulation) from the medicament container 3200 to the body provides naloxone bioavailability that is bioequivalent to naloxone bioavailability resulting from the delivery of a corresponding naloxone formulation from a manually actuated syringe. In some embodiments, the medicament delivery assembly 3300 is configured to deliver the dose of the medicament 3220 (i.e., the naloxone formulation) into the body such that the 90% confidence interval of at least one of the relative mean maximum naloxone plasma concentration after the dose is delivered into the body ($C_{max}$), time to reach the maximum naloxone plasma concentration ($T_{max}$), area under the plasma concentration-time curve from pre-dose (time 0) extrapolated to infinity ($AUC_{0-\infty}$), or area under the plasma concentration-time curve from pre-dose (time 0) to the time of the last quantifiable concentration ($T_{last}$) ($AUC_{0-t}$) of the delivered dose to a delivered dose of a corresponding naloxone composition delivered via a manually-actuated syringe is within 80% to 325%.

In yet other embodiments, the specific characteristics of the delivery device 3000 (or drug product) are such that a dose of the medicament 3220 (i.e., the naloxone formulation) is delivered from the medicament container 3200 and into the body of the patient such that the 90% confidence interval of at least one of the relative mean maximum naloxone plasma concentration after the dose is delivered into the body ($C_{max}$), time to reach the maximum naloxone plasma concentration ($T_{max}$), area under the plasma concentration-time curve from pre-dose (time 0) extrapolated to infinity ($AUC_{0-\infty}$), or area under the plasma concentration-time curve from pre-dose (time 0) to the time of the last quantifiable concentration ($T_{last}$) ($AUC_{0-t}$) of the delivered dose to a delivered dose of a corresponding naloxone composition delivered via a manually-actuated syringe is within 80% to 325%.

For example, in some embodiments, the medicament delivery assembly 3300 is configured to deliver a dose of the naloxone composition (i.e., any of the naloxone compositions described herein) having a delivered volume of at least about 0.34 ml at a faster delivery rate and/or at a higher delivery pressure than would result from the delivery of a corresponding dose via a manually-actuated syringe.

In such embodiments, the arrangement of the housing 3100 (e.g., the shoulders 3111) and the deformable portion 3376 can be such that the force F' exerted on the movable member 3330 decreases from a first amount at the start of a delivery event to a second amount at the end of the delivery event. In some embodiments, the force exerted on the movable member 3330 can decrease as a function of how the deformable portions 3376 are moved in response to the force F'. The decrease in the force can be, for example, linear, non-linear, exponential, and/or logarithmic over the duration of the delivery event. In contrast, as described above, a force exerted on a plunger of a manually-actuated syringe that is devoid of any deformable portions (such as the deformable portion 3376) can be substantially constant throughout the stroke of the syringe. As described herein, even when delivered with a different delivery and/or force profile, the delivery device 3000 (or drug product) delivers the dose of the naloxone composition such that at least one pharmacokinetic parameter of the naloxone composition is bioequivalent to the corresponding pharmacokinetic parameter resulting from the delivery of a corresponding dose of a corresponding naloxone formulation via a manually-actuated syringe.

Although the movable member 3330 is shown and described above as including the deformable portion 3376, in other embodiments, any suitable portion of the medicament delivery assembly 3300 can include a deformable portion 3376 that limits movement of the movable member 3300 and/or the elastomeric member 3217 until a force above a threshold value is applied. For example, in some embodiments, the medicament delivery assembly 3300 can include a carrier having a protrusion, surface or the like that is configured to deform to allow movement of the movable member (similar to the ribbed portion 2376 of the carrier 2370 described above with reference to the device 2000).

In some embodiments, the delivery member 3360 can be a needle, and the movable member 3330 is configured to move the needle from a first needle position to a second needle position before the deformation of the deformable portion 3376. In such embodiments, a distal end portion of the needle can be disposed outside of the housing when the needle is in the second needle position.

Although the force F' is described as being produced manually, in some embodiments, the medicament delivery device includes an energy storage member configured to produce the force on the movable member.

In some embodiments, the medicament delivery assembly 3300 is configured to deliver the dose in less than about two seconds. In some embodiments, the medicament delivery assembly 3300 is configured to deliver the dose in less than about 0.5 seconds.

Figure 58:
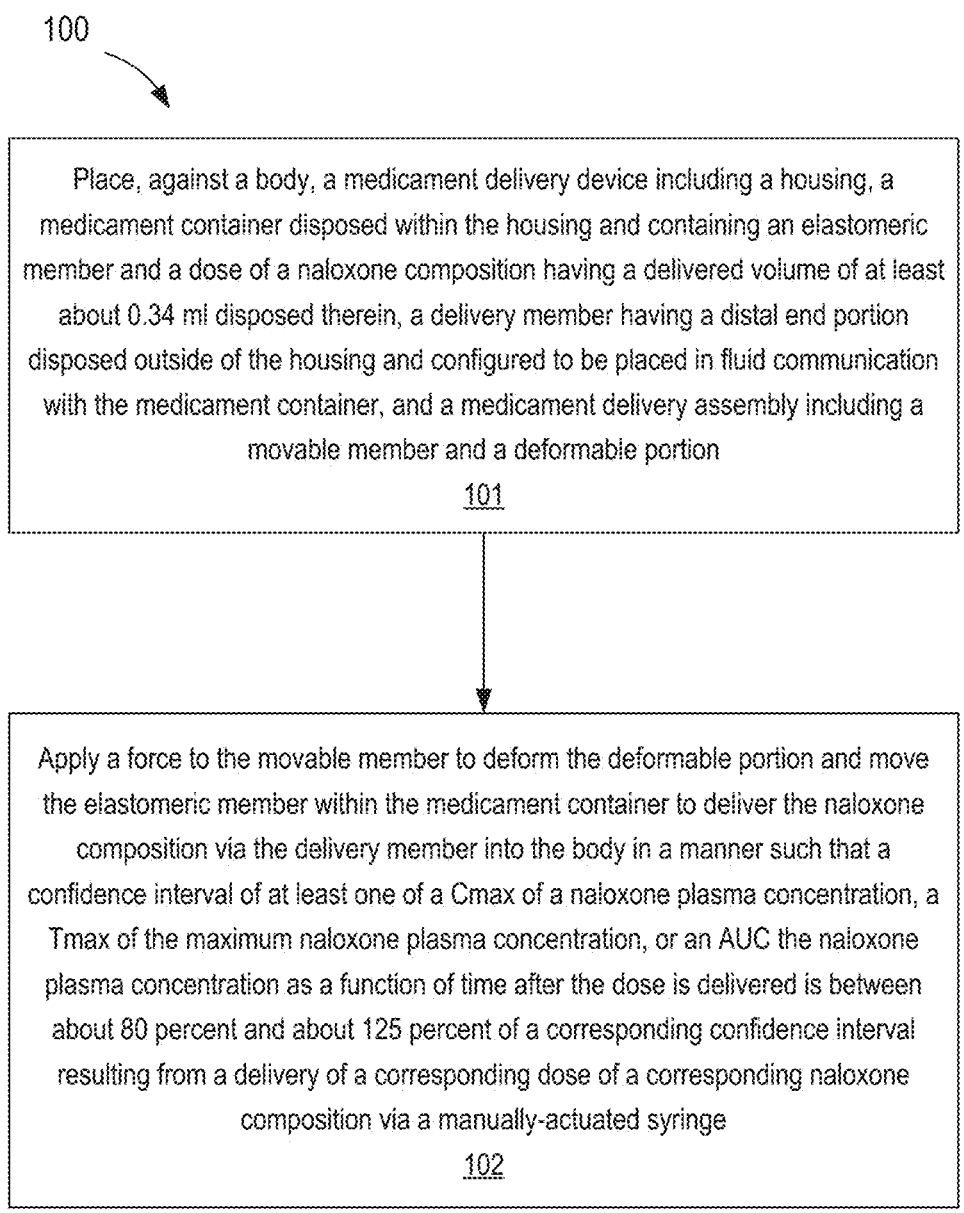
FIG. 58 is a flowchart illustrating a method of delivering an opioid antagonist to a body according to an embodiment.
Figure 59:
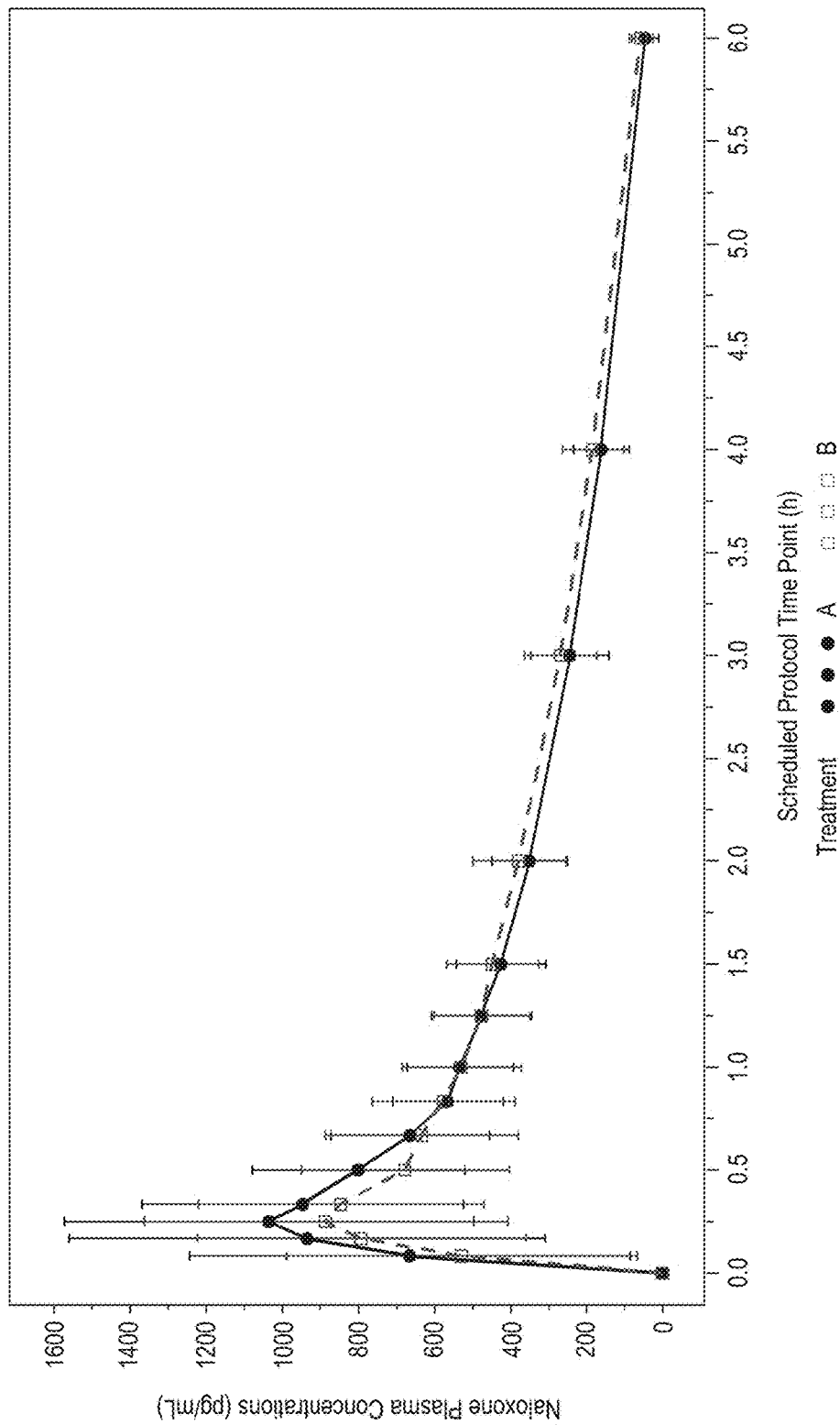
FIG. 59 is a graph illustrating the mean plasma-time concentration profile for naloxone plasma concentration data on a linear scale.

Referring now to FIG. 58, a flowchart is illustrated describing a method of using a delivery device to deliver a naloxone composition to a patient according to an embodiment. For example, a method 110 includes placing a medicament delivery device against a body, at 111. The medicament delivery device can be, for example substantially similar to and/or the same as the delivery device 2000 and/or 3000 described herein. Thus, the medicament delivery device includes a housing, a medicament container, a delivery member, and a medicament delivery assembly. The medicament container contains and/or stores a dose of the naloxone composition, such as those described herein, having a delivered volume of at least about 0.34 ml. In other embodiments, the dose of the naloxone composition can have any suitable delivered volume and/or fill volume such as, for example, a volume between about 0.3 ml and about 2.0 ml. The delivery member extends in a distal direction from the housing, and is configured to be placed in fluid communication with the medicament container. The medicament delivery assembly includes a movable member, such as the movable member 3330 described above, and a deformable portion. The deformable portion can a portion of the movable member 3330 or any other suitable portion of the medicament delivery assembly.

A force is applied to the movable member of the medicament delivery assembly to deform the deformable portion of the medicament delivery assembly and move an elastomeric member within the medicament container to deliver the naloxone composition via the delivery member, at 112. As described above with reference to the delivery device 3000, the naloxone composition can be delivered in a manner such that the 90% confidence interval of at least one of the relative mean maximum naloxone plasma concentration after the dose is delivered into the body ($C_{max}$), time to reach the maximum naloxone plasma concentration ($T_{max}$), area under the plasma concentration-time curve from pre-dose (time 0) extrapolated to infinity ($AUC_{0-\infty}$), or area under the plasma concentration-time curve from pre-dose (time 0) to the time of the last quantifiable concentration ($T_{last}$) ($AUC_{0-t}$) of the delivered dose to a delivered dose of a corresponding naloxone composition delivered via a manually-actuated syringe is within 80% to 125%. In some embodiments, the naloxone composition can be delivered in a manner such that the 90% confidence interval of at least one of the relative mean maximum naloxone plasma concentration after the dose is delivered into the body ($C_{max}$), time to reach the maximum naloxone plasma concentration ($T_{max}$), area under the plasma concentration-time curve from pre-dose (time 0) extrapolated to infinity ($AUC_{0-\infty}$), or area under the plasma concentration-time curve from pre-dose (time 0) to the time of the last quantifiable concentration ($T_{last}$) ($AUC_{0-t}$) of the delivered dose to a delivered dose of a corresponding naloxone composition delivered via a manually-actuated syringe is within 100% to 125%. In some embodiments, the naloxone composition can be delivered in a manner such that the 90% confidence interval of at least one of the relative mean maximum naloxone plasma concentration after the dose is delivered into the body ($C_{max}$), time to reach the maximum naloxone plasma concentration ($T_{max}$), area under the plasma concentration-time curve from pre-dose (time 0) extrapolated to infinity ($AUC_{0-\infty}$), or area under the plasma concentration-time curve from pre-dose (time 0) to the time of the last quantifiable concentration ($T_{last}$) ($AUC_{0-t}$) of the delivered dose to a delivered dose of a corresponding naloxone composition delivered via a manually-actuated syringe is within 110% to 125%. In some embodiments, the naloxone composition can be delivered in a manner such that the 90% confidence interval of at least one of the relative mean maximum naloxone plasma concentration after the dose is delivered into the body ($C_{max}$), time to reach the maximum naloxone plasma concentration ($T_{max}$), area under the plasma concentration-time curve from pre-dose (time 0) extrapolated to infinity ($AUC_{0-\infty}$), or area under the plasma concentration-time curve from pre-dose (time 0) to the time of the last quantifiable concentration ($T_{last}$) ($AUC_{0-t}$) of the delivered dose to a delivered dose of a corresponding naloxone composition delivered via a manually-actuated syringe is within 115% to 125%. Thus, in some embodiments, the delivery of the naloxone composition via the medicament delivery device can be substantially bioequivalent to a delivery of the naloxone composition (e.g., substantially the same dose) via the manually actuated syringe.

In some embodiments, the force can be manually applied to movable member. In other embodiments, the medicament delivery device includes an energy storage member configured to produce the force. In such embodiments, the force can be applied by actuating the energy storage member.

The embodiments described herein can be used with any suitable opioid antagonist such as, for example, naloxone compositions or a pharmaceutically acceptable salt thereof suitable for use in the medicament delivery devices disclosed herein. Such naloxone compositions can include any of the compositions described in U.S. Pat. No. 8,627,816 entitled "Medicament Delivery Device for Administration of Opioid Antagonists Including Formulations for Naloxone," which is incorporated herein by reference in its entirety. Accordingly, the present naloxone compositions may be adapted for various administration routes, depending on the apparatus in which such composition(s) are to be employed. For example, in some embodiments, the present compositions may be adapted for transmucosal administration as, e.g., a nasal spray, or alternatively as a sublingual or buccal spray. In other embodiments, the present naloxone compositions may be adapted for parenteral administration as, e.g., an injectable solution.

The present compositions generally comprise an effective amount of naloxone, i.e., 4,5-epoxy-3,14-dihydroxy-17-(2-propenyl) morphinan-6-one, or a pharmaceutically acceptable salt and/or ester thereof. As used herein, an "effective amount" is an amount sufficient to provide a desired therapeutic effect. For example, as described herein, the present naloxone compositions may be useful in treating respiratory depression and/or other indications associated with opioid toxicity. Accordingly, an effective amount of naloxone in the present compositions may be an amount sufficient to treat such respiratory depression and/or other indications associated with opioid toxicity. The present naloxone compositions typically have a concentration of 4,5-epoxy-3,14-dihydroxy-17-(2-propenyl)morphinan-6-one (or a salt and/or ester thereof) between about 0.01 mg/mL and about 10 mg/mL (e.g., between about 0.05 mg/mL and about 2 mg/mL, or any other value or range of values therein, including about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, about 1.0 mg/mL, about 1.1 mg/mL, about 1.2 mg/mL, about 1.3 mg/mL, about 1.4 mg/mL, about 1.5 mg/mL, about 1.6 mg/mL, about 1.7 mg/mL, about 1.8 mg/mL, or about 1.9 mg/mL).

In some embodiments, the present naloxone compositions comprise a pH-adjusting agent. In some embodiments, the pH-adjusting agent includes at least one of hydrochloric acid, citric acid, acetic acid, phosphoric acid, or combinations thereof. The pH-adjusting agent may comprise an organic and/or inorganic acid or salt thereof (e.g., alkali metal salts [Li, Na, K, etc.], alkaline earth metal [e.g., Ca, Mg, etc.] salts, ammonium salts, etc.). In other embodiments, the pH-adjusting agent includes mixtures of one or more acids and one or more salts thereof, e.g., citric acid and citrate salts, acetic acid and acetate salts, phosphoric acid and phosphate salts, etc. In certain embodiments, the pH-adjusting agent is added in an amount sufficient to provide a pH of the present naloxone compositions of from about 3 to about 5 (for example a pH of about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, or about 5.0). Accordingly, the present compositions may comprise naloxone salts of the pH-adjusting agent employed. For example, in one embodiment, the pH-adjusting agent is dilute aqueous hydrochloric acid, and the naloxone salt is naloxone HCl (e.g., 4,5-epoxy-3,14-dihydroxy-17-(2-propenyl)-morphinan-6-one hydrochloride).

Solvents suitable for use in the present compositions are not particularly limited, provided they are pharmaceutically acceptable. Accordingly, any pharmaceutically acceptable solvent in which the components of the present compositions are soluble, and which does not adversely affect the stability of the present compositions and/or the naloxone and/or naloxone salts contained therein may be employed. For example, in a typical composition, the solvent is sterile water (e.g., USP grade water for injection [WFI]).

In some embodiments, the present compositions may also comprise one or more tonicity-adjusting agents. For example, the tonicity-adjusting agent may include at least one of dextrose, glycerin, mannitol, potassium chloride, sodium chloride, or combinations thereof. The tonicity-adjusting agent(s) may be present in an amount of from about 0.1 mg/mL to about 50 mg/mL (e.g., including about 0.5 mg/mL, about 1.0 mg/mL, about 2.0 mg/mL, about 3.0 mg/mL, about 4.0 mg/mL, about 5.0 mg/mL, about 10 mg/mL, about 15 mg/mL, about 20 mg/mL, about 25 mg/mL, about 30 mg/mL, about 35 mg/mL, about 40 mg/mL, or about 45 mg/mL). In one embodiment, the tonicity-adjusting agent is sodium chloride, and the concentration thereof is between about 0.1 mg/mL and about 20 mg/mL. Generally, in naloxone compositions as described herein which are adapted for injection and/or intranasal delivery, tonicity-adjusting agents are added to provide a desired osmolality. In some embodiments, the osmolality of the naloxone compositions described herein is from about 250 to about 350 mOsm.

Because the naloxone compositions disclosed herein may be stored in the medicament container of the devices described herein for extended periods of time under varying storage conditions, in some embodiments the present compositions may further comprise stabilizers to prevent or inhibit decomposition of the naloxone during storage. Various types of pharmaceutically acceptable stabilizers can be used, including antioxidants (e.g. substituted phenols such as BHT, TBHQ, BHA, or propyl gallate; ascorbates such as ascorboyl palmitate, sodium ascorbate, ascorbic acid), complexing agents (e.g., cyclodextrins); or chelating agents such as EDTA (and its salts), D-gluconic acid δ-lactone, sodium or potassium gluconate, sodium triphosphate, and sodium hexametaphosphate.

Exemplary naloxone compositions suitable for use in the present invention are set forth in Table 1, below:

TABLE 1

Exemplary Naloxone Formulations.

| Lot | Initial WFI (g) | Order of Addition | API Added (mg) | API Mix Time (seconds) | NaCl Added (g) | NaCl Mix Time (seconds) | Initial pH | Adjusted pH | Final pH | Volume of pH Adjuster (mL) | Final Weight (g) |
|---|---|---|---|---|---|---|---|---|---|---|---|
| 1 | 400.01 | A | 554.73 | 110 | 4.5000 | 98 | 5.52 | 3.01 | 2.99 | 4.1 | 500.00 |
| 2 | 400.15 | B | 555.10 | 86 | 4.5269 | 69 | 5.41 | 6.51 | 6.51 | 0.5 | 502.14 |
| 3 | 400.13 | A | 554.95 | 104 | 4.5033 | 58 | 5.39 | 4.47 | 4.47 | 0.2 | 502.17 |
| 4 | 400.00 | B | 554.58 | 82 | 4.4999 | 87 | 5.37 | 3.01 | 3.01 | 4.0 | 502.15 |
| 5 | 399.99 | A | 554.59 | 85 | 4.5513 | 74 | 5.40 | 6.49 | 6.49 | 0.2 | 502.16 |
| 6 | 400.02 | B | 554.81 | 68 | 4.5020 | 70 | 5.45 | 4.50 | 4.49 | 0.2 | 502.19 |

Final Formulation Solution Density = 1.0043 g/mL (Determined during the formulation process for Lot 1)
Order of Addition:
A = Water, NaCl, naloxone hydrochloride, pH adjuster
B = Water, naloxone hydrochloride, NaCl, pH adjuster In some embodiments, a medicament delivery device such as those described herein can be configured to automatically deliver any of the naloxone compositions described herein. Similarly stated, in some embodiments, a medicament delivery device, after being actuated by the user, can automatically produce (i.e., produce without any further human intervention) a force or a range of forces to deliver the naloxone composition. In this manner, the force with which the naloxone composition is delivered is within a desired range, and is repeatable between different devices, users or the like. Moreover, the force and/or range of forces can deliver the naloxone composition into a portion of the body in such a manner that at least one PK parameter of the naloxone composition is bioequivalent to the corresponding PK parameter resulting from the delivery of a corresponding dose of a corresponding naloxone formulation via a manually-actuated syringe. Similarly stated, the delivery device (or drug product) is configured such that delivery of the naloxone composition into the body produces naloxone bioavailability that is bioequivalent to naloxone bioavailability resulting from the delivery of a corresponding naloxone formulation from a manually actuated syringe or the like.

While various embodiments have been described above, it should be understood that they have been presented by way of example only, and not limitation. Where schematics and/or embodiments described above indicate certain components arranged in certain orientations or positions, the arrangement of components may be modified. While the embodiments have been particularly shown and described, it will be understood that various changes in form and details may be made. Although various embodiments have been described as having particular features and/or combinations of components, other embodiments are possible having a combination of any features and/or components from any of embodiments as discussed above.

For example, the needles 1360 and 2360 described herein can have any diameter and/or length to facilitate the injection of the naloxone composition 1220 and 2220, respectively. For example, the needles 1360 and 2360 can have a length suitable to penetrate clothing and deliver the naloxone via a subcutaneous injection and/or an intramuscular injection. In some embodiments, the needles 1360 and 2360 can have a length of greater than 1 inch, greater than 1.5 inches, greater than 2 inches, greater than 2.5 inches or greater than 3 inches. In some embodiments, the needles 1360 and 2360 can have a lumen diameter of approximately between 19-gauge and 31-gauge.

In some embodiments, the outer surface 2815 of the needle sheath 2810 can include a cap or cover that has different material properties than the remainder of the needle sheath 2810. For example, in some embodiments, the outer surface 2815 can be constructed of a material having greater hardness and/or rigidity than the remainder of the needle sheath 2810. This arrangement allows for sufficient structural rigidity to assemble the needle sheath 2810 within the engagement portion 2720 of the safety lock 2700. In other embodiments, however, the needle sheath 2810 need not include an outer cover or cap. The use of a cap-less design can reduce manufacturing and/or assembly costs.

Although the devices 1000, 2000 and 3000 are specifically described above as being configured to deliver, for example, a naloxone composition, in other embodiments, the devices 1000, 2000 and/or 3000 can be configured to deliver any suitable medicament or therapeutic agent. In some embodiments, the medicament can be a vaccine, such as, for example, an influenza A vaccine, an influenza B vaccine, an influenza A (H1N1) vaccine, a hepatitis A vaccine, a hepatitis B vaccine, a haemophilus influenza Type B (HiB) vaccine, a measles vaccine, a mumps vaccine, a rubella vaccine, a polio vaccine, a human papilloma virus (HPV) vaccine, a tetanus vaccine, a diphtheria vaccine, a pertussis vaccine, a bubonic plague vaccine, a yellow fever vaccine, a cholera vaccine, a malaria vaccine, a smallpox vaccine, a pneumococcal vaccine, a rotavirus vaccine, a varicella vaccine, a rabies vaccine and/or a meningococcus vaccine. In yet other embodiments, the medicament can include peptide hormones such as insulin and glucagon, human growth hormone (HGH), erythropoiesis-stimulating agents (ESA) such as darbepoetin alfa, monoclonal antibodies such as denosumab and adalimumab, interferons, etanercept, pegfilgrastim, and other chronic therapies, or the like. In still other embodiments, the medicament can be a placebo substance (i.e., a substance with no active ingredients), such as water.

Although the delivery device 2000 is shown above as including a gas container 2410 that is actuated by a puncturer that moves within the housing 2100 with the release member 2550, in other embodiments a system actuation assembly 2500 can include a puncturer that is substantially fixed within the housing and a gas container that moves within the housing into contact with the puncturer upon actuation of the device.

Although the delivery devices 1000 and 2000 are shown and described above as being auto-injectors configured to deliver the naloxone compositions described herein via injection through a needle (e.g., the needle 1360 and the needle 2360, respectively), in other embodiments, a medicament delivery device can be configured to deliver the naloxone compositions described herein via any suitable delivery member, and in any suitable manner. For example, in some embodiments, a medicament delivery device can include a delivery member that delivers the naloxone composition into the body via inhalation and/or intranasal delivery, as shown, for example in delivery device 3000. For example, in some embodiments, an energy storage member is disposed within a housing of a delivery device (drug product), and is configured to produce a force to deliver the naloxone composition from the medicament container via a delivery member such that the delivery member atomizes the naloxone composition. In other embodiments, a device can include deformable portions such that the application of a manually-produced force can deliver the naloxone composition from the medicament container via a delivery member such that the delivery member atomizes the naloxone composition.

Although the delivery device 2000 includes the electronic circuit system cavity 2137, the gas cavity 2151, and/or the medicament cavity 2139 that are shown and described as being fluidically and/or physically isolated from each other, in other embodiments, any of the electronic circuit system cavity 2137, the gas cavity 2151, and/or the medicament cavity 2139 can be fluidically coupled to and/or share a common boundary with each other. In some embodiments, for example, a housing can define a single cavity within which a medicament container, an energy storage member and an electronic circuit system are disposed.

Although the delivery device 2000 includes the electronic circuit system 2900, in other embodiments, a delivery device and/or drug product need not include an electronic circuit system.

Although the electronic circuit system 2900 is shown and described above as producing an electronic output in response to the actuation of two irreversible switches (e.g., switch 2972 and switch 2973), in other embodiments, an electronic circuit system can produce an electronic output in response to an actuation of any number of reversible or irreversible switches and/or any other suitable input, command, or prompt. Suitable input for prompting an output can include, for example, an audible input by the user (e.g., the user's response to a voice prompt produced by the electronic circuit system), an input from a "start button" depressed by the user, an input from a sensor (e.g., a proximity sensor, a temperature sensor or the like), movement of (e.g., shaking) of the medicament delivery device, or the like. In some embodiments, an electronic circuit system can include a microphone and/or a voice recognition module to detect a user's vocal input.

Although medical devices having two LEDs and an audio output device have been shown, in other embodiments the medical device might have any number of LEDs and/or audio output devices. Additionally, other types of output devices, such as haptic output devices, can be used. In some embodiments, outputs from an electronic circuit system can include, for example, an audible or visual output related to the composition of the medicament (e.g., an indication of the expiration date, the symptoms requiring treatment with the medicament or the like), the use of the medicament delivery device, and/or post-administration procedures (e.g., a prompt to call 911, instructions for the disposal of the device or the like).

Although the electronic circuit system 2900 is shown and described herein as being coupled the housing 2100 of the medicament delivery device 2000, in other embodiments, all or a portion of an electronic circuit system can be coupled to a removable cover (e.g., cover 2190). For example, in some embodiments, such a cover can include an electronic circuit system (the "master ECS") including an audible output device, and the electronic circuit system can be configured to receive one or more signals from an electronic circuit system (the "slave ECS") coupled to the medicament delivery device. In this manner, the master ECS can receive indications of when the safety tab has been removed, when the device has been actuated or the like, and can produce an audible output as described herein. In some such embodiments, the master ECS and the slave ECS can be similar to the electronic circuit systems shown and described in U.S. Pat. No. 8,172,082, entitled "Devices, Systems and Methods for Medicament Delivery," filed on Feb. 5, 2007, which is incorporated herein by reference in its entirety.

Although the electronic circuit system 2900 is shown and described above as producing an electronic output in response to the removal of the safety lock 2700 and/or movement of the base 2510, in other embodiments, any suitable component within a medicament delivery device can function to actuate the electronic circuit system. For example, in some embodiments, a carrier (similar to the carrier 2370) can include a protrusion configured to engage a portion of an electronic circuit system such that the electronic circuit system produces an output in response to movement of the carrier. In other embodiments, an electronic circuit system can produce an electronic output in response to the deformation of a portion of a movable member (e.g., the engagement portion 2379 of the carrier 2370). In such embodiments, the deformable portion may be configured to engage a portion of the electronic circuit system or may be configured such that a portion of the electronic circuit system is disposed therein (e.g., a copper trace) to activate the electronic circuit system.

In some embodiments, the electronic circuit system 2900 can be used in either an actual medicament delivery device or a simulated medicament delivery device. A simulated medicament delivery device can, for example, correspond to an actual medicament delivery device and can be used, for example, to train a user in the operation of the corresponding actual medicament delivery device.

The simulated medicament delivery device can simulate the actual medicament delivery device in any number of ways, as shown and described in U.S. Patent Publication No. 2008/0059133, entitled "Medical Injector Simulation Device," which is incorporated herein by reference in its entirety. For example, in some embodiments, the simulated medicament delivery device can have a shape corresponding to a shape of the actual medicament delivery device, a size corresponding to a size of the actual medicament delivery device and/or a weight corresponding to a weight of the actual medicament delivery device. Moreover, in some embodiments, the simulated medicament delivery device can include components that correspond to the components of the actual medicament delivery device. In this manner, the simulated medicament delivery device can simulate the look, feel and sounds of the actual medicament delivery device. For example, in some embodiments, the simulated medicament delivery device can include external components (e.g., a housing, a needle guard, a sterile cover, a safety lock or the like) that correspond to external components of the actual medicament delivery device. In some embodiments, the simulated medicament delivery device can include internal components (e.g., an actuation mechanism, a compressed gas source, a medicament container or the like) that correspond to internal components of the actual medicament delivery device.

In some embodiments, however, the simulated medicament delivery device can be devoid of a medicament and/or those components that cause the medicament to be delivered (e.g., a needle, a nozzle or the like). In this manner, the simulated medicament delivery device can be used to train a user in the use of the actual medicament delivery device without exposing the user to a needle and/or a medicament. Moreover, the simulated medicament delivery device can have features to identify it as a training device to prevent a user from mistakenly believing that the simulated medicament delivery device can be used to deliver a medicament. For example, in some embodiments, the simulated medicament delivery device can be of a different color than a corresponding actual medicament delivery device. Similarly, in some embodiments, the simulated medicament delivery device can include a label clearly identifying it as a training device.

The actuation of the medicament delivery device configuration switch 2974 can configure the electronic circuit system 2900 to output a different electronic output when the medicament delivery device 2000 is a simulated delivery device than when the medicament delivery device 2000 is an actual delivery device. Said yet another way, the electronic circuit system 2900 can be configured to output a first series of electronic outputs when the electronic circuit system configuration switch 2974 is in the first state and a second series of electronic outputs when the electronic circuit system configuration switch 2974 is in the second state. In this manner, the electronic circuit system configuration switch 2974 can enable the same electronic circuit system 2900 to be used in both simulated medicament delivery devices and actual medicament delivery devices. When used on an actual medicament delivery device, for example, the housing can be devoid of the actuation protrusion 2165. The dual functionality of the electronic circuit system 2900 can decrease the cost of production of the electronic circuit system 2900 of the medicament delivery device 2000.

In other embodiments, moving the electronic circuit system configuration switch 2974 to the second state can place the electronic circuit system 2900 in any number of different functional configurations. For example, moving the electronic circuit system configuration switch 2974 from the first state to the second state can indicate the type of medicament in the medicament container, the dosage of the medicament and/or the language of the audible electronic outputs output by the electronic circuit system 2900.

In still other embodiments, any number of electronic circuit system configuration switches can be used. For example, multiple switches can be used to configure the electronic circuit system 2900 to output usage instructions in any number of languages. For example, if an electronic circuit system contained three configuration switches (e.g., switches A, B and C), switch A can correspond to English instructions, switch B to Spanish instructions and switch C to German instructions. Further, moving both switch A and B to the second state might correspond to French instructions. In this manner, a single electronic circuit system 2900 can be configured to output instructions in multiple languages.

Although the drug product 2000 is shown and described as include a gas container to produce the force for insertion and injection, in other embodiments, a drug product can include any suitable energy storage member, such as, for example, a spring.

Pharmacokinetic Analysis

A randomized, single-blind, single-dose, two-sequence, two-period crossover bioavailability, safety and tolerability study in fasted, healthy, male and female subjects to evaluate the PK of naloxone administered by injection using either the delivery device of present invention or a standard syringe was conducted. Thirty (30) healthy adult subjects completed the study. Subjects were randomized to receive one of the following treatments on Day 1 and the alternate treatment on Day 2:

Treatment A: A single injection of 0.4 mg naloxone HCl for injection USP administered using a delivery device of the present invention.

Treatment B: A single injection of 0.4 mg naloxone HCl for injection USP administered using a standard, manually-activated, syringe.

Randomization was instituted to reduce bias in treatment selection and in evaluation of treatments. The study was conducted in healthy adult males and females weighing between ≥50 kg and ≤100 kg. The 30 subjects were randomized to the two treatment sequences, with 15 subjects per sequence.

The second dose was administered at least 24 hours after the first dose to permit adequate wash-out between doses. Naloxone is rapidly distributed in the body and disappears from the serum in the initial distribution phase over a period of approximately 15 to 20 minutes. The elimination half-life is estimated to be between 30 and 90 minutes.

The Manual Injection Treatment was naloxone HCl injection USP administered via standard syringe. The Manual Injection Treatment was drawn from International Medicinal Systems (IMS), Limited's 2 mg/2 mL single dose disposable LUER-JET naloxone HCl injection USP pre-filled syringe (National Drug Code number: 0548-1469-00, Abbreviated New Drug Application #072076). The IMS product is a sterile, non-pyrogenic solution of naloxone HCl in water for injection. Each mL contains 1.0 mg naloxone HCl, 8.35 mg/mL sodium chloride to adjust tonicity in water and hydrochloric acid for pH adjustment; pH 3.0-4.5. The IMS product has been approved for IV, IM and SC administration.

The Auto-injection Treatment was naloxone HCl injection USP administered via a delivery device of the present invention. This formulation for the naloxone HCl injection USP utilizes drug substance meeting USP/National Formulary and European Pharmacopoeia specifications and the same excipients that are approved for the formulation of the Manual Injection. Each mL contains 1.0 mg naloxone HCl, 8.35 mg/mL sodium chloride to adjust tonicity in water and hydrochloric acid for pH adjustment; pH 3.0-4.5. The parenteral formulation was filled into a Type I borosilicate glass cartridge and enclosed with little-to-no headspace by an elastomeric plunger and elastomeric lined crimp seal (i.e., primary container closure). The materials that made up the primary container closure for the Auto-Injection Treatment were of the same general type as those used for the Manual Injection Treatment.

The delivery device and/or drug product had the structure as described above for the delivery device 2000 (e.g., the actuation assembly 2500, the medicament container 2200 and the delivery mechanism 2300). Moreover, the gas container included nominally 0.125 grams of Argon at a pressure of about 1100 psi (at 70° F.). The dynamic injection performance specifications of the drug product for the Auto-Injection Treatment are shown in Table 2:

TABLE 2

Device Performance Specifications:

| Test | Ave ± SD |
|---|---|
| Activation Force | 7.1 ± 0.5 |
| Volume Dispensed | 0.409 ± 0.005 |
| Dispensing Time | 0.254 ± 0.038 |
| Exposed Needle Length | 0.50 ± 0.01 |

Blood (approximately 7 mL) was collected 5 minutes prior to dosing and at 5, 10, 15, 20, 30, 40 and 50 minutes and 1, 1.25, 1.5, 2, 3, 4 and 6 hours post-dose for each dosing period. Blood was processed and plasma analyzed by validated methods for concentrations of naloxone and total naloxone (naloxone and its major metabolite, naloxone-3-glucuronide).

Pharmacokinetic Plasma Parameters

Pharmacokinetic parameters were calculated by non-compartmental analysis methods from the naloxone plasma concentration-time data using Phoenix® WinNonlin® version 6.2 (Pharsight, St. Louis, Mo., USA) following these guidelines:

Actual sampling times relative to dosing were used in the calculation of all derived PK parameters.

There was no imputation of missing data other than the substitution of concentrations that were BLQ as follows. All pre-dose BLQ and in the absorption phase prior to the first quantifiable concentration were substituted by zeros. Thereafter, BLQ values between quantifiable concentrations were substituted by ½ of the lower limit of quantification, before the calculation of the PK variables. The terminal BLQ values were disregarded.

The below PK parameters were estimated from plasma concentration-actual time profiles:

$C_{max}$: Maximum plasma naloxone concentration determined directly from the plasma concentration-time profile.

$T_{max}$: Time of maximum plasma naloxone concentration determined directly from the plasma concentration-time profile.

$AUC_{0-t}$: Area under the plasma concentration-time curve (AUC) from pre-dose (time 0) to the time of the last quantifiable concentration (Tlast) calculated using the linear-log trapezoidal rule.

$AUC_{0-\infty}$: AUC from pre-dose (time 0) extrapolated to infinite time ($AUC_{0-t}$+last observed quantifiable concentration in a given plasma concentration-time profile $[C_{last}]/\lambda_z$) calculated using the linear-log trapezoidal rule Lambda z ($\lambda_z$): Apparent terminal elimination rate constant $T_{1/2}$: Terminal elimination half-life calculated as: $\ln(2)/\lambda_z$ Analysis of Bioavailability For each of the naloxone PK parameters $C_{max}$, $AUC_{0-t}$ and $AUC_{0-\infty}$, analysis of variance (ANOVA) was applied to the logarithmically-transformed data and used to test the significance of the effects of sequence, period and treatment. In this analysis, subject nested within sequence was assumed to be a random effect; sequence, period and treatment were modeled as fixed factors. The treatment ratios (Test IMP/Reference IMP) for $C_{max}$, $AUC_{0-t}$ and $AUC_{0-\infty}$ were calculated by taking the anti-logarithm of the difference between treatment means.

A 90% CI for the treatment ratio was obtained by taking the anti-logarithm of the 90% CI endpoints for the mean difference. Bioequivalence was suggested when a 90% CI for the ratio of the geometric least squares (LS) means between treatments was contained in the equivalence limits (0.8, 1.25) for AUC and Cmax. These equivalence limits were used as a reference for comparing the bioavailability of the two treatments.

All available PK parameter data for AUC and $C_{max}$ was used for the assessment of bioavailability.

Figure 60:
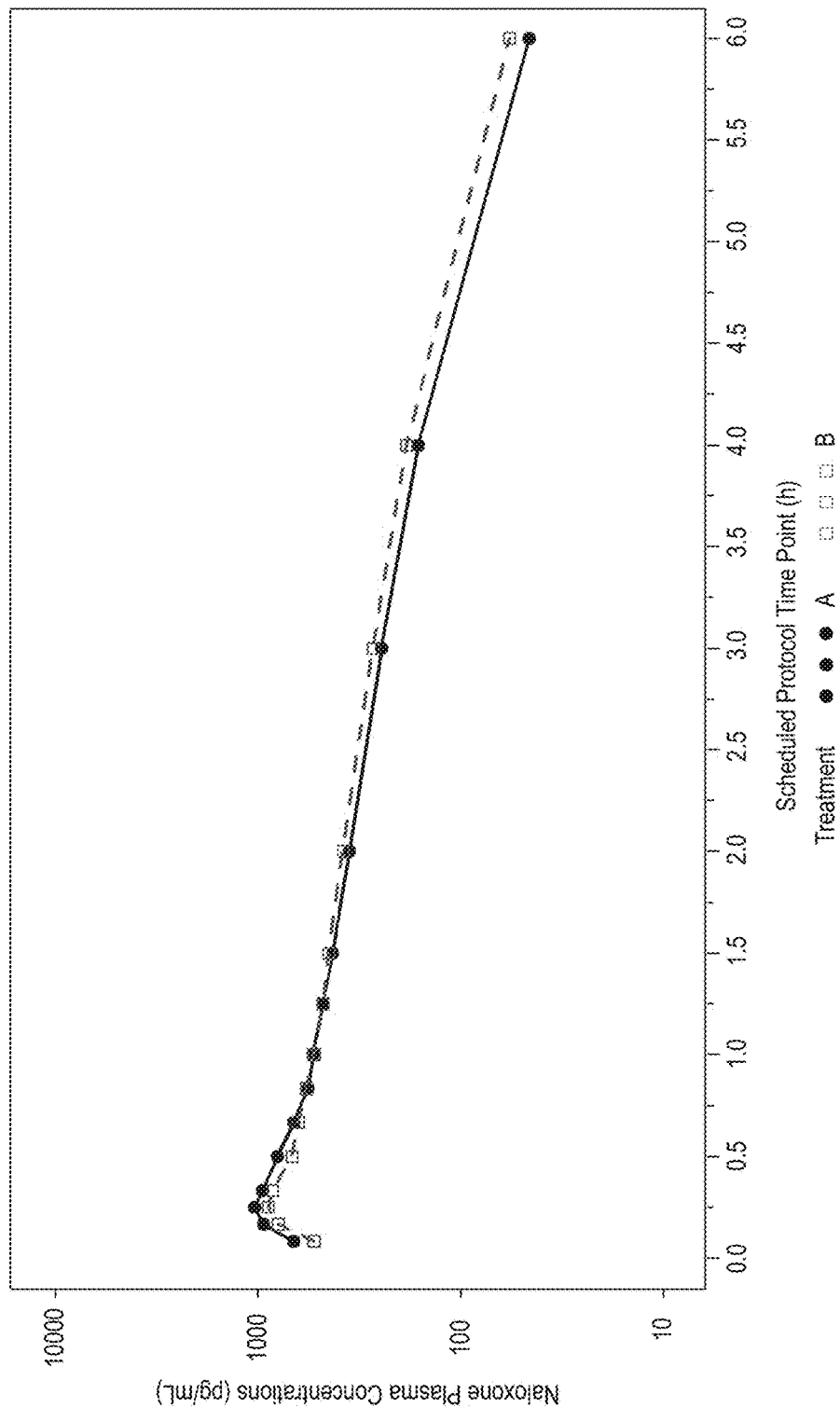
FIG. 60 is a graph illustrating the mean plasma-time concentration profile for naloxone plasma concentration data on a semi-logarithmic scale.

Mean plasma plasma concentration-time profiles for naloxone plasma concentration data are shown graphically in FIG. 58 (on a linear scale) and FIG. 60 (on a semi-logarithmic scale).

Figure 61:
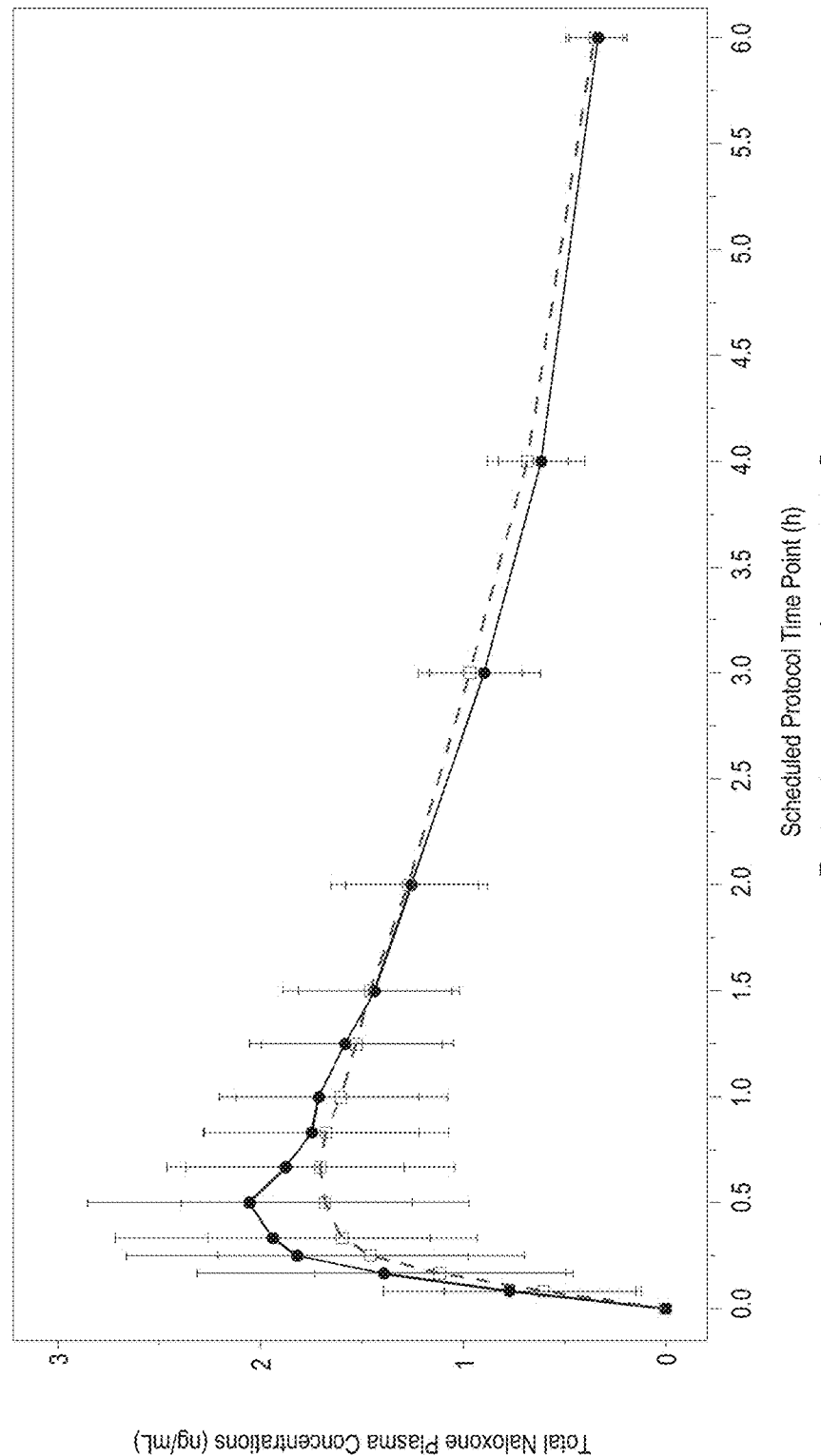
FIG. 61 is a graph illustrating the mean plasma-time concentration profile for total naloxone plasma concentration data on a linear scale.
Figure 62:
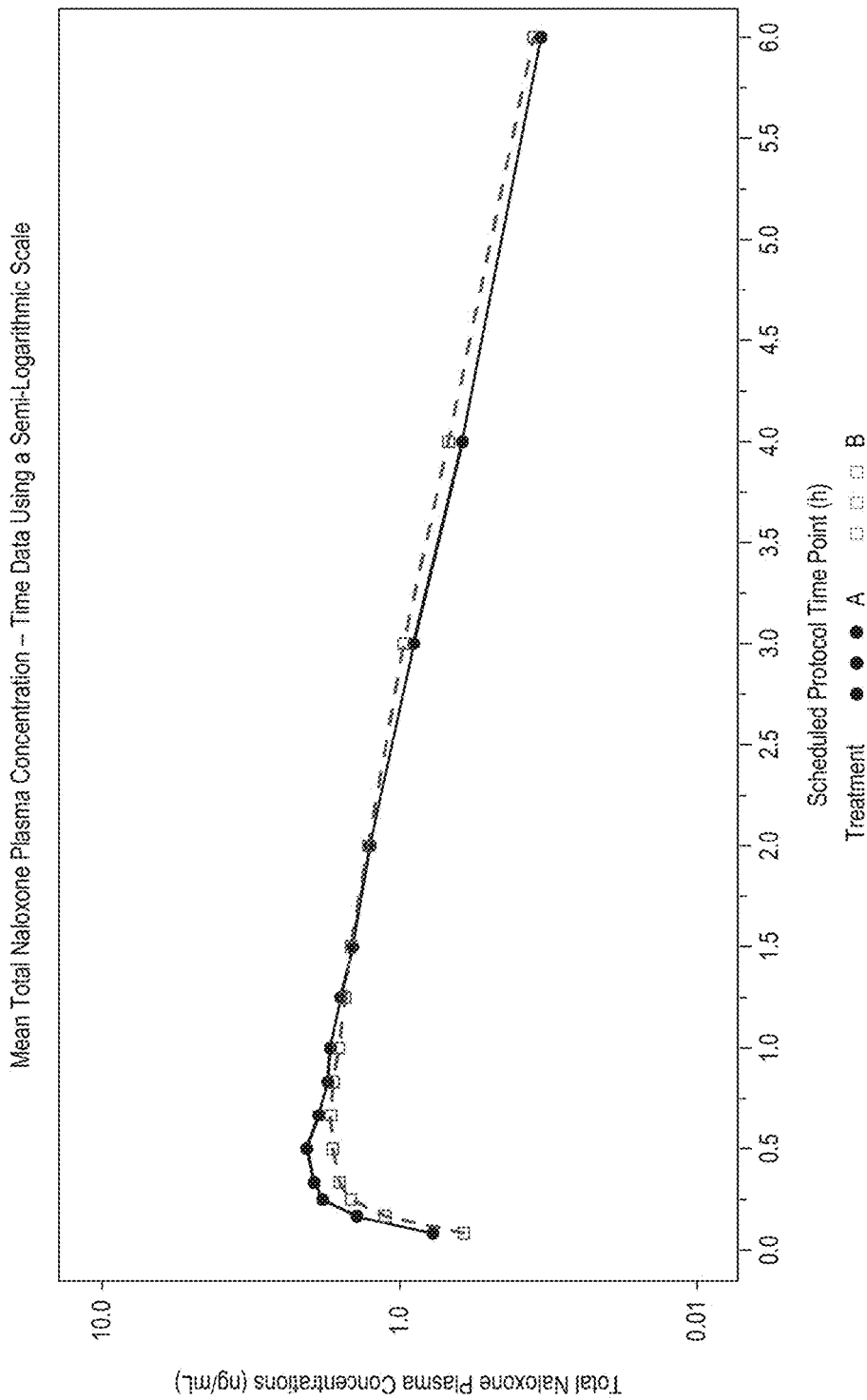
FIG. 62 is a graph illustrating the mean plasma-time concentration profile for total naloxone plasma concentration data on a semi-logarithmic scale.

Mean plasma plasma concentration-time profiles for total naloxone plasma concentration data (naloxone and its major metabolite, naloxone-3-glucuronide) are presented in FIG. 61 (on linear scales) and FIG. 62 (on semi-logarithmic scales).

Pharmacokinetic parameters are summarized descriptively by treatment in Table 3.

TABLE 3

Summary of Naloxone Plasma Pharmacokinetic Parameters

| Treatment | Statistic | $C_{max}$ (pg/mL) | $T_{max}$ (h) | $T_{1/2}$ (h) | $\lambda_z$ (1/h) | $AUC_{0-t}$ (pg.h/mL) | $AUC_{0-inf}$ (pg.h/mL) |
|---|---|---|---|---|---|---|---|
| A Auto-Injector | n | 30 | 30 | 30 | 30 | 30 | 30 |
| | Mean | 1240 | | 1.28 | 0.588 | 1830 | 1930 |
| | SD | 638 | | 0.485 | 0.136 | 397 | 453 |
| | %CV | 51.4 | | 38.0 | 23.2 | 21.7 | 23.4 |
| | Median | 1070 | 0.25 | 1.20 | 0.577 | 1790 | 1910 |
| | Min | 471 | 0.08 | 0.885 | 0.221 | 898 | 932 |
| | Max | 3110 | 1.23 | 3.13 | 0.783 | 2680 | 2960 |
| | Geometric %CV | 52.4 | | 29.2 | 29.2 | 23.1 | 24.7 |
| | Geometric Mean | 1100 | | 1.22 | 0.569 | 1780 | 1880 |
| B Manual | N | 30 | 30 | 30 | 30 | 30 | 30 |
| | Mean | 1070 | | 1.36 | 0.535 | 1850 | 1980 |
| | SD | 482 | | 0.319 | 0.110 | 452 | 495 |
| | %CV | 45.1 | | 23.5 | 20.6 | 24.4 | 25.0 |
| | Median | 959 | 0.33 | 1.28 | 0.542 | 1760 | 1840 |
| | Min | 294 | 0.08 | 0.894 | 0.295 | 859 | 922 |
| | Max | 2270 | 2.03 | 2.35 | 0.776 | 3040 | 3100 |
| | Geometric %CV | 53.2 | | 22.0 | 22.0 | 26.9 | 27.5 |

TABLE 3-continued

Summary of Naloxone Plasma Pharmacokinetic Parameters

| Treatment | Statistic | $C_{max}$ (pg/mL) | $T_{max}$ (h) | $T_{\%}$ (h) | $\lambda_z$ (1/h) | $AUC_{0-t}$ (pg.h/mL) | $AUC_{0-inf}$ (pg.h/mL) |
|---|---|---|---|---|---|---|---|
| | Geometric Mean | 957 | | 1.32 | 0.524 | 1800 | 1910 | h = hour(s); SD = Standard Deviation; %CV = Percentage coefficient of variation; HCl= Hydrochloride, USP = United States Pharmacopeia A summary of the statistical analysis of relative bioavailability of the treatment ratio (Treatment A/Treatment B) of $C_{max}$, $AUC_{0-t}$ and $AUC_{0-inf}$ is presented in Table 4.

TABLE 4

Statistical Analysis of Relative Bioavailability for Naloxone Plasma Pharmacokinetic Parameters

| Parameter (unit) | IMP | N | Geometric LS Means | Geometric LS Means 95% CI | Treatment Ratio (A/B) | 90% CI for Ratio of Geometric LS Means | Within Subject % CV |
|---|---|---|---|---|---|---|---|
| $C_{max}$ (pg/mL) | Test | 30 | 1100 | (918, 1320) | 1.15 | (0.97, 1.37) | 40.9 |
| | Reference | 30 | 957 | (797, 1150) | | | |
| $AUC_{0-t}$ (pg · h/mL) | Test | 30 | 1780 | (1620, 1960) | 0.993 | (0.94, 1.05) | 12.6 |
| | Reference | 30 | 1800 | (1640, 1970) | | | |
| $AUC_{0-inf}$ (pg · h/mL) | Test | 30 | 1880 | (1710, 2070) | 0.983 | (0.937, 103) | 10.9 |
| | Reference | 30 | 1910 | (1740, 2110) | | | |

CI = Confidence interval;
% CV = Percentage coefficient of variation;
LS: Least squares;
N = Number of subjects exposed to treatment;
HCl = Hydrochloride;
USP = United States Pharmacopeia

What is claimed is:

1. An apparatus, comprising:
a housing;
a medicament container disposed within the housing, the medicament container containing a dose of a naloxone composition, the dose having a delivered volume of at least 0.34 ml;
a needle configured to be placed in fluid communication with the medicament container when an end portion of the needle is extended outside of the housing; and
an actuation assembly including an energy storage member configured to produce a force on an elastomeric member within the medicament container to deliver the dose of the naloxone composition from the medicament container via the needle,
when actuated, the actuation assembly delivers the dose of the naloxone composition into a body in less than 0.5 seconds such that a 90% confidence interval of at least one of a relative mean maximum naloxone plasma concentration after the dose is delivered into the body ($C_{max}$), a time to reach a maximum naloxone plasma concentration ($T_{max}$), an area under a plasma concentration-time curve from pre-dose (time 0) extrapolated to infinity ($AUC_{0-\infty}$), or an area under the plasma concentration-time curve from pre-dose (time 0) to a time of a last quantifiable concentration ($T_{last}$) ($AUC_{0-t}$) of the delivered dose to a delivered dose of a corresponding naloxone composition via a manually-actuated syringe is within 80% to 125%.

2. The apparatus of claim 1, wherein the actuation assembly is configured such that the force on the elastomeric member decreases during delivery of the dose from a start force to an end force, the start force being between about between 30 pounds and 38 pounds, the end force being between 23 pounds and 31 pounds.

3. The apparatus of claim 1, wherein the needle is configured to move between a first needle position, in which the end portion of the needle is within the housing, and a second needle position, in which the end portion of the needle extends from the housing, the apparatus further comprising:
a retraction spring configured to urge the needle towards the first needle position; and
a release member configured to release the force from the elastomeric member after delivery of the dose, the actuation assembly and the release member configured such that at least 0.34 ml of the naloxone composition is delivered before the needle begins movement from the second needle position towards the first needle position.

4. The apparatus of claim 1, wherein the energy storage member is any one of a spring, a compressed gas container, or a propellant container.

5. The apparatus of claim 1, wherein:
the needle is configured to move between a first needle position, in which the end portion of the needle is within the housing, and a second needle position, in which the end portion of the needle extends from the housing; and
the force moves the needle from the first needle position to the second needle position.

6. The apparatus of claim 5, wherein the needle has a length sufficient to penetrate clothing and deliver any of a subcutaneous injection or an intramuscular injection of the dose of the naloxone composition.

7. The apparatus of claim 1, wherein an amount of the dose is between 0.2 mg and 10 mg.

8. The apparatus of claim 1, wherein the naloxone composition includes 4,5-epoxy-3,14-dihydroxy-17-(2-propenyl)morphinan-6-one in a concentration of between 0.01 mg/mL and 50 mg/mL.

9. The apparatus of claim 8, wherein the concentration of the 4,5-epoxy-3,14-dihydroxy-17-(2-propenyl)morphinan-6-one is between 0.01 mg/mL and 10 mg/mL.

10. The apparatus of claim 1, wherein the delivered volume is between 0.34 ml and 2 ml.

11. The apparatus of claim 1, wherein the energy storage member is any one of a compressed gas container or a propellant container that produces a pressurized gas within the housing to produce the force, the force moving the needle from a first needle position to a second needle position before the dose of the naloxone composition is delivered, the end portion of the needle being within the housing when the needle is in the first needle position, the end portion of the needle extended from the housing when the needle is in the second needle position, the apparatus further comprising:
a retraction spring configured to urge the needle towards the first needle position; and
a release member configured to release the pressurized gas from within the housing after delivery of the dose.

12. A method of delivering a dose of a naloxone composition, comprising:
placing a medicament injector against a body, the medicament injector including:
a housing;
a medicament container disposed within the housing, the medicament container containing the dose of the naloxone composition, the dose having a delivered volume of at least 0.34 ml;
a needle coupled to the medicament container; and
an actuation assembly including an energy storage member; and
actuating the medicament injector such that the energy storage member produces a force to move an elastomeric member within the medicament container to deliver the dose of the naloxone composition from the medicament container via the needle into the body in less than 0.5 seconds and in a manner such that a 90% confidence interval of at least one of a relative mean maximum naloxone plasma concentration after the dose is delivered into the body ($C_{max}$), a time to reach a maximum naloxone plasma concentration ($T_{max}$), an area under a plasma concentration-time curve from pre-dose (time 0) extrapolated to infinity ($AUC_{0-\infty}$), or an area under the plasma concentration-time curve from pre-dose (time 0) to a time of a last quantifiable concentration ($T_{last}$) ($AUC_{0-t}$) of the delivered dose to a delivered dose of a corresponding naloxone composition delivered via a manually-actuated syringe is within 80% to 125%.

13. The method of claim 12, wherein:
the actuating the medicament injector causes the force to move the needle from a first needle position to a second needle position before the dose of the naloxone composition is delivered, the end portion of the needle being within the housing when the needle is in the first needle position, the end portion of the needle extended from the housing when the needle is in the second needle position.

14. The method of claim 13, wherein:
the energy storage member is any one of a compressed gas container or a propellant container that produces a pressurized gas within the housing to produce the force; and
the medicament injector includes a retraction spring and a release member, the retraction spring configured to urge the needle towards the first needle position, the release member releasing the pressurized gas from within the housing after delivery of the dose.

15. The method of claim 13, wherein the end portion of the needle extends from the housing by a length sufficient to penetrate clothing and deliver any of a subcutaneous injection or an intramuscular injection of the dose of the naloxone composition.

16. The method of claim 12, wherein an amount of the dose is between 0.2 mg and 10 mg.

17. The method of claim 12, wherein the naloxone composition includes 4,5-epoxy-3,14-dihydroxy-17-(2-propenyl)morphinan-6-one in a concentration of between 0.01 mg/mL and 50 mg/mL.

18. The method of claim 17, wherein the concentration of the 4,5-epoxy-3,14-dihydroxy-17-(2-propenyl)morphinan-6-one is between 0.01 mg/mL and 10 mg/mL.

19. The method of claim 12, wherein the delivered volume is between 0.34 ml and 2 ml.

20. The method of claim 12, further comprising:
storing, before the placing, the medicament injector for at least six months.

21. The method of claim 20, wherein the storing includes storing the medicament injector within a case, the method further comprising:
removing, before the placing, the medicament injector from the case.

* * * * *